US011099195B2

(12) United States Patent
Estruch et al.

(10) Patent No.: US 11,099,195 B2
(45) Date of Patent: *Aug. 24, 2021

(54) METHODS OF DETECTING MARKERS FOR INFLAMMATORY CONDITIONS AND FOOD SENSITIVITY IN COMPANION ANIMALS

(71) Applicant: VETICA LABS, INC., San Diego, CA (US)

(72) Inventors: Juan Estruch, San Diego, CA (US); Genevieve Hansen, San Diego, CA (US)

(73) Assignee: VETICA LABS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/029,373

(22) Filed: Jul. 6, 2018

(65) Prior Publication Data

US 2018/0306809 A1    Oct. 25, 2018

Related U.S. Application Data

(60) Division of application No. 15/592,104, filed on May 10, 2017, now Pat. No. 10,041,958, which is a continuation-in-part of application No. PCT/US2016/060674, filed on Nov. 4, 2016.

(60) Provisional application No. 62/373,307, filed on Aug. 10, 2016, provisional application No. 62/252,266, filed on Nov. 6, 2015.

(51) Int. Cl.
| | |
|---|---|
| *G01N 33/68* | (2006.01) |
| *C07K 16/28* | (2006.01) |
| *C07K 16/12* | (2006.01) |
| *C07K 16/18* | (2006.01) |
| *G01N 33/50* | (2006.01) |
| *G01N 33/564* | (2006.01) |
| *A23K 50/40* | (2016.01) |
| *G01N 33/569* | (2006.01) |

(52) U.S. Cl.
CPC ......... *G01N 33/6893* (2013.01); *A23K 50/40* (2016.05); *C07K 16/12* (2013.01); *C07K 16/18* (2013.01); *C07K 16/28* (2013.01); *C07K 16/2839* (2013.01); *G01N 33/5005* (2013.01); *G01N 33/564* (2013.01); *G01N 33/56911* (2013.01); *G01N 33/6854* (2013.01); *G01N 2333/195* (2013.01); *G01N 2333/4727* (2013.01); *G01N 2333/4737* (2013.01); *G01N 2333/70546* (2013.01); *G01N 2333/79* (2013.01); *G01N 2800/06* (2013.01); *G01N 2800/24* (2013.01)

(58) Field of Classification Search
None
See application file for complete search history.

(56) References Cited

U.S. PATENT DOCUMENTS

| | | | |
|---|---|---|---|
| 4,277,250 A | 7/1981 | Melnick et al. | |
| 4,446,232 A | 5/1984 | Liotta | |
| 4,801,536 A | 1/1989 | Stahl et al. | |
| 4,868,108 A | 9/1989 | Bahar et al. | |
| 4,920,045 A | 4/1990 | Okuda et al. | |
| 6,019,944 A | 1/2000 | Buechler | |
| 6,033,864 A | 3/2000 | Braun | |
| 6,218,129 B1 | 4/2001 | Walsh et al. | |
| 6,309,643 B1 | 10/2001 | Braun et al. | |
| 6,406,862 B1 | 6/2002 | Krakauer et al. | |
| 6,838,250 B2 | 1/2005 | Scalice et al. | |
| 7,081,345 B1 | 7/2006 | Roecklin et al. | |
| 7,138,237 B1 | 11/2006 | Targan et al. | |
| 2003/0105060 A1 | 6/2003 | Esnault et al. | |
| 2006/0154276 A1 | 7/2006 | Lois et al. | |
| 2010/0094560 A1 | 4/2010 | Lois et al. | |
| 2010/0330190 A1 | 12/2010 | Compans et al. | |
| 2014/0135483 A1* | 5/2014 | Seito ................ A61K 38/00 530/387.9 |
| 2015/0110827 A1 | 4/2015 | Song et al. | |
| 2015/0376707 A1 | 12/2015 | Targan et al. | |
| 2017/0248614 A1 | 8/2017 | Estruch et al. | |

FOREIGN PATENT DOCUMENTS

| | | |
|---|---|---|
| CN | 102046198 A | 5/2011 |
| CN | 102488898 A | 6/2012 |
| CN | 102656276 A | 9/2012 |

(Continued)

OTHER PUBLICATIONS

Colman etal., 'Effects of amino acid sequence changes on antibody-antigen interactions,' Res. In Immunology 145:33-36 (1994).*
Abaza et al., 'Effects of amino acid substitutions outside an antigenis site on protein binding to monoclonal antibodies of predetermined specificity obtained by peptide immunization: demonstration with region 94-100 (antigenic site 3) of myoglobin,' J. Prot. Chem. 11:433-444 (1992).*
Lederrnan ei al., 'A single amino acid substitution in a common African allele of the cd4 molecule ablates binding of the monoclonal antibody, OKT4,' Molec. Immunolo. 28:1171-1181 (1991).*
Bateman et al., "IgA antibodies of coeliac disease patients recognize a dominant T cell epitope of A-gliadin." Gut. 2004, 53(9):1274-1278.

(Continued)

Primary Examiner — Nora M Rooney
(74) Attorney, Agent, or Firm — Hoxie & Associates LLC

(57) ABSTRACT

The present invention provides methods and systems to accurately detect and measure levels of endogenous antibodies, for examples endogenous IgA, to particular antigens in a biological sample from a companion animal, which is useful to diagnose inflammatory conditions, including bowel disease (IBD), gastrointestinal infections, and food sensitivities in companion animals, e.g., dogs or cats, and to distinguish among such gastrointestinal disorders. Such methods and systems identify whether a sample from the patient is associated with an inflammatory condition, infection, and/or food sensitivity condition, by using non-invasive means, thus conveniently providing information useful for guiding treatment decisions.

22 Claims, No Drawings

Specification includes a Sequence Listing.

(56) References Cited

FOREIGN PATENT DOCUMENTS

| WO | WO 2011/125015 A2 | | 10/2011 | | |
|---|---|---|---|---|---|
| WO | WO 2011/146479 | * | 11/2011 | ............. | C07K 16/00 |
| WO | WO 2013/001819 | * | 1/2013 | ............. | C07K 14/71 |
| WO | WO 2014/037588 A2 | * | 3/2014 | ............. | C07K 16/24 |
| WO | WO 2014/053996 A2 | | 4/2014 | | |
| WO | WO 2017/079653 A2 | | 5/2017 | | |

OTHER PUBLICATIONS

Cerquetella, M. et al., "Inflammatory Bowel Disease in the Dog: Differences and Similarities with Humans," World J. Gastroent, 2010, 16:1050-1056.

Colman et al., "Effects of amino acide sequence changes on antibody-antigen interactions." Res. Immunol., 1994, 145:33-35.

Felici et al., "Phage-Displayed Peptides as Tools for Characterization of Human Sera," Methods in Enzymology, 1996, 267:116-129.

Frosch et al., "NZB mouse system for production of monoclonal antibodies to weak bacterial antigens: Isolation of an IgG antibody to the polysaccharide capsules of *Escherichia coli* K1 and group B meningococci," Proc. Natl. Acad. Sci., 1985, 82:1194-1198.

Hall et al., "Immune responses to dietary antigens in gluten-sensitive enteropathy of Irish setters," Research in Veterinary Science, 1992, 53:293-299.

Hashida, et al., "More reliable diagnosis of infection with human immunodeficiency virus type 1 (HIV-1) by detection of antibody IgGs to pol and gag proteins of HIV-1 and p24 antigen of HIV-1 in urine, saliva, and/or serum with highly sensitive and specific enzyme immunoassay (immune complex transfer enzyme immunoassay): A review," J. Clin. Lab. Anal., 1997, 11:267-286.

International Search Report and Written Opinion for International Application No. PCT/US2016/060674, prepared by the International Searching Authority, dated Apr. 25, 2017, 15 pages.

Kikuchi et al., "Production and characterization of antibodies to the β-(1→6)-galactotetraosyl group and their interaction with arabinogalactan-proteins," Planta, 1993,190:525-535.

Lindberg et al., "Antibody (IgG, IgA, and IgM) to baker's yeast (*Saccharomyces cerevisiae*), yeast mannan, gliadin, ovalbumin and betalactoglobulin in monozygotic twins with inflammatory bowel disease," Gut, 1992, 33:909-913.

Nikaido, "Molecular Basis of Bacterial Outer Membrane Permeability Revisited," Mol. Biol. Rev., 2003, 67(4):593-656.

Nolan, J.P. & Condello, D., "Spectral Flow Cytometry," Curr Protoc Cytom., 2013, Unit 1.27, 1-18.

Nolan, J.P. & Mandy, F., "Multiplexed and Microparticle-based Analyses: Quantitative Tools for the Large-Scale Analysis of Biological Systems," F. Cytometry, 2006, 69A:318-325.

Sendid et al., "Specific Antibody Response to Oligomannosidic Epitopes in Crohn's Disease," Clin. Diagn. Lab. Immunol., 1996, 3(2):219-226.

Suchodolski, "Companion Animals Symposium: Microbes and gastrointestinal health of dogs and cats," J. Anim. Sci., 2011, 89:1520-1530.

Tsai et al., "Ultrasensitive Antibody Detection by Agglutination-PCR (ADAP)," ACS Cent. Sci., 2016, 2:139-147.

Xavier, R.J. and Podolsky, D.K., "Unravelling the Pathogenesis of Inflammatory Bowel Disease," Nature, 2007, 448:427-434.

Allenspach, K., "Diagnosis of Small Intestinal Disorders in Dogs and Cats," *Clin. Lab Med*, vol. 35, pp. 521-534, (2015).

GenBank Accession No. ACS66786.1, retrieved on Dec. 22, 2014 from https://www.ncbi.nlm.nih.gov/protein/ ACS66786.1, 1 page.

GenBank Accession No. AAC63948.1.1, retrieved on Sep. 27, 2020 from https://www.ncbi.nlm.nih.gov/protein/AAC63948.1, 4 pages.

GenBank Accession No. AJR10062.1, retrieved on Sep. 27, 2020 from https://www.ncbi.nlm.nih.gov/protein/AJR10062.1, 1 page.

GenBank Accession No. EEI48859.1, retrieved on Sep. 27, 2020 from https://www.ncbi.nlm.nih.gov/protein/EEI48859.1, 2 pages.

GenBank Accession No. WP_023533978.1, retrieved on Sep. 27, 2020 from https://www.ncbi.nlm.nih.gov/protein/ WP_023533978.1, 1 page.

GenBank Accession No. XP_004392420.1, retrieved on Sep. 27, 2020 from https://www.ncbi.nlm.nih.gov/protein/ XP_004392420.1, 2 pages.

GenBank Accession No. XP_004403099.2, retrieved on Sep. 27, 2020 from https://www.ncbi.nlm.nih.gov/protein/ XP_004403099.2, 2 pages.

GenBank Accession No. XP_004406290.1, retrieved on Sep. 27, 2020 from https://www.ncbi.nlm.nih.gov/protein/ XP_004406290.1, 2 pages.

GenBank Accession No. XP_004769005.2, retrieved on Sep. 27, 2020 from https://www.ncbi.nlm.nih.gov/protein/ XP_004769005.2, 2 pages.

GenBank Accession No. XP_008565858.1, retrieved on Sep. 27, 2020 from https://www.ncbi.nlm.nih.gov/protein/ XP_008565858.1, 2 pages.

GenBank Accession No. XP_008694896.1, retrieved on Sep. 27, 2020 from https://www.ncbi.nlm.nih.gov/protein/ 671008069, 2 pages.

Nanau et al., "In-Depth Review: Inflammatory Bowel Disease," *Translational Research*, vol. 160, No. 1, pp. 1-28, (2012).

Tang et al., "Value of Serological Markers in Diagnosis and Prognosis of Inflammatory Bowel Disease," *Chinese Journal of Practical Internal Medicine*, vol. 35, No. 9, 5 pages, (2015); English Abstract Only (Machine Translation).

Wdowiak et al., "Biomarkers in Canine Inflammatory Bowel Disease Diagnostics," *Polish Journal of Veterinary Sciences*, vol. 16, No. 3, pp. 601-609, (2013).

* cited by examiner

SEQUENCE LISTING

<160> NUMBER OF SEQ ID NOS: 66

<210> SEQ ID NO 1
<211> LENGTH: 21
<212> TYPE: DNA
<213> ORGANISM: Unknown
<220> FEATURE:
<223> OTHER INFORMATION: Unidentified Bacteria Species

<400> SEQUENCE: 1
gctttaactg taaacaccaa c                                        21

<210> SEQ ID NO 2
<211> LENGTH: 20
<212> TYPE: DNA
<213> ORGANISM: Unknown
<220> FEATURE:
<223> OTHER INFORMATION: Unidentified Bacteria Species

<400> SEQUENCE: 2
ctactgaagc agtttcagga                                          20

<210> SEQ ID NO 3
<211> LENGTH: 24
<212> TYPE: DNA
<213> ORGANISM: Unknown
<220> FEATURE:
<223> OTHER INFORMATION: Unidentified Bacteria Species

<400> SEQUENCE: 3
gctttatctg ttaataccaa catc                                     24

<210> SEQ ID NO 4
<211> LENGTH: 23
<212> TYPE: DNA
<213> ORGANISM: Unknown
<220> FEATURE:
<223> OTHER INFORMATION: Unidentified Bacteria Species

<400> SEQUENCE: 4
ttactgaagc agtttcagta ccg                                      23

<210> SEQ ID NO 5
<211> LENGTH: 21
<212> TYPE: DNA
<213> ORGANISM: Unknown
<220> FEATURE:
<223> OTHER INFORMATION: Unidentified Bacteria Species

<400> SEQUENCE: 5
gcacaagtca ttaataccaa c                                        21

<210> SEQ ID NO 6
<211> LENGTH: 21
<212> TYPE: DNA
<213> ORGANISM: Unknown
<220> FEATURE:
<223> OTHER INFORMATION: Unidentified Bacteria Species

<400> SEQUENCE: 6
ttaacgtaac agagacagaa c                                        21

<210> SEQ ID NO 7
<211> LENGTH: 21
<212> TYPE: DNA
<213> ORGANISM: Unknown

```
<220> FEATURE:
<223> OTHER INFORMATION: Unidentified Bacteria Species

<400> SEQUENCE: 7
gcacaagtca ttaataccaa c                                              21

<210> SEQ ID NO 8
<211> LENGTH: 18
<212> TYPE: DNA
<213> ORGANISM: Unknown
<220> FEATURE:
<223> OTHER INFORMATION: Unidentified Bacteria Species

<400> SEQUENCE: 8
ttaaccctgc agcagaga                                                  18

<210> SEQ ID NO 9
<211> LENGTH: 484
<212> TYPE: PRT
<213> ORGANISM: Unknown
<220> FEATURE:
<223> OTHER INFORMATION: Unidentified Bacteria Species

<400> SEQUENCE: 9
```

Met Ala Leu Thr Val Asn Thr Asn Ile Ala Ser Val Thr Thr Gln Val
1               5                   10                  15

Asn Leu Asn Lys Ala Ser Thr Ala Gln Thr Thr Ser Met Gln Arg Leu
            20                  25                  30

Ser Ser Gly Leu Arg Ile Asn Ser Ala Lys Asp Asp Ala Ala Gly Leu
        35                  40                  45

Gln Ile Ala Asn Arg Leu Thr Ser Gln Ile Asn Gly Leu Gly Gln Ala
    50                  55                  60

Val Lys Asn Ala Asn Asp Gly Ile Ser Ile Ala Gln Thr Ala Glu Gly
65                  70                  75                  80

Ala Met Gln Ala Ser Thr Asp Ile Leu Gln Lys Met Arg Thr Leu Ala
                85                  90                  95

Leu Ser Ser Ala Thr Gly Ser Leu Ser Pro Asp Asp Arg Lys Ser Asn
            100                 105                 110

Asn Asp Glu Tyr Gln Ala Leu Thr Ala Glu Leu Asn Arg Ile Ser Ala
        115                 120                 125

Thr Thr Thr Phe Gly Gly Gln Lys Leu Leu Asp Gly Ser Tyr Gly Thr
    130                 135                 140

Lys Ala Ile Gln Val Gly Ala Asn Ala Asn Glu Thr Ile Asn Leu Thr
145                 150                 155                 160

Leu Asp Asn Val Ser Ala Lys Ser Ile Gly Ser Gln Leu Lys Thr
                165                 170                 175

Gly Asn Ile Ser Ile Ser Lys Asp Gly Leu Ala Ala Gly Glu Leu Ala
            180                 185                 190

Val Thr Gly Asn Gly Gln Thr Lys Thr Val Asn Tyr Gly Pro Gly Ala
        195                 200                 205

Ser Ala Lys Asp Val Ala Ala Gln Leu Asn Gly Ala Ile Gly Gly Leu
    210                 215                 220

Thr Ala Thr Ala Ser Thr Glu Val Lys Leu Asp Ala Ser Gly Ala Thr
225                 230                 235                 240

Ala Ala Ala Pro Ala Asn Phe Asp Leu Thr Val Gly Gly Ser Thr Val
                245                 250                 255

Ser Phe Val Gly Val Thr Asp Asn Ala Ser Leu Ala Asp Gln Leu Lys
            260                 265                 270

-continued

Ser Asn Ala Ala Lys Leu Gly Ile Ser Val Asn Tyr Asp Glu Ser Thr
            275                 280                 285

Lys Asn Leu Glu Ile Lys Ser Asp Thr Gly Glu Asn Ile Thr Phe Ala
        290                 295                 300

Pro Lys Ala Gly Ala Pro Gly Val Lys Ile Ala Ala Lys Asn Gly Ser
305                 310                 315                 320

Gly Thr Tyr Gly Ala Ala Val Pro Leu Asn Ala Ala Gly Asp Lys
                325                 330                 335

Ser Val Val Thr Gly Gln Ile Ser Leu Asp Ser Ala Lys Gly Tyr Ser
            340                 345                 350

Ile Ala Asp Gly Ala Gly Ala Asn Gly Ala Gly Ser Thr Ala Ala Leu
            355                 360                 365

Tyr Gly Thr Gly Val Thr Ser Val Ser Ser Lys Lys Thr Asn Val Ser
        370                 375                 380

Asp Thr Asp Val Thr Ser Ala Thr Asn Ala Gln Asn Ala Val Ala Val
385                 390                 395                 400

Ile Asp Lys Ala Ile Gly Ser Ile Asp Ser Val Arg Ser Gly Leu Gly
                405                 410                 415

Ala Thr Gln Asn Arg Leu Thr Thr Thr Val Asp Asn Leu Gln Asn Ile
            420                 425                 430

Gln Lys Asn Ser Thr Ala Ala Arg Ser Thr Val Gln Asp Val Asp Phe
        435                 440                 445

Ala Ser Glu Thr Ala Glu Leu Thr Lys Gln Gln Thr Leu Gln Gln Ala
    450                 455                 460

Ser Thr Ala Ile Leu Ser Gln Ala Asn Gln Leu Pro Ser Ser Val Leu
465                 470                 475                 480

Lys Leu Leu Gln

<210> SEQ ID NO 10
<211> LENGTH: 476
<212> TYPE: PRT
<213> ORGANISM: Unknown
<220> FEATURE:
<223> OTHER INFORMATION: Unidentified Bacteria Species

<400> SEQUENCE: 10

Met Ala Leu Ser Val Asn Thr Asn Ile Ala Ser Ile Thr Thr Gln Gly
1               5                   10                  15

Asn Leu Thr Lys Ala Ser Thr Ala Gln Thr Thr Ser Met Gln Arg Leu
            20                  25                  30

Ser Ser Gly Leu Arg Ile Asn Ser Ala Lys Asp Asp Ala Ala Gly Leu
        35                  40                  45

Gln Ile Ser Asn Arg Leu Thr Ser Gln Ile Asn Gly Leu Gly Gln Ala
    50                  55                  60

Val Lys Asn Ala Asn Asp Gly Ile Ser Ile Ala Gln Thr Ala Glu Gly
65                  70                  75                  80

Ala Met Gln Ala Ser Thr Asp Ile Leu Gln Lys Met Arg Thr Leu Ala
                85                  90                  95

Leu Ser Ser Ala Thr Gly Ser Leu Ser Ala Asp Arg Lys Ser Asn
            100                 105                 110

Asn Asp Glu Tyr Gln Ala Leu Thr Ala Glu Leu Thr Arg Ile Ser Gln
        115                 120                 125

Thr Thr Thr Phe Gly Gly Gln Lys Leu Leu Asp Gly Ser Tyr Gly Thr
    130                 135                 140

-continued

```
Lys Ala Ile Gln Val Gly Asn Ala Asn Glu Thr Ile Asn Leu Thr
145                 150                 155                 160

Leu Asp Asn Val Ala Ala Asn Asn Ile Gly Ser Gln Gln Val Lys Ser
                165                 170                 175

Val Ala Ile Thr Pro Ser Ala Thr Gly Val Asp Ala Gly Thr Val Thr
            180                 185                 190

Val Thr Gly Asn Gly Gln Thr Lys Asp Val Thr Val Thr Ala Gly Asp
        195                 200                 205

Ser Ala Lys Thr Ile Ala Ala Asn Leu Asn Gly Ala Ile Gly Gly Leu
    210                 215                 220

Thr Ala Thr Ala Ser Thr Glu Val Gln Phe Ser Val Asp Lys Thr Ala
225                 230                 235                 240

Pro Ala Ala Asn Phe Glu Leu Thr Val Gly Ser Gln Lys Val Ser Phe
                245                 250                 255

Val Gly Val Thr Asp Thr Ala Ser Leu Ala Asp Gln Leu Lys Ser Asn
            260                 265                 270

Ala Ala Lys Leu Gly Ile Ser Val Asn Tyr Asp Glu Ser Asn Gly Gly
        275                 280                 285

Ser Leu Ser Val Lys Ser Asp Thr Gly Glu Asn Leu Val Phe Gly Ala
    290                 295                 300

Gly Asp Ala Ala Gln Ala Gly Ile Lys Val Asn Ala Lys Asp Gly
305                 310                 315                 320

Asn Gly Glu Tyr Ala Ala Ser Gly Thr Ala Leu Thr Ala Ala Asp Leu
                325                 330                 335

Tyr Val Thr Gly Ala Ile Ser Leu Asp Ser Ala Lys Gly Tyr Ser Leu
            340                 345                 350

Thr Gly Gly Gly Val Thr Lys Leu Phe Ser Ala Ala Gly Thr Ala Ala
        355                 360                 365

Thr Ser Val Lys Thr Thr Ile Ala Asp Thr Asp Val Thr Asp Ala Thr
    370                 375                 380

Lys Ala Gln Asn Ala Leu Ala Val Ile Asp Lys Ala Ile Gly Ser Ile
385                 390                 395                 400

Asp Ser Val Arg Ser Gly Leu Gly Ala Thr Gln Asn Arg Leu Gln Thr
                405                 410                 415

Thr Val Asp Asn Leu Gln Asn Ile Gln Lys Asn Ser Thr Ala Ala Arg
            420                 425                 430

Ser Thr Val Gln Asp Val Asp Phe Ala Ser Glu Thr Ala Glu Leu Thr
        435                 440                 445

Lys Gln Gln Thr Leu Gln Gln Ala Ser Thr Ala Ile Leu Ser Gln Ala
    450                 455                 460

Asn Gln Leu Pro Ser Ser Val Leu Lys Leu Leu Gln
465                 470                 475

<210> SEQ ID NO 11
<211> LENGTH: 365
<212> TYPE: PRT
<213> ORGANISM: Unknown
<220> FEATURE:
<223> OTHER INFORMATION: Unidentified Bacteria Species

<400> SEQUENCE: 11

Met Ala Gln Val Ile Asn Thr Asn Tyr Leu Ser Leu Val Thr Gln Asn
1               5                   10                  15

Asn Leu Asn Lys Ser Gln Gly Thr Leu Gly Ser Ala Ile Glu Arg Leu
            20                  25                  30
```

Ser Ser Gly Leu Arg Ile Asn Ser Ala Lys Asp Asp Ala Gly Gln
        35                  40                  45

Ala Ile Ala Asn Arg Phe Thr Ser Asn Val Asn Gly Leu Thr Gln Ala
 50                  55                  60

Ser Arg Asn Ala Asn Asp Gly Ile Ser Ile Ala Gln Thr Thr Glu Gly
 65                  70                  75                  80

Ala Leu Asn Glu Ile Asn Asn Leu Gln Arg Ile Arg Glu Leu Thr
                 85                  90                  95

Val Gln Ala Lys Asn Gly Thr Asn Ser Asn Ser Asp Ile Thr Ser Ile
                100                 105                 110

Gln Asn Glu Val Lys Glu Arg Leu Asp Glu Ile Asn Arg Ile Ser Glu
            115                 120                 125

Gln Thr Gln Phe Asn Gly Val Lys Val Leu Ser Gly Glu Lys Ser Glu
    130                 135                 140

Met Val Ile Gln Val Gly Thr Asn Asp Asn Glu Thr Ile Lys Phe Asn
145                 150                 155                 160

Leu Asp Lys Val Asp Asn Asp Thr Leu Gly Val Ala Ser Asp Lys Leu
                165                 170                 175

Phe Asp Thr Lys Thr Glu Lys Lys Gly Val Thr Glu Ala Gly Ala Ala
                180                 185                 190

Ile Asp Ala Lys Asp Ile Gly Val Thr Gly Ala Thr Lys Tyr Glu Gly
            195                 200                 205

Gly Thr Val Lys Glu Tyr Lys Val Asp Gly Lys Val Ser Ala Asp Lys
    210                 215                 220

Val Ile Phe Asn Asp Gly Thr Lys Asp Tyr Leu Val Ser Lys Ser Asp
225                 230                 235                 240

Phe Lys Leu Lys Ala Gly Thr Ala Asp Thr Ala Glu Phe Thr Gly Ser
                245                 250                 255

Lys Thr Thr Glu Phe Lys Ala Asp Ala Gly Lys Asp Val Lys Thr Leu
                260                 265                 270

Asn Val Lys Asp Asp Ala Leu Ala Thr Leu Asp Lys Ala Ile Asn Thr
            275                 280                 285

Ile Asp Glu Ser Arg Ser Lys Leu Gly Ala Ile Gln Asn Arg Phe Glu
    290                 295                 300

Ser Thr Ile Asn Asn Leu Asn Asn Thr Val Asn Asn Leu Ser Ala Ser
305                 310                 315                 320

Arg Ser Arg Ile Leu Asp Ala Asp Tyr Ala Thr Glu Val Ser Asn Met
                325                 330                 335

Ser Arg Gly Gln Ile Leu Gln Gln Ala Gly Thr Ser Val Leu Ala Gln
                340                 345                 350

Ala Asn Gln Val Pro Gln Thr Val Leu Ser Leu Leu Arg
    355                 360                 365

<210> SEQ ID NO 12
<211> LENGTH: 453
<212> TYPE: PRT
<213> ORGANISM: Unknown
<220> FEATURE:
<223> OTHER INFORMATION: Unidentified Bacteria Species

<400> SEQUENCE: 12

Met Ala Gln Val Ile Asn Thr Asn Ser Leu Ser Leu Ile Thr Gln Asn
1               5                   10                  15

Asn Ile Asn Lys Asn Gln Ser Ala Leu Ser Ser Ser Ile Glu Arg Leu
            20                  25                  30

```
Ser Ser Gly Leu Arg Ile Asn Ser Ala Lys Asp Asp Ala Gly Gln
        35                  40                  45

Ala Ile Ala Asn Arg Phe Thr Ser Asn Ile Lys Gly Leu Thr Gln Ala
50                  55                  60

Ala Arg Asn Ala Asn Asp Gly Ile Ser Leu Ala Gln Thr Thr Glu Gly
65                  70                  75                  80

Ala Leu Ser Glu Ile Asn Asn Asn Leu Gln Arg Val Arg Glu Leu Thr
                85                  90                  95

Val Gln Ala Thr Thr Gly Thr Asn Ser Asp Ser Asp Leu Ser Ser Ile
            100                 105                 110

Gln Asp Glu Ile Lys Ser Arg Leu Asp Glu Ile Asp Arg Val Ser Gly
        115                 120                 125

Gln Thr Gln Phe Asn Gly Val Asn Val Leu Ala Lys Asn Gly Thr Met
    130                 135                 140

Lys Ile Gln Val Gly Ala Asn Asp Gly Gln Thr Ile Ala Ile Asp Leu
145                 150                 155                 160

Gln Lys Ile Asp Ser Ser Thr Leu Gly Leu Asn Gly Leu Ser Val Ser
                165                 170                 175

Lys Asn Ser Leu Asn Val Ser Glu Pro Val Thr Gln Ile Asn Asn Ala
            180                 185                 190

Ala Asn Thr Ala Pro Leu Lys Val Asp Leu Ser Ala Val Ala Thr Asp
        195                 200                 205

Leu Gly Val Asp Ala Ser Ser Leu Thr Leu Ser Asn Val Leu Asp Lys
    210                 215                 220

Asp Gly Asn Ala Thr Lys Asn Tyr Val Val Lys Ser Gly Asn Asp Tyr
225                 230                 235                 240

Phe Ala Ala Ser Val Asp Arg Ala Thr Gly Lys Val Ala Leu Asn Lys
                245                 250                 255

Ala Asp Val Glu Tyr Thr Asp Pro Ala Asn Gly Leu Thr Thr Ala Ala
            260                 265                 270

Thr Gln Ala Gly Gln Phe Val Lys Val Ser Ala Asp Lys Asp Gly Asn
        275                 280                 285

Ala Thr Ala Phe Val Thr Phe Gln Gly Lys Asn Tyr Ala Ala Lys Ala
    290                 295                 300

Ala Ser Leu Val Asp Thr Gly Asp Ala Thr Thr Ala Ala Gln Gly Thr
305                 310                 315                 320

Ala Ala Thr Thr Asn Lys Val Thr Leu Gln Leu Ser Asp Lys Ala Ala
                325                 330                 335

Val Ile Gly Thr Gly Thr Ala Ala Asn Pro Gln Phe Pro Ala Thr Ser
            340                 345                 350

Ala Thr Ala Glu Phe Ala Gly Thr Ala Thr Asn Asp Pro Leu Ala Leu
        355                 360                 365

Leu Asp Lys Ala Ile Ala Ser Val Asp Lys Phe Arg Ser Ser Leu Gly
    370                 375                 380

Ala Val Gln Asn Arg Leu Ser Ser Ala Val Thr Asn Leu Asn Asn Thr
385                 390                 395                 400

Thr Thr Asn Leu Ser Glu Ala Gln Ser Arg Ile Gln Asp Ala Asp Tyr
                405                 410                 415

Ala Thr Glu Val Ser Asn Met Ser Lys Ala Gln Ile Val Gln Gln Ala
            420                 425                 430

Gly Asn Ser Val Leu Ser Lys Ala Asn Gln Val Pro Gln Gln Val Leu
        435                 440                 445

Ser Leu Leu Gln Gly
```

-continued

```
                    450

<210> SEQ ID NO 13
<211> LENGTH: 572
<212> TYPE: PRT
<213> ORGANISM: Unknown
<220> FEATURE:
<223> OTHER INFORMATION: Unidentified Bacteria Species

<400> SEQUENCE: 13

Met Ala Gln Val Ile Asn Thr Asn Ser Leu Ser Leu Ile Thr Gln Asn
1               5                   10                  15

Asn Ile Asn Lys Asn Gln Ser Ala Leu Ser Ser Ser Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ala Arg Asn Ala Asn Asp Gly Ile Ser Val Ala Gln Thr Thr Glu Gly
65                  70                  75                  80

Ala Leu Ser Glu Ile Asn Asn Asn Leu Gln Arg Val Arg Glu Leu Thr
                85                  90                  95

Val Gln Ala Thr Thr Gly Thr Asn Ser Gln Ser Asp Leu Asp Ser Ile
            100                 105                 110

Gln Asp Glu Ile Lys Ser Arg Leu Asp Glu Ile Asp Arg Val Ser Gly
        115                 120                 125

Gln Thr Gln Phe Asn Gly Val Asn Val Pro Ala Lys Asp Gly Ser Met
    130                 135                 140

Lys Ile Gln Val Gly Ala Asn Asp Gly Gln Thr Ile Thr Ile Asp Leu
145                 150                 155                 160

Lys Lys Ile Asp Ser Ser Thr Leu Lys Leu Thr Gly Phe Asn Val Asn
                165                 170                 175

Gly Ser Gly Ser Val Ala Asn Thr Ala Ala Thr Lys Ala Asp Leu Ala
            180                 185                 190

Ala Ala Ala Ile Gly Thr Pro Gly Ala Ala Asp Ser Thr Gly Ala Ile
        195                 200                 205

Ala Tyr Thr Val Ser Ala Gly Leu Thr Lys Thr Thr Ala Ala Asp Val
    210                 215                 220

Leu Ser Ser Leu Ala Asp Gly Thr Thr Ile Thr Ala Thr Gly Val Lys
225                 230                 235                 240

Asn Gly Phe Ala Ala Gly Ala Thr Ser Asn Ala Tyr Lys Leu Asn Lys
                245                 250                 255

Asp Asn Asn Thr Phe Thr Tyr Asp Thr Thr Ala Thr Ala Glu Leu
            260                 265                 270

Gln Ser Tyr Leu Thr Pro Lys Ala Gly Asp Thr Ala Thr Phe Ser Val
        275                 280                 285

Glu Ile Gly Gly Thr Thr Gln Asp Val Val Leu Ser Ser Asp Gly Lys
    290                 295                 300

Leu Thr Ala Lys Asp Gly Ser Lys Leu Tyr Ile Asp Thr Thr Gly Asn
305                 310                 315                 320

Leu Thr Gln Asn Gly Gly Asn Asn Gly Val Gly Thr Leu Ala Glu Ala
                325                 330                 335

Thr Leu Ser Gly Leu Ala Leu Asn Asn Asn Gly Ala Ala Ala Val
            340                 345                 350

Lys Ser Thr Ile Thr Thr Ala Asp Asn Thr Ser Ile Val Leu Asn Gly
```

```
                355                 360                 365
Ser Ser Asn Gly Thr Glu Gly Thr Ile Ala Val Thr Gly Ala Val Ile
    370                 375                 380

Ser Ser Ala Ala Leu Gln Ser Ala Ser Lys Thr Thr Gly Phe Thr Val
385                 390                 395                 400

Gly Thr Ala Asp Thr Ala Gly Tyr Ile Ser Val Gly Thr Asp Gly Ser
                405                 410                 415

Val Gln Ala Tyr Asp Val Ala Thr Ser Gly Asn Lys Asp Ser Tyr Thr
            420                 425                 430

Asn Thr Asp Gly Thr Leu Thr Thr Asp Asn Thr Thr Lys Leu Tyr Leu
        435                 440                 445

Gln Lys Asp Gly Ser Val Thr Asn Gly Ser Gly Lys Ala Val Tyr Val
    450                 455                 460

Glu Ala Asp Gly Asp Phe Thr Thr Asp Ala Ala Thr Lys Ala Ala Thr
465                 470                 475                 480

Thr Thr Asp Pro Leu Ala Ala Leu Asp Ala Ile Ser Gln Ile Asp
                485                 490                 495

Lys Phe Arg Ser Ser Leu Gly Ala Ile Gln Asn Arg Leu Asp Ser Ala
                500                 505                 510

Val Thr Asn Leu Asn Asn Thr Thr Thr Asn Leu Ser Glu Ala Gln Ser
            515                 520                 525

Arg Ile Gln Asp Ala Asp Tyr Ala Thr Glu Val Ser Asn Met Ser Lys
        530                 535                 540

Ala Gln Ile Ile Gln Gln Ala Gly Asn Ser Val Leu Ala Lys Ala Asn
545                 550                 555                 560

Gln Val Pro Gln Gln Val Leu Ser Leu Leu Gln Gly
                565                 570

<210> SEQ ID NO 14
<211> LENGTH: 20
<212> TYPE: DNA
<213> ORGANISM: Unknown
<220> FEATURE:
<223> OTHER INFORMATION: Unidentified Bacteria Species

<400> SEQUENCE: 14
ctgaagttta caacaaagac                                                 20

<210> SEQ ID NO 15
<211> LENGTH: 21
<212> TYPE: DNA
<213> ORGANISM: Unknown
<220> FEATURE:
<223> OTHER INFORMATION: Unidentified Bacteria Species

<400> SEQUENCE: 15
ttagaactgg taaaccagac c                                               21

<210> SEQ ID NO 16
<211> LENGTH: 355
<212> TYPE: PRT
<213> ORGANISM: Unknown
<220> FEATURE:
<223> OTHER INFORMATION: Unidentified Bacteria Species

<400> SEQUENCE: 16

Ala Glu Val Tyr Asn Lys Asp Gly Asn Lys Leu Asp Leu Tyr Gly Lys
1               5                   10                  15

Val Asp Gly Leu His Tyr Phe Ser Asp Asn Lys Ser Glu Asp Gly Asp
```

```
                    20                  25                  30
Gln Thr Tyr Val Arg Leu Gly Phe Lys Gly Glu Thr Gln Val Thr Asp
                35                  40                  45

Gln Leu Thr Gly Tyr Gly Gln Trp Glu Tyr Gln Ile Gln Gly Asn Thr
         50                  55                  60

Ser Glu Asp Asn Lys Glu Asn Ser Trp Thr Arg Val Ala Phe Ala Gly
 65                  70                  75                  80

Leu Lys Phe Gln Asp Val Gly Ser Phe Asp Tyr Gly Arg Asn Tyr Gly
                    85                  90                  95

Val Val Tyr Asp Val Thr Ser Trp Thr Asp Val Leu Pro Glu Phe Gly
                100                 105                 110

Gly Asp Thr Tyr Gly Ser Asp Asn Phe Met Gln Gln Arg Gly Asn Gly
                115                 120                 125

Phe Ala Thr Tyr Arg Asn Thr Asp Phe Phe Gly Leu Val Asp Gly Leu
                130                 135                 140

Asn Phe Ala Val Gln Tyr Gln Gly Lys Asn Gly Ser Val Ser Gly Glu
145                 150                 155                 160

Gly Met Thr Asn Asn Gly Arg Gly Ala Leu Arg Gln Asn Gly Asp Gly
                165                 170                 175

Val Gly Gly Ser Ile Thr Tyr Asp Tyr Glu Gly Phe Gly Ile Gly Ala
                180                 185                 190

Ala Val Ser Ser Lys Arg Thr Asp Gln Asn Gly Ser Tyr Thr
                195                 200                 205

Ser Asn Gly Val Val Arg Asn Tyr Ile Gly Thr Gly Asp Arg Ala Glu
            210                 215                 220

Thr Tyr Thr Gly Gly Leu Lys Tyr Asp Ala Asn Asn Ile Tyr Leu Ala
225                 230                 235                 240

Ala Gln Tyr Thr Gln Thr Tyr Asn Ala Thr Arg Val Gly Ser Leu Gly
                245                 250                 255

Trp Ala Asn Lys Ala Gln Asn Phe Glu Ala Val Ala Gln Tyr Gln Phe
                260                 265                 270

Asp Phe Gly Leu Arg Pro Ser Leu Ala Tyr Leu Gln Ser Lys Gly Lys
                275                 280                 285

Asn Leu Gly Val Ile Asn Gly Arg Asn Tyr Asp Asp Glu Asp Ile Leu
            290                 295                 300

Lys Tyr Val Asp Val Gly Ala Thr Tyr Tyr Phe Asn Lys Asn Met Ser
305                 310                 315                 320

Thr Tyr Val Asp Tyr Lys Ile Asn Leu Leu Asp Asp Asn Gln Phe Thr
                325                 330                 335

Arg Asp Ala Gly Ile Asn Thr Asp Asn Ile Val Ala Leu Gly Leu Val
                340                 345                 350

Tyr Gln Phe
        355

<210> SEQ ID NO 17
<211> LENGTH: 346
<212> TYPE: PRT
<213> ORGANISM: Unknown
<220> FEATURE:
<223> OTHER INFORMATION: Unidentified Bacteria Species

<400> SEQUENCE: 17

Ala Glu Val Tyr Asn Lys Asp Gly Asn Lys Leu Asp Leu Tyr Gly Lys
1               5                   10                  15

Val Asp Gly Leu His Tyr Phe Ser Asp Asn Lys Asp Val Asp Gly Asp
```

```
                    20                  25                  30
Gln Thr Tyr Met Arg Leu Gly Phe Lys Gly Glu Thr Gln Val Thr Asp
            35                  40                  45

Gln Leu Thr Gly Tyr Gly Gln Trp Glu Tyr Gln Ile Gln Gly Asn Ser
        50                  55                  60

Ala Glu Asn Glu Asn Ser Trp Thr Arg Val Ala Phe Ala Gly Leu
65                  70                  75                  80

Lys Phe Gln Asp Val Gly Ser Phe Asp Tyr Gly Arg Asn Tyr Gly Val
                85                  90                  95

Val Tyr Asp Val Thr Ser Trp Thr Asp Val Leu Pro Glu Phe Gly Gly
            100                 105                 110

Asp Thr Tyr Gly Ser Asp Asn Phe Met Gln Arg Gly Asn Gly Phe
        115                 120                 125

Ala Thr Tyr Arg Asn Thr Asp Phe Phe Gly Leu Val Asp Gly Leu Asn
        130                 135                 140

Phe Ala Val Gln Tyr Gln Gly Lys Asn Gly Ser Val Ser Gly Glu Gly
145                 150                 155                 160

Met Thr Asn Asn Gly Arg Gly Ala Leu Arg Gln Asn Gly Asp Gly Val
                165                 170                 175

Gly Gly Ser Ile Thr Tyr Asp Tyr Glu Gly Phe Gly Ile Gly Gly Ala
            180                 185                 190

Ile Ser Ser Ser Lys Arg Thr Asp Asp Gln Asn Ser Pro Leu Tyr Ile
        195                 200                 205

Gly Asn Gly Asp Arg Ala Glu Thr Tyr Thr Gly Gly Leu Lys Tyr Asp
    210                 215                 220

Ala Asn Asn Ile Tyr Leu Ala Ala Gln Tyr Thr Gln Thr Tyr Asn Ala
225                 230                 235                 240

Thr Arg Val Gly Ser Leu Gly Trp Ala Asn Lys Ala Gln Asn Phe Glu
                245                 250                 255

Ala Val Ala Gln Tyr Gln Phe Asp Phe Gly Leu Arg Pro Ser Val Ala
            260                 265                 270

Tyr Leu Gln Ser Lys Gly Lys Asn Leu Gly Val Ile Asn Gly Arg Asn
        275                 280                 285

Tyr Asp Asp Glu Asp Ile Leu Lys Tyr Val Asp Val Gly Ala Thr Tyr
    290                 295                 300

Tyr Phe Asn Lys Asn Met Ser Thr Tyr Val Asp Tyr Lys Ile Asn Leu
305                 310                 315                 320

Leu Asp Asp Asn Gln Phe Thr Arg Asp Ala Gly Ile Asn Thr Asp Asn
                325                 330                 335

Ile Val Ala Leu Gly Leu Val Tyr Gln Phe
            340                 345

<210> SEQ ID NO 18
<211> LENGTH: 343
<212> TYPE: PRT
<213> ORGANISM: Unknown
<220> FEATURE:
<223> OTHER INFORMATION: Unidentified Bacteria Species

<400> SEQUENCE: 18

Ala Glu Val Tyr Asn Lys Asp Gly Asn Lys Leu Asp Leu Tyr Gly Lys
1               5                   10                  15

Val Asp Gly Leu His Tyr Phe Ser Asp Asn Asp Ser Lys Asp Gly Asp
            20                  25                  30

Lys Thr Tyr Met Arg Leu Gly Phe Lys Gly Glu Thr Gln Val Thr Asp
```

```
                    35                  40                  45
Gln Leu Thr Gly Tyr Gly Gln Trp Glu Tyr Gln Ile Gln Gly Asn Glu
             50                  55                  60
Pro Glu Ser Asp Asn Ser Ser Trp Thr Arg Val Ala Phe Ala Gly Leu
 65                  70                  75                  80
Lys Phe Gln Asp Val Gly Ser Phe Asp Tyr Gly Arg Asn Tyr Gly Val
                 85                  90                  95
Val Tyr Asp Val Thr Ser Trp Thr Asp Val Leu Pro Glu Phe Gly Gly
            100                 105                 110
Asp Thr Tyr Asp Ser Asp Asn Phe Met Gln Gln Arg Gly Asn Gly Phe
            115                 120                 125
Ala Thr Tyr Arg Asn Thr Asp Phe Phe Gly Leu Val Asp Gly Leu Asp
            130                 135                 140
Phe Ala Val Gln Tyr Gln Gly Lys Asn Gly Ser Ala His Gly Glu Gly
145                 150                 155                 160
Met Thr Thr Asn Gly Arg Asp Asp Val Phe Glu Gln Asn Gly Asp Gly
                165                 170                 175
Val Gly Gly Ser Ile Thr Tyr Asn Tyr Glu Gly Phe Gly Ile Gly Ala
            180                 185                 190
Ala Val Ser Ser Ser Lys Arg Thr Trp Asp Gln Asn Asn Thr Gly Leu
            195                 200                 205
Ile Gly Thr Gly Asp Arg Ala Glu Thr Tyr Thr Gly Gly Leu Lys Tyr
210                 215                 220
Asp Ala Asn Asn Ile Tyr Leu Ala Ala Gln Tyr Thr Gln Thr Tyr Asn
225                 230                 235                 240
Ala Thr Arg Val Gly Ser Leu Gly Trp Ala Asn Lys Ala Gln Asn Phe
                245                 250                 255
Glu Ala Val Ala Gln Tyr Gln Phe Asp Phe Gly Leu Arg Pro Ser Leu
            260                 265                 270
Ala Tyr Leu Gln Ser Lys Gly Lys Asn Leu Gly Arg Gly Tyr Asp Asp
            275                 280                 285
Glu Asp Ile Leu Lys Tyr Val Asp Val Gly Ala Thr Tyr Tyr Phe Asn
290                 295                 300
Lys Asn Met Ser Thr Tyr Val Asp Tyr Lys Ile Asn Leu Leu Asp Asp
305                 310                 315                 320
Asn Arg Phe Thr Arg Asp Ala Gly Ile Asn Thr Asp Asp Ile Val Ala
                325                 330                 335
Leu Gly Leu Val Tyr Gln Phe
            340

<210> SEQ ID NO 19
<211> LENGTH: 243
<212> TYPE: PRT
<213> ORGANISM: Artificial Sequence
<220> FEATURE:
<223> OTHER INFORMATION: Hetero-chimeric S100A8/S100A9

<400> SEQUENCE: 19

Met Gly Ser Ser His His His His His His Gly Leu Thr Glu Leu Glu
 1               5                  10                  15
Ser Ala Ile Asn Ser Leu Ile Glu Val Tyr His Lys Tyr Ser Leu Val
                20                  25                  30
Lys Gly Asn Tyr His Ala Leu Tyr Arg Asp Asp Leu Lys Lys Leu Leu
            35                  40                  45
Glu Thr Glu Cys Pro Gln Tyr Met Lys Lys Lys Asp Ala Asp Thr Trp
```

```
                  50                  55                  60
Phe Gln Glu Leu Asp Val Asn Ser Asp Gly Ala Ile Asn Phe Glu Glu
 65                  70                  75                  80

Phe Leu Ile Leu Val Ile Lys Val Gly Val Ala Ser His Lys Asp Ile
                     85                  90                  95

His Lys Glu Gly Gly Gly Ser Gly Gly Gly Ser Gly Gly
                100                 105                 110

Gly Ser Ala Asp Gln Met Ser Gln Leu Glu Cys Ser Ile Glu Thr Ile
                115                 120                 125

Ile Asn Ile Phe His Gln Tyr Ser Val Arg Leu Glu His Pro Asp Lys
                130                 135                 140

Leu Asn Gln Lys Glu Met Lys Gln Leu Val Lys Glu Leu Pro Asn
145                 150                 155                 160

Phe Leu Lys Lys Gln Lys Lys Asn Asp Asn Ala Ile Asn Lys Ile Met
                165                 170                 175

Glu Asp Leu Asp Thr Asn Gly Asp Lys Glu Leu Asn Phe Glu Glu Phe
                180                 185                 190

Ser Ile Leu Val Ala Arg Leu Thr Val Ala Ser His Glu Glu Met His
                195                 200                 205

Lys Asn Ala Pro Glu Gly Glu Gly His Ser His Gly Pro Gly Phe Gly
                210                 215                 220

Glu Gly Ser Gln Gly His Cys His Ser His Gly Gly His Gly His Gly
225                 230                 235                 240

His Ser His

<210> SEQ ID NO 20
<211> LENGTH: 102
<212> TYPE: PRT
<213> ORGANISM: Artificial Sequence
<220> FEATURE:
<223> OTHER INFORMATION: S100A12

<400> SEQUENCE: 20

Met Gly Ser Ser His His His His His His Gly Thr Lys Leu Glu Asp
 1               5                  10                  15

His Leu Glu Gly Ile Val Asp Val Phe His Arg Tyr Ser Ala Arg Val
                 20                  25                  30

Gly His Pro Asp Thr Leu Ser Lys Gly Glu Met Lys Gln Leu Ile Ile
                 35                  40                  45

Arg Glu Leu Pro Asn Thr Leu Lys Asn Thr Lys Asp Gln Ala Thr Val
 50                  55                  60

Asp Lys Leu Phe Gln Asp Leu Asp Ala Asp Lys Asp Gly Gln Val Asn
 65                  70                  75                  80

Phe Asn Glu Phe Ile Ser Leu Val Ser Val Val Leu Asp Thr Ser His
                 85                  90                  95

Lys Asn Thr His Lys Glu
                100

<210> SEQ ID NO 21
<211> LENGTH: 99
<212> TYPE: PRT
<213> ORGANISM: Artificial Sequence
<220> FEATURE:
<223> OTHER INFORMATION: S100A8

<400> SEQUENCE: 21

Met Gly Ser Ser His His His His His His Gly Leu Thr Glu Leu Glu
```

```
                1               5                  10                 15
Ser Ala Ile Asn Ser Leu Ile Glu Val Tyr His Lys Tyr Ser Leu Val
                        20                 25                 30

Lys Gly Asn Tyr His Ala Leu Tyr Arg Asp Asp Leu Lys Lys Leu Leu
                35                 40                 45

Glu Thr Glu Cys Pro Gln Tyr Met Lys Lys Lys Ala Asp Thr Trp
         50                 55                 60

Phe Gln Glu Leu Asp Val Asn Ser Asp Gly Ala Ile Asn Phe Glu Glu
 65                 70                 75                 80

Phe Leu Ile Leu Val Ile Lys Val Gly Val Ala Ser His Lys Asp Ile
                        85                 90                 95

His Lys Glu

<210> SEQ ID NO 22
<211> LENGTH: 140
<212> TYPE: PRT
<213> ORGANISM: Artificial Sequence
<220> FEATURE:
<223> OTHER INFORMATION: S100A9
<220> FEATURE:
<221> NAME/KEY: misc_feature
<222> LOCATION: (130)..(130)
<223> OTHER INFORMATION: Xaa can be any naturally occurring amino acid

<400> SEQUENCE: 22

Met Gly Ser Ser His His His His His Gly Ala Asp Gln Met Ser
 1               5                  10                 15

Gln Leu Glu Cys Ser Ile Glu Thr Ile Ile Asn Ile Phe His Gln Tyr
                20                 25                 30

Ser Val Arg Leu Glu His Pro Asp Lys Leu Asn Gln Lys Glu Met Lys
                35                 40                 45

Gln Leu Val Lys Lys Glu Leu Pro Asn Phe Leu Lys Lys Gln Lys Lys
         50                 55                 60

Asn Asp Asn Ala Ile Asn Lys Ile Met Glu Asp Leu Asp Thr Asn Gly
 65                 70                 75                 80

Asp Lys Glu Leu Asn Phe Glu Glu Phe Ser Ile Leu Val Ala Arg Leu
                85                 90                 95

Thr Val Ala Ser His Glu Glu Met His Lys Asn Ala Pro Glu Gly Glu
                100                105                110

Gly His Ser His Gly Pro Gly Phe Gly Glu Gly Ser Gln Gly Phe Phe
                115                120                125

Ile Xaa His Gly Gly His Gly His Gly His Ser His
         130                135                140

<210> SEQ ID NO 23
<211> LENGTH: 21
<212> TYPE: DNA
<213> ORGANISM: Unknown
<220> FEATURE:
<223> OTHER INFORMATION: Unidentified Bacteria Species

<400> SEQUENCE: 23
gtgtctgcct ctcgacctcg g                                          21

<210> SEQ ID NO 24
<211> LENGTH: 27
<212> TYPE: DNA
<213> ORGANISM: Unknown
<220> FEATURE:
<223> OTHER INFORMATION: Unidentified Bacteria Species
```

-continued

<400> SEQUENCE: 24
cagagaattg aaggatttca aatcagc                              27

<210> SEQ ID NO 25
<211> LENGTH: 27
<212> TYPE: DNA
<213> ORGANISM: Unknown
<220> FEATURE:
<223> OTHER INFORMATION: Unidentified Bacteria Species

<400> SEQUENCE: 25
ttatgtgaaa tgacgtttgg gtctttg                              27

<210> SEQ ID NO 26
<211> LENGTH: 21
<212> TYPE: DNA
<213> ORGANISM: Unknown
<220> FEATURE:
<223> OTHER INFORMATION: Unidentified Bacteria Species

<400> SEQUENCE: 26
gaattggatg ccaagatctc c                                    21

<210> SEQ ID NO 27
<211> LENGTH: 27
<212> TYPE: DNA
<213> ORGANISM: Unknown
<220> FEATURE:
<223> OTHER INFORMATION: Unidentified Bacteria Species

<400> SEQUENCE: 27
ttacagtgtg tgcagctcca cagtcag                              27

<210> SEQ ID NO 28
<211> LENGTH: 24
<212> TYPE: DNA
<213> ORGANISM: Unknown
<220> FEATURE:
<223> OTHER INFORMATION: Unidentified Bacteria Species

<400> SEQUENCE: 28
ttagtgatcc gcgcctctct cttg                                 24

<210> SEQ ID NO 29
<211> LENGTH: 909
<212> TYPE: PRT
<213> ORGANISM: Unknown
<220> FEATURE:
<223> OTHER INFORMATION: Unidentified Bacteria Species

<400> SEQUENCE: 29

Trp Leu Val Val Gly Ala Pro Thr Ala Arg Trp Leu Ala Asn Ala Ser
1               5                   10                  15

Val Val Asn Pro Gly Ala Ile Tyr Arg Cys Arg Ile Gly Gly Asn Pro
            20                  25                  30

Gly Leu Thr Cys Glu Gln Leu Gln Leu Gly Ser Pro Ser Gly Glu Pro
        35                  40                  45

Cys Gly Lys Thr Cys Leu Glu Glu Arg Asp Asn Gln Trp Leu Gly Val
    50                  55                  60

Thr Leu Ser Arg Gln Pro Gly Glu Asn Gly Ser Ile Val Thr Cys Gly
65                  70                  75                  80

His Arg Trp Lys Asn Ile Phe Tyr Ile Lys Asn Glu Asn Lys Leu Pro

```
                85                  90                  95
Met Gly Val Cys Tyr Gly Met Pro Ser Asp Leu Arg Thr Glu Leu Ser
                100                 105                 110

Lys Arg Ile Ala Pro Cys Tyr Gln Asp Tyr Val Arg Lys Phe Gly Glu
            115                 120                 125

Asn Phe Ala Ser Cys Gln Ala Gly Ile Ser Ser Phe Tyr Thr Glu Asp
        130                 135                 140

Leu Ile Val Met Gly Ala Pro Gly Ser Ser Tyr Trp Thr Gly Ser Leu
145                 150                 155                 160

Phe Val Tyr Asn Ile Thr Thr Asn Lys Tyr Lys Ala Phe Leu Asp Arg
                165                 170                 175

Gln Asn Gln Val Lys Phe Gly Ser Tyr Leu Gly Tyr Ser Val Gly Ala
            180                 185                 190

Gly His Phe Arg Ser Pro His Thr Thr Glu Val Val Gly Gly Ala Pro
        195                 200                 205

Gln His Glu Gln Ile Gly Lys Ala Tyr Ile Phe Ser Ile Glu Ala Lys
    210                 215                 220

Glu Leu Ser Ile Leu His Glu Met Lys Gly Lys Lys Leu Gly Ser Tyr
225                 230                 235                 240

Phe Gly Ala Ser Val Cys Ala Val Asp Leu Asn Ala Asp Gly Phe Ser
                245                 250                 255

Asp Leu Leu Val Gly Ala Pro Met Gln Ser Thr Ile Arg Glu Glu Gly
            260                 265                 270

Arg Val Phe Val Tyr Ile Asn Ser Gly Ser Gly Ala Val Met Asn Glu
        275                 280                 285

Met Glu Thr Glu Leu Ile Gly Ser Asp Lys Tyr Ala Ala Arg Phe Gly
    290                 295                 300

Glu Ser Ile Val Asn Leu Gly Asp Ile Asp Asn Asp Gly Phe Glu Asp
305                 310                 315                 320

Val Ala Val Gly Ala Pro Gln Glu Asp Leu Arg Gly Ala Val Tyr
                325                 330                 335

Ile Tyr Asn Gly Arg Ala Asp Gly Ile Ser Thr Ala Phe Ser Gln Arg
            340                 345                 350

Ile Glu Gly Phe Gln Ile Ser Lys Ser Leu Ser Met Phe Gly Gln Ser
        355                 360                 365

Ile Ser Gly Gln Ile Asp Ala Asp Asn Gly Tyr Val Asp Val Ala
    370                 375                 380

Val Gly Ala Phe Arg Ser Asp Ser Ala Val Leu Leu Arg Thr Arg Pro
385                 390                 395                 400

Val Val Ile Val Glu Val Ser Leu Asn His Pro Glu Ser Val Asn Arg
                405                 410                 415

Thr Asn Phe Asp Cys Val Glu Asn Gly Leu Pro Ser Val Cys Met Asp
            420                 425                 430

Leu Thr Leu Cys Phe Ser Tyr Lys Gly Lys Glu Val Pro Gly Tyr Ile
        435                 440                 445

Val Leu Leu Tyr Asn Met Ser Leu Asp Val Asn Arg Lys Ile Asp Ser
    450                 455                 460

Pro Ser Arg Phe Tyr Phe Ser Asn Gly Thr Ser Asp Val Ile Thr
465                 470                 475                 480

Gly Ser Met Lys Val Ser Ser Lys Val Pro Asn Cys Arg Thr His Gln
                485                 490                 495

Ala Phe Met Arg Lys Asp Val Arg Asp Ile Leu Thr Pro Ile Gln Ile
            500                 505                 510
```

Glu Ala Ala Tyr Arg Leu Gly Gln His Val Ile Arg Lys Arg Ser Thr
            515                 520                 525
Glu Glu Phe Pro Pro Leu Gln Pro Ile Leu Gln Gln Lys Lys Glu Arg
            530                 535                 540
Asp Ile Ile Glu Lys Thr Ile Asn Phe Ala Arg Phe Cys Ala His Glu
545                 550                 555                 560
Asn Cys Ser Ala Asp Leu Gln Val Ser Ala Arg Ile Gly Phe Leu Lys
            565                 570                 575
Pro His Glu Asn Lys Thr Tyr Val Ala Val Gly Ser Met Lys Thr Val
            580                 585                 590
Met Leu Asn Val Ser Leu Phe Asn Ala Gly Asp Ala Tyr Glu Thr
            595                 600                 605
Ala Leu His Ile Arg Leu Pro Ser Gly Leu Tyr Phe Ile Lys Ile Leu
            610                 615                 620
Asp Leu Glu Glu Lys Gln Ile Asn Cys Glu Val Thr Asp Ser Ser Gly
625                 630                 635                 640
Ser Val Lys Leu Asp Cys Ser Ile Gly Tyr Ile Tyr Met Asp Arg Leu
            645                 650                 655
Ser Arg Met Asp Ile Ser Phe Leu Leu Asp Val Ser Ser Leu Ser Gln
            660                 665                 670
Ala Glu Glu Asp Leu Ser Leu Thr Val His Ala Thr Cys Ala Asn Glu
            675                 680                 685
Arg Glu Met Asp Asn Leu Asn Lys Val Thr Leu Ala Ile Pro Leu Lys
            690                 695                 700
Tyr Glu Val Met Leu Ser Val His Gly Phe Val Asn Pro Thr Ser Phe
705                 710                 715                 720
Ile Tyr Gly Pro Lys Glu Glu Asn Glu Pro Asp Thr Cys Met Ala Glu
            725                 730                 735
Lys Met Asn Phe Thr Phe His Val Ile Asn Thr Gly His Ser Met Ala
            740                 745                 750
Pro Asn Val Ser Val Glu Ile Met Val Pro Asn Ser Phe Ala Pro Gln
            755                 760                 765
Thr Asp Lys Leu Phe Asn Ile Leu Asp Val Gln Pro Ala Gly Glu Cys
            770                 775                 780
His Phe Lys Thr Tyr Gln Arg Lys Cys Ala Leu Glu Gln Glu Lys Gly
785                 790                 795                 800
Ala Met Lys Ile Leu Lys Asp Ile Phe Thr Phe Leu Ser Lys Thr Asp
            805                 810                 815
Lys Lys Leu Leu Phe Cys Met Lys Ala Asp Pro Tyr Cys Leu Thr Ile
            820                 825                 830
Leu Cys His Leu Gly Lys Met Glu Ser Gly Lys Glu Ala Ser Val His
            835                 840                 845
Ile Gln Leu Glu Gly Arg Pro Tyr Leu Ser Glu Met Asp Glu Thr Ser
            850                 855                 860
Ala Leu Lys Phe Glu Val Arg Val Thr Ala Phe Pro Glu Pro Asn Pro
865                 870                 875                 880
Lys Val Ile Glu Leu Asn Lys Asp Glu Asn Val Ala His Val Leu Leu
            885                 890                 895
Glu Gly Leu His His Gln Arg Pro Lys Arg His Phe Thr
            900                 905

<210> SEQ ID NO 30
<211> LENGTH: 1015

<212> TYPE: PRT
<213> ORGANISM: Unknown
<220> FEATURE:
<223> OTHER INFORMATION: Unidentified Bacteria Species

<400> SEQUENCE: 30

| | | | | | | | | | | | | | | | |
|---|---|---|---|---|---|---|---|---|---|---|---|---|---|---|---|
| Val | Ser | Ala | Ser | Arg | Pro | Arg | Pro | Gly | Ser | Thr | Pro | Pro | Pro | Pro |
| 1 | | | | 5 | | | | | 10 | | | | | 15 |
| Trp | Gln | Val | Tyr | Pro | Val | Ala | Glu | Ala | Trp | Glu | Gly | Gly | Ala | Ser | Ser |
| | | | 20 | | | | | 25 | | | | | 30 | | |
| Ser | Gly | Ser | Gly | Glu | Gln | Gly | Pro | Arg | Ala | Gly | Gly | Cys | Gly | Ala | Pro |
| | | | 35 | | | | | 40 | | | | | 45 | | |
| Ala | Gly | Ser | Ser | Pro | Lys | Val | Leu | Val | Ala | Lys | Ser | Gly | Ala | Arg | Gly |
| | 50 | | | | | 55 | | | | | 60 | | | | |
| Leu | Ser | Ser | Ser | Trp | Trp | Gly | Arg | Arg | Gly | Asp | Ala | Gln | Ala | Arg | Gly |
| 65 | | | | | 70 | | | | | 75 | | | | | 80 |
| Phe | Gly | Ala | Gly | Ser | Trp | Glu | Leu | Glu | Gly | Asp | Leu | Ala | His | Val | Cys |
| | | | | 85 | | | | | 90 | | | | | 95 | |
| Ala | His | Leu | His | Gly | Cys | Pro | Leu | Gly | Leu | Trp | Leu | Val | Val | Gly | Ala |
| | | | 100 | | | | | 105 | | | | | 110 | | |
| Pro | Thr | Ala | Arg | Trp | Leu | Ala | Asn | Ala | Ser | Val | Val | Asn | Pro | Gly | Ala |
| | | | 115 | | | | | 120 | | | | | 125 | | |
| Ile | Tyr | Arg | Cys | Arg | Ile | Gly | Gly | Asn | Pro | Gly | Leu | Thr | Cys | Glu | Gln |
| | 130 | | | | | 135 | | | | | 140 | | | | |
| Leu | Gln | Leu | Gly | Ser | Pro | Ser | Gly | Glu | Pro | Cys | Gly | Lys | Thr | Cys | Leu |
| 145 | | | | | 150 | | | | | 155 | | | | | 160 |
| Glu | Glu | Arg | Asp | Asn | Gln | Trp | Leu | Gly | Val | Thr | Leu | Ser | Arg | Gln | Pro |
| | | | | 165 | | | | | 170 | | | | | 175 | |
| Gly | Glu | Asn | Gly | Ser | Ile | Val | Thr | Cys | Gly | His | Arg | Trp | Lys | Asn | Ile |
| | | | 180 | | | | | 185 | | | | | 190 | | |
| Phe | Tyr | Ile | Lys | Asn | Glu | Asn | Lys | Leu | Pro | Met | Gly | Val | Cys | Tyr | Gly |
| | | | 195 | | | | | 200 | | | | | 205 | | |
| Met | Pro | Ser | Asp | Leu | Arg | Thr | Glu | Leu | Ser | Lys | Arg | Ile | Ala | Pro | Cys |
| | 210 | | | | | 215 | | | | | 220 | | | | |
| Tyr | Gln | Asp | Tyr | Val | Arg | Lys | Phe | Gly | Glu | Asn | Phe | Ala | Ser | Cys | Gln |
| 225 | | | | | 230 | | | | | 235 | | | | | 240 |
| Ala | Gly | Ile | Ser | Ser | Phe | Tyr | Thr | Glu | Asp | Leu | Ile | Val | Met | Gly | Ala |
| | | | | 245 | | | | | 250 | | | | | 255 | |
| Pro | Gly | Ser | Ser | Tyr | Trp | Thr | Gly | Ser | Leu | Phe | Val | Tyr | Asn | Ile | Thr |
| | | | 260 | | | | | 265 | | | | | 270 | | |
| Thr | Asn | Lys | Tyr | Lys | Ala | Phe | Leu | Asp | Arg | Gln | Asn | Gln | Val | Lys | Phe |
| | | | 275 | | | | | 280 | | | | | 285 | | |
| Gly | Ser | Tyr | Leu | Gly | Tyr | Ser | Val | Gly | Ala | Gly | His | Phe | Arg | Ser | Pro |
| | 290 | | | | | 295 | | | | | 300 | | | | |
| His | Thr | Thr | Glu | Val | Val | Gly | Gly | Ala | Pro | Gln | His | Glu | Gln | Ile | Gly |
| 305 | | | | | 310 | | | | | 315 | | | | | 320 |
| Lys | Ala | Tyr | Ile | Phe | Ser | Ile | Glu | Ala | Lys | Glu | Leu | Ser | Ile | Leu | His |
| | | | | 325 | | | | | 330 | | | | | 335 | |
| Glu | Met | Lys | Gly | Lys | Lys | Leu | Gly | Ser | Tyr | Phe | Gly | Ala | Ser | Val | Cys |
| | | | 340 | | | | | 345 | | | | | 350 | | |
| Ala | Val | Asp | Leu | Asn | Ala | Asp | Gly | Phe | Ser | Asp | Leu | Leu | Val | Gly | Ala |
| | | | 355 | | | | | 360 | | | | | 365 | | |
| Pro | Met | Gln | Ser | Thr | Ile | Arg | Glu | Glu | Gly | Arg | Val | Phe | Val | Tyr | Ile |
| | 370 | | | | | 375 | | | | | 380 | | | | |

```
Asn Ser Gly Ser Gly Ala Val Met Asn Glu Met Glu Thr Glu Leu Ile
385                 390                 395                 400

Gly Ser Asp Lys Tyr Ala Ala Arg Phe Gly Glu Ser Ile Val Asn Leu
            405                 410                 415

Gly Asp Ile Asp Asn Asp Gly Phe Glu Asp Val Ala Val Gly Ala Pro
        420                 425                 430

Gln Glu Asp Asp Leu Arg Gly Ala Val Tyr Ile Tyr Asn Gly Arg Ala
        435                 440                 445

Asp Gly Ile Ser Thr Ala Phe Ser Gln Arg Ile Glu Gly Phe Gln Ile
    450                 455                 460

Ser Lys Ser Leu Ser Met Phe Gly Gln Ser Ile Ser Gly Gln Ile Asp
465                 470                 475                 480

Ala Asp Asn Asn Gly Tyr Val Asp Val Ala Val Gly Ala Phe Arg Ser
                485                 490                 495

Asp Ser Ala Val Leu Leu Arg Thr Arg Pro Val Val Ile Val Glu Val
            500                 505                 510

Ser Leu Asn His Pro Glu Ser Val Asn Arg Thr Asn Phe Asp Cys Val
        515                 520                 525

Glu Asn Gly Leu Pro Ser Val Cys Met Asp Leu Thr Leu Cys Phe Ser
    530                 535                 540

Tyr Lys Gly Lys Glu Val Pro Gly Tyr Ile Val Leu Leu Tyr Asn Met
545                 550                 555                 560

Ser Leu Asp Val Asn Arg Lys Ile Asp Ser Pro Ser Arg Phe Tyr Phe
                565                 570                 575

Ser Ser Asn Gly Thr Ser Asp Val Ile Thr Gly Ser Met Lys Val Ser
            580                 585                 590

Ser Lys Val Pro Asn Cys Arg Thr His Gln Ala Phe Met Arg Lys Asp
        595                 600                 605

Val Arg Asp Ile Leu Thr Pro Ile Gln Ile Glu Ala Ala Tyr Arg Leu
    610                 615                 620

Gly Gln His Val Ile Arg Lys Arg Ser Thr Glu Phe Pro Pro Leu
625                 630                 635                 640

Gln Pro Ile Leu Gln Gln Lys Lys Glu Arg Asp Ile Ile Glu Lys Thr
            645                 650                 655

Ile Asn Phe Ala Arg Phe Cys Ala His Glu Asn Cys Ser Ala Asp Leu
        660                 665                 670

Gln Val Ser Ala Arg Ile Gly Phe Leu Lys Pro His Glu Asn Lys Thr
    675                 680                 685

Tyr Val Ala Val Gly Ser Met Lys Thr Val Met Leu Asn Val Ser Leu
690                 695                 700

Phe Asn Ala Gly Asp Asp Ala Tyr Glu Thr Ala Leu His Ile Arg Leu
705                 710                 715                 720

Pro Ser Gly Leu Tyr Phe Ile Lys Ile Leu Asp Leu Glu Glu Lys Gln
            725                 730                 735

Ile Asn Cys Glu Val Thr Asp Ser Ser Gly Ser Val Lys Leu Asp Cys
        740                 745                 750

Ser Ile Gly Tyr Ile Tyr Met Asp Arg Leu Ser Arg Met Asp Ile Ser
    755                 760                 765

Phe Leu Leu Asp Val Ser Ser Leu Ser Gln Ala Glu Glu Asp Leu Ser
        770                 775                 780

Leu Thr Val His Ala Thr Cys Ala Asn Glu Arg Glu Met Asp Asn Leu
785                 790                 795                 800

Asn Lys Val Thr Leu Ala Ile Pro Leu Lys Tyr Glu Val Met Leu Ser
```

```
                805                 810                 815
Val His Gly Phe Val Asn Pro Thr Ser Phe Ile Tyr Gly Pro Lys Glu
            820                 825                 830

Glu Asn Glu Pro Asp Thr Cys Met Ala Glu Lys Met Asn Phe Thr Phe
            835                 840                 845

His Val Ile Asn Thr Gly His Ser Met Ala Pro Asn Val Ser Val Glu
        850                 855                 860

Ile Met Val Pro Asn Ser Phe Ala Pro Gln Thr Asp Lys Leu Phe Asn
865                 870                 875                 880

Ile Leu Asp Val Gln Pro Ala Gly Glu Cys His Phe Lys Thr Tyr Gln
                885                 890                 895

Arg Lys Cys Ala Leu Glu Gln Glu Lys Gly Ala Met Lys Ile Leu Lys
            900                 905                 910

Asp Ile Phe Thr Phe Leu Ser Lys Thr Asp Lys Lys Leu Leu Phe Cys
            915                 920                 925

Met Lys Ala Asp Pro Tyr Cys Leu Thr Ile Leu Cys His Leu Gly Lys
        930                 935                 940

Met Glu Ser Gly Lys Glu Ala Ser Val His Ile Gln Leu Glu Gly Arg
945                 950                 955                 960

Pro Tyr Leu Ser Glu Met Asp Glu Thr Ser Ala Leu Lys Phe Glu Val
                965                 970                 975

Arg Val Thr Ala Phe Pro Glu Pro Asn Pro Lys Val Ile Glu Leu Asn
            980                 985                 990

Lys Asp Glu Asn Val Ala His Val  Leu Leu Glu Gly Leu  His His Gln
        995                 1000                 1005

Arg Pro  Lys Arg His Phe Thr
    1010                 1015

<210> SEQ ID NO 31
<211> LENGTH: 440
<212> TYPE: PRT
<213> ORGANISM: Unknown
<220> FEATURE:
<223> OTHER INFORMATION: Unidentified Bacteria Species

<400> SEQUENCE: 31

Glu Leu Asp Ala Lys Ile Ser Ser Ala Glu Lys Ala Thr Glu Trp Arg
1               5                   10                  15

Asp Pro Asp Leu Ser Leu Leu Gly Ser Cys Gln Pro Ala Pro Ser Cys
            20                  25                  30

Arg Glu Cys Ile Leu Ser His Pro Ser Cys Ala Trp Cys Lys Gln Leu
        35                  40                  45

Phe Trp Gly Leu Gly Ile Arg Asp Gln Asp Ala Ser Pro Phe Gly Ser
    50                  55                  60

Trp Gly Gly Pro Ser Pro Trp Pro Ala His Arg Cys Arg Pro Ala Leu
65                  70                  75                  80

Trp Cys Leu Phe Cys Asp Pro Pro Pro Pro Ala Ser Ala Pro
                85                  90                  95

Arg Leu Ser Pro Gly Pro Ser Arg Arg Cys Thr Leu Asp Pro Leu Leu
            100                 105                 110

Cys Arg Arg Leu His Arg Ala Pro Cys Ala Leu Cys Pro Ala Pro Cys
        115                 120                 125

Thr Leu His Pro Ala Leu Arg Leu Gly Thr Pro Cys Ala Thr Ser Thr
    130                 135                 140

Trp Pro Ala Arg Pro Leu Ala Gln Pro Ser Pro Cys Pro Leu Pro Gly
```

```
                145                 150                 155                 160
        Phe Gly Ser Phe Val Asp Lys Thr Val Leu Pro Phe Val Ser Thr Val
                        165                 170                 175

Pro Ala Lys Leu Arg His Pro Cys Pro Thr Arg Leu Glu Arg Cys Gln
                        180                 185                 190

Pro Pro Phe Ser Phe Arg His Val Leu Ser Leu Thr Gly Asp Ala Thr
                        195                 200                 205

Ala Phe Glu Arg Glu Val Gly Arg Gln Ser Val Ser Gly Asn Leu Asp
                210                 215                 220

Ser Pro Glu Gly Gly Phe Asp Ala Ile Leu Gln Ala Ala Leu Cys Gln
        225                 230                 235                 240

Glu Lys Ile Gly Trp Arg Asn Val Ser Arg Leu Leu Val Phe Thr Ser
                        245                 250                 255

Asp Asp Thr Phe His Thr Ala Gly Asp Gly Lys Leu Gly Ile Phe
                        260                 265                 270

Met Pro Ser Asp Gly His Cys His Leu Asp Ser Asn Gly Leu Tyr Ser
                        275                 280                 285

Arg Ser Pro Glu Phe Asp Tyr Pro Ser Val Gly Gln Val Ala Gln Ala
                290                 295                 300

Leu Ser Thr Ala Asn Ile Gln Pro Ile Phe Ala Val Thr Ser Ala Thr
        305                 310                 315                 320

Leu Pro Val Tyr Gln Glu Leu Ser Lys Leu Ile Pro Lys Ser Ala Val
                        325                 330                 335

Gly Glu Leu Ser Glu Asp Ser Ser Asn Val Val Gln Leu Ile Met Asp
                        340                 345                 350

Ala Tyr Asn Ser Leu Ser Ser Thr Val Thr Leu Glu His Ser Ala Leu
                        355                 360                 365

Pro Pro Gly Val His Ile Ser Tyr Glu Ser Leu Cys Gly Asp Pro Glu
                        370                 375                 380

Lys Arg Glu Ala Glu Ala Gly Asp Arg Gly Gln Cys Ser His Val Pro
        385                 390                 395                 400

Ile Asn His Thr Val Asn Phe Leu Val Thr Leu Gln Ala Thr Arg Cys
                        405                 410                 415

Leu Pro Glu Pro His Leu Leu Arg Leu Arg Ala Leu Gly Phe Ser Glu
                        420                 425                 430

Glu Leu Thr Val Glu Leu His Leu
                        435                 440

<210> SEQ ID NO 32
<211> LENGTH: 691
<212> TYPE: PRT
<213> ORGANISM: Unknown
<220> FEATURE:
<223> OTHER INFORMATION: Unidentified Bacteria Species

<400> SEQUENCE: 32

Glu Leu Asp Ala Lys Ile Ser Ser Ala Glu Lys Ala Thr Glu Trp Arg
        1               5                   10                  15

Asp Pro Asp Leu Ser Leu Leu Gly Ser Cys Gln Pro Ala Pro Ser Cys
                        20                  25                  30

Arg Glu Cys Ile Leu Ser His Pro Ser Cys Ala Trp Cys Lys Gln Leu
                        35                  40                  45

Phe Trp Gly Leu Gly Ile Arg Asp Gln Asp Ala Ser Pro Phe Gly Ser
                        50                  55                  60

Trp Gly Gly Pro Ser Pro Trp Pro Ala His Arg Cys Arg Pro Ala Leu
```

```
            65                  70                  75                  80
Trp Cys Leu Phe Cys Asp Pro Pro Pro Pro Ala Ser Ala Pro
                85                  90                  95
Arg Leu Ser Pro Gly Pro Ser Arg Arg Cys Thr Leu Asp Pro Leu Leu
                100                 105                 110
Cys Arg Arg Leu His Arg Ala Pro Cys Ala Leu Cys Pro Ala Pro Cys
                115                 120                 125
Thr Leu His Pro Ala Leu Arg Leu Gly Thr Pro Cys Ala Thr Ser Thr
    130                 135                 140
Trp Pro Ala Arg Pro Leu Ala Gln Pro Ser Pro Cys Pro Leu Pro Gly
145                 150                 155                 160
Phe Gly Ser Phe Val Asp Lys Thr Val Leu Pro Phe Val Ser Thr Val
                165                 170                 175
Pro Ala Lys Leu Arg His Pro Cys Pro Thr Arg Leu Glu Arg Cys Gln
                180                 185                 190
Pro Pro Phe Ser Phe Arg His Val Leu Ser Leu Thr Gly Asp Ala Thr
                195                 200                 205
Ala Phe Glu Arg Glu Val Gly Arg Gln Ser Val Ser Gly Asn Leu Asp
    210                 215                 220
Ser Pro Glu Gly Gly Phe Asp Ala Ile Leu Gln Ala Ala Leu Cys Gln
225                 230                 235                 240
Glu Lys Ile Gly Trp Arg Asn Val Ser Arg Leu Leu Val Phe Thr Ser
                245                 250                 255
Asp Asp Thr Phe His Thr Ala Gly Asp Gly Lys Leu Gly Gly Ile Phe
                260                 265                 270
Met Pro Ser Asp Gly His Cys His Leu Asp Ser Asn Gly Leu Tyr Ser
                275                 280                 285
Arg Ser Pro Glu Phe Asp Tyr Pro Ser Val Gly Gln Val Ala Gln Ala
    290                 295                 300
Leu Ser Thr Ala Asn Ile Gln Pro Ile Phe Ala Val Thr Ser Ala Thr
305                 310                 315                 320
Leu Pro Val Tyr Gln Glu Leu Ser Lys Leu Ile Pro Lys Ser Ala Val
                325                 330                 335
Gly Glu Leu Ser Glu Asp Ser Ser Asn Val Val Gln Leu Ile Met Asp
                340                 345                 350
Ala Tyr Asn Ser Leu Ser Ser Thr Val Thr Leu Glu His Ser Ala Leu
                355                 360                 365
Pro Pro Gly Val His Ile Ser Tyr Glu Ser Leu Cys Gly Asp Pro Glu
    370                 375                 380
Lys Arg Glu Ala Glu Ala Gly Asp Arg Gly Gln Cys Ser His Val Pro
385                 390                 395                 400
Ile Asn His Thr Val Asn Phe Leu Val Thr Leu Gln Ala Thr Arg Cys
                405                 410                 415
Leu Pro Glu Pro His Leu Leu Arg Leu Arg Ala Leu Gly Phe Ser Glu
                420                 425                 430
Glu Leu Thr Val Glu Leu His Thr Leu Cys Asp Cys Asn Cys Ser Asp
                435                 440                 445
Thr Gln Pro Gln Ala Pro His Cys Ser Asp Gly Gln Gly Leu Leu Gln
    450                 455                 460
Cys Gly Val Cys Ser Cys Ala Pro Gly Arg Leu Gly Arg Leu Cys Glu
465                 470                 475                 480
Cys Ser Glu Ala Glu Leu Ser Ser Pro Asp Leu Glu Ser Gly Cys Arg
                485                 490                 495
```

```
Ala Pro Asn Gly Thr Gly Pro Leu Cys Ser Gly Lys Gly Arg Cys Gln
            500                 505                 510

Cys Gly Arg Cys Ser Cys Ser Gly Gln Ser Ser Gly Pro Leu Cys Glu
        515                 520                 525

Cys Asp Ala Ser Cys Glu Arg His Glu Gly Ile Leu Cys Gly Gly
    530                 535                 540

Phe Gly His Cys Gln Cys Gly Arg Cys His Cys His Ala Asn Arg Thr
545                 550                 555                 560

Gly Ser Ala Cys Glu Cys Ser Met Asp Thr Asp Ser Cys Leu Gly Pro
            565                 570                 575

Glu Gly Glu Val Cys Ser Gly His Gly Asp Cys Lys Cys Asn Arg Cys
            580                 585                 590

Gln Cys Arg Asp Gly Tyr Phe Gly Ala Leu Cys Glu Gln Cys Ser Gly
        595                 600                 605

Cys Lys Thr Ser Cys Glu Arg His Arg Asp Cys Ala Glu Cys Gly Ala
    610                 615                 620

Phe Gly Thr Gly Pro Leu Ala Thr Asn Cys Ser Val Ala Cys Ala His
625                 630                 635                 640

Tyr Asn Val Thr Leu Ala Leu Val Pro Val Leu Asp Asp Gly Trp Cys
            645                 650                 655

Lys Glu Arg Thr Leu Asp Asn Gln Leu Leu Phe Phe Leu Val Glu Glu
        660                 665                 670

Glu Ala Gly Gly Met Val Val Leu Thr Val Arg Pro Gln Glu Arg Gly
    675                 680                 685

Ala Asp His
    690

<210> SEQ ID NO 33
<211> LENGTH: 119
<212> TYPE: PRT
<213> ORGANISM: Artificial Sequence
<220> FEATURE:
<223> OTHER INFORMATION: TAG

<400> SEQUENCE: 33

Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
        35                  40                  45

Val Ser Asp Gly Ser Ser Glu Ile Phe Phe Lys Ile Lys Lys Thr Thr
    50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
            85                  90                  95

Gln Thr Pro Glu Asp Leu Asp Met Glu Asp Asn Asp Ile Ile Glu Ala
        100                 105                 110

His Arg Glu Gln Ile Gly Gly
        115

<210> SEQ ID NO 34
<211> LENGTH: 602
<212> TYPE: PRT
<213> ORGANISM: Artificial Sequence
```

<220> FEATURE:
<223> OTHER INFORMATION: Flagellin

<400> SEQUENCE: 34

```
Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
        35                  40                  45

Val Ser Asp Gly Ser Ser Glu Ile Phe Phe Lys Ile Lys Lys Thr Thr
    50                  55                  60

Pro Leu Arg Arg Leu Met Glu Ala Phe Ala Lys Arg Gln Gly Lys Glu
65              70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

His Arg Glu Gln Ile Gly Gly Ala Leu Thr Val Asn Thr Asn Ile Ala
        115                 120                 125

Ser Val Thr Thr Gln Val Asn Leu Asn Lys Ala Ser Thr Ala Gln Thr
    130                 135                 140

Thr Ser Met Gln Arg Leu Ser Ser Gly Leu Arg Ile Asn Ser Ala Lys
145                 150                 155                 160

Asp Asp Ala Ala Gly Leu Gln Ile Ala Asn Arg Leu Thr Ser Gln Ile
                165                 170                 175

Asn Gly Leu Gly Gln Ala Val Lys Asn Ala Asn Asp Gly Ile Ser Ile
            180                 185                 190

Ala Gln Thr Ala Glu Gly Ala Met Gln Ala Ser Thr Asp Ile Leu Gln
        195                 200                 205

Lys Met Arg Thr Leu Ala Leu Ser Ser Ala Thr Gly Ser Leu Ser Pro
    210                 215                 220

Asp Asp Arg Lys Ser Asn Asn Asp Glu Tyr Gln Ala Leu Thr Ala Glu
225                 230                 235                 240

Leu Asn Arg Ile Ser Ala Thr Thr Thr Phe Gly Gly Gln Lys Leu Leu
                245                 250                 255

Asp Gly Ser Tyr Gly Thr Lys Ala Ile Gln Val Gly Ala Asn Ala Asn
            260                 265                 270

Glu Thr Ile Asn Leu Thr Leu Asp Asn Val Ser Ala Lys Ser Ile Gly
        275                 280                 285

Ser Gln Gln Leu Lys Thr Gly Asn Ile Ser Ile Ser Lys Asp Gly Leu
    290                 295                 300

Ala Ala Gly Glu Leu Ala Val Thr Gly Asn Gly Gln Thr Lys Thr Val
305                 310                 315                 320

Asn Tyr Gly Pro Gly Ala Ser Ala Lys Asp Val Ala Ala Gln Leu Asn
                325                 330                 335

Gly Ala Ile Gly Gly Leu Thr Ala Thr Ala Ser Thr Glu Val Lys Leu
            340                 345                 350

Asp Ala Ser Gly Ala Thr Ala Ala Pro Ala Asn Phe Asp Leu Thr
        355                 360                 365

Val Gly Gly Ser Thr Val Ser Phe Val Gly Val Thr Asp Asn Ala Ser
    370                 375                 380

Leu Ala Asp Gln Leu Lys Ser Asn Ala Ala Lys Leu Gly Ile Ser Val
385                 390                 395                 400
```

-continued

Asn Tyr Asp Glu Ser Thr Lys Asn Leu Glu Ile Lys Ser Asp Thr Gly
            405                 410                 415

Glu Asn Ile Thr Phe Ala Pro Lys Ala Gly Ala Pro Gly Val Lys Ile
            420                 425                 430

Ala Ala Lys Asn Gly Ser Gly Thr Tyr Gly Ala Ala Val Pro Leu Asn
            435                 440                 445

Ala Ala Ala Gly Asp Lys Ser Val Val Thr Gly Gln Ile Ser Leu Asp
450                 455                 460

Ser Ala Lys Gly Tyr Ser Ile Ala Asp Gly Ala Gly Ala Asn Gly Ala
465                 470                 475                 480

Gly Ser Thr Ala Ala Leu Tyr Gly Thr Gly Val Thr Ser Val Ser Ser
            485                 490                 495

Lys Lys Thr Asn Val Ser Asp Thr Asp Val Thr Ser Ala Thr Asn Ala
            500                 505                 510

Gln Asn Ala Val Ala Val Ile Asp Lys Ala Ile Gly Ser Ile Asp Ser
            515                 520                 525

Val Arg Ser Gly Leu Gly Ala Thr Gln Asn Arg Leu Thr Thr Thr Val
            530                 535                 540

Asp Asn Leu Gln Asn Ile Gln Lys Asn Ser Thr Ala Ala Arg Ser Thr
545                 550                 555                 560

Val Gln Asp Val Asp Phe Ala Ser Glu Thr Ala Glu Leu Thr Lys Gln
            565                 570                 575

Gln Thr Leu Gln Gln Ala Ser Thr Ala Ile Leu Ser Gln Ala Asn Gln
            580                 585                 590

Leu Pro Ser Ser Val Leu Lys Leu Leu Gln
            595                 600

<210> SEQ ID NO 35
<211> LENGTH: 474
<212> TYPE: PRT
<213> ORGANISM: Artificial Sequence
<220> FEATURE:
<223> OTHER INFORMATION: OMPC

<400> SEQUENCE: 35

Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
            35                  40                  45

Val Ser Asp Gly Ser Ser Glu Ile Phe Phe Lys Ile Lys Lys Thr Thr
50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
            85                  90                  95

Gln Thr Pro Glu Asp Leu Asp Met Glu Asp Asn Asp Ile Ile Glu Ala
            100                 105                 110

His Arg Glu Gln Ile Gly Gly Ala Glu Val Tyr Asn Lys Asp Gly Asn
            115                 120                 125

Lys Leu Asp Leu Tyr Gly Lys Val Asp Gly Leu His Tyr Phe Ser Asp
            130                 135                 140

Asn Lys Ser Glu Asp Gly Asp Gln Thr Tyr Val Arg Leu Gly Phe Lys
145                 150                 155                 160

Gly Glu Thr Gln Val Thr Asp Gln Leu Thr Gly Tyr Gly Gln Trp Glu
            165                 170                 175
Tyr Gln Ile Gln Gly Asn Thr Ser Glu Asp Asn Lys Glu Asn Ser Trp
        180                 185                 190
Thr Arg Val Ala Phe Ala Gly Leu Lys Phe Gln Asp Val Gly Ser Phe
    195                 200                 205
Asp Tyr Gly Arg Asn Tyr Gly Val Val Tyr Asp Val Thr Ser Trp Thr
210                 215                 220
Asp Val Leu Pro Glu Phe Gly Asp Thr Tyr Gly Ser Asp Asn Phe
225                 230                 235                 240
Met Gln Gln Arg Gly Asn Gly Phe Ala Thr Tyr Arg Asn Thr Asp Phe
                245                 250                 255
Phe Gly Leu Val Asp Gly Leu Asn Phe Ala Val Gln Tyr Gln Gly Lys
            260                 265                 270
Asn Gly Ser Val Ser Gly Glu Gly Met Thr Asn Asn Gly Arg Gly Ala
        275                 280                 285
Leu Arg Gln Asn Gly Asp Gly Val Gly Gly Ser Ile Thr Tyr Asp Tyr
    290                 295                 300
Glu Gly Phe Gly Ile Gly Ala Ala Val Ser Ser Ser Lys Arg Thr Asp
305                 310                 315                 320
Asp Gln Asn Gly Ser Tyr Thr Ser Asn Gly Val Val Arg Asn Tyr Ile
                325                 330                 335
Gly Thr Gly Asp Arg Ala Glu Thr Tyr Thr Gly Gly Leu Lys Tyr Asp
            340                 345                 350
Ala Asn Asn Ile Tyr Leu Ala Ala Gln Tyr Thr Gln Thr Tyr Asn Ala
        355                 360                 365
Thr Arg Val Gly Ser Leu Gly Trp Ala Asn Lys Ala Gln Asn Phe Glu
    370                 375                 380
Ala Val Ala Gln Tyr Gln Phe Asp Phe Gly Leu Arg Pro Ser Leu Ala
385                 390                 395                 400
Tyr Leu Gln Ser Lys Gly Lys Asn Leu Gly Val Ile Asn Gly Arg Asn
                405                 410                 415
Tyr Asp Asp Glu Asp Ile Leu Lys Tyr Val Asp Val Gly Ala Thr Tyr
            420                 425                 430
Tyr Phe Asn Lys Asn Met Ser Thr Tyr Val Asp Tyr Lys Ile Asn Leu
        435                 440                 445
Leu Asp Asp Asn Gln Phe Thr Arg Asp Ala Gly Ile Asn Thr Asp Asn
    450                 455                 460
Ile Val Ala Leu Gly Leu Val Tyr Gln Phe
465                 470

<210> SEQ ID NO 36
<211> LENGTH: 11
<212> TYPE: PRT
<213> ORGANISM: Artificial Sequence
<220> FEATURE:
<223> OTHER INFORMATION: Poly-His tag

<400> SEQUENCE: 36

Met Gly Ser Ser His His His His His His Gly
1               5                   10

<210> SEQ ID NO 37
<211> LENGTH: 57
<212> TYPE: PRT
<213> ORGANISM: Unknown

```
<220> FEATURE:
<223> OTHER INFORMATION: Gliadin

<400> SEQUENCE: 37

Gln Pro Gln Pro Gln Pro Gln Pro Gln Pro Gln Met Asn Thr Cys Ala
1               5                   10                  15

Ala Phe Leu Gln Gln Cys Ser Gln Thr Ala Tyr Val Gln Ser Gln Met
            20                  25                  30

Trp Gln Ala Ser Gly Cys Gln Leu Met Arg Gln Cys Cys Gln Pro
        35                  40                  45

Leu Ala Gln Ile Ser Glu Gln Ala Arg
    50                  55

<210> SEQ ID NO 38
<211> LENGTH: 6
<212> TYPE: PRT
<213> ORGANISM: Unknown
<220> FEATURE:
<223> OTHER INFORMATION: Gliadin

<400> SEQUENCE: 38

Gln Gln Gln Gly Gln Arg
1               5

<210> SEQ ID NO 39
<211> LENGTH: 26
<212> TYPE: PRT
<213> ORGANISM: Unknown
<220> FEATURE:
<223> OTHER INFORMATION: Gliadin

<400> SEQUENCE: 39

Phe Gly Gln Pro Gln Gln Gln Gly Gln Ser Phe Gly Gln Pro Gln
1               5                   10                  15

Gln Gln Val Pro Val Glu Ile Met Gly Met
            20                  25

<210> SEQ ID NO 40
<211> LENGTH: 18
<212> TYPE: PRT
<213> ORGANISM: Unknown
<220> FEATURE:
<223> OTHER INFORMATION: Gliadin

<400> SEQUENCE: 40

Val Phe Leu Gln Gln Gln Cys Ser Pro Val Ala Met Pro Gln His Leu
1               5                   10                  15

Ala Arg

<210> SEQ ID NO 41
<211> LENGTH: 15
<212> TYPE: PRT
<213> ORGANISM: Unknown
<220> FEATURE:
<223> OTHER INFORMATION: Amylase inhibitor

<400> SEQUENCE: 41

Ala Phe Gln Val Pro Ala Leu Pro Ala Cys Arg Pro Leu Leu Arg
1               5                   10                  15

<210> SEQ ID NO 42
<211> LENGTH: 28
<212> TYPE: PRT
<213> ORGANISM: Unknown
```

```
<220> FEATURE:
<223> OTHER INFORMATION: Amylase Inhibitor

<400> SEQUENCE: 42

Leu Gln Cys Asn Gly Ser Gln Val Pro Glu Ala Val Leu Arg Asp Cys
1               5                   10                  15

Cys Gln Gln Leu Ala His Ile Ser Glu Trp Cys Arg
            20                  25

<210> SEQ ID NO 43
<211> LENGTH: 16
<212> TYPE: PRT
<213> ORGANISM: Unknown
<220> FEATURE:
<223> OTHER INFORMATION: Amylase inhibitor

<400> SEQUENCE: 43

Glu His Gly Ala Gln Glu Gly Gln Ala Gly Thr Gly Ala Phe Pro Arg
1               5                   10                  15

<210> SEQ ID NO 44
<211> LENGTH: 27
<212> TYPE: PRT
<213> ORGANISM: Unknown
<220> FEATURE:
<223> OTHER INFORMATION: Amylase inhibitor

<400> SEQUENCE: 44

Leu Thr Ala Ala Ser Ile Thr Ala Val Cys Arg Leu Pro Ile Val Val
1               5                   10                  15

Asp Ala Ser Gly Asp Gly Ala Tyr Val Cys Lys
            20                  25

<210> SEQ ID NO 45
<211> LENGTH: 18
<212> TYPE: PRT
<213> ORGANISM: Unknown
<220> FEATURE:
<223> OTHER INFORMATION: Amylase inhibitor

<400> SEQUENCE: 45

Tyr Lys Glu His Gly Ala Gln Glu Gly Gln Ala Gly Thr Gly Ala Phe
1               5                   10                  15

Pro Arg

<210> SEQ ID NO 46
<211> LENGTH: 13
<212> TYPE: PRT
<213> ORGANISM: Unknown
<220> FEATURE:
<223> OTHER INFORMATION: Zein

<400> SEQUENCE: 46

Ala Thr Ile Phe Pro Gln Cys Ser Gln Ala Pro Ile Ala
1               5                   10

<210> SEQ ID NO 47
<211> LENGTH: 5
<212> TYPE: PRT
<213> ORGANISM: Unknown
<220> FEATURE:
<223> OTHER INFORMATION: Zein

<400> SEQUENCE: 47

Pro Tyr Leu Pro Ser
```

-continued

<210> SEQ ID NO 48
<211> LENGTH: 30
<212> TYPE: PRT
<213> ORGANISM: Unknown
<220> FEATURE:
<223> OTHER INFORMATION: Zein

<400> SEQUENCE: 48

Ile Ile Ala Ser Ile Cys Glu Asn Pro Ala Leu Gln Pro Tyr Arg Leu
1               5                   10                  15

Gln Gln Ala Ile Ala Ala Ser Asn Ile Pro Leu Ser Pro Leu
            20                  25                  30

<210> SEQ ID NO 49
<211> LENGTH: 9
<212> TYPE: PRT
<213> ORGANISM: Unknown
<220> FEATURE:
<223> OTHER INFORMATION: Zein

<400> SEQUENCE: 49

Leu Phe Gln Gln Ser Pro Ala Leu Ser
1               5

<210> SEQ ID NO 50
<211> LENGTH: 10
<212> TYPE: PRT
<213> ORGANISM: Unknown
<220> FEATURE:
<223> OTHER INFORMATION: Zein

<400> SEQUENCE: 50

Leu Val Gln Ser Leu Val Gln Thr Ile Arg
1               5                   10

<210> SEQ ID NO 51
<211> LENGTH: 12
<212> TYPE: PRT
<213> ORGANISM: Unknown
<220> FEATURE:
<223> OTHER INFORMATION: Zein

<400> SEQUENCE: 51

Ser Gln Gln Gln Gln Phe Leu Pro Phe Asn Gln Leu
1               5                   10

<210> SEQ ID NO 52
<211> LENGTH: 16
<212> TYPE: PRT
<213> ORGANISM: Unknown
<220> FEATURE:
<223> OTHER INFORMATION: Zein

<400> SEQUENCE: 52

Ser Gln Leu Ala Thr Ala Tyr Ser Gln Gln Gln Gln Leu Leu Pro Phe
1               5                   10                  15

<210> SEQ ID NO 53
<211> LENGTH: 30
<212> TYPE: PRT
<213> ORGANISM: Unknown
<220> FEATURE:
<223> OTHER INFORMATION: Zein

<400> SEQUENCE: 53

Gln Ile Leu Leu Pro Phe Ser Gln Leu Ala Ala Asn Arg Ala Ser
1               5                   10                  15

Phe Leu Thr Gln Gln Gln Leu Leu Pro Phe Tyr Gln Gln Phe
            20                  25                  30

<210> SEQ ID NO 54
<211> LENGTH: 14
<212> TYPE: PRT
<213> ORGANISM: Unknown
<220> FEATURE:
<223> OTHER INFORMATION: Zein

<400> SEQUENCE: 54

Ala Ala Asn Pro Ala Thr Leu Leu Gln Leu Gln Gln Leu Leu
1               5                   10

<210> SEQ ID NO 55
<211> LENGTH: 15
<212> TYPE: PRT
<213> ORGANISM: Unknown
<220> FEATURE:
<223> OTHER INFORMATION: Zein

<400> SEQUENCE: 55

Val Gln Leu Ala Leu Thr Asp Pro Ala Ala Ser Tyr Gln Gln His
1               5                   10                  15

<210> SEQ ID NO 56
<211> LENGTH: 7
<212> TYPE: PRT
<213> ORGANISM: Unknown
<220> FEATURE:
<223> OTHER INFORMATION: Zein

<400> SEQUENCE: 56

Ile Ile Gly Gly Ala Leu Phe
1               5

<210> SEQ ID NO 57
<211> LENGTH: 11
<212> TYPE: PRT
<213> ORGANISM: Unknown
<220> FEATURE:
<223> OTHER INFORMATION: Zein

<400> SEQUENCE: 57

Ala Gln Gln Leu Gln Gln Leu Val Leu Ala Asn
1               5                   10

<210> SEQ ID NO 58
<211> LENGTH: 113
<212> TYPE: PRT
<213> ORGANISM: Artificial Sequence
<220> FEATURE:
<223> OTHER INFORMATION: Gliadin

<400> SEQUENCE: 58

Met Gly Ser Ser His His His His His Gly Gln Pro Gln Pro Gln
1               5                   10                  15

Pro Gln Pro Gln Pro Gln Met Asn Thr Cys Ala Ala Phe Leu Gln Gln
            20                  25                  30

Cys Ser Gln Thr Ala Tyr Val Gln Ser Gln Met Trp Gln Ala Ser Gly
        35                  40                  45

Cys Gln Leu Met Arg Gln Gln Cys Cys Gln Pro Leu Ala Gln Ile Ser

```
                 50                  55                  60
Glu Gln Ala Arg Cys Gln Ala Val Cys Ser Val Ala Gln Ile Ile Met
 65                  70                  75                  80

Arg Gln Gln Gly Gln Arg Phe Gly Gln Pro Gln Gln Gln Gly
                 85                  90                  95

Gln Ser Phe Gly Gln Pro Gln Gln Val Pro Val Glu Ile Met Gly
                100                 105                 110

Met

<210> SEQ ID NO 59
<211> LENGTH: 117
<212> TYPE: PRT
<213> ORGANISM: Artificial Sequence
<220> FEATURE:
<223> OTHER INFORMATION: Amylase inhibitor

<400> SEQUENCE: 59

Met Gly Ser Ser His His His His His His Gly Ala Phe Gln Val Pro
 1               5                  10                  15

Ala Leu Pro Ala Cys Arg Pro Leu Leu Arg Leu Gln Cys Asn Gly Ser
                20                  25                  30

Gln Val Pro Glu Ala Val Leu Arg Asp Cys Cys Gln Gln Leu Ala His
            35                  40                  45

Ile Ser Glu Trp Cys Arg Cys Gly Ala Leu Tyr Ser Met Leu Asp Ser
 50                  55                  60

Met Tyr Lys Glu His Gly Ala Gln Glu Gly Gln Ala Gly Thr Gly Ala
 65                  70                  75                  80

Phe Pro Arg Cys Arg Arg Glu Val Val Lys Leu Thr Ala Ala Ser Ile
                85                  90                  95

Thr Ala Val Cys Arg Leu Pro Ile Val Val Asp Ala Ser Gly Asp Gly
            100                 105                 110

Ala Tyr Val Cys Lys
        115

<210> SEQ ID NO 60
<211> LENGTH: 209
<212> TYPE: PRT
<213> ORGANISM: Artificial Sequence
<220> FEATURE:
<223> OTHER INFORMATION: Zein

<400> SEQUENCE: 60

Met Gly Ser Ser His His His His His His Gly Ile Ile Ala Ser Ile
 1               5                  10                  15

Cys Glu Asn Pro Ala Leu Gln Pro Tyr Arg Leu Gln Gln Ala Ile Ala
                20                  25                  30

Ala Ser Asn Ile Pro Leu Ser Pro Leu Leu Phe Gln Gln Ser Pro Ala
            35                  40                  45

Leu Ser Leu Val Gln Ser Leu Val Gln Thr Ile Arg Ala Gln Gln Leu
         50                  55                  60

Gln Gln Leu Val Leu Pro Leu Ile Asn Gln Val Ala Leu Ala Asn Leu
 65                  70                  75                  80

Ser Pro Tyr Ser Gln Gln Gln Phe Leu Pro Phe Asn Gln Leu Ser
                85                  90                  95

Thr Leu Asn Pro Ala Ala Tyr Leu Gln Gln Gln Leu Leu Pro Phe Ser
            100                 105                 110

Gln Leu Ala Thr Ala Tyr Ser Gln Gln Gln Gln Leu Leu Pro Phe Asn
```

```
            115                 120                 125
Gln Leu Ala Ala Leu Asn Pro Ala Ala Tyr Leu Gln Gln Gln Ile Leu
    130                 135                 140

Leu Pro Phe Ser Gln Leu Ala Ala Ala Asn Arg Ala Ser Phe Leu Thr
145                 150                 155                 160

Gln Gln Gln Leu Leu Pro Phe Tyr Gln Gln Phe Ala Ala Asn Pro Ala
                165                 170                 175

Thr Leu Leu Gln Leu Gln Gln Leu Leu Pro Phe Val Gln Leu Ala Leu
            180                 185                 190

Thr Asp Pro Ala Ala Ser Tyr Gln Gln His Ile Ile Gly Gly Ala Leu
        195                 200                 205

Phe

<210> SEQ ID NO 61
<211> LENGTH: 21
<212> TYPE: DNA
<213> ORGANISM: Unknown
<220> FEATURE:
<223> OTHER INFORMATION: TTG2

<400> SEQUENCE: 61
gccgaggatc tggttctcga g                                            21

<210> SEQ ID NO 62
<211> LENGTH: 21
<212> TYPE: DNA
<213> ORGANISM: Unknown
<220> FEATURE:
<223> OTHER INFORMATION: TTG2

<400> SEQUENCE: 62
ttaggcggga ccaatgagga c                                            21

<210> SEQ ID NO 63
<211> LENGTH: 805
<212> TYPE: PRT
<213> ORGANISM: Artificial Sequence
<220> FEATURE:
<223> OTHER INFORMATION: TTG2

<400> SEQUENCE: 63

Met Gly Ser Ser His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
        35                  40                  45

Val Ser Asp Gly Ser Ser Glu Ile Phe Phe Lys Ile Lys Lys Thr Thr
    50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

His Arg Glu Gln Ile Gly Gly Ala Glu Asp Leu Val Leu Glu Lys Cys
        115                 120                 125

Asp Leu Glu Leu Glu Ala Asn Gly Arg Asp His His Thr Ala Gly Leu
    130                 135                 140
```

```
Cys Gln Gly Arg Leu Val Val Arg Arg Gly Gln Pro Phe Trp Leu Thr
145                 150                 155                 160

Leu His Phe Thr Gly Arg Ser Tyr Glu Ser Ser Val Asp Ser Leu Thr
            165                 170                 175

Phe Ser Ala Val Thr Gly Pro Asp Pro Ser Glu Glu Ala Gly Thr Lys
        180                 185                 190

Ala Arg Phe Ser Leu Ser Ser Ala Val Glu Glu Gly Ala Trp Thr Ala
    195                 200                 205

Val Val Met Asp Gln Gln Asp Ser Val Leu Ser Leu Gln Leu Ser Thr
210                 215                 220

Pro Pro Asn Ala Pro Val Gly Leu Tyr Arg Leu Ser Leu Glu Ala Ser
225                 230                 235                 240

Thr Gly Tyr Gln Gly Ser Ser Phe Val Leu Gly His Phe Thr Leu Leu
            245                 250                 255

Phe Asn Ser Trp Cys Pro Ala Asp Ala Val Tyr Leu Asp Ser Asp Glu
            260                 265                 270

Glu Arg Arg Glu Tyr Val Leu Ser Gln Gln Gly Phe Ile Tyr Gln Gly
        275                 280                 285

Ser Val Lys Phe Ile Lys Ser Ile Pro Trp Asn Phe Gly Gln Phe Glu
290                 295                 300

Asp Gly Ile Leu Asp Ile Cys Leu Met Leu Leu Asp Arg Asn Pro Lys
305                 310                 315                 320

Phe Leu Lys Asp Ala Cys Arg Asp Cys Ser Ser Arg Ser Asn Pro Ile
            325                 330                 335

Tyr Val Gly Arg Val Val Ser Ala Met Val Asn Cys Asn Asp Asp Gln
            340                 345                 350

Gly Val Leu Leu Gly Arg Trp Asp Asn Asn Tyr Lys Asp Gly Ile Ser
        355                 360                 365

Pro Met Phe Trp Ile Gly Ser Val Asp Ile Leu Arg Arg Trp Lys Thr
        370                 375                 380

Ser Gly Cys Gln Arg Val Lys Tyr Gly Gln Cys Trp Val Phe Ala Ala
385                 390                 395                 400

Val Ala Cys Thr Val Leu Arg Cys Leu Gly Ile Pro Thr Arg Val Val
            405                 410                 415

Thr Asn Phe Asn Ser Ala His Asp Gln Asn Ser Asn Leu Leu Ile Glu
            420                 425                 430

Tyr Val Tyr Asn Lys Phe Gly Glu Ile Gln Lys Glu Lys Ser Glu Met
        435                 440                 445

Ile Trp Asn Tyr His Cys Trp Val Glu Ser Trp Met Ser Arg Pro Asp
        450                 455                 460

Leu Gln Pro Gly Tyr Glu Gly Trp Gln Ala Leu Asp Pro Thr Pro Gln
465                 470                 475                 480

Glu Lys Ser Glu Gly Thr Tyr Cys Cys Gly Pro Val Pro Val Arg Ala
            485                 490                 495

Ile Lys Glu Gly Asp Leu Ser Thr Lys Tyr Asp Ala Ala Phe Val Phe
            500                 505                 510

Ala Glu Val Asn Ala Asp Val Val Asn Trp Ile Gln Gln Asp Asp Gly
        515                 520                 525

Ser Leu Cys Lys Ser Thr Asn Asn Ser Gln Thr Val Gly Met Lys Ile
        530                 535                 540

Ser Thr Lys Ser Val Gly Arg Asp Glu Arg Glu Asp Ile Thr His Asn
545                 550                 555                 560
```

-continued

Tyr Lys Tyr Pro Glu Gly Ser Pro Glu Arg Glu Ala Phe Arg Lys
            565                 570                 575

Ala Asn His Leu Asn Lys Leu Thr Glu Lys Glu Thr Gly Leu Ala
            580                 585                 590

Met Arg Ile Arg Val Ser Glu Ser Met Ser Met Gly Ser Asp Phe Asp
            595                 600                 605

Val Phe Ala Tyr Ile Asn Asn Asn Thr Ser Glu Ser His Ser Cys Arg
        610                 615                 620

Leu Leu Leu His Ala Arg Thr Val Ser Tyr Asn Gly Ile Leu Gly Pro
625                 630                 635                 640

Glu Cys Gly Thr Lys Asp Leu Leu Asn Leu Ser Leu Glu Pro Phe Ser
                645                 650                 655

Glu Lys Ser Ile Pro Leu Arg Ile Leu Tyr Glu Lys Tyr Cys Glu Cys
            660                 665                 670

Leu Thr Glu Ser Asn Leu Ile Lys Val Arg Gly Leu Leu Val Glu Gln
        675                 680                 685

Ala Ala Asn Asn Tyr Leu Leu Ala Glu Arg Asp Ile Tyr Leu Glu Asn
690                 695                 700

Pro Glu Ile Lys Ile Arg Ile Leu Gly Glu Pro Lys Gln Asn Arg Lys
705                 710                 715                 720

Leu Val Ala Glu Ala Ser Leu Arg Asn Pro Leu Thr Val Pro Leu Leu
                725                 730                 735

Gly Cys Ser Phe Thr Met Glu Gly Ala Gly Leu Thr Glu Glu Gln Lys
            740                 745                 750

Val Met Asp Val Pro Asp Pro Val Glu Ala Gly Glu Val Lys Val
        755                 760                 765

Arg Val Asp Leu Leu Pro Arg His Val Gly Arg His Lys Leu Val Val
        770                 775                 780

Asn Phe Glu Ser Asp Lys Leu Lys Ala Val Lys Gly Phe Arg Asn Val
785                 790                 795                 800

Leu Ile Gly Pro Ala
            805

<210> SEQ ID NO 64
<211> LENGTH: 24
<212> TYPE: DNA
<213> ORGANISM: Unknown
<220> FEATURE:
<223> OTHER INFORMATION: TG3

<400> SEQUENCE: 64
acggctttag aaccccagag tatc                                          24

<210> SEQ ID NO 65
<211> LENGTH: 24
<212> TYPE: DNA
<213> ORGANISM: Unknown
<220> FEATURE:
<223> OTHER INFORMATION: TG3

<400> SEQUENCE: 65
cttcactcgg ccacgtcaat ggac                                          24

<210> SEQ ID NO 66
<211> LENGTH: 598
<212> TYPE: PRT
<213> ORGANISM: Artificial Sequence
<220> FEATURE:
<223> OTHER INFORMATION: TG3

<400> SEQUENCE: 66

Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
        35                  40                  45

Val Ser Asp Gly Ser Ser Glu Ile Phe Phe Lys Ile Lys Lys Thr Thr
    50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

His Arg Glu Gln Ile Gly Gly Thr Ala Leu Glu Pro Gln Ser Ile Asn
        115                 120                 125

Trp Gln Ala Thr Ser Asn Arg Arg Ala His His Thr Asp Arg Phe Ser
    130                 135                 140

Ser Gln Glu Pro Ile Leu Arg Arg Gly Gln Ser Phe Asn Phe Ser Leu
145                 150                 155                 160

Ser Leu Asn Arg Ser Leu Gly Thr Gly Glu Ser Leu Gly Phe Val Val
                165                 170                 175

Ser Thr Gly Pro Gln Pro Ser Glu Ser Ala Arg Thr Lys Ala Val Phe
            180                 185                 190

Pro Leu Ser Asn Arg Thr Ser Arg Gly Trp Ser Ala Glu Leu Val
        195                 200                 205

Ser Asn Lys Asp Asn Ile Leu Thr Ile Ser Ile Ser Ser Pro Val Asn
    210                 215                 220

Ala Pro Val Gly Trp Tyr Thr Leu Ser Thr Gln Ile Ser Ser Gln Gly
225                 230                 235                 240

Lys Asp Phe Ile Leu Lys Leu Gly Met Phe Ile Leu Leu Phe Asn Pro
                245                 250                 255

Trp Leu Gln Glu Asp Gly Val Phe Met Asp Asn His Val Glu Arg Glu
            260                 265                 270

Glu Tyr Val Leu Glu Asp Ala Gly Ile Ile Tyr Val Gly Ser Thr Asn
        275                 280                 285

Arg Ile Gly Met Val Gly Cys Asn Phe Gly Gln Phe Glu Glu Gly Ile
    290                 295                 300

Leu Asn Ile Cys Leu Ser Ile Leu Asp His Ser Leu Asn Phe Arg Arg
305                 310                 315                 320

Asp Pro Ala Thr Asp Val Ala Arg Arg Asn Asp Pro Lys Tyr Val Gly
                325                 330                 335

Arg Val Leu Ser Ala Met Val Asn Gly Asn Asp Asp Asn Gly Val Leu
            340                 345                 350

Ser Gly Asn Trp Ser Gly Asn Tyr Thr Gly Gly Arg Asp Pro Arg Asn
        355                 360                 365

Trp Asn Gly Ser Val Glu Ile Leu Lys Glu Trp Lys Lys Ser Gly Phe
    370                 375                 380

Arg Pro Val Arg Phe Gly Gln Cys Trp Val Phe Ala Gly Thr Leu Asn
385                 390                 395                 400

Thr Val Leu Arg Ser Phe Gly Ile Pro Ser Arg Val Val Thr Asn Phe

-continued

```
                    405                     410                     415
Asn Ser Ala His Asp Thr Asp Arg Asn Leu Ser Val His Val Tyr Tyr
            420                     425                 430

Asp Pro Tyr Gly Arg Pro Met Asp Lys Gly Ser Asp Ser Val Trp Asn
        435                     440                 445

Phe His Val Trp Asn Glu Ala Trp Phe Val Arg Thr Asp Leu Gly Pro
    450                     455                 460

Leu Tyr Asn Gly Trp Gln Val Leu Asp Ala Thr Pro Gln Glu Arg Ser
465                     470                     475                 480

Gln Gly Val Phe Gln Cys Gly Pro Ala Ser Val Ala Ala Val Arg Glu
                485                     490                 495

Gly Asp Val Asn Leu Asp Phe Asp Met Pro Phe Val Phe Ala Glu Val
                500                     505                 510

Asn Ala Asp Arg Ile Thr Trp Ile Tyr Asp Val Tyr Asn Ser Thr Gln
            515                     520                 525

Lys Gln Asn Ala Ser Asp Ala His Ser Ile Gly Arg Tyr Ile Ser Thr
            530                     535                 540

Lys Ala Val Gly Ser Asn Ser Arg Met Asp Ile Thr Glu Lys Tyr Lys
545                     550                     555                 560

His Pro Glu Gly Ser Ser Gln Glu Arg Gln Val Phe Glu Lys Ala Leu
                565                     570                 575

Gly Lys Leu Lys Pro His Ala Ser Phe Gly Ala Thr Ser Ala Arg His
                580                     585                 590

Leu Ala Asp Lys Leu Arg
                595
```

METHODS OF DETECTING MARKERS FOR INFLAMMATORY CONDITIONS AND FOOD SENSITIVITY IN COMPANION ANIMALS

RELATED APPLICATIONS

This application is divisional application of U.S. application Ser. No. 15/592,104, filed May 10, 2017, which is a Continuation-in-Part of International Application PCT/US16/60674, filed Nov. 4, 2016, designating the US and claiming the benefit of U.S. Provisional Application No. 62/373,307, filed Aug. 10, 2016, and U.S. Provisional Application No. 62/252,266, filed Nov. 6, 2015, the entire contents of which applications are incorporated herein by reference.

FIELD OF THE INVENTION

The invention relates generally to the fields of inflammation and immunology, for example inflammatory bowel disease, and more specifically to serological methods and specific algorithms for diagnosing and distinguishing inflammatory conditions, such as inflammatory bowel disease, from other diseases in companion animals, and also to food sensitivity, gastrointestinal related disorders and immunology and more specifically to serological methods and specific algorithms for detecting and distinguishing food sensitivity from other diseases in companion animals, particularly comprising detecting and measuring endogenous antibodies, as well as diagnostic kits for carrying out such methods, and methods of treating companion animals so diagnosed.

BACKGROUND OF THE INVENTION

Inflammatory Conditions in Companion Animals:

Inflammation is usually a normal, healthy response to injury or infection, but sometimes the inflammatory response is disproportionate or abnormal, so that the inflammation, rather than promoting healing, seriously damages normal tissues, resulting in chronic pain, contributing to a wide variety of serious disorders, and in some cases even causing death. Inflammatory bowel disease (IBD), for example, is a debilitating and progressive disease involving inflammation of the gastrointestinal tract. Symptoms include abdominal pain, cramping, diarrhea and bleeding.

One indication of such inflammatory diseases is the presence of inflammatory cells such as neutrophils and macrophages at local sites of inflammation. Inflammation is a response of vascularized tissue to infection and/or injury and it is affected by adhesion of leukocytes to the endothelial cells of blood vessels and their infiltration into the surrounding tissues. Such local concentrations can be detected by invasive methods requiring biopsy procedures and pathology analysis. The inflammatory state can also be systemic, i.e. polypeptides secreted by inflammatory cells become detectable in the blood serum.

Inflammatory bowel disease (IBD) describes idiopathic gastrointestinal disorders characterized by persistent or recurrent gastrointestinal (GI) signs and histological evidence of GI inflammation for which no underlying cause can be found. Effective treatment of IBD requires differentiating the condition from other gastrointestinal disorders that do not necessarily involve chronic inflammation. While certain diagnostics have been developed for humans, these diagnostics are not always accurate, and the lack of accurate diagnostics is even more acute for companion animals such as dogs and cats. Inflammatory bowel disease is typically identified by veterinarians as being the most common cause of intestinal disease in companion animals, but accurate data on its prevalence is lacking mainly because diagnosis of the disease is challenging. The disease varies greatly, not only in severity but also in its anatomical distribution throughout the GI of companion animals, particularly lower GI, and perhaps most importantly the type of inflammatory reaction involved. Lymphoplasmacytic enteritis (LPE) is the most common form reported in companion animals followed by eosinophilic gastroenteritis (EGE) that is less common, and granulomatous enteritis (GE) that is rare.

Canine and feline IBD bear little resemblance clinically or histologically to the human IBD forms (Xavier and Podolsky, *Nature*, 448:427-434 (2007); Cerquetella et al., *World J. Gastroent.*, 16: 1050-1056 (2010). IBD and IBD-related conditions are likely to affect a significant portion of companion animals during their lifetime, and when left untreated, leads to an increase of morbidity, deteriorating quality of life and in some cases cancer. Prompt and accurate diagnosis of the condition is likely to result on rapid and adequate interventions leading to significant improvement in the quality of life of companion animals.

The most common clinical signs in companion animal IBD are vomiting and diarrhea, although the disease can present broader clinical signs including but not limited to abdominal pain, altered appetite and weight loss, bloating and cramping, and even flatulence. All these clinical symptoms are general in nature and overlap with many other potential conditions making definitive diagnosis extremely difficult. The difficulty in diagnosing IBD and differentiating from other superficially similar conditions such as irritable bowel syndrome (IBS), food sensitivities and/or gastrointestinal infections hampers early and effective treatment.

The best current methodology to diagnose IBD in companion animals requires using relatively costly, labor-intensive and intrusive clinical, radiographic, endoscopic, and/or histological techniques. And despite all these techniques, there is a high degree of subjectivity. Histopathological assessment of gastrointestinal biopsies remain the gold standard to diagnose GI inflammation in companion animals. However, the quality of specimens may vary, agreement between pathologists might be lacking, and differentiation between tissues affected by different conditions may be difficult requiring significant intervention, cost and time. The term IBD includes cases in which histological evidence of inflammation is found without obvious underlying cause, and all other etiologies have been excluded. Overall, the diagnosis of IBD remains a process of exclusion, and thus, represents a lengthy and costly process, which also contributes to unnecessary companion animal suffering and morbidity.

Inflammatory bowel disease (IBD) in companion animals poses a major challenge to veterinarians. The initial symptoms are often confused with non-IBD acute or chronic bowel conditions, particularly for those veterinarians unfamiliar with the disease. Therefore, IBD remains undiagnosed and untreated. In the worst case scenario, IBD is misdiagnosed and companion animals are potentially receiving inadequate medical care resulting in increased morbidity and associated companion animal owner discomfort.

Only a few immunological and inflammatory markers have been validated for use in companion animals. There is therefore a need for markers that are both sensitive and specific for companion animals with chronic inflammatory diseases, such as IBD. The availability of rapid and less intrusive methods to diagnose IBD tailored specifically for companion animals would represent a major clinical advance in veterinary medicine and would facilitate earlier and more appropriate therapeutic intervention to treat diseased companion animals. There is a need for a more effective, less intrusive diagnostic method tailored specifically for companion animals to rule out inflammation related IBD if it is not the underlying condition or to rule in IBD.

A further challenge is distinguishing among inflammatory conditions, food sensitivities, and other gastrointestinal disorders.

Food Sensitivities in Companion Animals:

Food sensitivity is a unique disorder that is defined as an adverse reaction to specific foods that may cause severe illness. Food sensitivity, in its chronic form, is an immunologic sensitivity to a food involving T and B lymphocytes as part of the chronic cell mediated immune system (also called delayed or type IV hypersensitivity) that may include noticeable symptoms such as abdominal pain, diarrhea, constipation, and weight loss, and may also include less noticeable effects due to malabsorption of fluids and dietary nutrients, such as osteoporosis, anemia, or vitamin deficiencies. Without proper diagnostic testing, which currently is limited to invasive means such as endoscopic intestinal biopsy and the presence of symptoms which can be confounded with other gastrointestinal related diseases, the subject may unknowingly continue to consume the food triggering the chain of reactions which may have long term health implications.

One such immunologic food sensitivity is gluten sensitivity where subjects display an immunologic reaction to dietary gluten contained in wheat, barley, rye, and oats, that results in any degree of intestinal histopathology. The gluten-induced immunologic process causes villous atrophy and inflammation of the small intestine, in turn, resulting in diarrhea and weight loss from malabsorption of fluids, electrolytes, and dietary nutrients. Despite the fact that chronic diarrhea is the most common symptom of food sensitivity to gluten in its classic, villous atrophic, form, there have been no studies of the prevalence of gluten related sensitivity or other food sensitivities in companion animals presenting to veterinarians with chronic diarrhea or other common gastrointestinal symptoms. Additionally, there are no adequate methods in the prior art to diagnose for food sensitivities when the patient presents with little or no common gastrointestinal symptoms or when the symptoms are also attributable to other diseases. This frequently results in either no diagnosis or misdiagnosis of a food sensitivity.

In addition to the gastrointestinal issues triggered by food sensitivities, they have also been associated with other diverse conditions in humans such as dermatopathies (e.g. dermatitis herpetiformis) and neurological disorders such as gluten ataxia. In cases of gluten ataxia, although less than 10% show gastrointestinal signs of disease, over 34% will have evidence of enteropathy on biopsy.

Elimination diets in which controlled proteins and carbohydrates are used as sources remain the main approach used by veterinarians to diagnose food sensitivities. The elimination diet approach has significant challenges though. These diets have to be maintained for at least 12 weeks to be effective with significant compliance issues. Further, because there is no current robust methodology to determine the specific source of sensitivity, veterinarians favor the introduction of pan-hypoallergenic diets with highly hydrolyzed proteins which are costly and lack clear determination of which ingredient or ingredients are causing the sensitivity.

Food sensitivity in some cases can be defined as an intolerance to proteins including storage proteins from grains such as wheat and corn. The food sensitivity is characterized by a chronic inflammatory state of the proximal small intestinal mucosa that heals when foods containing prolamins rich proteins are excluded from the diet and returns when these foods are reintroduced. Complex adaptive and innate immune reactions result in chronic inflammation of the mucosa and result in various structural and functional changes. There is atrophy of the small intestinal villi, deepening of the crypts, and infiltration of the lamina propria and intraepithelial compartments with chronic inflammatory cells. The functional changes include decreased digestion of food, decreased absorption of macronutrients and micronutrients, and increased net secretion of water and solute. Although the mucosal damage is primarily cellular, untreated food sensitivity is also associated with a humoral immune response that consists of both secreted intestinal and circulating serologic antibodies directed against the reticulin and endomysium of connective tissue such as endomysial antibodies, and against various peptides derived predominantly from wheat, "anti-gliadin antibodies" and from corn "anti-zein antibodies".

Prolamins are a group of proteins soluble in 40-70% ethanol and are the major storage proteins of all cereal grains. Prolamins are further classified in sub-families based on differences in aqueous solubility and ability to form disulfide interactions. Most prolamins share common structural features including the presence of amino acid sequences consisting of repeated blocks based on one or more short peptide motifs, or enriched in specific amino acid residues. These features are responsible for the high proportions of glutamine, proline and other specific amino acids (e.g. histidine, glycine, methionine, and phenylalanine).

The gluten proteins of wheat consist of an approximately equal amount mixture of monomeric gliadins and polymeric glutenin subunits forming 80% of the total storage protein content in the wheat kernel. The remainder is albumins (12%) and globulins (8%). The highly seed storage proteins of wheat and barley are classified on the basis of their solubility into water-soluble albumins, salt-soluble globulins, alcohol-soluble (40%-70%) gliadins, and alcohol-insoluble glutenins. In wheat, the alcohol insoluble fraction of prolamins is comprised of the High Molecular Weight (HMW) glutenin subunits (650-850 residues long) and the Low Molecular Weight (LMW) glutenin subunits (270-330 residues long), whereas the alcohol soluble fraction is comprised of gliadins (250-720 residues long) further separated into sulphur-poor w-gliadins and the sulphur-rich α/β and γ gliadins. In barley the homologous proteins are named D-, C-, B- and γ-hordeins, respectively. Glutamine (Gln or Q) and proline (Pro or P) are two major amino acids that comprise 35 and 15% of the gluten proteins, respectively, and as such are also classified prolamins.

The prolamins of maize, called zeins, and of other panicoid cereals such as sorghum and millets are comprised of one major group of proteins (α-zeins) rich in glutamine, proline, alanine, and leucine residues accounting for 70% of the total zein fraction and several minor groups (β, γ, δ-zeins). Amino acid sequence comparisons demonstrate that the β, γ and δ-zeins are all members of the prolamin superfamily, but only the γ-zeins contain repeated amino acid sequences (either two or eight tandem repeats of Pro-Pro-Pro-Val-His-Leu). The β-zeins and δ-zeins are both rich in methionine. The α-zeins contain only one or two cysteine residues per molecule and are present in the grain as monomers or oligomers, while the β-, γ- and δ-zeins are all richer in cysteine and form polymers.

The amino acid composition of the prolamin polypeptides makes them highly resistant to gastric and pancreatic proteases. The partially digested polypeptides move from the stomach into the intestine, where they are incompletely hydrolyzed by the exopeptidases of the brush border membrane. The immunogenicity of these peptides may be intensified by deamidation of selected glutamine residues by tissue transglutaminase 2 (tTG2). These polypeptide complexes may trigger mucosal inflammation and loss of absorptive surface area manifested by a broad spectrum of symptoms and nutritional deficiencies in subjects with active food sensitivity.

Alpha-Amylase inhibitors also present in grains of the cereal family are composed of 120-160 amino-acid residues forming five disulfide bonds. These inhibitors may cause upon repeated exposure harmful effects.

Transglutaminase 2 is a multifunctional enzyme that belongs to transglutaminases which catalyze the crosslinking of proteins by epsilon-(gamma-glutamyl) lysine isopeptide bonds. Tissue transglutaminase 2 (tTG2 or TTG2), identified as an endomysial autoantigens, is an intestinal digestive enzyme which deamidates already partially digested dietary gluten e.g. gliadin peptides. In food sensitivity predisposed subjects, tTG2 triggers autoimmune responses that are characterized by the production of tTG2 antibodies. Epidermal transglutaminase (eTG 3 or TTG3) is another member of the transglutaminase family that can also function as an autoantigen that is manifested by a skin rash clinically known as dermatitis herpetiformis (DH).

Food sensitivity in companion animals poses a major challenge to veterinarians. The most common clinical signs in pet food sensitivity are vomiting and diarrhea, although the disease can present broader clinical signs including but not limited to abdominal pain, altered appetite and weight loss, bloating and cramping, and even flatulence. All these clinical symptoms are general in nature and overlap with many other potential conditions making definitive diagnosis extremely difficult. The difficulty in differentially diagnosing food sensitivity and differentiate from other similar conditions such as inflammatory bowel disease (IBD), irritable bowel syndrome (IBS), and/or gastrointestinal infections hampers early and effective treatment of these diseases.

The best current methodology to diagnose food sensitivity in companion animals either requires using relatively costly, labor-intensive and intrusive clinical, radiographic, endoscopic, and/or histological techniques and/or the implementation of diet elimination trials followed by the re-introduction of specific ingredients to confirm the food sensitivity. The term food sensitivity includes cases in which histological evidence of inflammation is found without obvious underlying cause, and all other etiologies have been excluded. Overall, the diagnosis of food sensitivity remains a process of exclusion, and thus, represents a lengthy and costly process that also contributes to unnecessary pet suffering and morbidity.

Veterinarians need rapid, accurate and relatively non-intrusive methods to detect, distinguish and diagnose chronic food sensitivity, inflammatory bowel disease (IBD), irritable bowel syndrome (IBS), and/or gastrointestinal infections, which may present with similar symptoms but which require very different therapeutic interventions. Despite the significant and long-felt need for effective diagnostic methods tailored specifically for companion animals, the tools to differentially diagnose these conditions in companion animals remain unavailable, hampering the early and effective treatment of these diseases.

The present invention addresses these needs and provides related advantages as well.

SUMMARY OF THE INVENTION

The present invention provides novel markers and novel methods for detecting them, to aid in diagnosis and monitoring of gastrointestinal inflammatory diseases in companion animals. The invention further provides novel markers to identify food sensitivity, e.g., as related to wheat and corn, as well as other food sensitivities, such as sensitivity to albumin and to beef and derivatives of beef.

The detection of different biomarkers in combination, for example inflammatory markers and food sensitivity biomarkers, allows veterinarians to distinguish among chronic food sensitivity, inflammatory conditions such as inflammatory bowel disease (IBD), irritable bowel syndrome (MS), and/or gastrointestinal infections, allowing them to provide appropriate treatment.

In one embodiment, the invention provides novel methods for detecting the presence and/or level of one or more endogenous antibodies associated with inflammation in a sample obtained from a companion animal. The endogenous antibodies may include autoantibodies to proteins such as calprotectin, β-integrins, lactoferritin, and C-reactive protein, and/or may also include endogenous antibodies to polymorphonuclear leukocytes (PMNs or granulocytes, including neutrophil granulocytes) and/or to microbes found in the gut.

For example, it has surprisingly been discovered that companion animals, when suffering from inflammatory conditions, produce autoantibodies to proteins such as calprotectin, β-integrins, lactoferritin, and C-reactive protein, which are known to be associated with inflammation. Such autoantibodies have not previously been discovered or characterized, and it is unexpected and counter-intuitive that the body would produce antibodies to its own anti-inflammatory proteins, or that such antibodies could serve as markers for pathological inflammatory conditions such as IBD.

The invention thus provides in another embodiment methods which comprise measuring the immunoglobulin levels to inflammation markers, such as calprotectin and β-integrins, lactoferritin, and/or C-reactive protein, to detect inflammation either on a systemic basis and/or on a localized basis such as in the gastrointestinal tract. These inflammation-associated autoantibodies may be used as markers on their own to identify and characterize inflammatory conditions, or in conjunction with the anti-PMN antibody, anti-microbial antibody, calprotectin and combinations thereof as are known or described herein.

In certain embodiments, the invention provides novel methods for detecting the presence and/or level of one or more inflammation-associated autoantibodies in a sample obtained from a companion animal, wherein the inflammation-associated autoantibodies are endogenous antibodies to an inflammatory marker, e.g., selected from one or more of autoantibodies to a calprotectin, an integrin, a lactoferritin, and a C-reactive protein; e.g., wherein the inflammation-associated autoantibodies are IgA antibodies, e.g. wherein the patient is a dog or a cat.

In the case of IBD in canines and felines, we have also identified certain novel types of endogenous antibodies to polymorphonuclear leukocytes (PMNs) and to microbes found in the gut. These endogenous antibodies can be used to diagnose IBD and to distinguish it from other gastrointestinal disorders. In certain embodiments, measuring endogenous antibodies to polymorphonuclear leukocytes (PMNs) and to microbes found in the gut is coupled with measurement of one or more other markers of inflammation including measuring calprotectin levels directly, and measuring autoantibodies to inflammation markers, such as calprotectin and β-integrins, lactoferritin, and/or C-reactive protein In some embodiments, the present invention provides novel methods of detecting inflammation-associated endogenous antibodies in a companion animal, for example screening for presence or absence of IBD in companion animals by detecting specific autoantibodies and classifying whether a sample from a companion animal is associated with inflammatory bowel disease (IBD) or not. As a non-limiting example, the present invention is useful for classifying a sample from a companion animal as an IBD sample using empirical data and/or a statistical algorithm. The present invention is also useful for differentiating between IBD subtypes using empirical data and/or a statistical algorithm.

In one aspect, the present invention provides a method for classifying whether companion animals are associated with IBD, the method comprising: (a) determining the presence or level of at least one marker selected from the group consisting of an anti-polymorphonuclear leukocyte (PMN) antibody, antimicrobial antibody, calprotectin and combinations thereof in the sample; and (b) classifying the sample as an IBD sample or non-IBD sample using a statistical algorithm based upon the presence or level of at least one marker.

In a related aspect, the present invention provides a method for classifying whether companion animals are associated with a clinical subtype of IBD, the method comprising: (a) determining the presence or level of at least one marker selected from the group consisting of an anti-PMN antibody, antimicrobial antibody, calprotectin and combinations thereof in the sample; and (b) classifying the sample lymphoplasmacytic (LPE) IBD, eosinophilic gastroenterocolitis (EGE) IBD or granulomatous (GE) IBD or non-IBD sample using a statistical algorithm based upon the presence or level of the at least one marker.

In another aspect, the present invention provides a method for monitoring the progression or regression of IBD in companion animals, the method comprising: (a) determining the presence or level of at least one marker selected from the group consisting of an anti-PMN antibody, antimicrobial antibody, calprotectin and combinations thereof in a sample from the individual; and (b) determining the presence or severity of IBD in companion animals using a statistical algorithm based upon the presence or level of the at least one marker.

In a related aspect, the present invention provides a method for monitoring drug efficacy in companion animals receiving drugs useful for treating IBD, the method comprising: (a) determining the presence or level of at least one marker selected from the group consisting of an anti-PMN antibody, antimicrobial antibody, calprotectin and combinations thereof in a sample from the individual; and (b) determining the presence or severity of IBD in the individual using a statistical algorithm based upon the presence or level of the at least one marker.

Thus, in accordance with the methods of the present invention, the level of the different markers in a sample from IBD companion animals is determined and compare to the presence or absence of the same markers in non-IBD companion animals. The methods of the present invention are performed using immunochemical reagents, for example, to detect endogenous antimicrobial antibodies, anti-PMN antibodies and the like. Thus, there are an array of different immunoassay formats in which the methods of the present invention may be performed. Also provided by the present invention are kits for screening companion animal IBD. Suitable kits include immunochemical reagents useful for determining certain endogenous antibodies in a sample.

Food sensitivity has an immunological basis and it is not possible to distinguish a food that elicits an immunological response from the related intestinal disease or body's reaction to the food itself. Therefore, the immunologic food sensitivity of these animals may not be properly diagnosed using known testing methods, such as endoscopic intestinal biopsy or other testing methods that lack specificity. Additionally, these animals may present with other immunologic diseases such as the autoimmune diseases of skin, liver, joints, kidneys, pancreas, and thyroid gland, or microscopic colitis. In some embodiments the invention provides methods for detecting immunological food sensitivities in companion animals by collecting serum and detecting the presence or absence of at least one of an IgA, IgM or IgG antibody to well-defined chemical components of food ingredient or compositions, and specific epitopes responsible for such immunological response. Diagnosing an immunologic food sensitivity based on the presence of such antibody, is then effected.

Thus in another embodiment, the invention provides novel methods of detecting endogenous antibodies associated with food sensitivities in a companion animal, for example screening for presence or absence of antibodies to endogenous antibodies to gliadin, zein, tissue transglutaminase, or amylase inhibitor in companion animals and classifying whether a sample from a companion animal is associated with food sensitivity or not. As a non-limiting example, the present invention is useful for classifying a sample from a companion animal as food sensitivity sample using empirical data and/or a statistical algorithm. The present invention is also useful for differentiating between inflammatory conditions such as IBD and food sensitivity conditions such as sensitivity to wheat or corn, using empirical data and/or a statistical algorithm.

Thus, for example, in some embodiments, the invention provides methods for detecting the presence and/or level of one or more endogenous antibodies associated with inflammation and/or food sensitivity in a sample obtained from a companion animal patient, wherein the endogenous antibodies are selected from one or more of a. autoantibodies to a calprotectin,
b. autoantibodies to a β-integrin,
c. autoantibodies to a lactoferritin,
d. autoantibodies to a C-reactive protein,
e. autoantibodies to polymorphonuclear leukocytes (PMNs or granulocytes, including neutrophil granulocytes),
f. endogenous antibodies to microbes found in the gut,
g. endogenous antibodies to plant proteins or immunogenic fragments thereof, wherein the plant proteins are selected from the group consisting of zeins, gliadins, or amylase inhibitors, and combinations thereof, and/or
h. autoantibodies to tissue transglutaminase, comprising contacting one or more antigens with said sample, wherein the one or more antigens are specific for the endogenous antibody of interest, and wherein the one or more antigens are bound to a substrate or detectable label, and detecting the binding of said one or more one or more endogenous antibodies associated with inflammation to the one or more antigens;

and optionally further comprising classifying said sample as "consistent" or "not consistent" with inflammation and/or food sensitivity, wherein the presence or level of the one or one or more endogenous antibodies, separately or in combination, correlates with the presence of inflammation and/or food sensitivity.

In certain instances, the methods and systems of the present invention compose a step having a "transformation" or "machine" associated therewith. For example, an ELISA technique may be performed to measure the presence or concentration level of many of the markers described herein. An ELISA includes transformation of the marker, e.g., an endogenous-antibody, into a complex between the marker (e.g., the endogenous antibody) and a binding agent (e.g., antigen), which can then be measured with a labeled secondary antibody. In many instances, the label is an enzyme which transforms a substrate into a detectable product. The detectable product measurement can be performed using a plate reader such as a spectrophotometer. In other instances, genetic markers are determined using various amplification techniques such as PCR. Method steps including amplification such as PCR result in the transformation of single or double strands of nucleic acid into multiple strands for detection. The detection can include the use of a fluorophore, which is performed using a machine such as a fluorometer.

Further areas of applicability of the present invention will become apparent from the detailed description provided hereinafter. It should be understood that the detailed description and specific examples, while indicating certain embodiments of the invention, are intended for purposes of illustration only and are not intended to limit the scope of the invention.

DETAILED DESCRIPTION OF THE INVENTION

The following description of different embodiments is merely exemplary in nature and is in no way intended to limit the invention, its application, or uses.

I. Definitions

As used herein, the following terms have the meanings ascribed to them unless specified otherwise.
Antibodies As used herein, the term "antibody" includes a population of immunoglobulin molecules, which can be polyclonal or monoclonal and of any class and isotype, or a fragment of an immunoglobulin molecule. There are five major classes of immunoglobulins: IgA, IgD, IgE, IgG, and IgM, and several of these may be further divided into subclasses (isotypes), e.g., IgG1, IgG2, IgG3, IgG4, IgA1 (human), IgA2 (human), IgAa (canine), IgAb (canine), IgAc (canine), and IgAd (canine). Such fragment generally comprises the portion of the antibody molecule that specifically binds an antigen. For example, a fragment of an immunoglobulin molecule known in the art as Fab, Fab' or F(ab')2 is included within the meaning of the term antibody.

As used herein, the term "endogenous antibodies" refers to antibodies made by or originating from the patient, which can be isolated from the patient's blood or tissue. Typically, endogenous antibodies are generated in response to a foreign antigen, for example in response to a bacterial antigen, as part of the body's natural defense against infection. In certain cases, however, the patient may generate endogenous antibodies against the body's own proteins, such endogenous antibodies being referred to herein as "autoantibodies". In the context of this application, therefore, endogenous antibodies may refer to autoantibodies to proteins such as calprotectin, β-integrins, lactoferritin, and C-reactive protein, and/or may also include endogenous antibodies to polymorphonuclear leukocytes (PMNs or granulocytes, including neutrophil granulocytes) and/or to microbes found in the gut. Where the patient is a dog, the endogenous antibodies would be canine antibodies, and where the patient is a cat, the endogenous antibodies would be feline antibodies.

The term "endogenous antibodies" is used herein to distinguish from therapeutic or diagnostic antibodies, derived from a source other than the patient, which may for example be administered to the patient or used to detect the presence of antigens in a biological sample (e.g., blood, plasma, urine, tissue, saliva, etc.) from the patient. Therapeutic or diagnostic antibodies would typically be monoclonal antibodies propagated in cell lines, usually derived from antibodies made in other species, e.g., from rodents, or using phage display techniques. Therapeutic antibodies could be complete antibodies or antibody fragments.

"Autoantibody", as used herein, refers to an endogenous antibody made by the patient against an endogenous antigen, for example against an endogenous protein. The examples herein, for example, describe autoantibodies against endogenous inflammation-related proteins such as calprotectin, integrin, lactoferrin, and/or CRP. Accordingly, where the autoantibody binds to an inflammation-related protein, both the autoantibody and the inflammation-related protein antigen would be from the same individual and the same species, e.g., where the patient is a dog, the autoantibodies generated by the patient are canine antibodies, and the endogenous antigen would be a canine peptide, e.g., canine calprotectin or canine integrin. In other embodiments, the examples herein, for example, describe autoantibodies against tissue transglutaminase-related proteins. Accordingly, where the autoantibody binds to a tissue transglutaminase-related protein, both the autoantibody and the protein antigen would be from the same individual and the same species, e.g., where the patient is a dog, the autoantibodies generated by the patient are canine antibodies, and the endogenous antigen would be a canine peptide, e.g., canine TTG. The autoantibody in such a case can be isolated and characterized by its binding to a protein having the same binding epitope as the endogenous antigen.

The autoantibody in such a case can be isolated and characterized by its binding to a protein having the same binding epitope as the endogenous antigen.

"Class switching" or "isotype switching" means a change in the phenotype of an immunoglobulin producing cell. Immunoglobulin class switching is a critical step in the generation of the diversified biological effector functions of the antibody response. During the course of an antibody mediated immune response, immunoglobulin producing cells are induced to undergo genetic rearrangements, a process known as class switch recombination (CSR) that results in "switching" of a variable region to different constant region sequence. The identity of the heavy-chain class to which an immunoglobulin-producing cell is switched is believed to be regulated by cytokines. For example, IgA class switching is the process whereby an immunoglobulin-producing cell acquire the expression of IgA, the most abundant antibody isotype in mucosal secretions.

"Food sensitivity-associated antibody" or "Food-related antigen antibody" can be used interchangeably and refer to an antibody class in the serum of the companion animal patient to be diagnosed or treated, which is associated with the presence, severity or type of food sensitivity, and so can be considered a marker for food sensitivity. Food sensitivity-associated antibodies include for example antibodies as described herein, such as anti-gliadin antibodies (AGA), anti-zein antibodies (AZA), and the like.

"IBD-associated antibody" refers to an antibody in the serum of the companion animal patient to be diagnosed or treated, which is associated with the presence, severity or type of IBD, and so can be considered a marker for IBD. IBD-associated antibodies include for example antibodies as described herein, such as anti-PMN antibodies, anti-yeast antibodies, antimicrobial antibodies, for example antibodies to bacterial OmpC or flagellin proteins, as well as autoantibodies against endogenous inflammation-related proteins such as calprotectin, integrin, lactoferrin, and/or CRP.

Indications

The term "patient" or "subject" in the context of this application refers to mammalian companion animals or pets, including e.g. dogs, cats, and horses.

The term "food sensitivity" refers to an immune-mediated reaction to food arising from immune responses that occur reproducibly on exposure to a given set of epitopes derived from food. The reactive immune response are characterized as types I, II, III or IV depending on the mechanism involved and the delayed nature of such response. Food sensitivity may involve types II, III or IV in which more complex set of immune cells are involved and may take between hours and weeks between the exposure and the response, and such response can be chronic in nature.

By contrast, the term "food allergy" refers to the type I food responses that are mediated by IgE and occur less than two hours after exposure or consumption of the allergen.

The term "gluten-induced disease" refers to any disorder or condition induced by gluten that can be associated with autoantibodies against tissue transglutaminase TTG and/or seropositivity to gliadin extracts (or specific gliadin-derived oligopeptides). Gluten-induced diseases often cause enteropathies. However, the existence of non-enteropathy gluten-induced disease are known, and therefore autoantibodies against TTG2 and/or seropositivity to gliadins can potentially be better indicators for such conditions.

"Inflammation" or "inflammatory condition" as used herein refers to a immunovascular response to a stimuli, for example an immune response to an antigen, a pathogen, or a damaged cell, which is mediated by white blood cells (leukocytes). In some embodiments, the inflammation may be chronic. In some embodiments, the inflammation may be an autoimmune condition, where the immune system causes damage to otherwise normal, non-foreign tissue, as is seen for example in rheumatoid arthritis, multiple sclerosis, and other autoimmune diseases.

The term "inflammatory bowel disease" or "IBD" refers to a chronic inflammation of all or part of the gastrointestinal tract, include, without limitation, the following sub-types: lymphoplasmacytic enteritis (LPE), eosinophilic gastroenteritis (EGE) and granulomatous enteritis (GE) Inflammatory bowel diseases are distinguished from all other disorders, syndromes, and abnormalities of the gastroenterological tract, including irritable bowel syndrome (IBS) and transient GI infections, in being characterized by chronic inflammation.

The term "diagnosing IBD" includes the use of the methods, systems, and code of the present invention to determine the presence or absence of IBD in a companion animal patient. The term also includes methods, systems, and code for assessing the level of disease activity in a companion animal patient. The term "monitoring the progression or regression of IBD" includes the use of the methods, systems, and code of the present invention to determine the disease state (e.g., presence or severity of IBD) of a companion animal patient. In certain instances, the results of a statistical algorithm are compared to those results obtained for the same companion animal patient at an earlier time. In some aspects, the methods, systems, and code of the present invention can also be used to predict the progression of IBD, e.g., by determining a likelihood for IBD to progress either rapidly or slowly in a companion animal based on the presence or level of at least one marker in a sample. In other aspects, the methods, systems, and code of the present invention can also be used to predict the regression of IBD, e.g., by determining a likelihood for IBD to regress either rapidly or slowly in a companion animal patient based on the presence or level of at least one marker in a sample.

The term "diagnosing an inflammatory condition" includes the use of the methods, systems, and code of the present invention to determine the presence or absence of an inflammatory condition in a companion animal patient, e.g. a horse, dog or cat. The term also includes methods, systems, and code for assessing the level of disease activity in the patient. The term "monitoring the progression or regression of inflammation" includes the use of the methods, systems, and code of the present invention to determine the disease state (e.g., presence or severity of inflammation) of the patient. In certain instances, the results of a statistical algorithm are compared to those results obtained for the same patient at an earlier time. In some aspects, the methods, systems, and code of the present invention can also be used to predict the progression of inflammation, e.g., by determining a likelihood for the inflammation to progress either rapidly or slowly in the patient based on the presence or level of at least one marker in a sample. In other aspects, the methods, systems, and code of the present invention can also be used to predict the regression of inflammation, e.g., by determining a likelihood for inflammation to regress either rapidly or slowly in the patient based on the presence or level of at least one marker in a sample.

The term "diagnosing food sensitivity" includes the use of the methods, systems, and code of the present invention to determine the presence or absence of food sensitivity in a pet patient. The term also includes methods, systems, and code for assessing the level of disease activity in a pet patient. The term "monitoring the progression or regression of food sensitivity" includes the use of the methods, systems, and code of the present invention to determine the disease state (e.g., presence or severity of food sensitivity) of a pet patient. In certain instances, the results of a statistical algorithm are compared to those results obtained for the same pet patient at an earlier time. In some aspects, the methods, systems, and code of the present invention can also be used to predict the progression of food sensitivity, e.g., by determining a likelihood for food sensitivity to progress either rapidly or slowly in a pet based on the presence or level of at least one marker in a sample. In other aspects, the methods, systems, and code of the present invention can also be used to predict the regression of food sensitivity, e.g., by determining a likelihood for food sensitivity to regress either rapidly or slowly in a pet patient based on the presence or level of at least one marker in a sample.

Methods

The term "sample" includes any biological specimen obtained from a companion animal patient. Suitable samples for use in the present invention include, without limitation, whole blood, plasma, serum, saliva, urine, stool, tears, any other bodily fluid, tissue samples (e.g., biopsy), and cellular extracts thereof (e.g., red blood cellular extract). The use of samples such as serum, saliva, and urine is well known in the art (Hashida et al. *J. Clin. Lab. Anal.,* 11:267-286 (1997). One skilled in the art will appreciate that samples such as serum samples can be diluted prior to the analysis of marker levels. In particular embodiments the samples are whole blood or plasma from companion animals.

The term "marker" includes any biochemical marker, serological marker, genetic marker, or other clinical or echographic characteristic that can be used to classify a sample from a companion animal patient as being associated with an inflammatory condition, such as IBD. Non-limiting examples of markers suitable for use in the present invention are described below and include anti-PMN antibodies (e.g., APMNA, pAPMNA, cAPMNA, ANSNA, ASAPPA, and the like), antimicrobial antibodies (e.g., anti-Outer-Membrane Protein, anti-OmpC antibodies (ACA), anti-flagellin antibodies (AFA), and the like), lactoferrin, elastase, C-reactive protein (CRP), calprotectin, hemoglobin, and the like and combinations thereof, as well as autoantibodies to endogenous inflammation-related proteins such as calprotectin, integrin, lactoferrin, and/or CRP. The recitation of specific examples of markers associated with inflammatory conditions is not intended to exclude other markers as known in the art and suitable for use in the present invention.

The term "classifying" includes "associating" or "categorizing" a sample or a patient with a disease state or prognosis. In certain instances, "classifying" is based on statistical evidence, empirical evidence, or both. In certain embodiments, the methods and systems of classifying use a so-called training set of samples from patients with known disease states or prognoses. Once established, the training data set serves as a basis, model, or template against which the features of an unknown sample from a patient are compared, in order to classify the unknown disease state or provide a prognosis of the disease state in the patient. In some instances, "classifying" is akin to diagnosing the disease state and/or differentiating the disease state from another disease state. In other instances, "classifying" is akin to providing a prognosis of the disease state in a patient diagnosed with the disease state.

The term "marker profile" includes one, two, three, four, five, six, seven, eight, nine, ten, or more diagnostic and/or prognostic marker(s), wherein the markers can be a serological marker, a protein marker, a genetic marker, and the like. In some embodiments, the marker profile together with a statistical analysis can provide veterinarians valuable diagnostic and prognostic insight. In other embodiments, the marker profile with optionally a statistical analysis provides a projected response to biological therapy. Combining information from multiple diagnostic predictors is often useful, because combining data on multiple markers may provide a more sensitive and discriminating tool for diagnosis or screening applications than any single marker on its own. By using multiple markers (e.g., serological, protein, genetic, etc.) in conjunction with statistical analyses, the assays described herein provide diagnostic, prognostic and therapeutic value by identifying patients with IBD or a clinical subtype thereof, predicting risk of developing complicated disease, assisting in assessing the rate of disease progression (e.g., rate of progression to complicated disease or surgery), and assisting in the selection of therapy.

The term "label," as used herein, refers to a detectable compound, composition, or solid support, which can be conjugated directly or indirectly (e.g., via covalent or non-covalent means, alone or encapsulated) to a monoclonal antibody or a protein. The label may be detectable by itself (e.g., radioisotope labels, chemiluminescent dye, electro- chemical labels, metal chelates, latex particles, or fluorescent labels) or, in the case of an enzymatic label, may catalyze chemical alteration of a substrate compound or composition which is detectable (e.g., enzymes such as horseradish peroxidase, alkaline phosphatase, and the like). The label employed in the current invention could be, but is not limited to alkaline phosphatase; glucose-6-phosphate dehydrogenase ("G6PDH"); horseradish peroxidase (HRP); chemiluminescers such as isoluminol, fluorescers such as fluorescein and rhodamine compounds; ribozymes; and dyes. The label may also be a specific binding molecule which itself may be detectable (e.g., biotin, avidin, streptavidin, digioxigenin, maltose, oligohistidine, e.g., hex-histidine, 2,4-dinitrobenzene, phenylarsenate, ssDNA, dsDNA, and the like). The utilization of a label produces a signal that may be detected by means such as detection of electromagnetic radiation or direct visualization, and that can optionally be measured.

A monoclonal antibody can be linked to a label using methods well known to those skilled in the art, e.g., Immunochemical Protocols; Methods in Molecular Biology, Vol. 295, edited by R. Burns (2005)). For example, a detectable monoclonal antibody conjugate may be used in any known diagnostic test format like ELISA or a competitive assay format to generate a signal that is related to the presence or amount of an IBD-associated antibody in a test sample.

"Substantial binding" or "substantially binding" refer to an amount of specific binding or recognizing between molecules in an assay mixture under particular assay conditions. In its broadest aspect, substantial binding relates to the difference between a first molecule's incapability of binding or recognizing a second molecule, and the first molecules capability of binding or recognizing a third molecule, such that the difference is sufficient to allow a meaningful assay to be conducted to distinguish specific binding under a particular set of assay conditions, which includes the relative concentrations of the molecules, and the time and temperature of an incubation. In another aspect, one molecule is substantially incapable of binding or recognizing another molecule in a cross-reactivity sense where the first molecule exhibits a reactivity for a second molecule that is less than 25%, e.g. less than 10%, e.g., less than 5% of the reactivity exhibited toward a third molecule under a particular set of assay conditions, which includes the relative concentration and incubation of the molecules. Specific binding can be tested using a number of widely known methods, e.g, an immunohistochemical assay, an enzyme-linked immunosorbent assay (ELISA), a radioimmunoassay (RIA), or a western blot assay.

As used herein, the term "substantially the same amino acid sequence" includes an amino acid sequence that is similar, but not identical to, the naturally-occurring amino acid sequence. For example, an amino acid sequence, i.e., polypeptide, that has substantially the same amino acid sequence as a flagellin protein can have one or more modifications such as amino acid additions, deletions, or substitutions relative to the amino acid sequence of the naturally-occurring flagellin protein, provided that the modified polypeptide retains substantially at least one biological activity of flagellin such as immunoreactivity. The "percentage similarity" between two sequences is a function of the number of positions that contain matching residues or conservative residues shared by the two sequences divided by the number of compared positions times 100. In this regard, conservative residues in a sequence is a residue that is physically or functionally similar to the corresponding reference residue, e.g., that has a similar size, shape, electric charge, chemical properties, including the ability to form covalent or hydrogen bonds, or the like.

"Amino acid consensus sequence," as used herein, refers to a hypothetical amino acid sequence that can be generated using a matrix of at least two, for example, more than two, aligned amino acid sequences, and allowing for gaps in the alignment, such that it is possible to determine the most frequent amino acid residue at each position. The consensus sequence is that sequence which comprises the amino acids which are most frequently represented at each position. In the event that two or more amino acids are equally represented at a single position, the consensus sequence includes both or all of those amino acids. In some cases, amino acid consensus sequences correspond to a sequence or subsequence found in nature. In other cases, amino acid consensus sequences are not found in nature, but represent only theoretical sequences.

"Homology" is an indication that two nucleotide sequences represent the same gene or a gene product thereof, and typically means that that the nucleotide sequence of two or more nucleic acid molecules are partially, substantially or completely identical. When from the same organism, homologous polynucleotides are representative of the same gene having the same chromosomal location, even though there may be individual differences between the polynucleotide sequences (such as polymorphic variants, alleles and the like).

The term "heterologous" refers to any two or more nucleic acid or polypeptide sequences that are not normally found in the same relationship to each other in nature. For instance, a heterologous nucleic acid is typically recombinantly produced, having two or more sequences, e.g., from unrelated genes arranged to make a new functional nucleic acid, e.g., a promoter from one source and a coding region from another source. Similarly, a heterologous polypeptide will often refer to two or more subsequences that are not found in the same relationship to each other in nature (e.g., a fusion protein).

As used herein, the term "fragment" includes a peptide, polypeptide or protein segment of amino acids of the full-length protein, provided that the fragment retains reactivity with at least one antibody in sera of disease patients. In some embodiments, the antigen or fragment thereof comprises at the amino-terminus and/or carboxyl-terminus one or more or a combination of tags such as a polyhistidine tag (e.g., 6×His tag, optionally together with solubility enhancing residues, for example an N-terminal sequence of SEQ ID NO 33 or SEQ ID NO 36), a Small Ubiquitin-like Modifier (SUMO), a glutathione 5-transferase (GST), and the like. An "antigenic fragment" is a fragment of a full-length protein that comprises an antibody binding epitope, for example an epitope to which an antibody of interest exhibits substantial binding.

An "epitope" is the antigenic determinant on a polypeptide that is recognized for binding by a paratope on antibodies specific to the polypeptide, for example, an IBD-associated antibody. Antibodies in the context of the invention may recognize particular epitopes having a sequence of 3 to 11, e.g., 5 to 7, amino acids. The antibody may further be characterized by its binding affinity to the protein, polypeptide or peptide applied in the methods and kits of the invention, and the binding affinity ($K_D$) is, for example, in the nanomolar range, e.g., $K_D$ $10^{-7}$ or less, for example, to $K_D$ $10^{-9}$ to $10^{-10}$. Particular antibodies used in the invention are the IBD-associated antibody found in the serum of animals with IBD, and monoclonal or polyclonal antibodies directed against antibodies, used as detection antibodies.

The term "clinical factor" includes a symptom in a patient that is associated with IBD. Examples of clinical factors include, without limitation, diarrhea, abdominal pain and/or discomfort, cramping, fever, anemia, hypoproteinemia, weight loss, anxiety, lethargy, and combinations thereof. In some embodiments, a diagnosis of IBD is based upon a combination of analyzing the presence or level of one or more markers in a patient using statistical algorithms and determining whether the patient has one or more clinical factors.

The term "prognosis" includes a prediction of the probable course and outcome of IBD or the likelihood of recovery from the disease. In some embodiments, the use of statistical algorithms provides a prognosis of IBD in a patient. For example, the prognosis can be surgery, development of a clinical subtype of IBD, development of one or more clinical factors, development of intestinal cancer, or recovery from the disease.

The term "prognostic profile" includes one, two, three, four, five, six, seven, eight, nine, ten, or more marker(s) of a companion animal patient, wherein the marker(s) can be a serological marker, a protein marker, a genetic marker, and the like. A statistical analysis transforms the marker profile into a prognostic profile. An example of statistical analysis can be defined, but not limited to, analysis by quartile scores and the quartile score for each of the markers can be summed to generate a quartile sum score.

As used herein, the term "sensitivity" refers to the probability that a diagnostic method, system, or code of the present invention gives a positive result when the sample is positive, e.g., having IBD or a clinical subtype thereof or chronic food sensitivity. Sensitivity is calculated as the number of true positive results divided by the sum of the true positives and false negatives. Sensitivity essentially is a measure of how well a method, system, or code of the present invention correctly identifies those with IBD or a clinical subtype thereof or chronic food sensitivity from those without the disease. The statistical algorithms can be selected such that the sensitivity of classifying IBD or a clinical subtype thereof, or of classifying food sensitivity or a clinical subtype thereof, is at least about 60%, and can be, for example, at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The term "specificity" refers to the probability that a diagnostic method, system, or code of the present invention gives a negative result when the sample is not positive, e.g., not having IBD or a clinical subtype thereof or food sensitivity or a clinical subtype thereof. Specificity is calculated as the number of true negative results divided by the sum of the true negatives and false positives. Specificity essentially is a measure of how well a method, system, or code of the present invention excludes those who do not have IBD, or a clinical subtype thereof, or food sensitivity or a clinical subtype thereof, from those who have the disease. The statistical algorithms can be selected such that the specificity of classifying IBD or a clinical subtype thereof is at least about 50%, for example, at least about 50%, 55%, 60%, 65%, 70%, 75%, 80%, 85%, 86%, 87%, 88%, 89%, 90%, 91%, 92%, 93%, 94%, 95%, 96%, 97%, 98%, or 99%.

As used herein, the term "negative predictive value" or "NPV" refers to the probability that an individual identified as not having IBD or a clinical subtype thereof or food sensitivity or a clinical subtype thereof actually does not have the disease. Negative predictive value can be calculated as the number of true negatives divided by the sum of the true negatives and false negatives. Negative predictive value is determined by the characteristics of the diagnostic method, system, or code as well as the prevalence of the disease in the companion animal population analyzed. The statistical algorithms can be selected such that the negative predictive value in a population having a disease prevalence is in the range of about 50% to about 99% and can be, for example, at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The term "positive predictive value" or "PPV" refers to the probability that an individual identified as having IBD or a clinical subtype thereof or food sensitivity or a clinical subtype thereof actually has the disease. Positive predictive value can be calculated as the number of true positives divided by the sum of the true positives and false positives. Positive predictive value is determined by the characteristics of the diagnostic method, system, or code as well as the prevalence of the disease in the companion animal population analyzed. The statistical algorithms can be selected such that the positive predictive value in a population having a disease prevalence is in the range of about 70% to about 99% and can be, for example, at least about 70%, 75%, 80%, 85%, 86%, 87%, 88%, 89%, 90%, 91%, 92%, 93%, 94%, 95%, 96%, 97%, 98%, or 99%.

Predictive values, including negative and positive predictive values, are influenced by the prevalence of the disease in the companion animal population analyzed. In the methods, systems, and code of the present invention, the statistical algorithms can be selected to produce a desired clinical parameter for a clinical population with a particular IBD prevalence or food sensitivity prevalence. For example, learning statistical classifier systems can be selected for an IBD or food sensitivity prevalence of up to about 1%, 2%, 3%, 4%, 5%, 6%, 7%, 8%, 9%, 10%, 15%, 20%, 25%, 30%, 35%, 40%, 45%, 50%, 55%, 60%, 65%, or 70%, which can be seen, e.g., in a veterinarian office.

As used herein, the term "overall agreement" or "overall accuracy" refers to the accuracy with which a method, system, or code of the present invention classifies a disease state. Overall accuracy is calculated as the sum of the true positives and true negatives divided by the total number of sample results and is affected by the prevalence of the disease in the companion animal population analyzed. For example, the statistical algorithms can be selected such that the overall accuracy in a patient population having a disease prevalence is at least about 60%, and can be, for example, at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%.

The term "correlating" as used herein in reference to the use of biomarkers refers to comparing the presence or amount of the biomarker(s) in a companion animal patient to its presence or amount in companion animals known to suffer from, or known to be at risk of, a given condition; or in companion animals known to be free of a given condition. Often, this takes the form of comparing an assay result in the form of a biomarker concentration to a predetermined threshold selected to be indicative of the occurrence or nonoccurrence of a disease or the likelihood of some future outcome.

Population studies may also be used to select a decision threshold using Receiver Operating Characteristic ("ROC") analysis to distinguish a diseased subpopulation from a nondiseased subpopulation. A false positive in this case occurs when the sample tests positive, but actually does not have the disease. A false negative, on the other hand, occurs when the sample tests negative, suggesting they are healthy, when they actually do have the disease. To draw a ROC curve, the true positive rate (TPR) and false positive rate (FPR) are determined. Since TPR is equivalent with sensitivity and FPR is equal to 1-specificity, the ROC graph is sometimes called the sensitivity vs (1-specificity) plot. A perfect test will have an area under the ROC curve of 1.0; a random test will have an area of 0.5. A threshold is selected to provide an acceptable level of specificity and sensitivity.

These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

The term "statistical algorithm" or "statistical process" includes any of a variety of statistical analyses used to determine relationships between variables. In the present invention, the variables are the presence or level of at least one marker of interest. Any number of markers can be analyzed using a statistical algorithm described herein. For example, the presence or levels of 1, 2, 3, 4, 5, 6, 7, 8, 9, 10, 11, 12, 13, 14, 15, 16, 17, 18, 19, 20, 25, 30, 35, 40, 45, 50, or more markers can be included in a statistical algorithm. In one embodiment, logistic regression is used. In another embodiment, linear regression is used. In certain instances, the statistical algorithms of the present invention can use a quantile measurement of a particular marker within a given population as a variable. Quantiles are a set of "cut points" that divide a sample of data into groups containing (as far as possible) equal numbers of observations. For example, quartiles are values that divide a sample of data into four groups containing (as far as possible) equal numbers of observations. The lower quartile is the data value a quarter way up through the ordered data set; the upper quartile is the data value a quarter way down through the ordered data set. Quintiles are values that divide a sample of data into five groups containing (as far as possible) equal numbers of observations. The present invention can also include the use of percentile ranges of marker levels (e.g., textiles, quartile, quintiles, etc.), or their cumulative indices (e.g., quartile sums of marker levels, etc.) as variables in the algorithms (just as with continuous variables).

The statistical algorithms of the present invention comprise one or more learning statistical classifier systems. As used herein, the term "learning statistical classifier system" includes a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used. Examples of learning statistical classifier systems include, but are not limited to, those using inductive learning (e.g., decision/classification trees such as random forests, classification and regression trees (C&RT), boosted trees, etc.), and genetic algorithms and evolutionary programming.

The learning statistical classifier systems described herein can be trained and tested using a cohort of samples (e.g., serological samples) from healthy and IBD companion animals. For example, samples from companion animals diagnosed by a veterinarian as having IBD using a biopsy and/or endoscopy are suitable for use in training and testing the learning statistical classifier systems of the present invention. Samples from healthy companion animals can include those that were not identified as IBD or food sensitivity samples. One skilled in the art will know of additional techniques and diagnostic criteria for obtaining a cohort of companion animal samples that can be used in training and testing the learning statistical classifier systems of the present invention.

The term "optimizing therapy in a companion animal having IBD" includes the use of methods, systems, and code of the present invention to determine the course of therapy for a companion animal patient before a therapeutic intervention (e.g., anti-inflammatory or other IBD drug) has been administered. In certain instances, the results of a statistical algorithm are compared to those results obtained for the same companion animal patient at an earlier time during the course of therapy. As such, a comparison of the results provides an indication for the need to change the course of therapy or an indication for the need to increase or decrease the dose of the current course of therapy. The term "course of therapy" includes any therapeutic approach taken to relieve or prevent one or more symptoms (i.e., clinical factors) associated with the condition to be treated, e.g., IBD. The term encompasses administering any compound, drug, procedure, or regimen useful for improving the health of a companion animal with IBD or food allergy and includes any of the therapeutic interventions (e.g., administration of IBD drugs or special diets) described above as well as surgery.

The term "therapeutically effective amount or dose" includes a dose of a drug that is capable of achieving a therapeutic effect in a companion animal patient in need thereof. For example, a therapeutically effective amount of a drug useful for treating IBD can be the amount that is capable of preventing or relieving one or more symptoms associated with IBD. The exact amount can be ascertainable by one skilled in the art using known techniques broadly reported in pharmaceutical dosage and compounding books.

The term "therapeutic profile" includes one, two, three, four, five, six, seven, eight, nine, ten, or more marker(s) of an individual, wherein the marker(s) can be a serological marker, a protein marker, a genetic marker, and the like. A statistical analysis transforms the marker profile into a therapeutic profile. An example of statistical analysis can be defined, but not limited to, by quartile scores and the quartile score for each of the markers can be summed to generate a quartile sum score.

The term "efficacy profile" includes one, two, three, four, five, six, seven, eight, nine, ten, or more marker(s) of an individual, wherein the markers can be a serological marker, a protein marker, a genetic marker, and the like, and wherein each of the markers changes with therapeutic administration. In certain instances, the marker profile is compared to the efficacy profile in order to assess therapeutic efficacy. In certain aspects, the efficacy profile is equivalent to the marker profile, but wherein the markers are measured later in time. In certain other aspects, the efficacy profile corresponds to a marker profile from inflammation patients, including IBD patients who responded to a particular therapeutic agent or drug. In these aspects, similarities or differences between the test marker profile and the reference efficacy profile indicate whether that particular drug is suitable or unsuitable for the treatment of inflammation, e.g., IBD.

In certain instances, the methods of the invention are used in order to prognosticate the progression of IBD. The methods can be used to monitor the disease, both progression and regression. The term "monitoring the progression or regression of IBD" includes the use of the methods and marker profiles to determine the disease state (e.g., presence or severity of IBD) of a companion animal. In certain instances, the results of a statistical analysis are compared to those results obtained for the same companion animal at an earlier time. In some aspects, the methods, systems, and code of the present invention can also be used to predict the progression of IBD, e.g., by determining a likelihood for the condition to progress either rapidly or slowly in a companion animal based on the presence or level of at least one marker in a sample. In other aspects, the methods, systems, and code of the present invention can also be used to predict the regression of IBD, e.g., by determining a likelihood for the condition to regress either rapidly or slowly in an individual based on the presence or level of at least one marker in a sample.

The term "monitoring drug efficacy in a companion animal patient receiving a drug useful for treating IBD" includes the determination of a marker profile, alone or in combination with the application of a statistical analysis, to determine the disease state (e.g., presence or severity of IBD) of a companion animal after a therapeutic agent for treating IBD has been administered.

In certain instances, the methods of the invention are used in order to prognosticate the progression of an inflammatory condition. The methods can be used to monitor the disease, both progression and regression. The term "monitoring the progression or regression of inflammation" includes the use of the methods and marker profiles to determine the disease state (e.g., presence or severity of inflammation) of a patient. In certain instances, the results of a statistical analysis are compared to those results obtained for the same companion animal at an earlier time. In some aspects, the methods, systems, and code of the present invention can also be used to predict the progression of inflammation, e.g., by determining a likelihood for inflammation to progress either rapidly or slowly in the patient based on the presence or level of at least one marker in a sample. In other aspects, the methods, systems, and code of the present invention can also be used to predict the regression of IBD, e.g., by determining a likelihood for inflammation to regress either rapidly or slowly in the patient based on the presence or level of at least one marker in a sample.

In certain instances, the methods of the invention are used in order to prognosticate the progression of food sensitivity. The methods can be used to monitor the disease, both progression and regression. The term "monitoring the progression or regression of food sensitivity" includes the use of the methods and marker profiles to determine the disease state (e.g., presence or severity of food sensitivity) of a pet. In certain instances, the results of a statistical analysis are compared to those results obtained for the same pet at an earlier time. In some aspects, the methods, systems, and code of the present invention can also be used to predict the progression of food sensitivity, e.g., by determining a likelihood for food sensitivity to progress either rapidly or slowly in a pet based on the presence or level of at least one marker in a sample. In other aspects, the methods, systems, and code of the present invention can also be used to predict the regression of food sensitivity, e.g., by determining a likelihood for food sensitivity to regress either rapidly or slowly in an individual based on the presence or level of at least one marker in a sample.

The term "optimizing therapy in a pet having food sensitivity" includes the use of methods, systems, and code of the present invention to determine the course of therapy for a pet patient before a therapeutic agent has been administered. In certain instances, the results of a statistical algorithm are compared to those results obtained for the same pet patient at an earlier time during the course of therapy. As such, a comparison of the results provides an indication for the need to change the course of therapy or an indication for the need to increase or decrease the dose of the current course of therapy. The term "course of therapy" includes any therapeutic approach taken to relieve or prevent one or more symptoms (i.e., clinical factors) associated with food sensitivity. The term encompasses administering any compound, drug, procedure, or regimen useful for improving the health of a pet with food sensitivity and includes any of the therapeutic agents (e.g., food sensitivity drugs) described above as well as surgery.

The term "monitoring treatment efficacy in a pet patient receiving a therapy useful for treating food sensitivity" includes the determination of a marker profile, alone or in combination with the application of a statistical analysis, to determine the disease state (e.g., presence or severity of food sensitivity) of a pet after a therapeutic agent, special diet or other therapy for treating food sensitivity has been administered.

II. Diagnosing IBD in Companion Animals

In particular embodiments, the present invention provides methods and systems for detecting and measuring markers associated with IBD, for example endogenous IBD-associated antibodies. Determining the presence and/or level of such markers is useful for accurately classifying whether a sample from a companion animal is associated with IBD or a clinical subtype thereof. In some embodiments, the present invention is useful for classifying a sample from a companion animal as an IBD sample using empirical data (e.g., the presence or level of an IBD marker) and/or a statistical algorithm. The present invention is also useful for differentiating between different IBD sub-types using empirical data (e.g., the presence or level of an IBD marker) and/or a statistical algorithm. Accordingly, the present invention provides an accurate diagnostic prediction of IBD or a clinical subtype thereof and prognostic information useful for guiding treatment decisions.

In one aspect, the present invention provides a method for classifying whether a sample from a companion animal is associated with IBD, the method comprising: (a) determining the presence or level of at least one marker selected from the group consisting of an anti-PMN antibody, antimicrobial antibody, calprotectin and combinations thereof in the sample; and (b) classifying the sample as an IBD sample or non-IBD sample using a statistical algorithm based upon the presence or level of the at least one marker.

In a related aspect, the present invention provides a method for classifying whether a sample from a companion animal is associated with a clinical subtype of IBD, the method comprising: (a) determining the presence or level of at least one marker selected from the group consisting of an anti-PMN antibody, antimicrobial antibody, calprotectin and combinations thereof in the sample; and (b) classifying the sample as a LPE sample, EGE sample, GE sample, other IBD subtypes or non-IBD sample using a statistical algorithm based upon the presence or level of the at least one marker. In certain embodiments, the at least one marker may alternatively be or may comprise one or more autoantibodies against endogenous inflammation-related proteins such as calprotectin, integrin, lactoferrin, and/or CRP.

In some embodiments, the presence or level of at least two, three, four, five, six, seven, eight, nine, ten, or more IBD markers are determined in the companion animal's sample. In certain instances, the anti-PMN antibody comprises an anti-PMN antibody (APMNA), perinuclear anti-PMN antibody (pAPMNA), cytoplasmic anti-PMN antibody (cAPMNA), PMN-specific nuclear antibody (NSNA), speckling anti-pan polymorphonuclear antibody (SAPPA), and combinations thereof. In certain instances, the presence or level of APMNA and/or pAPMNA is determined in the companion animal's sample. In certain other instances, the anti-PMN antibody (APMNA) comprises anti-PMN immunoglobulin A (APMNA-IgA), comprises anti-PMN immunoglobulin G (APMNA-IgG), comprises anti-PMN immunoglobulin G1 (APMNA-G1), comprises anti-PMN immunoglobulin G2 (APMNA-G2), comprises anti-PMN immunoglobulin M (APMNA-IgM), and/or combinations thereof. In certain other instances, the antimicrobial antibody comprises an anti-outer membrane protein C (ACA) antibody. In certain instances, the anti-outer membrane protein C antibody (ACA) comprises anti-OmpC immunoglobulin A (ACA-IgA), anti-OmpC immunoglobulin G (ACA-IgG), anti-OmpC immunoglobulin G1 (ACA-IgG1), anti-OmpC immunoglobulin G2 (ACA-IgG2), anti-OmpC immunoglobulin M (ACA-IgM), and/or combinations thereof. In certain other instances, the antimicrobial antibody comprises an anti-flagellin (ACA) antibody. In certain instances, the anti-flagellin antibody (AFA) comprises anti-flagellin immunoglobulin A (AFA-IgA), anti-flagellin immunoglobulin G (AFA-IgG), anti-flagellin immunoglobulin G1 (AFA-IgG1), anti-flagellin immunoglobulin G2 (AFA-IgG2), anti-flagellin immunoglobulin M (AFA-IgM), and/or combinations thereof.

In other embodiments, at least one marker further comprises one, two, three, four, five, six, seven, eight, nine, ten, or more IBD markers in addition to anti-PMN antibodies, and/or antimicrobial antibodies. Examples of such IBD markers include, but are not limited to, lactoferrin, anti-lactoferrin antibodies, elastase, C-reactive protein (CRP), calprotectin, hemoglobin, and combinations thereof.

In certain embodiments, at least one marker comprises one or more autoantibodies against endogenous inflammation-related proteins such as calprotectin, integrin, lactoferrin, and/or CRP.

The sample used for detecting or determining the presence or level of at least one marker is typically whole blood, plasma, serum, saliva, urine, stool (i.e., feces), tears, and any other bodily fluid, or a tissue sample (i.e., biopsy) such as a small intestine or colon sample. In some embodiments, the sample is serum, whole blood, plasma, stool, urine, or a tissue biopsy. In certain instances, the method of the present invention further comprises obtaining the sample from the companion animal patient prior to detecting or determining the presence or level of at least one marker in the sample.

In other embodiments, the method of the present invention comprises determining the presence or level of APMNA, ACA, AFA, calprotectin and/or pAPMNA in a sample such as serum, plasma, whole blood, or stool. A panel consisting of one or more of the IBD markers described above may be constructed and used for classifying the sample as an IBD sample or as a non-IBD sample.

In certain instances, the presence or level of at least one marker is determined using an immunoassay or an immunohistochemical assay. A non-limiting example of an immunoassay suitable for use in the method of the present invention includes an enzyme-linked immunosorbent assay (ELISA). Examples of immunohistochemical assays suitable for use in the method of the present invention include, but are not limited to, immunofluorescence assays such as direct fluorescent antibody assays, indirect fluorescent antibody (IFA) assays, anticomplement immunofluorescence assays, and avidin-biotin immunofluorescence assays. Other types of immunohistochemical assays include immunoperoxidase assays.

In some embodiments, the present invention is useful for classifying a sample from a companion animal as an IBD sample using a statistical algorithm (e.g., a learning statistical classifier system) and/or empirical data (e.g., the presence or level of an IBD marker). The present invention is also useful for differentiating between LPE, EGE, and GE using a statistical algorithm (e.g., a learning statistical classifier system) and/or empirical data (e.g., the presence or level of an IBD marker).

In certain instances, the statistical algorithm is a single learning statistical classifier system that can comprise a tree-based statistical algorithm such as a C&RT or RF. As a non-limiting example, a single learning statistical classifier system can be used to classify the sample as an IBD sample or non-IBD sample based upon a prediction or probability value and the presence or level of the at least one IBD marker. The use of a single learning statistical classifier system typically classifies the sample as an IBD (e.g. LPE, EGE, or others) sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In certain embodiments, the method of the present invention further comprises sending the IBD classification results to a veterinarian. In another embodiment, the method of the present invention further provides a diagnosis in the form of a probability that the companion animal patient has IBD or a clinical subtype thereof. For example, the patient can have about a 0%, 5%, 10%, 15%, 20%, 25%, 30%, 35%, 40%, 45%, 50%, 55%, 60%, 65%, 70%, 75%, 80%, 85%, 90%, 95%, or greater probability of having IBD or a clinical subtype thereof. In yet another embodiment, the method of the present invention further provides a prognosis of IBD in the companion animal patient. For example, the prognosis can be surgery, development of a clinical subtype of IBD (e.g., LPE or GE), development of one or more symptoms, development of intestinal cancer, or recovery from the disease. In some instances, the method of classifying a sample as an IBD sample is further based on the symptoms (i.e., clinical factors) of the patient from which the sample is obtained. The symptoms or group of symptoms can be, for example, diarrhea, abdominal pain, cramping, fever, anemia, weight loss, anxiety, depression, and combinations thereof.

In some embodiments, the diagnosis of a companion animal patient as having IBD or a clinical subtype thereof is followed by administering to the companion animal a therapeutically effective amount of a drug useful for treating one or more symptoms associated with IBD or the IBD subtype. Suitable IBD drugs include, but are not limited to, aminosalicylates (e.g., mesalazine, sulfasalazine, and the like), corticosteroids (e.g., prednisone), thiopurines (e.g., azathioprine, 6-mercaptopurine, and the like), methotrexate, monoclonal antibodies (e.g., infliximab), free bases thereof, pharmaceutically acceptable salts thereof, derivatives thereof, analogs thereof, and combinations thereof.

In certain instances, the statistical algorithms of the present invention can be used to differentiate a LPE sample from an EGE sample in a companion animal patient previously identified as having IBD. In certain other instances, the statistical algorithms of the present invention can be used to classify a sample from a companion animal patient not previously diagnosed with IBD as a LPE sample, EGE sample, GE sample or non-IBD sample.

In another aspect, the present invention provides a method for monitoring the progression or regression of IBD in a companion animal patient, the method comprising: (a) determining the presence or level of at least one marker selected from the group consisting of an anti-PMN antibody, antimicrobial antibody, calprotectin and combinations thereof in a sample from the companion animal; and (b) determining the presence or severity of IBD in the companion animal patient using a statistical algorithm based upon the presence or level of the at least one marker.

In a related aspect, the present invention provides a method for monitoring drug efficacy in a companion animal patient receiving a drug useful for treating IBD, the method comprising: (a) determining the presence or level of at least one marker selected from the group consisting of an anti-PMN antibody, antimicrobial antibody, calprotectin and combinations thereof in a sample from the companion animal patient; and (b) determining the presence or severity of IBD in the patient using a statistical algorithm based upon the presence or level of the at least one marker.

The sample used for detecting or determining the presence or level of at least one marker is typically whole blood, plasma, serum, saliva, urine, stool (i.e., feces), tears, and any other bodily fluid, or a tissue sample (i.e., biopsy) such as a small intestine or colon sample. The sample may be serum, whole blood, plasma, stool, urine, or a tissue biopsy. In certain instances, the method of the present invention further comprises obtaining the sample from the companion animal patient prior to detecting or determining the presence or level of at least one marker in the sample.

In other embodiments, the method of the present invention comprises determining the presence or level of APMNA, anti-OmpC antibody (ACA), anti-flagellin antibody (AFA), calprotectin and/or pAPMNA, in a sample such as serum, plasma, whole blood, or stool, and optionally additionally determining the presence or level of autoantibodies to inflammation markers, e.g., autoantibodies to calprotectin, β-integrins, lactoferritin, and/or C-reactive protein. A panel consisting of one or more of the IBD markers described above may be constructed and used for determining the presence or severity of IBD in the companion animal patient.

In certain instances, the presence or level of at least one marker is determined using an immunoassay or an immunohistochemical assay. A non-limiting example of an immunoassay suitable for use in the method of the present invention includes an ELISA. Examples of immunohistochemical assays suitable for use in the method of the present invention include, but are not limited to, immunofluorescence assays such as direct fluorescent antibody assays, IFA assays, anticomplement immunofluorescence assays, and avidin-biotin immunofluorescence assays. Other types of immunohistochemical assays include immunoperoxidase assays.

In certain embodiments, the methods of the present invention can further comprise comparing the presence or severity of IBD determined in step (b) to the presence or severity of IBD in the companion animal patient at an earlier time. As a non-limiting example, the presence or severity of IBD determined for a companion animal patient receiving a therapeutic agent useful for treating IBD can be compared to the presence or severity of IBD determined for the same companion animal patient before initiation of use of the therapeutic agent or at an earlier time in therapy. In certain other embodiments, the method can further comprise sending the IBD monitoring results to a veterinarian.

In yet another aspect, the present invention provides a computer-readable medium including code for controlling one or more processors to classify whether a sample from a companion animal patient is associated with IBD, the code including instructions to apply a statistical process to a data set indicating the presence or level of at least one marker selected from the group consisting of an anti-PMN antibody, antimicrobial antibody, calprotectin and combinations thereof in the sample to produce a statistically derived decision classifying the sample as an IBD sample or non-IBD sample based upon the presence or level of the at least one marker.

In a related aspect, the present invention provides a computer-readable medium including code for controlling one or more processors to classify whether a sample from a companion animal patient is associated with a clinical subtype of IBD, the code including instructions to apply a statistical process to a data set indicating the presence or level of at least one marker selected from the group consisting of an anti-PMN antibody, antimicrobial antibody, calprotectin and combinations thereof in the sample to produce a statistically derived decision classifying the sample as a LPE sample, EGE sample, GE sample, other subtypes of IBD or non-IBD sample based upon the presence or level of the at least one marker.

In a further aspect, the present invention provides a system for classifying whether a sample from a companion animal patient is associated with IBD, the system comprising: (a) a data acquisition module configured to produce a data set indicating the presence or level of at least one marker selected from the group consisting of an anti-PMN antibody, antimicrobial antibody, calprotectin and combinations thereof in the sample; (b) a data processing module configured to process the data set by applying a statistical process to the data set to produce a statistically derived decision classifying the sample as an IBD sample or non-IBD sample based upon the presence or level of the at least one marker; and (c) a display module configured to display the statistically derived decision. In a related aspect, the present invention provides a system for classifying whether a sample from a companion animal patient is associated with a clinical subtype of IBD, the system comprising: (a) a data acquisition module configured to produce a data set indicating the presence or level of at least one marker selected from the group consisting of an anti-PMN antibody, antimicrobial antibody, calprotectin and combinations thereof in the sample; (b) a data processing module configured to process the data set by applying a statistical process to the data set to produce a statistically derived decision classifying the sample as a LPE sample, EGE sample, GE sample, other IBD subtype or non-IBD sample based upon the presence or level of the at least one marker; and (c) a display module configured to display the statistically derived decision. In one embodiment, the statistical process is a learning statistical classifier system. Examples of learning statistical classifier systems suitable for use in the present invention are described above. In certain instances, the statistical process is a single learning statistical classifier system. In certain other instances, the statistical process is a combination of at least two learning statistical classifier systems. In some instances, the data obtained from using the learning statistical classifier system or systems can be processed using a processing algorithm.

III. Clinical Subtypes of IBD in Companion Animals

IBD in companion animals is often a mixed inflammatory response in which certain cells predominate and/or appear increased and the different forms recognized in companion animals are based primarily on their histological description. In the case of IBD, the changes observed in the GI are related to true inflammation and not merely to a reactive response. The canine and feline IBD type diseases bear little resemblance clinically or histologically to the human forms of IBD (i.e., Crohn's and ulcerative colitis) (E J Hall, 2009).

The most common histological type of IBD in companion animals is lymphoplasmacytic enteritis ("LPE"), which is mostly affecting the small intestine and/or the stomach with less frequency. The clinical symptoms of LPE are indistinguishable from those of other IBD subtypes. LPE is characterized by mucosal structural changes associated with infiltrates of lymphocytes and plasma cells. Complete or partial villus atrophy may be present, with villus fusion and crypt abscessation presented in most severe cases. The degree of inflammation is variable, may be patchy in nature and with edema as complication. The relative proportion of lymphocytes and plasma cells varies between cases, but the significance of such variation in the pattern of lymphocyte distribution remains unknown.

In canine LPE, marked increases in lamina propria T cells, IgG plasma cells, macrophages and granulocytes are reported and range in severity from mild to severe infiltration. Significant alterations of cytokines and increased expression of Th1 type, Th2 type, pro-inflammatory and immunoregulatory cytokines have been reported. Increase concentrations of acute-phase proteins reflect the inflammatory response and may normalize after treatment.

Eosinophilic gastroenteritis ("EGE") is the second most common form of idiopathic IBD in dogs and cats. Evidence of mucosal architectural disturbances like villus atrophy is present in conjunction with a mixed infiltrate of inflammatory cells where eosinophils predominate. Diagnostic criteria vary among pathologists with some defining EGE based only on subjective increases in mucosal eosinophil numbers, whereas others require the increase to specifically occur in the lamina propria. The clinical signs depend on the area of the GI tract involved. Mucosal erosion/ulceration may occur more frequently in EGE than in any other forms of IBD, and so a number of GI tract complications such as hematemesis, melena, or even perforations of the GI tract requiring immediate intervention. EGE may be seen in dogs and cats of any breed and age, although it is most common in younger adult animals. An increased incidence in German Shepherds has been suggested and Boxers and Dobermans may be predisposed.

Granulomatous enteritis ("GE") is a less common form of IBD characterized by mucosal infiltration with macrophages, resulting in the formation of granulomas. The distribution of inflammation can be patchy. While this condition has some similarities with the Crohn's Disease (CD) in humans, CD tends to be more extensive causing intestinal obstruction and enter cutaneous fistulation, which may not be characteristics in companion animals.

In dogs, the development of IBD is thought to originate as a consequence of a deregulation of mucosal immunity in predisposed animals. The concentration of lymphocytes in the lamina propia is a feature that defines certain types of canine IBD which is very distinctive from other species including humans. The increased concentration of eosinophils and mast cells in the case of EGE when compared to healthy dogs is further evidence of the involvement of hypersensitivity reactions in the pathogenesis of canine IBD.

IV. Gut Microbiome and GI Health

The intestinal microbiota is defined as the aggregate of all live micro-organisms that inhabit the gastrointestinal tract. The gastrointestinal tract of animals is colonized by a heterogenous group of microorganisms known as GI microbiota. There is a growing number of studies of the GI microbiota in animals, especially in dogs and cats (Suchodolski, 2011) because it is involved in many critical processes in the host such as equilibrium between health and disease.

In monogastric animals the intestine contains the most abundant, diverse, and metabolically relevant group of bacteria in the GI tract. Bacteria may represent as much as 98% of all fecal microbiota, with Archeaea, Eukaryotes and viruses representing the rest. The bacterial groups that are most abundant in canine and feline are within the phyla Firmicutes and Bacteriodetes, but the proportions vary widely depending on the studies. For example, percentages of Firmicutes range between 25 and 95% depending on extraction methods and PCR protocols between studies (Suchodolski, 2011).

V. IBD Markers

The diagnosis of inflammatory bowel disease (IBD) in companion animals poses a clinical challenge for veterinarians due to the similarity in symptoms between IBD and other diseases or disorders. For example, companion animals with symptoms of an acute infection of the bowel experiencing irritable bowel syndrome (IBS) such as bloating, diarrhea, constipation, and abdominal pain can be difficult to distinguish from companion animals with IBD. As a result, the similarity in symptoms between IBD and IBS renders rapid and accurate diagnosis difficult and hampers early and effective treatment of the disease.

The present invention is based, in part, upon the surprising discovery that the diagnosis of IBD in companion animals can be achieved by detecting the presence or level of certain diagnostic markers such as anti-polymorphonuclear leukocyte (PMN) antibodies (APMNA), antimicrobial antibodies (e.g. anti-Outer-Membrane Protein OmpC antibodies (ACA) and/or anti-flagellin antibodies (AFA)), and proteins associated with inflammatory conditions (e.g., calprotectin). In some aspects, the present invention uses statistical algorithms to aid in the classification of a companion animal sample as an IBD sample or non-IBD sample. By combining multiple markers that are associated with the disease in companion animals, a more accurate and sensitive diagnosis of IBD for companion animals can be achieved. In other aspects, the present invention uses the combination of markers as well as statistical algorithms to aid in the classification of a sample as a LPE, EGE or GE IBD samples and non-IBD samples. The present invention has yielded a unique set of markers as exemplified by the empirical testing of markers that have been described for humans with no applicability to companion animals as well as by the need to identify companion animal-specific and/or diseased companion animal-derived bacterial strains (i.e. bacteria isolated from dogs and cats that have been diagnosed as having IBD by endoscopy/biopsy) from the relevant antigens were isolated and used in the present invention.

These diagnostic markers, such as anti-PMN antibodies and antimicrobial antibodies, e.g. anti-Outer-Membrane Protein OmpC antibodies and/or anti-flagellin antibodies, and as well as proteins associated with inflammatory conditions (e.g., calprotectin) can optionally be measured in conjunction with measurement of autoantibodies to inflammatory markers as described above, for example, measuring the levels of autoantibodies to calprotectin, β-integrins, lactoferritin, and/or C-reactive protein, The methods of the present invention are also useful for screening companion animal patients prior or after onset of clinical symptoms allowing veterinarians to diagnose the disease earlier (instead of waiting for its chronicity), identify companion animals in need of additional testing and/or make decisions on therapy earlier.

A variety of inflammatory bowel disease (IBD) markers, such as biochemical markers, serological markers, genetic markers, or other clinical or echographic characteristics, are suitable for use in the statistical algorithms of the present invention for ruling out or ruling in IBD, e.g., by classifying a sample from a patient as an IBD sample. The IBD markers described herein are also suitable for use in the statistical algorithms of the present invention for differentiating between clinical subtypes of IBD, e.g., by classifying a sample from a patient LPE, EGE, GE or others. Examples of markers suitable for use in the present invention include, but are not limited to, anti-PMN antibodies (e.g., APMNA, pPMNA, cPMNA, NSNA, SAPPA, etc.), anti-microbial antibodies e.g., anti-OmpC antibodies, anti-flagellin antibodies, etc.), lactoferrin, anti-lactoferrin antibodies, elastase, C-reactive protein (CRP), calprotectin, hemoglobin, and combinations thereof. One skilled in the art will know of additional markers suitable for use in the statistical algorithms of the present invention.

The determination of APMNA levels and/or the presence or absence of pPMNA in a sample is useful in the present invention. As used herein, the term "anti-PMN antibody" or "APMNA" includes antibodies directed to cytoplasmic and/or nuclear components of PMNs. APMNA activity can be divided into several broad categories based upon the APMNA staining pattern in PMNs: (1) cytoplasmic PMN staining without perinuclear highlighting (cPMNA); (2) perinuclear staining around the outside edge of the nucleus (pPMNA); (3) perinuclear staining around the inside edge of the nucleus (NSNA); and (4) diffuse staining with speckling across the entire PMN (SAPPA), in certain instances, pPMNA staining is sensitive to DNase treatment. The term APMNA encompasses all varieties of anti-PMN reactivity, including, but not limited to, cPMN, pPMN, NSNA, and SAPPA. Similarly, the term APMNA encompasses all immunoglobulin isotypes including, without limitation, immunoglobulin A and G.

APMNA levels in a sample from a companion animal patient can be determined, for example, using an immunoassay such as an enzyme-linked immunosorbent assay (ELISA) with alcohol-fixed PMNs. The presence or absence of a particular category of APMNA such as pPMNA can be determined, for example, using an immunohistochemical assay such as an indirect fluorescent antibody (WA) assay. The presence or absence of pPMNA in a sample can be determined using an immunofluorescence assay with DNase-treated, fixed PMNs. In addition to fixed PMNs, antigens specific for APMNA that are suitable for determining APMNA levels include, without limitation, unpurified or partially purified PMN extracts; purified proteins, protein fragments, or synthetic peptides such as histone H1 or pPMNA-reactive fragments thereof (see, e.g. U.S. Pat. No. 6,033,864); secretory vesicle antigens or APMNA-reactive fragments thereof (see, e.g. U.S. Pat. No. 6,218,129); and anti-APMNA idiotypic antibodies. One skilled in the art will appreciate that the use of additional antigens specific for APMNA is within the scope of the present invention.

The determination of AYA (AYA-IgA, AYA-IgG, AYA-IgG1, AYA-IgG2, and/or AYA-IgM) levels in a sample is also useful in the present invention. As used herein, the term "anti-yeast immunoglobulin A" or "AYA-IgA" includes antibodies of the immunoglobulin A isotype that react specifically with yeast cell wall. Similarly, the term "anti-yeast immunoglobulin G" or "AYA-IgG," the term "anti-yeast immunoglobulin G1" or "AYA-IgG1," the term "anti-yeast immunoglobulin G2" or "AYA-IgG" include antibodies of the immunoglobulin G isotype, of the immunoglobulin G1 isotype, and of the immunoglobulin G2 isotype respectively that react specifically with yeast cell wall. Similarly, the term "anti-yeast immunoglobulin M" or "AYA-IgM" includes antibodies of the immunoglobulin M isotype that react specifically with yeast cell wall.

The determination of whether a sample is positive for AYA-IgA, AYA-IgG, AYA-IgG1, AYA-IgG2, AYA-IgM is made using an antigen specific for AYA. Such an antigen can be any antigen or mixture of antigens that is bound specifically by AYA-IgA, AYA-IgG and/or AYA-IgM. Although AYA antibodies were initially characterized by their ability to bind yeast, those of skill in the art will understand that an antigen that is bound specifically by AYA can be obtained from yeast or from a variety of other sources so long as the antigen is capable of binding specifically to AYA antibodies. Accordingly, exemplary sources of an antigen specific for AYA, which can be used to determine the levels of AYA-IgA, AYA-IgG, AYA-IgG1, AYA-IgG2, and/or AYA-IgM in a sample, include, without limitation, whole killed yeast cells such as *Saccharomyces* or *Candida* cells; yeast cell wall mannan such as phosphopeptidomannan; oligosaccharides such as oligomannosides; neoglycolipids; anti-AYA idiotypic antibodies; and the like. Different species and strains of yeast, such as *S. cerevisiae* strain SuI, Su2, CBS 1315, or BM 156, or *Candida albicans* strain VW32, are suitable for use as an antigen specific for AYA-IgA, AYA-IgG, and AYA-IgM. Different species and strains of yeast isolated from the microbiome of a subject or a pool of different species and stains of yeast isolated from the microbiome of a subject and/or from a collection of species and strains are also suitable for use in determining the levels of AYA-IgA, AYA-IgG, and AYA-IgM in a sample. A pool of Purified and synthetic antigens specific for AYA are also suitable for use in determining the levels of AYA-IgA, AYA-IgG, and AYA-IgM in a sample. Examples of purified antigens include, without limitation, purified oligosaccharide antigens such as oligomannosides. Examples of synthetic antigens include, without limitation, synthetic oligomannosides such as those described in U.S. Patent Publication No. 20030105060, e.g., D-Man β(1-2) D-Man β(1-2) D-Man β(1-2) D-Man-OR, D-Mati α(1-2) D-Man α(1-2) D-Man α(1-2) D-Man-OR, and D-Man α(1-3) D-Man α(1-2) D-Man α(1-2) D-Man-OR, wherein R is a hydrogen atom, a C1 to C20 alkyl, or an optionally labeled connector group.

Preparations of yeast cell wall mannans, e.g., can be used in determining the levels of AYA-IgA, AYA-IgG, and AYA-IgM in a sample. Such water-soluble surface antigens can be prepared by any appropriate extraction technique known in the art, including, for example, by autoclaving, or by enzymatic digestion, or by alkaline extraction, or by acid extraction, or by a combination of extraction methods, or can be obtained commercially (see, e.g., Lindberg et al, *Gut*, 33:909-913 (1992).

Purified oligosaccharide antigens such as oligomannosides can also be useful in determining the levels of AYA-IgA, AYA-IgG and AYA-IgM in a sample. One skilled in the art understands that the reactivity of such an oligomannoside antigen with AYA can be optimized by varying the mannosyl chain length (Frosh et al., *Proc. Natl. Acad. Sci. USA*, 82:1194-1198 (1985); the anomeric configuration (Fukazawa, Y. In "Immunology of Fungal Disease," E. Kurstak et al. (eds.), Marcel Dekker Inc., New York, pp. 37-62 (1989); or the position of the linkage (Kikuchi et al., *Planta*, 190:525-535 (1993).

The determination of anti-OmpC antibody levels in a sample is also useful in the present invention. As used herein, the term "anti-outer membrane protein C antibody" or "anti-OmpC antibody" includes antibodies directed to a bacterial outer membrane porin (Nikaido, H. *Microbiol. Mol. Biol. Rev.* 67: 593-656 (2003). The term "outer membrane protein C" or "OmpC" includes a bacterial porin that is immunoreactive with an anti-OmpC antibody.

As used herein, the term "anti-outer membrane protein immunoglobulin A" or "ACA-IgA" includes antibodies of the immunoglobulin A isotype that react specifically with outer membrane protein. Similarly, the term "anti-outer membrane protein immunoglobulin G" or "ACA-IgG", the term "anti-outer membrane protein G1" or "ACA-IgG1", the term "anti-outer membrane protein immunoglobulin G2" or "ACA-IgG" include antibodies of the immunoglobulin G isotype, of the immunoglobulin G1 isotype, and of the immunoglobulin G2 isotype respectively that react specifically with outer membrane protein. Similarly, the term "anti-outer membrane protein immunoglobulin M" or "ACA-IgM" includes antibodies of the immunoglobulin M isotype that react specifically with outer membrane protein.

The level of anti-OmpC antibody present in a sample from a companion animal patient can be determined using an OmpC protein or a fragment thereof such as an immunoreactive fragment thereof. Suitable OmpC antigens useful in determining anti-OmpC antibody levels in a companion animal sample include, without limitation, an OmpC protein, an OmpC polypeptide having substantially the same amino acid sequence as the OmpC protein, or a fragment thereof such as an immunoreactive fragment thereof. As used herein, an OmpC polypeptide generally describes polypeptides having an amino acid sequence with greater than about 50% identity, e.g., greater than about 60% identity, for example greater than about 70% identity, e.g., greater than about 80%, 85%, 90%, 95%, 96%, 97%, 98%, or 99% amino acid sequence identity with an OmpC protein, with the amino acid identity determined using a sequence alignment program such as CLUSTALW. Such antigens can be prepared, for example, by purification from enteric bacteria such as *E. coli*, by recombinant expression of a nucleic acid, by synthetic means such as solution or solid phase peptide synthesis, or by using phage display.

The anti-flagellin antibody (AFA) levels in a companion animal sample are also determined in the present invention. As used herein, the term "anti-flagellin antibody" includes antibodies directed to a protein component of bacterial flagella. The term "flagellin" includes a bacterial flagellum protein that is immunoreactive with an anti-flagellin antibody. Microbial flagellins are proteins found in bacterial flagellum that arrange themselves in a hollow cylinder to form the filament.

As used herein, the term "anti-flagellin protein immunoglobulin A" or "AFA-IgA" includes antibodies of the immunoglobulin A isotype that react specifically with flagellin protein. Similarly, the term "anti-flagellin protein immunoglobulin G" or "AFA-IgG", the term "anti-flagellin protein G1" or "AFA-IgG1", the term "anti-flagellin protein immunoglobulin G2" or "AFA-IgG" include antibodies of the immunoglobulin G isotype, of the immunoglobulin G1 isotype, and of the immunoglobulin G2 isotype respectively that react specifically with flagellin protein. Similarly, the term "anti-flagellin protein immunoglobulin M" or "AFA-IgM" includes antibodies of the immunoglobulin M isotype that react specifically with flagellin.

The level of anti-flagellin antibody present in a companion animal sample can be determined using a flagellin protein or a fragment thereof such as an immunoreactive fragment thereof. Suitable flagellin antigens useful in determining anti-flagellin antibody levels in a sample include, without limitation, a flagellin protein, fragments thereof, and combinations thereof, a flagellin polypeptide having substantially the same amino acid sequence as the flagellin protein, or a fragment thereof such as an immunoreactive fragment thereof. As used herein, a flagellin polypeptide generally describes polypeptides having an amino acid sequence with greater than about 50% identity, e.g., greater than about 60% identity, for example. greater than about 70% identity, e.g., greater than about 80%, 85%, 90%, 95%, 96%, 97%, 98%, or 99% amino acid sequence identity with a naturally-occurring flagellin protein, with the amino acid identity determined using a sequence alignment program such as CLUSTALW. Such flagellin antigens can be prepared from bacterium of at least one genus such as *Pseudomonas, Proteus, Escherichia coli, Helicobacter, Salmonella, Klebsiellia, Butyrivibrio, Brevundimonas, Enterococcus, Streptomyces, Enterobacter, Acinetobacter, Staphylococcus, Rhodococcus, Stenotrophomonas*, and the like. The source of bacterium can be from a subject. Preparations include purification of flagellins from bacterium or purification by recombinant expression of a nucleic acid encoding a flagellin antigen, by synthetic means such as solution or solid phase peptide synthesis, or by using phage display.

The determination of the presence or level of C-reactive protein (CRP) in a companion animal sample is also useful in the present invention. In certain instances, the presence or level of CRP is detected at the level of mRNA expression with an assay such as, for example, a hybridization assay or an amplification-based assay. In certain other instances, the presence or level of CRP is detected at the level of protein expression using, for example, an immunoassay (e.g., ELISA) or an immunohistochemical assay. For example, a sandwich colorimetric ELISA assay available from Alpco Diagnostics (Salem, N.H.) can be used to determine the level of CRP in a serum, plasma, urine, or stool sample. Similarly, an ELISA kit available from Biomeda Corporation (Foster City, Calif.) can be used to detect CRP levels in a sample. Other methods for determining CRP levels in a sample are described in e.g., U.S. Pat. Nos. 6,838,250 and 6,406,862.

In addition, hemoccult, fecal occult blood, is often indicative of gastrointestinal illness and various kits have been developed to monitor gastrointestinal bleeding. For example, Hemoccult SENSA, a Beckman Coulter product, is a diagnostic aid for gastrointestinal bleeding, iron deficiency, peptic ulcers, ulcerative colitis, and, in some instances, in screening for colorectal cancer. This particular assay is based on the oxidation of guaiac by hydrogen peroxide to produce a blue color. A similar colorimetric assay is commercially available from Helena Laboratories (Beaumont, Tex.) for the detection of blood in stool samples. Other methods for detecting occult blood in a stool sample by determining the presence or level of hemoglobin or heme activity are described in, e.g., U.S. Pat. Nos. 4,277,250, 4,920,045.

Calprotectin is a calcium and zinc-binding protein found in all cells, tissues, and fluids in the body. Calprotectin is a major protein in granulocytes and macrophages and accounts for as much as 60% of the total protein in the cytosolic fraction of these cells. It is therefore a surrogate marker of PMN turnover. Its concentration in stool correlates with the intensity of PMN infiltration of the intestinal mucosa and with the severity of inflammation. Calprotectin can be measured with an ELISA.

Integrins are cell adhesion receptors that are involved in immune patrolling and tissue-tropic mechanisms, and their determination can also be useful in the present invention. They are transmembrane proteins located in memory T-cells that facilitate the migration of lymphocytes through specific tissues like skin, CNS and gut. For example, memory T lymphocytes expressing $\alpha 4\beta 7$ integrin preferentially migrate into the gastrointestinal tract.

The method may further comprise measuring the levels of autoantibodies to inflammation markers, such as calprotectin and $\beta$-integrins, lactoferrin, and/or C-reactive protein.

Additional clinical indicia may be combined with the IBD marker assay result(s) of the present invention. These include other biomarkers related to disease of the gastrointestinal tract and/or inflammation. Examples include the following: Acute phase proteins such as C-reactive protein (CRP), serum amyloid A, albumin, transferrin among and the like whose serum/plasma concentrations increase or decrease in response to inflammation; Cytokines such as IL-6, IL-beta 1 and the like that are secreted by immune cells that regulate a range of immune system functions including inflammatory response and microbial response; Defensins such as alpha and beta defensins (i.e. DEFB1 and DEFB2) that are implicated in resistance of epithelial surfaces to microbial colonization; Cadherins such as E-cadherin and the like that mediates bacterial adhesion to mammalian cells followed by internalization; Cellular adhesion molecules such as ICAM-1 and VCAM-1 that are involved in the recruitment of lymphocytes to the infected tissue and the adhesion of such white cells to the vascular endothelium.

Other clinical indicia which may be combined with the IBD marker assay result(s) of the present invention includes demographic information (e.g., weight, gender, age, breed), veterinary history (e.g., clinical factors, pre-existing disease such as chronic diarrhea, food sensitivities, others).

Combining assay results/clinical indicia in this manner can comprise the use of multivariate logistical regression including, but not limited to, log linear modeling, neural network analysis, n-of-m analysis, decision tree analysis.

VI. Diagnosing Food Sensitivity in Companion Animas

In certain embodiments, this invention provides methods of diagnosis of pet patients that are undergoing immunological food sensitivities based on the presence of circulating antibodies against specific food-related antigenic determinants. One of the most prominent food sensitivity is the gluten sensitivity, and although gluten is commonly cited as food allergen for dogs, the current methods of detection may not be sufficiently sensitive. For instance, gluten sensitivity has only been demonstrated in a single Irish Setter cohort. In this cohort, the gluten sensitivity was detected by histopathology of the gut exhibiting partial-villous atrophy with intraepithelial lymphocyte infiltration but there was no increased levels of anti-gliadin antibodies as described in as described in Hall, et al. *Res. Vet. Sci.,* 1992, 53 (3), pp 293-299.

This disclosure includes methods to detect the presence of anti-gliadin antibodies in patients with gastrointestinal symptoms that are consistent with food sensitivity. The normal assimilation of these dietary proteins by the pet's gut require their full proteolysis in the stomach followed by a highly efficient cleavage in the upper small intestine (duodenum). Further processing of the oligopeptide fragments by exopeptidases and endopeptidases in the jejunum results in mostly free amino acids (also dipeptides and tripeptides) that are absorbed across the epithelial cells into the lamina propia from where these nutrients enter the bloodstream and are distributed throughout the body. As described in the examples below, during normal digestion, stomach resistant oligopeptides remain after exposure of gliadins. These oligopeptides are believed to act as antigens for T cells in humans suffering from gluten sensitivity related conditions. This disclosure addresses the resistance of certain gliadin-derived peptides when subjected to dog gastric fluids, the isolation and identification of these oligopeptides, and their use as baits to identify seropositivity in cohorts of dog patients that show symptoms consistent with gluten sensitivity. This method relies in the detection of circulating antibodies against these gliadin oligopeptides resistant to dog gastric fluid.

This invention also provides methods to detect seropositivity against zeins in pet patients with gastrointestinal symptoms consistent with food sensitivity. Grain proteins like gliadins and zeins, and other grain-related proteins are main ingredients in standard commercial food for pets. Other common antigenic determinants in pet food composition originate from beef.

Tissue transglutaminases are a family of enzymes that catalyze the deamidation of glutamine residues to glutamic acid. The process results in the creation of new epitopes that could play a pivotal role in the immune-pathogenesis of gluten sensitivity. This invention further comprises methods to detect anti-pet tissue transglutaminase antibodies. In pet patients with gluten-induced disease, TTG is known to be involved in mediating specific epitope deamination resulting in an increase immunogenicity against the TTG itself as well as against specific gliadin-derived oligopeptides. In methods based on seropositivity for circulating antibodies, the exposure of the right epitopes becomes critical as the antibodies recognize preferentially conformational antigen determinants for which they display the highest avidity. Thus, this invention comprises sequences of canine transglutaminase and the sequences of the gliadin-derived oligopeptides resistant to dog gastric fluid. These are key components contributing the crucial antigens that enable the detection of specific circulating antibodies, which would in turn provide a new method to diagnose and monitor the underlying condition.

The determination of anti-gliadin antibody levels in a sample is also useful in the present invention. As used herein, the term "anti-gliadin" or "anti-gliadin antibody" or "AGA" includes antibodies directed to gliadin extract immunoreactive with an anti-gliadin antibody.

As used herein, the term "anti-gliadin-immunoglobulin A" or "AGA-IgA" includes antibodies of the immunoglobulin A isotype that react specifically with gliadin. The term "anti-gliadin-IgAb", "anti-gliadin-IgAc" and anti-gliadin-IgAd" includes antibodies of the allelic variants b, c, d of immunoglobulin A isotype. Similarly, the term "anti-gliadin immunoglobulin G" or "AGA-IgG", the term "anti-gliadin immunoglobulin G1" or "AGA-IgG1", the term "anti-gliadin immunoglobulin G2" or "AGA-IgG" include antibodies of the immunoglobulin G isotype, of the immunoglobulin G1 isotype, and of the immunoglobulin G2 isotype respectively that react specifically with gliadin extract. Similarly, the term "anti-gliadin immunoglobulin M" or "AGA-IgM" includes antibodies of the immunoglobulin M isotype that react specifically with gliadin.

The level of anti-gliadin antibody present in a sample from a pet can be determined using a gliadin extract, a gliadin polypeptide or a fragment thereof such as an immunoreactive fragment thereof. Suitable gliadin antigens useful in determining anti-gliadin antibody levels in a pet sample include, without limitation, a gliadin extract, a gliadin protein, a gliadin polypeptide having substantially the same amino acid sequence as the gliadin protein, or a fragment thereof such as an immunoreactive fragment thereof. As used herein, a gliadin polypeptide generally describes polypeptides having an amino acid sequence with greater than about 50% identity, e.g., greater than about 60% identity, for example greater than about 70% identity, e.g., greater than about 80%, 85%, 90%, 95%, 96%, 97%, 98%, or 99% amino acid sequence identity with a gliadin protein, with the amino acid identity determined using a sequence alignment program such as CLUSTALW. Such antigens can be prepared, for example, by purification from wheat grains, by recombinant expression of a nucleic acid, by digestion with gastric, pancreatic and intestinal fluids separately or in combination, by synthetic means such as solution or solid phase peptide synthesis, or by using phage display.

The determination of anti-zein antibody levels in a sample is also useful in the present invention. As used herein, the term "anti-zein" or "anti-zein antibody" or "AZA" includes antibodies directed zein extract immunoreactive with an anti-zein antibody.

As used herein, the term "anti-zein-immunoglobulin A" or "AZA-IgA" includes antibodies of the immunoglobulin A isotype that react specifically with zein. The term "anti-zein-IgAb", "anti-zein-IgAc" and anti-zein-IgAd" includes antibodies of the allelic variants b, c, d of immunoglobulin A isotype. Similarly, the term "anti-zein immunoglobulin G" or "AZA-IgG", the term "anti-zein immunoglobulin G1" or "AZA-IgG1", the term "anti-zein immunoglobulin G2" or "AZA-IgG" include antibodies of the immunoglobulin G isotype, of the immunoglobulin G1 isotype, and of the immunoglobulin G2 isotype respectively that react specifically with zein extract. Similarly, the term "anti-zein immunoglobulin M" or "AZA-IgM" includes antibodies of the immunoglobulin M isotype that react specifically with zein.

The level of anti-zein antibody present in a sample from a pet patient can be determined using a zein extract, a zein polypeptide or a fragment thereof such as an immunoreactive fragment thereof. Suitable zein antigens useful in determining anti-zein antibody levels in a pet sample include, without limitation, a zein protein, a zein polypeptide having substantially the same amino acid sequence as the zein protein, or a fragment thereof such as an immunoreactive fragment thereof. As used herein, a zein polypeptide generally describes polypeptides having an amino acid sequence with greater than about 50% identity, e.g., greater than about 60% identity, for example greater than about 70% identity, e.g., greater than about 80%, 85%, 90%, 95%, 96%, 97%, 98%, or 99% amino acid sequence identity with a zein protein, with the amino acid identity determined using a sequence alignment program such as CLUSTALW. Such antigens can be prepared, for example, by purification from corn grains, by recombinant expression of a nucleic acid, by digestion with gastric, pancreatic and intestinal fluids separately or in combination, by synthetic means such as solution or solid phase peptide synthesis, or by using phage display.

The determination of anti-recombinant gliadin antibody levels in a sample is also useful in the present invention. As used herein, the term "anti-recombinant gliadin" or "anti-recombinant gliadin antibody" or "ARGA" includes antibodies directed to recombinant gliadin immunoreactive with an anti-gliadin antibody.

As used herein, the term "anti-recombinant gliadin-immunoglobulin A" or "ARGA-IgA" includes antibodies of the immunoglobulin A isotype that react specifically with recombinant gliadin and the likes. The term "anti-recombinant gliadin-IgAb", "anti-recombinant gliadin-IgAc" and anti-recombinant gliadin-IgAd" includes antibodies of the allelic variants b, c, d of immunoglobulin A isotype. Similarly, the term "anti-recombinant gliadin immunoglobulin G" or "ARGA-IgG", the term "anti-recombinant gliadin immunoglobulin G1" or "ARGA-IgG1", the term "anti-recombinant gliadin immunoglobulin G2" or "ARGA-IgG" include antibodies of the immunoglobulin G isotype, of the immunoglobulin G1 isotype, and of the immunoglobulin G2 isotype respectively that react specifically with recombinant gliadin polypeptides. Similarly, the term "anti-recombinant gliadin immunoglobulin M" or "ARGA-IgM" includes antibodies of the immunoglobulin M isotype that react specifically with recombinant gliadin polypeptides or fragment thereof.

The level of anti-recombinant gliadin antibody present in a sample from a pet can be determined using a recombinant gliadin polypeptide or a fragment thereof such as an immunoreactive fragment thereof. Suitable recombinant gliadin antigens useful in determining anti-gliadin antibody levels in a pet sample include, without limitation, a recombinant gliadin protein, a recombinant gliadin polypeptide having substantially the same amino acid sequence as the recombinant gliadin polypeptide, or a fragment thereof such as an immunoreactive fragment thereof. As used herein, a recombinant gliadin polypeptide generally describes polypeptides having an amino acid sequence with greater than about 50% identity, e.g., greater than about 60% identity, for example greater than about 70% identity, e.g., greater than about 80%, 85%, 90%, 95%, 96%, 97%, 98%, or 99% amino acid sequence identity with a recombinant gliadin polypeptide, with the amino acid identity determined using a sequence alignment program such as CLUSTALW. Such antigens can be prepared, for example, by recombinant expression of a nucleic acid or by using phage display.

The determination of anti-recombinant zein antibody levels in a sample is also useful in the present invention. As used herein, the term "anti-recombinant zein" or "anti-zein antibody" or "ARZA" includes antibodies directed to recombinant zein immunoreactive with an anti-gliadin antibody.

As used herein, the term "anti-recombinant zein-IgA" or "ArZA-IgA" includes antibodies of the immunoglobulin A isotype that react specifically with recombinant zein and the likes. The term "anti-recombinant zein-IgAb", "anti-recombinant zein-IgAc" and anti-recombinant zein-IgAd" includes antibodies of the allelic variants b, c, d of immunoglobulin A isotype. Similarly, the term "anti-recombinant zein immunoglobulin G" or "ARZA-IgG", the term "anti-recombinant zein immunoglobulin G1" or "ARZA-IgG1", the term "anti-recombinant zein immunoglobulin G2" or "ARZA-IgG" include antibodies of the immunoglobulin G isotype, of the immunoglobulin G1 isotype, and of the immunoglobulin G2 isotype respectively that react specifically with recombinant zein polypeptides. Similarly, the term "anti-recombinant zein immunoglobulin M" or "ARZA-IgM" includes antibodies of the immunoglobulin M isotype that react specifically with recombinant zein polypeptides.

The level of anti-recombinant zein antibody present in a sample from a pet can be determined using a recombinant zein polypeptide or a fragment thereof such as an immunoreactive fragment thereof. Suitable recombinant zein antigens useful in determining anti-zein antibody levels in a pet sample include, without limitation, a zein protein, a zein polypeptide having substantially the same amino acid sequence as the recombinant zein polypeptide, or a fragment thereof such as an immunoreactive fragment thereof. As used herein, a recombinant zein polypeptide generally describes polypeptides having an amino acid sequence with greater than about 50% identity, e.g., greater than about 60% identity, for example greater than about 70% identity, e.g., greater than about 80%, 85%, 90%, 95%, 96%, 97%, 98%, or 99% amino acid sequence identity with a recombinant zein polypeptide, with the amino acid identity determined using a sequence alignment program such as CLUSTALW. Such antigens can be prepared, for example, by recombinant expression of a nucleic acid or by using phage display.

The determination of anti-recombinant amylase inhibitor antibody levels in a sample is also useful in the present invention. As used herein, the term "anti-recombinant amylase inhibitor" or "anti-amylase inhibitor antibody" includes antibodies directed to recombinant amylase inhibitor immunoreactive with an anti-amylase inhibitor antibody. As used herein, the term "anti-recombinant amylase inhibitor-IgA" or "ARAA-IgA" includes antibodies of the immunoglobulin A isotype that react specifically with amylase inhibitor and the likes. The term "anti-recombinant amylase inhibitor-IgAb", "anti-recombinant amylase inhibitor-IgAc" and anti-recombinant amylase inhibitor-IgAd" includes antibodies of the allelic variants b, c, d of immunoglobulin A isotype. Similarly, the term "anti-recombinant amylase inhibitor immunoglobulin G" or "ARAA-IgG", the term "anti-recombinant amylase inhibitor immunoglobulin G1" or "ARAA-IgG1", the term "anti-recombinant amylase immunoglobulin G2" or "ARAA-IgG" include antibodies of the immunoglobulin G isotype, of the immunoglobulin G1 isotype, and of the immunoglobulin G2 isotype respectively that react specifically with recombinant amylase inhibitor polypeptides. Similarly, the term "anti-recombinant amylase inhibitor immunoglobulin M" or "ARAA-IgM" includes antibodies of the immunoglobulin M isotype that react specifically with recombinant amylase inhibitor polypeptides.

The level of anti-recombinant amylase inhibitor antibody present in a sample from a pet can be determined using a recombinant amylase inhibitor polypeptide or a fragment thereof such as an immunoreactive fragment thereof. Suitable amylase inhibitor antigens useful in determining anti-amylase inhibitor antibody levels in a pet sample include, without limitation, a amylase inhibitor protein, a amylase inhibitor polypeptide having substantially the same amino acid sequence as the recombinant amylase inhibitor polypeptide, or a fragment thereof such as an immunoreactive fragment thereof. As used herein, a recombinant amylase inhibitor polypeptide generally describes polypeptides having an amino acid sequence with greater than about 50% identity, e.g., greater than about 60% identity, for example greater than about 70% identity, e.g., greater than about 80%, 85%, 90%, 95%, 96%, 97%, 98%, or 99% amino acid sequence identity with a recombinant amylase inhibitor polypeptide, with the amino acid identity determined using a sequence alignment program such as CLUSTALW. Such antigens can be prepared, for example, by recombinant expression of a nucleic acid or by using phage display.

The determination of anti-tissue transglutaminase antibody levels in a sample is also useful in the present invention. As used herein, the term "anti-tissue transglutaminase antibody" or "anti-TTG antibody" or "ATTGA" includes antibodies directed to a TTG polypeptide immunoreactive with an anti-TTG antibody.

As used herein, the term "anti-ATTGA-immunoglobulin A" or "ATTGA-IgA" includes antibodies of the immunoglobulin A isotype that react specifically with TTG. The term "ATTGA-IgAb", "ATTGA-IgAc" and ATTGA-IgAd" includes antibodies of the allelic variants b, c, d of immunoglobulin A isotype. Similarly, the term "anti-TTGA immunoglobulin G" or "ATTGA-IgG", the term "anti-TTG immunoglobulin G1" or "ATTGA-IgG1", the term "anti-TTG immunoglobulin G2" or "ATTGA-IgG" include antibodies of the immunoglobulin G isotype, of the immunoglobulin G1 isotype, and of the immunoglobulin G2 isotype respectively that react specifically with TTG protein. Similarly, the term "anti-TTGA immunoglobulin M" or "ATTGA-IgM" includes antibodies of the immunoglobulin M isotype that react specifically with TTG.

The level of anti-TTG antibody present in a sample from a pet patient can be determined using a TTG polypeptide or a fragment thereof such as an immunoreactive fragment thereof. Suitable TTG antigens useful in determining anti-TTG antibody levels in a pet sample include, without limitation, a TTG protein, a TTG polypeptide having substantially the same amino acid sequence as the TTG protein, or a fragment thereof such as an immunoreactive fragment thereof. As used herein, a TTG polypeptide generally describes polypeptides having an amino acid sequence with greater than about 50% identity, e.g., greater than about 60% identity, for example greater than about 70% identity, e.g., greater than about 80%, 85%, 90%, 95%, 96%, 97%, 98%, or 99% amino acid sequence identity with a TTG protein, with the amino acid identity determined using a sequence alignment program such as CLUSTALW. Such antigens can be prepared, for example, by purification from tissues, by recombinant expression of a nucleic acid, by synthetic means such as solution or solid phase peptide synthesis, or by using phage display.

VII. Autoantibodies as Markers for Inflammatory Conditions in Mammals

Inflammation is a crucial process in the normal defense mechanisms against various pathogens, and leukocytes are the principal cellular mediators of inflammation. Inflammation is characterized histologically by the accumulation of leukocytes in the affected tissue due to migration of circulating leukocytes out of the vasculature, a process which is actively mediated and precisely controlled by leukocytes, the cytokines they produce, and the vascular endothelium. However, excessive or uncontrolled inflammatory responses can lead to the pathologic inflammation seen in many rheumatologic and inflammatory disorders.

Calprotectin and integrins are two classes of proteins that are intimately related to these physiological processes, with their expression, activation and accumulation being tightly controlled under normal conditions. Dysregulation of these proteins have been associated with specific disease conditions like dysregulation of $\alpha4\beta1$, $\alpha4\beta7$, and $\alpha E\beta7$ integrins may all play a contributory role in the progression of chronic forms of demyelinating disease leading to some forms of multiple sclerosis; dysregulation of $\alpha1\beta2$ associated with psoriasis; and $\alpha4$-type integrins being associated with celiac and other skin-related, gluten-sensitivity diseases.

Calprotectin has commonly been used as a marker to distinguish between organic and functional gastrointestinal disease and for the early diagnosis of inflammatory bowel disease. Calprotectin is a 24 kDa dimer of calcium binding polypeptides S100A8 and S100A9. The complex accounts for up to 60% of the soluble polypeptide content of the neutrophil cytosol and is resistant to enzymatic degradation, and can be measured in feces. A number of assays for calprotectin detection and quantification are already known and generally used to determine calprotectin levels in different body fluids and feces. S100 polypeptides, specially calprotectin and S100A12 have been studied extensively in human IBD populations and their serum and mucosal levels have been shown to be elevated with IBD. Some studies on calprotectin levels in serum and feces have also been performed in non-human animals and similar trends have been reported, albeit they are very limited.

All estimations of calprotectin in the different body fluids have been done by direct measurement of the polypeptide in different formats but mostly based on the use of antibodies against calprotectin itself, wherein the antibodies are typically monoclonal antibodies, usually murine, made for the purpose of detecting and measuring calprotectin.

Endogenous antibodies to calprotectin, as described herein, have not been described, or associated with inflammatory conditions. The present invention includes methods that determine and quantify endogenous immunoglobulin levels to calprotectin and its complexes in defined cohorts and associating those levels to defined clinical profiles.

Integrins are heterodimeric cell surface receptors which enable adhesion, proliferation, and migration of cells by recognizing binding motifs in extracellular matrix (ECM) polypeptides. As transmembrane linkers between the cytoskeleton and the ECM, they are able to recruit a huge variety of polypeptides and to influence cell processes. Integrins mediate cell-to-cell interactions and are critical homing mechanisms for many biological processes. Alpha-4 integrin is expressed by circulating leukocytes and forms heterodimeric receptors in conjunction with either the beta-1 or the beta-7 integrin subunit. Both alpha-4 beta-1 ($\alpha4\beta1$, or very late antigen-4 (VLA-4)) and alpha-4 beta-7 ($\alpha4\beta7$) dimers play a role in the migration of leukocytes across the vascular endothelium and contribute to cell activation and survival within the parenchyma. The $\alpha4\beta7$ integrin, known as the gut mucosal homing receptor, acts as a homing receptor that mediates lymphocyte migration from gut inductive sites were the immune responses are first induced to the lamina propria.

Integrin-mediated interactions with the extracellular matrix (ECM) are required for the attachment, cytoskeletal organization, mechanosensing, migration, proliferation, differentiation and survival of cells in the context of a multitude of biological processes including fertilization, implantation and embryonic development, immune response, bone resorption and platelet aggregation. Integrins also function in pathological processes such as inflammation, wound healing, angiogenesis, and tumor metastasis.

Many integrins are circulating receptors that are constantly redistributed, internalized and turned over. Because of this, their direct quantification as target antigens is very challenging and has limited its direct measurement to be associated with any clinical conditions.

Endogenous antibodies to integrins as described herein have not been previously described, nor are they known to be associated with inflammatory conditions. The present invention includes methods that enable the quantification of endogenous immunoglobulin levels to integrins by measuring the titers of antibodies specifically recognizing the integrin, and associating them to defined clinical profiles.

Lactoferrin is a protein originally isolated from milk but later found to be present in various other secretory fluids such as saliva, tears and mucosal secretions, and in the granules of neutrophils. Lactoferrin is a potent antimicrobial agent. By sequestering free iron, it can starve bacteria of this essential nutrient. It also binds to bacterial LPS and bacterial cell surface proteins, interfering with bacterial adhesion and disrupting bacterial cell walls or membranes. In inflammatory conditions, plasma levels of lactoferrin may be substantially elevated due to the release of lactoferrin from neutrophil granules.

Endogenous antibodies to lactoferrins as described herein have not been previously described, nor are they known to be associated with inflammatory conditions. The present invention includes methods that enable the quantification of endogenous immunoglobulin levels to lactoferrins by measuring the titers of antibodies specifically recognizing the lactoferrin, and associating them to defined clinical profiles.

C-reactive protein (CRP) is a pentameric protein released by the liver in response to IL-6 released by macrophages and T cells. It binds to the phosphocholine expressed on the surface of dead or dying cells, including some bacteria, and activates the complement system, promoting phagocytosis by macrophages, which clears necrotic and apoptotic cells and bacteria. CRP levels rise rapidly and dramatically in response to inflammation, so it is a good marker for inflammation, and various techniques have been developed to measure CRP levels in order to diagnose and monitor inflammation.

Endogenous antibodies to CRP as described herein have not been previously described, or associated with inflammatory conditions. The present invention includes methods that enable the quantification of endogenous immunoglobulin levels to CRP by measuring the titers of antibodies specifically recognizing the CRP, and associating them to defined clinical profiles.

In each case, the correlation between inflammation and the presence and level of autoantibodies to the foregoing inflammatory markers is particularly marked for IgA autoantibodies to the inflammatory markers.

VIII. Assays

Any of a variety of assays, techniques, and kits known in the art can be used to determine the presence or level of one or more markers in a sample to classify whether the sample is associated with IBD or a clinical subtype thereof.

The present invention relies, in part, on determining the presence or level of at least one marker in a sample obtained from a companion animal patient. As used herein, the term "determining the presence of at least one marker" includes determining the presence of each marker of interest by using any quantitative or qualitative assay known to one of skill in the art. In certain instances, qualitative assays that determine the presence or absence of a particular trait, variable, or biochemical or serological substance (e.g., protein or antibody) are suitable for detecting each marker of interest. In certain other instances, quantitative assays that determine the presence or absence of RNA, protein, antibody, or activity are suitable for detecting each marker of interest. As used herein, the term "determining the level of at least one marker" includes determining the level of each marker of interest by using any direct or indirect quantitative assay known to one of skill in the art. In certain instances, quantitative assays that determine, for example, the relative or absolute amount of RNA, protein, antibody, or activity are suitable for determining the level of each marker of interest. One skilled in the art will appreciate that any assay useful for determining the level of a marker is also useful for determining the presence or absence of the marker.

Flow cytometry can be used to determine the presence or level of one or more markers in a sample. Such flow cytometry assays, including bead based immunoassays (see, e.g. Nolan, J. P. and Mandy, F. *Cytometry* 69:318-325 (2006).

Phage display technology for expressing a recombinant antigen specific for a marker can also be used to determine the presence or level of one or more markers in a sample. Phage particles expressing an antigen specific for, e.g., an antibody marker can be anchored, if desired, to a multi-well plate using an antibody such as an anti-phage monoclonal antibody (Felici et al, "Phage-Displayed Peptides as Tools for Characterization of Human Sera" in Abelson (Ed.), *Methods Enzymol.* 267:116-129 (1996).

A variety of immunoassay techniques, including competitive and non-competitive immunoassays (e.g., The immunoassay handbook $4^{th}$ edition, David Wild ed. Newnes, 2013) can be used to determine the presence or level of one or more markers in a sample. The term immunoassay encompasses techniques including, without limitation, enzyme immunoassays (EIA) such as enzyme multiplied immunoassay technique (EMIT), enzyme-linked immunosorbent assay (ELISA), direct ELISA, antigen capture ELISA, sandwich ELISA, IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). Liposome immunoassays, such as flow-injection liposome immunoassays and liposome immunosensors, are also suitable for use in the present invention. In addition, nephelometry assays, in which the formation of protein/antibody complexes results in increased light scatter that is converted to a peak rate signal as a function of the marker concentration, are suitable for use in the present invention. Nephelometry assays are commercially available from Beckman Coulter (Brea, Calif.; Kit #449430) and can be performed using a Behring Nephelometer Analyzer.

Antigen capture ELISA can be useful for determining the presence or level of one or more markers in a sample. For example, in an antigen capture ELISA, an antibody directed to a marker of interest is bound to a solid phase and sample is added such that the marker is bound by the antibody. After unbound proteins are removed by washing, the amount of bound marker can be quantitated using, e.g., a radioimmunoassay (see, e.g., Harlow and Lane, Antibodies: A Laboratory Manual, Cold Spring Harbor Laboratory, New York, 1988)). Sandwich ELISA can also be suitable for use in the present invention. For example, in a two-antibody sandwich assay, a first antibody is bound to a solid support, and the marker of interest is allowed to bind to the first antibody. The amount of the marker is quantitated by measuring the amount of a second antibody that binds the marker. The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

A radioimmunoassay using, for example, an iodine-125 ($^{125}$I) labeled secondary antibody (Harlow and Lane, supra) is also suitable for determining the presence or level of one or more markers in a sample. A secondary antibody labeled with a chemiluminescent marker can also be suitable for use in the present invention. A chemiluminescence assay using a chemiluminescent secondary antibody is suitable for sensitive, non-radioactive detection of marker levels. Such secondary antibodies can be obtained commercially from various sources, e.g., Amersham Lifesciences, Inc. (Arlington Heights, Ill.).

The immunoassays described above are particularly useful for determining the presence or level of one or more markers in a sample. As a non-limiting example, a fixed PMN ELISA is useful for determining whether a companion animal sample is positive for APMNA or for determining APMNA levels. Similarly, an ELISA using yeast cell wall phosphopeptidomannan is useful for determining whether a companion animal sample is positive for AYA-IgA, AYA-IgG, and/or AYA-IgM, or for determining AYA-IgA, AYA-IgG, and/or AYA-IgM levels. An ELISA using OmpC protein or a fragment thereof is useful for determining whether a companion animal sample is positive for anti-OmpC antibodies, or for determining anti-OmpC antibody levels. An ELISA using flagellin protein or a fragment thereof is useful for determining whether a companion animal sample is positive for anti-flagellin antibodies, or for determining anti-flagellin antibody levels. An ELISA using calprotectin or a fragment thereof is useful for determining whether a companion animal sample is positive for calprotectin antibodies, or for determining calprotectin antibody levels. In addition, the immunoassays described above are particularly useful for determining the presence or level of other markers in a companion animal sample.

In other embodiments, a gliadin extract is used for determining whether the pet sample is positive for AGA-IgA, AGA-IgG, and/or AGA-IgM and/or determining AGA antibody levels. Similarly, an ELISA using zein extract is useful for determining whether a pet sample is positive for AZA-IgA, AZA-IgG, and/or AZA-IgM and/or determining AZA antibody levels. An ELISA using TTG protein or a fragment thereof is useful for determining whether a pet sample is positive for ATTGA-IgA, ATTGA-IgG, and/or ATTGA-IgM and/or determining ATTGA antibody levels. In addition, the immunoassays described above are particularly useful for determining the presence or level of other markers in a pet sample.

Specific immunological binding of the antibody to the marker of interest can be detected directly or indirectly. Direct labels include fluorescent or luminescent tags, metals, dyes, radionuclides, and the like, attached to the antibody. An antibody labeled with iodine-125 ($^{125}$I) can be used for determining the levels of one or more markers in a sample. A chemiluminescence assay using a chemiluminescent antibody specific for the marker is suitable for sensitive, non-radioactive detection of marker levels. An antibody labeled with fluorochrome is also suitable for determining the levels of one or more markers in a sample. Examples of fluorochromes include, without limitation, DAPI, fluorescein, Hoechst 33258, R-phycocyanin, B-phycoerythrin, R-phycoerythrin, rhodamine, Texas red, and lissamine. Secondary antibodies linked to fluorochromes can be obtained commercially, e.g., goat F(ab')2 anti-human IgG-FITC is available from Tago Immunologicals (Burlingame, Calif.).

Indirect labels include various enzymes well-known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.). A useful secondary antibody linked to an enzyme can be obtained from a number of commercial sources, e.g., goat anti-dog IgG-alkaline phosphatase can be purchased from Jackson ImmunoResearch (West Grove, Pa.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis of the amount of marker levels can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

Quantitative western blotting can also be used to detect or determine the presence or level of one or more markers in a sample. Western blots can be quantitated by well-known methods such as scanning densitometry or phosphorimaging. As a non-limiting example, protein samples are electrophoresed on 10% SDS-PAGE Laemmli gels. Primary murine monoclonal antibodies are reacted with the blot, and antibody binding can be confirmed to be linear using a preliminary slot blot experiment. Goat anti-mouse horseradish peroxidase-coupled antibodies (BioRad) are used as the secondary antibody, and signal detection performed using chemiluminescence, for example, with the Renaissance chemiluminescence kit (New England Nuclear; Boston, Mass.) according to the manufacturer's instructions. Autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art.

Alternatively, a variety of immunohistochemical assay techniques can be used to determine the presence or level of one or more markers in a sample. The term "immunohistochemical assay" encompasses techniques that utilize the visual detection of fluorescent dyes or enzymes coupled (i.e., conjugated) to antibodies that react with the marker of interest using fluorescent microscopy or light microscopy and includes, without limitation, direct fluorescent antibody assay, indirect fluorescent antibody (IFA) assay, anticomplement immunofluorescence, avidin-biotin immunofluorescence, and immunoperoxidase assays. An IFA assay, for example, is useful for determining whether a companion animal sample is positive for APMNA, the level of APMNA, whether a companion animal sample is positive for p APMNA, the level of pAPMNA, and/or an APMNA staining pattern (e.g., cAPMNA, pAPMNA, NSNA, and/or SAPPA staining pattern). The concentration of APMNA in a sample can be quantitated, e.g., through endpoint titration or through measuring the visual intensity of fluorescence compared to a known reference standard.

In another embodiment, the detection of antibodies may utilize Agglutination-PCR (ADAP), e.g., as described in Tsai, et al. *ACS Cent. Sci.*, 2016, 2 (3), pp 139-147, e.g., using a qPCR assay to ultra-sensitively detect antibodies using antigen-DNA conjugates.

Alternatively, the presence or level of a marker of interest can be determined by detecting or quantifying the amount of the purified marker. Purification of the marker can be achieved, for example, by high pressure liquid chromatography (HPLC), alone or in combination with mass spectrometry (e.g., MALDI/MS, MALDI-TOF/MS, tandem MS, etc.). Qualitative or quantitative detection of a marker of interest can also be determined by well-known methods including, without limitation, Bradford assays, Coomassie blue staining, silver staining, assays for radiolabeled protein, and mass spectrometry.

The analysis of a plurality of markers may be carried out separately or simultaneously with one test sample. For separate or sequential assay of markers, suitable apparatuses include clinical laboratory analyzers such as the ElecSys (Roche), the AxSym (Abbott), the Access (Beckman), the AD VIA®, the CENTAUR® (Bayer), and the NICHOLS ADVANTAGE® (Nichols Institute) immunoassay systems. Particularly useful physical formats comprise surfaces having a plurality of discrete, addressable locations for the detection of a plurality of different markers. Such formats include protein microarrays, or "protein chips" and certain capillary devices (see, e.g., U.S. Pat. No. 6,019,944). In these embodiments, each discrete surface location may comprise antibodies to immobilize one or more markers for detection at each location. Surfaces may alternatively comprise one or more discrete particles (e.g., microparticles or nanoparticles) immobilized at discrete locations of a surface, where the microparticles comprise antibodies to immobilize one or more markers for detection.

As for the format of the test, it is understood that other diagnostic test devices may be adapted for the use of the present invention. For example, a strip test assay is well known in the art where the sample is applied to one end of the strip and the fluid migrates by capillary action up to the test zone. A sample can be any solution including body fluids (e.g. whole blood, serum or plasma, urine and the like).

In certain embodiments, the test zone contains an immobilized bound reagent for the detection of the desired analyte. Reagents can be immobilized via any suitable technique as will be apparent to those skilled in the art. Direct attachment methods include nondiffusive adsorption, nondiffusive absorption, attachment to microparticles that are themselves entrapped in the appropriate position, and covalent binding, such as by use of cyanogen bromide, carbonyl diimidazole, or glutaraldehyde. If the test result is positive, then the test zone will display a positive result; i.e., it will change color, altering the bar code by "adding" an additional stripe. In a similar embodiment, the test zone might be configured such that detection of an analyte will result in disappearance of the test zone stripe, such that the data encoded in the bar code is changed as well.

In general, the sample is suspected of containing an analyte. An analyte will typically be one member of a specific binding pair, while the test zone of the strip test will contain a second member of a specific binding pair. A member of a specific binding pair can include, for example, substances such as antigens, antibodies, receptors, peptides, proteins, ligands, single-stranded and double-stranded DNA, oligonucleotides, cDNA, mRNA, RNA, and the like. The analyte can be monovalent (monoepitopic) or polyvalent (polyepitopic), synthetic or natural, antigenic or haptenic, and may be a single compound or plurality of compounds which share at least one common epitopic or determinant site. The detection of a specific binding pair may occur simultaneously with the test, or may occur in one or more subsequent steps, depending on the test.

The formation of a specific binding pair between the analyte of interest and the reagent immobilized in the test zone may be detected by visual readout or machine-assisted readout. The detectable indication can be a color change, if a visible result is desired. In other embodiments, the detectable indication is created by enzymes, fluorophores, chromophores, radioisotopes, dyes, colloidal gold, colloidal carbon, latex particles, and chemiluminescent agents. In some embodiments, the detectable indication is not visible to the eye, but is detected by suitable equipment. Such is the case when the specific binding pair is fluorescent, or radioactive.

Methods to detect antibodies, including autoantibodies, are known, for example using immunodiffusion methods. Immunodiffusion techniques can be useful in analyzing a large number of biological components, including antibodies, proteins, enzymes and nucleic acids, depending on the particular binding agents employed. For example, where the analyte is an antibody, typical binding agents are antigens, and vice versa. Such techniques involve screening for the presence of an analyte by diffusing a solution suspected of containing the analyte through a support and by diffusing the antigen. The analyte contained in the sample eventually reacts with the antigen in solution producing a complex analyte-antigen. This complex between the antigen and analyte can be detected by a variety of indicators. For example, sandwich immunoassay techniques involve the formation of a three-member complex of antigen-analyte-label that can be detected via visual, radioactive, spectroscopic, or other methods. In yet another example, the complex analyte-antigen can create zones of precipitation resulting from immunodiffusion that can be subjected to direct quantitative measurements such as quantitative photooptical measurements of the light intensity.

Enzyme-linked immunosorbent assay (ELISA) methods are described above. For detection of the endogenous antibodies of the invention, for example, antigens to the endogenous antigens are attached to a surface. Then, the sample is contacted with the antigens, which act as bait to bind the endogenous antibodies, and a further specific antibody is applied over the surface, which can bind to the endogenous antibodies. This antibody is linked to an enzyme, and, in the final step, a substance containing the enzyme's substrate is added. The subsequent reaction produces a detectable signal, most commonly a color change in the substrate.

Western blot techniques can be useful in analyzing a large number of biological components. For example, an antigen or an antigenic mixture of interest is solubilized, usually with sodium dodecyl sulfate (SDS), urea, and, alternatively, with reducing agents such as 2-mercaptoethanol or the likes. Following solubilization, the material is separated on a polyacrylamide gel by electrophoresis and the antigens are then electrophoretically transferred to a support, where they are bound irreversibly. The membrane is exposed to the sample suspected of containing the analyte. The analyte contained in the sample eventually reacts with the antigen producing a complex analyte-antigen. The complex between the antigen and analyte can be detected by a variety of indicators such as a labeled detected antibody. In another example, the antigen is placed in contact with the sample suspected of containing the analyte. This complex is then run on a non-denaturing polyacrylamide gel by electrophoresis and the antigens are then electrophoretically transferred to a support, where it is bound irreversibly. The complex between the antigen and analyte can be detected by a variety of indicators such as a labeled detection antibody. In yet another example, the antigen is placed in contact with the sample suspected of containing the analyte. This complex is then transferred to a support, where it is bound irreversibly. The complex between the antigen and analyte can be detected by a variety of indicators such as a labeled detection antibody.

Anti-idiotypic antibodies techniques can be useful in analyzing a large number of biological components. For example, antibodies that bind IBD-associated antigens are isolated from one or more subjects and injected into a mammal such as mice, goats, rabbit, and the likes. The resulting anti-idiotypic polyclonal or monoclonal antibodies are used in assays to detect antibodies to IBD-associated antigens in subjects. For example, the assay is a competitive method for detecting the present of analyte contained in a sample. The assay includes incubating the antigen with an anti-idiotypic antibody and an unknown amount of analyte present in the sample collected from a subject wherein the antigen is either enzyme labelled or indirectly detected, whereby the presence of analyte in the sample is determined by comparing the extent to which its binding to the antigen is displaced by the addition of the anti-idiotypic antibody with a calibration curve obtained with a known amount of analyte or derivatives thereof.

Techniques based on mobility shift assay can be used to detect and quantify autoantibodies or any other type of antibodies against specific antigens present in any kind of samples. The sample can be subjected to differential separation by using size exclusion chromatography (either regular or high performance liquid chromatography) or any of the methods that relies on different mobility properties. Basically, the sample to be analyzed will be put in contact with the specific antigen which has been labeled with any standard labeling method (i.e. fluorophores, colored substrates, enzymes, or others), and further subjected to size exclusion chromatography or any other method based on the differential physico-properties of free versus bound antigen.

In addition to the above-described assays for determining the presence or level of various markers of interest, analysis of marker mRNA levels using routine techniques such as Northern analysis, reverse-transcriptase polymerase chain reaction (RT-PCR), or any other methods based on hybridization to a nucleic acid sequence that is complementary to a portion of the marker coding sequence (e.g., slot blot hybridization) are also within the scope of the present invention. General nucleic acid hybridization methods are described in Anderson, "Nucleic Acid Hybridization," BIOS Scientific Publishers, 1999. Amplification or hybridization of a plurality of transcribed nucleic acid sequences (e.g., mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi, P and G. Westley, "DNA Microarrays and Gene Expression: From Experiments to Data Analysis and Modeling," Cambridge University Press, 2002.

Analysis of the genotype of a marker such as a genetic marker can be performed using techniques known in the art including, without limitation, polymerase chain reaction (PCR)-based analysis, sequence analysis, and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing, solid-phase sequencing, sequencing with mass spectrometry such as matrix-assisted laser desorption/ionization time-of-flight mass spectrometry (MALDI-TOF/MS), and sequencing by hybridization. Non-limiting examples of electrophoretic analysis include slab gel electrophoresis such as agarose or polyacrylamide gel electrophoresis, capillary electrophoresis, and denaturing gradient gel electrophoresis. Other methods for genotyping an individual at a polymorphic site in a marker include, e.g., the INVADER® assay from Third Wave Technologies, Inc., restriction fragment length polymorphism (RFLP) analysis, allele-specific oligonucleotide hybridization, a heteroduplex mobility assay, and single strand conformational polymorphism (SSCP) analysis.

Several markers of interest may be combined into one test for efficient processing of a multiple of samples. In addition, one skilled in the art would recognize the value of testing multiple samples (e.g., at successive time points, etc.) from the same patient. Such testing of serial samples can allow the identification of changes in marker levels over time. Increases or decreases in marker levels, as well as the absence of change in marker levels, can also provide useful information to classify IBD or to differentiate between clinical subtypes of IBD.

A panel consisting of one or more of the markers described above may be constructed to provide relevant information related to the approach of the present invention for classifying a companion animal sample as being associated with IBD or a clinical subtype thereof or associated with a food sensitivity. Such a panel maybe constructed using 1, 2, 3, 4, 5, 6, 7, 8, 9, 10, 11, 12, 13, 14, 15, 16, 17, 18, 19, 20, 25, 30, 35, 40, or more individual markers. The analysis of a single marker or subsets of markers can also be carried out by one skilled in the art in various clinical settings.

The analysis of markers could be carried out in a variety of physical formats as well. For example, the use of microtiter plates or automation could be used to facilitate the processing of large numbers of test samples. Alternatively, single sample formats could be developed to facilitate treatment and diagnosis in a timely fashion.

In one aspect the invention relates to a kit for the detection of antibodies as described above, e.g., inflammation-associated autoantibodies and/or IBD-associated antibodies, and/or food sensitivity-related autoantibodies, in a sample comprising:

i. one or more peptide reagents as described above; and
ii. a means for detection of a complex formed between the peptide and an IBD-associated antibody and/or inflammation-associated autoantibody and/or a food sensitivity associated antibody.

In a particular embodiment, the kit provides
a. at least one peptide reagent binding to an inflammation-associated autoantibody, e.g., a peptide comprising epitopes from a companion animal calprotectin;
b. at least one peptide reagent binding to an IBD-associated endogenous antibody, e.g., a peptide comprising epitopes from a bacterial protein from one or more intestinal bacteria from a companion animal, e.g., a bacterial OmpC or flagellin; and
c. at least one peptide reagent binding to a food sensitivity associated endogenous antibody, e.g., a peptide comprising epitopes from one or more of gliadin, zein, amylase inhibitor, TTG2, or TG3, e.g., from a gliadin or zein;
together with a means for detection of a complex formed between the peptide and an IBD-associated antibody and/or inflammation-associated autoantibody and/or a food sensitivity associated antibody, e.g., wherein the antibodies detected are of the IgA class.

The kit may contain ready to use reagents and the test results are advantageously obtained within several hours, e.g., less than six hours. For example, the kit may contain all ready to use reagents including coated plates, negative and positive controls, wash solution, sample diluent, conjugate, TMB and stop solutions. In some embodiments the solid phase of the test is coated with peptide antigen as described above. The peptide antigen can be chemically synthesized or expressed in *E. coli* or other suitable bacterial expression line. In the method and test kit any known and useful solid phase may be used. For example, MaxiSorp or PolySorp (Thermo Fisher Scientific) may be used and coated by applying a coating buffer which has a pH of, for example, 5, 7 or 9.5. The antigen is applied in a quantity of 0.1, 0.5, 1, 2, 3 or 4 ug/ml. A diluent may be used, for example (i) 0.14M NaCl, 2.7 mM KCl, Kathon 0.03%, Tween 20 0.1%; or (ii) 2% MgCl2, 6% Tween20 and 6% AO, 0.5% Casein sodium salt. The detection antibody is diluted, for example 1:10000 or 1:20000.

The method steps will be applied as required and may vary depending to the particular reagents applied. In a one embodiment the conditions and method steps are as follows:
a) Sample (1:10) in sample diluent (MgCl2 2%, AO 6%, Tween20 6%, Casein 0.5%), 100 µl/well;
b) Incubate 1 h, room temperature in humid chamber;
c) 3× wash (phosphate buffered saline with 0.1% Tween20);
d) Conjugate ready-to-use, 100 µl/well;
e) Incubate 1 h, room temperature in humid chamber;
f) 3× wash (phosphate buffered saline with 0.1% Tween20);
g) TMB 100 ul/well, incubate 10 mins, room temperature;
h) Add stop solution (100 µl/well); and
i) Read out at 450 nm In some embodiments the sample diluent contains casein sodium salt in a concentration of between 0.1 to 0.55%. For example, the sample diluent may contain 0.5% casein sodium salt and MgCl2, e.g., at a concentration of 2%.

In some embodiments the method of detection and/or the kit, is characterized by the inclusion of specific compounds, the use of particular dilutions of the capturing antigen and/or a particular amount and quality of capturing antigen coated onto the solid support used in the method of detection and the kit of the invention.

In some embodiments, the dilution of the antigen is chosen to be in the coating solution in a concentration of 0.25 to 5 µg/ml, for example, 0.5 to 1 µg/ml. The coating step is, for example, performed at pH 5 to 10, e.g. about 5, 7 or 9.5. The antigen as described in the specification and Examples, in some embodiments is used in amounts of 0.1, 0.5, 1, 2, or 4 µg/ml, e.g., 1 µg/ml.

In some embodiments, the method of detection and kit contains Tween, e.g. a Tween 20, or a comparable substance, e.g., a detergent with comparable characteristics. For example, the substance is contained in an amount of 0.05 to 0.5%, for example 0.1 to 0.2%.

In some embodiments the wash solution of the coating step contains NaCl 0.14M, KCl 2.7 mM; Kathon 0.03%, Tween20 0.1%, sample diluent comprises MgCl2 2%, aminoxid (AO) 6%, Tween20 6% and 0.5% casein. For example, the conjugate (where the patient is a dog, the anti-canine Ab conjugate) is used in a dilution of 1:10 000 to 1:30 000, e.g., 1:20 000 in a conjugate stabilizing buffer as a ready to use format.

The immunoassays described herein may be configured in a reagent impregnated test strip in which a specific binding assay is performed in a rapid and convenient manner with a minimum degree of skills and involvement.

For example, the test strip is prepared with one or multiple detection zones in which the specific binding reagents (labeled or unlabeled) for an analyte suspected of being in the sample is immobilized. A sample of serum (or any other body fluid) is applied to one portion of the test strip comprising of a dry carrier (such as nitrocellulose or any other bibulous, porous or fibrous material capable of absorbing liquid rapidly) and is allowed to permeate through the strip material with the aid of an eluent such as phosphate buffer or the like. The sample progresses through the detection zone wherein a specific binding reagent has been immobilized.

In certain embodiments, the immobilized agents can comprise an antigen or a plurality of antigens that will bind to certain IBD-associated antibodies present in a sample from a dog having IBD, for example OmpC and/or flagellin antigen, for example, (i) a bacterial Omp C protein or antigenic fragment thereof comprising at least 10 (e.g., at least 20, e.g., at least 30) consecutive amino acids in a sequence selected from SEQ ID NOS 16, 17, and 18; and/or (ii) a bacterial flagellin protein or antigenic fragment thereof comprising at least 10 (e.g., at least 20, e.g., at least 30) consecutive amino acids in a sequence selected from SEQ ID NOS 9-13. In a particular embodiment, the immobilized agent contains at least one OmpC antigen and at least one flagellin antigen.

In some embodiments, the immobilized agents can additionally or alternatively comprise an antigen or a plurality of antigens that will bind to certain inflammation-associated autoantibodies present in a sample from a patient having an inflammatory condition, for example a calprotectin or antigenic fragment thereof, comprising at least 10 (e.g., at least 20, e.g., at least 30) consecutive amino acids in a sequence from a wild type calprotectin, e.g., from a companion animal calprotectin, for example, any of SEQ ID NO: 19, SEQ ID NO: 20, SEQ ID NO: 21, SEQ ID NO: 22 or any combination thereof, and/or an integrin or antigenic fragment thereof, comprising at least 10 (e.g., at least 20, e.g., at least 30) consecutive amino acids in a sequence from a wild type integrin, e.g. from a companion animal integrin, for example, any of SEQ ID NO: 29, SEQ ID NO: 30, SEQ ID NO: 31, SEQ ID NO: 32, or any combination thereof.

In some embodiments, the immobilized agents will further comprise a positive control, for example, a common antigen that will bind antibodies present in the serum or all or nearly all the companion animal species.

The inflammation-associated autoantibodies and/or IBD-associated antibodies and/or food sensitivity associated antibodies present in the sample can therefore become bound within the detection zone to the immobilized antigen. The antibody thus bound is capable of participating in a sandwich reaction where a second labeled binding reagent (e.g., a secondary antibody covalently linked to horseradish peroxidase or alkaline phosphatase or the like) is applied that operates as a specific binding partner for the given analyte. The labeled reagent, the analyte (if present) and the immobilized unlabeled specific binding reagent cooperate together in a sandwich reaction. The two binding reagents must have specificities for different epitopes on the analyte. The color generated at the detection zone can be read by eye or using a light refractometer. A quantitative variant of the test can be developed by testing mixtures of specific binding reagent. Alternatively, polymer particles (e.g., latex) can be colored and sensitized with reagents (e.g., proteinaceous antigens or antibodies) and used to detect specific analytes present in samples that have been deposited in detecting zones. Color development at test site may be compared with color of one or more standards or internal controls.

Broadly, the strip test cell and process of this example can be used to detect any analyte which has heretofore been assayed using known immunoassay procedures, or known to be detectable by such procedures, using polyclonal or monoclonal antibodies or other proteins comprising binding sites for such analytes. Various specific assay protocols, reagents, and analytes useful in the practice of the example invention are known per se, see, e.g., U.S. Pat. Nos. 4,446,232 and 4,868,108.

IX. Statistical Algorithms

In some aspects, the present invention provides methods, systems, and code for classifying whether a companion animal sample is associated with IBD using a statistical algorithm or process to classify the sample as an IBD sample or non-IBD sample, in other aspects, the present invention provides methods, systems, and code for classifying whether a sample is associated with a clinical subtype of IBD (i.e., differentiating between LPE, EGE or GE) using a statistical algorithm or process to classify the sample as a LPE sample, EGE sample, GE sample or non-IBD sample. The statistical algorithms or processes independently can comprise one or more learning statistical classifier systems. As described herein, a combination of learning statistical classifier systems advantageously provides improved sensitivity, specificity, negative predictive value, positive predictive value, and/or overall accuracy for classifying whether a sample is associated with IBD or a clinical subtype thereof.

X. Methods of Detecting Food Sensitivity in a Companion Animal

In another embodiment, the invention provides a method (Method 1) for detecting the presence and/or level of one or more endogenous antibodies associated with food sensitivity in a sample (e.g., a sample is selected from one or more of whole blood, serum, plasma, stool, and intestinal tissue) obtained from a companion animal patient, e.g., a dog or a cat, wherein the endogenous antibodies are selected from one or more of endogenous antibodies to one or more proteins associated with food sensitivity, e.g., selected from one or more of gliadin, zein, amylase inhibitor, or tissue transglutaminase (e.g. TTG2, or TG3), and optionally additionally autoantibodies to a calprotectin, autoantibodies to a β-integrin, autoantibodies to a lactoferritin, autoantibodies to a C-reactive protein, endogenous antibodies to polymorphonuclear leukocytes (PMNs or granulocytes, including neutrophil granulocytes), and/or endogenous antibodies to microbes found in the gut;

comprising contacting one or ore antigens with said sample, wherein the one or more antigens are specific for the endogenous antibody of interest, and wherein the one or more antigens are bound to a substrate or detectable label, and detecting the binding of said one or more one or more endogenous antibodies associated with inflammation to the one or more antigens, and optionally, classifying said sample as classifying the sample as positive or negative for food sensitivity, wherein the presence or level of the one or one or more endogenous antibodies associated with food sensitivity, separately or in combination, correlates with the presence of food sensitivity. For example 1.1. Method 1 which is a method for detecting the presence and/or level of one or more endogenous antibodies associated with a food sensitivity, for example endogenous antibodies to one or more of gliadin, zein, amylase inhibitor, or tissue transglutaminase (e.g. TTG2, or TG3), in a sample obtained from a patient, for example a companion animal patient, e.g., a dog or cat, for example wherein the sample is selected from one or more of whole blood, serum, plasma, stool, and intestinal tissue; the method comprising the steps of
  a. Contacting one or more antigens bound to a substrate or detectable label with said sample and detecting the binding of said one or more endogenous antibodies associated with a food sensitivity;
  b. Contacting a labeled antibody with said sample, wherein the labeled antibody specifically binds immunoglobulin from the species of the companion animal, and detecting binding of the labeled antibody to said one or more endogenous antibodies associated with a food sensitivity;
  c. Optionally, classifying said sample as positive or negative for food sensitivity, wherein the presence of level of the one or more food sensitivity-associated antibodies, separately or in combination, correlates with food sensitivity.

1.2. Any preceding method comprising the step of using a labeled antibody that specifically binds immunoglobulin from the species of the patient to detect the one or more endogenous antibodies associated with food sensitivity bound to the antigen.

1.3. Any preceding method, wherein the companion animal patient is a cat, a dog, or a horse, for example a dog.

1.4. Any preceding method wherein the sample is whole blood, serum or plasma.

1.5. Any preceding method wherein the presence, severity and/or type of food sensitivity in the patient is associated with antibody class switching from IgG to IgA, for example such that the proportion of one or more endogenous IgA antibodies associated with food sensitivity is lower in healthy animals and higher in animals with food sensitivity.

1.6. Any preceding method wherein one or more endogenous antibodies associated with food sensitivity are IgA antibodies.

1.7. Any preceding method which is an immunoassay selected from an enzyme-linked immunosorbent assay (ELISA), an immunohistochemical assay, and an immunofluorescence assay.

1.8. Any preceding method wherein the patient is a dog or cat, wherein the endogenous antibodies comprise antibodies to one or more of gliadin, zein, amylase inhibitor, tissue transglutaminase (e.g. TTG2, or TG3).

1.9. Any preceding method wherein the companion animal patient exhibits one or more of the following symptoms:
a. Blood in the stool;
b. Anemia;
c. Diarrhea;
d. Vomiting
e. Inappetence; or
f. Significant recent weight loss.

1.10. Any preceding method wherein the companion animal patient is a purebred cat or a pure or mixed breed dog of a breed selected from German Shepherds, Yorkshire Terriers, Cocker Spaniels, Basenjis, Soft-coated Wheaten Terriers, and Shar-Peis, e.g., wherein the breed of the dog is taken into account when classifying the sample.

1.11. Any preceding method wherein the companion animal patient is at greater than two, e.g., greater than 5 years of age.

1.12. Any preceding method wherein said patient has not responded to treatment with antibiotics.

1.13. Any preceding method wherein the presence, severity and/or type of food sensitivity in the companion animal patient is associated with antibody class switching from IgG to IgA, for example, wherein the proportion of IgG antibodies to a food sensitivity antigen, e,g, gliadin or zein antigen, e.g., relative to IgA antibodies to the same antigen, is higher in healthy animals and lower in animals with food sensitivity.

1.14. Any preceding method further comprising applying a statistical algorithm to said presence or level of one or more food sensitivity-associated endogenous antibodies to obtain a diagnostic or prognostic profile for said patient, wherein the presence or relative levels of particular food sensitivity-associated antibodies correlates with the presence, type or severity of food sensitivity.

1.15. Any preceding method wherein the one or more food sensitivity-associated endogenous antibodies are selected from the group consisting of antibodies to gliadin, zein, amylase inhibitor, tissue transglutaminase (e.g. TTG2, or TG3) and combinations thereof.

1.16. Any preceding method, wherein the one or more food sensitivity-associated endogenous antibodies comprise antibodies to gliadin.

1.17. Any preceding method, wherein the one or more food sensitivity-associated endogenous antibodies comprise antibodies recognizing an amino acid sequence selected from SEQ ID NOS 37-66 and/or combinations thereof.

1.18. Any preceding method, wherein the one or more food sensitivity-associated endogenous antibodies comprise antibodies to gliadin which bind to an amino acid sequence selected from the group consisting of SEQ ID NO 37, 38, 39, 40, and 58.

1.19. Any preceding method, wherein the one or more food sensitivity-associated endogenous antibodies comprise antibodies to gliadin which bind to an amino acid sequence which is a fusion peptide comprising at least two sequences selected from the group consisting of SEQ ID NO 37, 38, 39, and 40.

1.20. Any preceding method, wherein the one or more food sensitivity-associated endogenous antibodies comprise antibodies to gliadin which bind to an amino acid sequence comprising SEQ ID NO 58.

1.21. Any preceding method, wherein the one or more food sensitivity-associated endogenous antibodies comprise antibodies to zein which bind to an amino acid sequence selected from the group consisting of SEQ ID NO 46, 47, 48, 49, 50, 51, 52, 53, 54, 55, 56, 57 or 60.

1.22. Any preceding method, wherein the one or more food sensitivity-associated endogenous antibodies comprise antibodies to zein which bind to an amino acid sequence which is a fusion peptide comprising at least two sequences selected from the group consisting of SEQ ID NO 46, 47, 48, 49, 50, 51, 52, 53, 54, 55, 56, and 57.

1.23. Any preceding method, wherein the one or more food sensitivity-associated endogenous antibodies comprise antibodies to zein which bind to an amino acid sequence comprising SEQ ID NO 60.

1.24. Any preceding method, wherein the one or more food sensitivity-associated endogenous antibodies comprise antibodies to amylase inhibitor which bind to an amino acid sequence selected from the group consisting of SEQ ID NO 41, 42, 43, 44, 45, and 59.

1.25. Any preceding method, wherein the one or more food sensitivity-associated endogenous antibodies comprise antibodies to amylase inhibitor which bind to an amino acid sequence which is a fusion peptide comprising at least two sequences selected from the group consisting of SEQ ID NO 41, 42, 43, 44, and 45.

1.26. Any preceding method, wherein the one or more food sensitivity-associated endogenous antibodies comprise antibodies to amylase inhibitor which bind to an amino acid sequence comprising SEQ ID NO 59.

1.27. Any preceding method, wherein the one or more food sensitivity-associated endogenous antibodies comprise antibodies to canine TTG2.

1.28. Any preceding method, wherein the one or more food sensitivity-associated endogenous antibodies comprise antibodies to canine TTG2 which bind to an amino acid sequence which is encoded by a canine gene sequence amplifiable by primers comprising SEQ ID NO 61 and 62.

1.29. Any preceding method, wherein the one or more food sensitivity-associated endogenous antibodies comprise antibodies to canine TTG2 which bind to an amino acid sequence comprising SEQ ID NO 63.

1.30. Any preceding method, wherein the one or more food sensitivity-associated endogenous antibodies comprise antibodies to canine TG3.

1.31. Any preceding method, wherein the one or more food sensitivity-associated endogenous antibodies comprise antibodies to canine TG3 which bind to an amino acid sequence which is encoded by a canine gene sequence amplifiable by primers comprising SEQ ID NO 64 and 65.

1.32. Any preceding method, wherein the one or more food sensitivity-associated endogenous antibodies comprise antibodies to canine TG3 which bind to an amino acid sequence comprising SEQ ID NO 66.

1.33. Any preceding method, wherein said the one or more food sensitivity-associated endogenous antibodies are IgA antibodies.

1.34. Any preceding method, wherein the immunoassay to detect the presence or level of the one or more food sensitivity-associated endogenous antibodies is an enzyme-linked immunosorbent assay (ELISA).

1.35. Any preceding method, wherein the immunoassay to detect the presence or level of the one or more food sensitivity-associated endogenous antibodies is an immunohistochemical assay.

1.36. Any preceding method, wherein the immunoassay to detect the presence or level of the one or more food sensitivity-associated endogenous antibodies is an immunofluorescence assay.

1.37. Any preceding method, wherein said sample is selected from the group consisting of serum, plasma, and whole blood.

1.38. Any preceding method, wherein the step of classifying the sample as positive or negative for food sensitivity is carried out using a statistical algorithm selected from the group consisting of a classification and regression tree, boosted tree, neural network, random forest, support vector machine, general chi-squared automatic interaction detector model, interactive tree, multiadaptive regression spline, machine learning classifier, and combinations thereof.

1.39. Any preceding method, comprising: (a) determining the presence or level of at least one marker selected from the group consisting of endogenous antibodies to one or more of gliadin, zein, amylase inhibitor, tissue transglutaminase (e.g. TTG2, or TG3) and combinations thereof in the sample; and (b) classifying the sample as positive or negative for food sensitivity using a statistical algorithm based upon the presence or level of at least one marker.

1.40. Any preceding method comprising detecting a complex comprising an endogenous antibody associated with food sensitivity and an antigen, using a labeled antibody that binds to the endogenous antibody.

1.41. Any preceding method wherein the one or more antigens bound to a substrate or detectable label comprise any of Reagent 1, as hereinafter described.

1.42. Any preceding method wherein the one or more antigens bound to a substrate comprise an isolated zein peptide comprising one or more sequences which do not contain a protease cleavage site recognized by a protease in canine gastric fluid but not comprising sequences that contain such a protease cleavage site, e.g.,
  a. wherein the isolated zein peptide comprises one or more sequences selected from SEQ ID NOS 46-57;
  b. wherein the isolated zein peptide is a fusion peptide comprising two or more sequences selected from SEQ ID NOS 46-57;
  c. wherein the isolated zein peptide is bound to one or more of a label, a purification tag, a solid substrate, or another protein or fragment thereof; for example, wherein the isolated zein peptide is bound to a poly-histidine tag, for example an N-terminal hexa-histadine tag, e.g., optionally comprising one or more solubility enhancing residues;
  d. wherein the isolated zein peptide is bound to an N-terminal hexa-histadine tag of SEQ ID NO: 36; and/or
  e. wherein the isolated zein peptide comprises SEQ ID NO: 60.

1.43. Any preceding method wherein the one or more antigens bound to a substrate comprise an isolated gliadin peptide comprising one or more sequences which do not contain a protease cleavage site recognized by a protease in canine gastric fluid but not comprising sequences that contain such a protease cleavage site, e.g.,
  a. wherein the isolated gliadin peptide comprises one or more sequences selected from SEQ ID NOS 37-40;
  b. wherein the isolated gliadin peptide is a fusion peptide comprising two or more sequences selected from SEQ ID NOS 37-40;
  c. wherein the isolated zein peptide is bound to one or more of a label, a purification tag, a solid substrate, or another protein or fragment thereof; for example, wherein the isolated zein peptide is bound to a poly-histidine tag, for example an N-terminal hexa-histadine tag, e.g., optionally comprising one or more solubility enhancing residues;
  d. wherein the isolated gliadin peptide is bound to an N-terminal hexa-histadine tag of SEQ ID NO: 36; and/or
  e. wherein the isolated gliadin peptide comprises SEQ ID NO: 58.

1.44. Any preceding method wherein the one or more antigens bound to a substrate comprise an isolated amylase inhibitor peptide comprising one or more sequences which do not contain a protease cleavage site recognized by a protease in canine gastric fluid but not comprising sequences that contain such a protease cleavage site, e.g.,
  a. wherein the isolated amylase inhibitor peptide comprises one or more sequences selected from SEQ ID NOS 41-45;
  b. wherein the isolated amylase inhibitor peptide is a fusion peptide comprising two or more sequences selected from SEQ ID NOS 41-45;
  c. wherein the isolated amylase inhibitor peptide is bound to one or more of a label, a purification tag, a solid substrate, or another protein or fragment thereof; for example, wherein the isolated amylase inhibitor peptide is bound to a poly-histidine tag, for example an N-terminal hexa-histadine tag, e.g., optionally comprising one or more solubility enhancing residues;
  d. wherein the isolated amylase inhibitor peptide is bound to an N-terminal hexa-histadine tag of SEQ ID NO: 36; and/or
  e. wherein the isolated amylase inhibitor peptide comprises SEQ ID NO: 58.

1.45. Any preceding method wherein the one or more antigens bound to a substrate comprise an isolated canine tissue transglutaminase peptide comprising one or more antigenic sequences from canine TTG2 or TG3, e.g.,
  a. wherein the isolated canine tissue transglutaminase peptide comprises an amino acid sequence encoded by a canine TTG2 nucleic acid sequence amplifiable by primers comprising SEQ ID NO 61 and 62;
  b. wherein the isolated canine tissue transglutaminase peptide comprises an amino acid sequence encoded by a canine TG3 nucleic acid sequence amplifiable by primers comprising SEQ ID NO 64 and 65;
  c. wherein the isolated canine tissue transglutaminase peptide is bound to one or more of a label, a purification tag, a solid substrate, or another protein or fragment thereof; for example, wherein the isolated canine tissue transglutaminase peptide is bound to a poly-histidine tag, for example an N-terminal hexa-histadine tag, e.g., optionally comprising one or more solubility enhancing residues;
  d. wherein the isolated canine tissue transglutaminase peptide is bound to an N-terminal hexa-histadine tag of SEQ ID NO: 36;
  e. wherein the isolated canine tissue transglutaminase peptide comprises SEQ ID NO: 63; and/or
  f. wherein the isolated canine tissue transglutaminase peptide comprises SEQ ID NO: 66.

1.46. Any preceding method further comprising detecting the presence or level of autoantibodies to one or more inflammatory markers, e.g., selected from autoantibodies to calprotectin, β-integrins, lactoferritin, and C-reactive protein, e.g., in accordance with any of Method 3, et seq., including any of Method 3-1, et seq.

1.47. Any preceding method further comprising detecting the presence or level of endogenous antibodies to one or more bacterial antigens, e.g., in accordance with any of Methods 2, et seq.

1.48. Any preceding method wherein the one or more antigens are bound to one or more substrates, wherein the substrates comprise one or more microwell plates, such that where detecting binding to different antigens is desired, the different antigens are on different microwell plates or in different wells of the same microwell plate; e.g. wherein the microwell plate is a flat plate or strip with multiple sample wells, e.g., 6, 24, 96, 384 or 1536 sample wells, e.g., wherein each well of the microwell plate has a volume between 10 nl to 1 ml, for example between 50 μl and 500 μl.

1.49. Any preceding method, wherein the one or more antigens are bound to one or more substrates, comprising the steps of
   a. Affixing the one or more antigens to their respective substrates,
   b. Blocking any uncoated surfaces of the substrates with protein, e.g., bovine serum albumin
   c. Exposing the antigens to the sample to allow formation of antigen-antibody complexes,
   d. Exposing the antigen-antibody complexes thus formed to the labeled antibody to a labeled antibody that binds the immunoglobulin, e.g., IgA, from the patient species, e.g., e.g., horseradish peroxidase (HRP)-anti-IgA antibody
   e. Detecting binding of the labeled antibody to the antigen-antibody complexes,
e.g., wherein the substrate is washed with buffer after each of steps a-d.

1.50. Any foregoing method wherein the labeled antibody is labeled with an enzyme, 1.51. Any foregoing method wherein the labeled antibody is an anti-dog IgA antibody linked to an enzyme.

1.52. Any foregoing method wherein the labeled antibody is an anti-dog IgA antibody linked to an enzyme and the step of detecting binding of the labeled antibody to the antigen-antibody complexes is carried out by (i) contacting the endogenous IgA bound to antigen with the labeled antibody, (ii) providing a substrate for the enzyme, and (iii) measuring the increase in optical density caused by the reaction of the enzyme with the substrate for the enzyme, wherein the increase in optical density correlates with the presence and amount of endogenous IgA bound to antigen.

1.53. The foregoing method wherein the enzyme is horseradish peroxidase (HRP) and the substrate is 3,3',5,5'-Tetramethylbenzidine (TMB).

1.54. Any preceding method comprising classifying the sample from the patient as "consistent" with food sensitivity in the patient or "not consistent" with food sensitivity, wherein the presence and/or level of IgA in the sample that binds to the one or more antigens, separately or in combination, correlates with the presence of food sensitivity in the patient.

1.55. Any preceding method wherein the antigen comprises epitopes from one or more proteins associated with food sensitivity, e.g., selected from one or more of gliadin, zein, amylase inhibitor, TTG2, or TG3.

1.56. Any preceding method wherein the antigen comprises an antigen selected from one or more of the group consisting of SEQ ID NOS: 37-60, 63 and 66.

1.57. Any preceding method comprising classifying the sample from the patient as "consistent" with a food sensitivity in the patient, e.g., to zein or gliadin, or "not consistent" with food sensitivity, wherein the presence and/or level of endogenous IgA in the sample that binds to the one or more antigens comprising comprises epitopes from one or more proteins associated with food sensitivity, e.g., selected from one or more of gliadin, zein, amylase inhibitor, TTG2, or TG3, separately or in combination, correlates with the presence of the food sensitivity condition in the patient.

In another embodiment, the invention provides a method of diagnosing food sensitivity comprising detecting the presence and/or level of the one or more food sensitivity-associated antibodies, separately or in combination, in accordance with any of Method 1, et seq.

For example, in certain embodiments, the invention provides a method of diagnosing food sensitivity, and optionally differentiating food sensitivity from other gastrointestinal conditions, e.g., inflammation (for example, IBD or other inflammatory condition) or gastrointestinal infection, in a canine patient, comprising detecting the presence or level of endogenous IgA to a protein associated with food sensitivity, e.g., selected from gliadin, zein, amylase inhibitor, TTG2, TG3, and combinations thereof, e.g., in accordance with any of Method 1, et seq. and diagnosing food sensitivity when relatively high levels of endogenous IgA to the protein associated with food sensitivity are detected in the serum of the patient.

In certain embodiments, the invention provides a method of treating food sensitivity in a canine patient, comprising diagnosing the patient in accordance with the method of diagnosing food sensitivity in a canine patient as set forth in the preceding paragraph, and when food sensitivity is diagnosed, placing the patient on a grain-free diet or hypoallergenic diet.

In another aspect, the present invention provides a method for monitoring the progression or regression of food sensitivity in companion animals, the method comprising: (a) determining the presence or level of endogenous antibodies to one or more of gliadin, zein, amylase inhibitor, or tissue transglutaminase (e.g. TTG2, or TG3), in a sample from the individual; and (b) determining the presence or severity of food sensitivity in companion animals using a statistical algorithm based upon the presence or level of the endogenous antibodies; e.g. using any of Method 1, et seq.

In a related aspect, the present invention provides a method for monitoring treatment efficacy in companion animals receiving drugs or special diet useful for treating food sensitivity, the method comprising: (a) determining the presence or level of at least one marker selected from the group consisting of endogenous antibodies to gliadin, zein, amylase inhibitor, TTG2, or TG3; and (b) determining the presence or severity of food sensitivity in the individual using a statistical algorithm based upon the presence or level of the at least one marker.

In another embodiment, the invention provides a reagent (Reagent 1) comprising an amino acid sequence from one or more of
   a. An isolated zein peptide comprising one or more sequences from zein that do not contain a protease cleavage site recognized by a protease in canine gastric fluid but not comprising sequences from zein that do contain such a protease cleavage site, e.g.,
      i. wherein the isolated zein peptide comprises one or more sequences selected from SEQ ID NOS 46-57;
      ii. wherein the isolated zein peptide is a fusion peptide comprising two or more sequences selected from SEQ ID NOS 46-57;

iii. wherein the isolated zein peptide is bound to one or more of a label, a purification tag, a solid substrate, or another protein or fragment thereof; for example, wherein the isolated zein peptide is bound to a poly-histidine tag, for example an N-terminal hexa-histadine tag, e.g., optionally comprising one or more solubility enhancing residues;
iv. wherein the isolated zein peptide is bound to an N-terminal hexa-histadine tag of SEQ ID NO: 36; and/or
v. wherein the isolated zein peptide comprises SEQ ID NO: 60.

b. An isolated gliadin peptide comprising one or more sequences from gliadin which do not contain a protease cleavage site recognized by a protease in canine gastric fluid but not comprising sequences from gliadin that contain such a protease cleavage site, e.g.,
i. wherein the isolated gliadin peptide comprises one or more sequences selected from SEQ ID NOS 37-40;
ii. wherein the isolated gliadin peptide is a fusion peptide comprising two or more sequences selected from SEQ ID NOS 37-40;
iii. wherein the isolated zein peptide is bound to one or more of a label, a purification tag, a solid substrate, or another protein or fragment thereof; for example, wherein the isolated zein peptide is bound to a poly-histidine tag, for example an N-terminal hexa-histadine tag, e.g., optionally comprising one or more solubility enhancing residues;
iv. wherein the isolated gliadin peptide is bound to an N-terminal hexa-histadine tag of SEQ ID NO: 36; and/or
v. wherein the isolated gliadin peptide comprises SEQ ID NO: 58.

c. An isolated amylase inhibitor peptide comprising one or more sequences from amylase inhibitor protein which do not contain a protease cleavage site recognized by a protease in canine gastric fluid but not comprising sequences from amylase inhibitor protein that contain such a protease cleavage site, e.g.,
i. wherein the isolated amylase inhibitor peptide comprises one or more sequences selected from SEQ ID NOS 41-45;
ii. wherein the isolated amylase inhibitor peptide is a fusion peptide comprising two or more sequences selected from SEQ ID NOS 41-45;
iii. wherein the isolated amylase inhibitor peptide is bound to one or more of a label, a purification tag, a solid substrate, or another protein or fragment thereof; for example, wherein the isolated amylase inhibitor peptide is bound to a poly-histidine tag, for example an N-terminal hexa-histadine tag, e.g., optionally comprising one or more solubility enhancing residues;
iv. wherein the isolated amylase inhibitor peptide is bound to an N-terminal hexa-histadine tag of SEQ ID NO: 36; and/or
v. wherein the isolated amylase inhibitor peptide comprises SEQ ID NO: 58.

d. An isolated canine tissue transglutaminase peptide comprising one or more antigenic sequences from canine TTG2 or TG3, e.g.,
i. wherein the isolated canine tissue transglutaminase peptide comprises an amino acid sequence encoded by a canine TTG2 nucleic acid sequence amplifiable by primers comprising SEQ ID NO 61 and 62;
ii. wherein the isolated canine tissue transglutaminase peptide comprises an amino acid sequence encoded by a canine TG3 nucleic acid sequence amplifiable by primers comprising SEQ ID NO 64 and 65;
iii. wherein the isolated canine tissue transglutaminase peptide is bound to one or more of a label, a purification tag, a solid substrate, or another protein or fragment thereof; for example, wherein the isolated canine tissue transglutaminase peptide is bound to a poly-histidine tag, for example an N-terminal hexa-histadine tag, e.g., optionally comprising one or more solubility enhancing residues;
iv. wherein the isolated canine tissue transglutaminase peptide is bound to an N-terminal hexa-histadine tag of SEQ ID NO: 36;
v. wherein the isolated canine tissue transglutaminase peptide comprises SEQ ID NO: 63; and/or
vi.
vii.
viii. wherein the isolated canine tissue transglutaminase peptide comprises SEQ ID NO: 66.

In another embodiment the invention provides a diagnostic kit comprising a reagent according to Reagent 1; for example, a diagnostic kit for the detection of endogenous antibodies associated with food sensitivity in a sample from a dog, the kit comprising: (i) one or more reagents of Reagent 1 as described in the preceding two paragraphs; and (ii) means for detection of a complex formed between the reagent and the endogenous antibody. In some embodiments, the diagnostic kit is an ELISA assay. In some embodiments the kit is a strip assay, wherein antigens, e.g., according to Reagent 1, are bound to specific regions of the strip.

In another embodiment the invention provides the use of any reagent as described in Reagent 1 in the manufacture of a kit or component of a kit for carrying out a diagnostic method according to any of Methods 1, et seq.

In another embodiment, the invention provides any reagent described in Reagent 1 as a reagent for use in diagnosis, e.g. diagnosis of food sensitivity in a companion animal patient, e.g., in a diagnostic method according to any of Methods 1, et seq.

In another embodiment, the invention provides a complex comprising an antigen, an endogenous antibody associated with food sensitivity bound to the antigen, and a labeled antibody bound to the endogenous antibody, for example wherein the antigen is a reagent according to Reagent 1, as hereinbefore described.

In another embodiment, the invention provides a bacterial expression construct which expresses an antigen in accordance with any of Reagent 1, e.g., a bacterial expression construct comprising a promoter operably linked to an open reading frame encoding one or more of amino acid sequence from one or more of a. An isolated zein peptide comprising one or more sequences which do not contain a protease cleavage site recognized by a protease in canine gastric fluid but not comprising sequences from zein which do contain such a protease cleavage site, e.g.,
i. wherein the isolated zein peptide comprises one or more sequences selected from SEQ ID NOS 46-57;
ii. wherein the isolated zein peptide is a fusion peptide comprising two or more sequences selected from SEQ ID NOS 46-57;
iii. wherein the isolated zein peptide is bound to one or more of a label, a purification tag, a solid substrate, or another protein or fragment thereof; for example, wherein the isolated zein peptide is bound to a poly-histidine tag, for example an N-terminal hexa-histidine tag, e.g., optionally comprising one or more solubility enhancing residues;
iv. wherein the isolated zein peptide is bound to an N-terminal hexa-histadine tag of SEQ ID NO: 36; and/or
v. wherein the isolated zein peptide comprises SEQ ID NO: 60.
b. An isolated gliadin peptide comprising one or more sequences from gliadin which do not contain a protease cleavage site recognized by a protease in canine gastric fluid but not comprising sequences from gliadin which do contain such a protease cleavage site, e.g.,
i. wherein the isolated gliadin peptide comprises one or more sequences selected from SEQ ID NOS 37-40;
ii. wherein the isolated gliadin peptide is a fusion peptide comprising two or more sequences selected from SEQ ID NOS 37-40;
iii. wherein the isolated zein peptide is bound to one or more of a label, a purification tag, a solid substrate, or another protein or fragment thereof; for example, wherein the isolated zein peptide is bound to a poly-histidine tag, for example an N-terminal hexa-histidine tag, e.g., optionally comprising one or more solubility enhancing residues;
iv. wherein the isolated gliadin peptide is bound to an N-terminal hexa-histadine tag of SEQ ID NO: 36; and/or
v. wherein the isolated gliadin peptide comprises SEQ ID NO: 58.
c. An isolated amylase inhibitor peptide comprising one or more sequences from amylase inhibitor protein which do not contain a protease cleavage site recognized by a protease in canine gastric fluid but not comprising sequences from amylase inhibitor protein which do contain such a protease cleavage site, e.g.,
i. wherein the isolated amylase inhibitor peptide comprises one or more sequences selected from SEQ ID NOS 41-45;
ii. wherein the isolated amylase inhibitor peptide is a fusion peptide comprising two or more sequences selected from SEQ ID NOS 41-45;
iii. wherein the isolated amylase inhibitor peptide is bound to one or more of a label, a purification tag, a solid substrate, or another protein or fragment thereof; for example, wherein the isolated amylase inhibitor peptide is bound to a poly-histidine tag, for example an N-terminal hexa-histidine tag, e.g., optionally comprising one or more solubility enhancing residues;
iv. wherein the isolated amylase inhibitor peptide is bound to an N-terminal hexa-histadine tag of SEQ ID NO: 36; and/or
v. wherein the isolated amylase inhibitor peptide comprises SEQ ID NO: 58.
d. An isolated canine tissue transglutaminase peptide comprising one or more antigenic sequences from canine TTG2 or TG3, e.g.,
i. wherein the isolated canine tissue transglutaminase peptide comprises an amino acid sequence encoded by a canine TTG2 nucleic acid sequence amplifiable by primers comprising SEQ ID NO 61 and 62;
ii. wherein the isolated canine tissue transglutaminase peptide comprises an amino acid sequence encoded by a canine TG3 nucleic acid sequence amplifiable by primers comprising SEQ ID NO 64 and 65;
iii. wherein the isolated canine tissue transglutaminase peptide is bound to one or more of a label, a purification tag, a solid substrate, or another protein or fragment thereof; for example, wherein the isolated canine tissue transglutaminase peptide is bound to a poly-histidine tag, for example an N-terminal hexa-histadine tag, e.g., optionally comprising one or more solubility enhancing residues;
iv. wherein the isolated canine tissue transglutaminase peptide is bound to an N-terminal hexa-histadine tag of SEQ ID NO: 36;
v. wherein the isolated canine tissue transglutaminase peptide comprises SEQ ID NO: 63; and/or
vi. wherein the isolated canine tissue transglutaminase peptide comprises SEQ ID NO: 66.

In another embodiment, the invention provides a bacterial cell line, for example an *E. coli* line, comprising the bacterial expression construct of the preceding paragraph.

XI. Methods of Detecting IBD Markers in Companion Animals

In another embodiment, the invention provides a method (Method 2) for detecting the presence and/or level of one or more endogenous antibodies associated with inflammation in a sample (e.g., a sample is selected from one or more of whole blood, serum, plasma, stool, and intestinal tissue) obtained from a companion animal patient, e.g., a dog or a cat, wherein the endogenous antibodies are selected from one or more of endogenous antibodies to polymorphonuclear leukocytes (PMNs or granulocytes, including neutrophil granulocytes) and endogenous antibodies to microbes found in the gut;
and optionally further selected from autoantibodies to a calprotectin, autoantibodies to a β-integrin, autoantibodies to a lactoferritin, autoantibodies to a C-reactive protein, and/or optionally further selected from endogenous antibodies to one or more proteins associated with food sensitivity, e.g., selected from one or more of gliadin, zein, amylase inhibitor, TTG2, or TG3.
comprising
contacting one or more antigens with said sample, wherein the one or more anti s a specific for the endogenous antibody of interest, and wherein the one or more antigens are bound to a substrate or detectable label, and
detecting the binding of said one or more one or more endogenous antibodies associated with inflammation to the one or more antigens,
and optionally, classifying said sample as an inflammation sample or non-inflammation sample, wherein the presence or level of the one or one or more endogenous antibodies associated with inflammation, separately or in combination, correlates with the presence of inflammation.
For example
2.1. Method 2 which is a method for detecting the presence and/or level of one or more endogenous antibodies associated with an inflammatory condition, for example, endogenous antibodies associated with inflammatory bowel disease (IBD-associated antibodies), [for example selected from endogenous antibodies to polymorphonuclear leukocytes (PMNs or granulocytes, including neutrophil granulocytes) and/or endogenous antibodies to microbes found in the gut] in a sample obtained from a patient, for example a companion animal patient, e.g., a dog or cat, for example wherein the sample is selected from one or more of whole blood, serum, plasma, stool, and intestinal tissue; the method comprising the steps of a. Contacting one or more antigens bound to a substrate or detectable label with said sample and detecting the binding of said one or more IBD-associated antibodies and/or one or more food sensitivity associated antibodies to said one or more antigens; and/or b. Contacting a labeled antibody with said sample, wherein the labeled antibody specifically binds immunoglobulin from the species of the companion animal, and detecting binding of the labeled antibody to said one or more IBD-associated antibodies;

c. Optionally, classifying said sample as an IBD sample or non-IBD sample, or food sensitivity sample or non-food sensitivity sample, wherein the presence or level of the one or more IBD-associated antibodies, separately or in combination, correlates with the presence of IBD and the presence of level of the one or more food sensitivity-associated antibodies, separately or in combination, correlates with food sensitivity.

2.2. Any preceding method comprising the step of using a labeled antibody that specifically binds immunoglobulin from the species of the patient to detect the one or more one or more endogenous antibodies associated with inflammation bound to the antigen.

2.3. Any preceding method, wherein the companion animal patient is a cat, a dog, or a horse, for example a dog.

2.4. Any preceding method wherein the sample is whole blood, serum or plasma.

2.5. Any preceding method wherein the presence, severity and/or type of inflammation in the patient is associated with antibody class switching from IgG to IgA, for example such that the proportion of one or more endogenous antibodies associated with inflammation is higher in healthy animals and lower in animals with inflammation, or for example such that the proportion of one or more endogenous antibodies associated with food sensitivity is higher in healthy animals and lower in animals with inflammation.

2.6. Any preceding method wherein one or more endogenous antibodies associated with inflammation or food sensitivity are IgA antibodies.

2.7. Any preceding method which is an immunoassay selected from an enzyme-linked immunosorbent assay (ELISA), an immunohistochemical assay, and an immunofluorescence assay.

2.8. Any preceding method wherein the patient is a dog or cat, wherein the inflammation is inflammation associated with IBD, and wherein the endogenous antibodies comprise one or more IBD-associated antibodies selected from antibodies to polymorphonuclear leukocytes (PMNs or granulocytes, including neutrophil granulocytes) and/or endogenous antibodies to microbes found in the gut.

2.9. Any preceding method wherein the endogenous antibodies comprise one or more IBD-associated antibodies, wherein the one or more IBD-associated antibodies are selected from the group consisting of an anti-PMN antibody, anti-yeast antibody, antimicrobial antibody, and combinations thereof in said sample.

2.10. Any preceding method wherein the endogenous antibodies comprise one or more IBD-associated antibodies, wherein the one or more IBD-associated antibodies comprise one or more of
a) anti-PMN antibody selected from the group consisting of an anti-PMN antibody (APMNA), perinuclear anti-PMN antibody (pAPMNA), and combinations thereof;
b) anti-yeast antibody selected from the group consisting of anti-yeast immunoglobulin A (AYA-IgA), anti-yeast immunoglobulin G (AYA-IgG), anti-yeast immunoglobulin M (AYA-IgM) and combinations thereof;
c) antimicrobial antibody selected from the group consisting of an anti-outer membrane protein C (ACA) antibody, anti-flagellin antibody (AFA), and combinations thereof.

2.11. Any preceding method wherein the endogenous antibodies comprise one or more IBD-associated antibodies, wherein the one or more IBD-associated antibodies comprise anti-flagellin antibody (AFA) which binds to one or more epitopes on a bacterial flagellin encoded by a gene which is capable of being amplified by a first primer selected from one or more of SEQ ID NOS 1, 3, 5, and 7 and a second primer selected from one or more of SEQ ID NOS 2, 4, 6, and 8.

2.12. Any preceding method wherein the endogenous antibodies comprise one or more IBD-associated antibodies, wherein the one or more IBD-associated antibodies comprise anti-flagellin antibody (AFA) which binds to one or more epitopes on a bacterial flagellin protein or fragment thereof comprising at least 10 (e.g., at least 20, e.g., at least 30) consecutive amino acids in a sequence selected from SEQ ID NOS 9-13.

2.13. Any preceding method wherein the endogenous antibodies comprise one or more IBD-associated antibodies, wherein the one or more IBD-associated antibodies comprise anti-outer membrane protein C antibody (ACA) which binds to one or more epitopes on a bacterial outer membrane protein C encoded by a gene which is capable of being amplified by primers corresponding to SEQ ID NOS 14 and 15.

2.14. Any preceding method wherein the endogenous antibodies comprise one or more IBD-associated antibodies, wherein the one or more IBD-associated antibodies comprise anti-outer membrane protein C antibody (ACA) which binds to one or more epitopes on a bacterial outer membrane protein C or fragment thereof comprising at least 10 (e.g., at least 20, e.g., at least 30) consecutive amino acids in a sequence selected from SEQ ID NOS 16, 17, and 18.

2.15. Any preceding method wherein the endogenous antibodies comprise one or more IBD-associated antibodies, wherein said the one or more IBD-associated antibodies are selected from APMNA, pAPMNA, AYA-IgA, AYA-IgG, ACA, or AFA.

2.16. Any preceding method wherein the companion animal patient exhibits symptoms of gastrointestinal disorder, for example one or more of the following symptoms:
a. Blood in the stool;
b. Elevated levels of fecal calprotectin;
c. Elevated levels of fecal lactoferrin;
d. Anemia;
e. Diarrhea;
f. Vomiting
g. Inappetence; or
h. Significant recent weight loss.

2.17. Any preceding method further comprising determining the presence or level of calprotectin or lactoferrin in feces, for example, determining the presence or level of calprotectin in feces, e.g., wherein the level of calprotectin is correlated with inflammation in the bowel.

2.18. Any preceding method wherein the companion animal patient is a purebred cats or a pure or mixed breed dog of a breed selected from German Shepherds, Yorkshire Terriers, Cocker Spaniels, Basenjis, Soft-coated Wheaten Terriers, and Shar-Peis, e.g., wherein the breed of the dog is taken into account when classifying the sample.

2.19. Any preceding method wherein the companion animal patient is at greater than two, e.g., greater than 5 years of age.

2.20. Any preceding method wherein said patient has not responded to treatment with antibiotics.

2.21. Any preceding method wherein the presence, severity and/or type of IBD in the companion animal patient is associated with antibody class switching from IgG to IgA, for example, wherein the proportion of IgG antibodies to an bacterial antigen, e.g., an OmpC or flagellin antigen, e.g., relative to IgA antibodies to the same antigen is higher in healthy animals and lower in animals with IBD.

2.22. Any preceding method further comprising applying a statistical algorithm to said presence or level of one or more IBD-associated antibodies to obtain a diagnostic or prognostic profile for said patient, wherein the presence or relative levels of particular IBD-associated antibodies correlates with the presence, type or severity of IBD.

2.23. Any preceding method further comprising applying a statistical algorithm to said the presence or level of one or more IBD-associated antibodies in combination with the presence or level of one or more of fecal calprotectin or fecal lactoferrin to obtain a diagnostic or prognostic profile for said patient, wherein the presence or relative levels of particular IBD-associated antibodies in combination with the presence or level of one or more of fecal calprotectin or fecal lactoferrin correlates with the presence, type or severity of IBD.

2.24. Any preceding method wherein said patient is diagnosed with lymphoplasmacytic enteritis (LPE), eosinophilic gastroenteritis (EGE) or granulomatous enteritis (GE).

2.25. Any preceding method wherein the one or more IBD-associated antibodies are selected from the group consisting of an anti-PMN antibody, anti-yeast antibody, antimicrobial antibody, and combinations thereof in said sample.

2.26. Any preceding method, wherein the one or more IBD-associated antibodies comprise anti-PMN antibody selected from the group consisting of an anti-PMN antibody (APMNA), perinuclear anti-PMN antibody (pAPMNA), and combinations thereof.

2.27. Any preceding method wherein the one or more IBD-associated antibodies comprise anti-yeast antibody selected from the group consisting of anti-yeast immunoglobulin A (AYA-IgA), anti-yeast immunoglobulin G (AYA-IgG), anti-yeast immunoglobulin M (AYA-IgM) and combinations thereof.

2.28. Any preceding method, wherein the one or more IBD-associated antibodies comprise antimicrobial antibody selected from the group consisting of an anti-outer membrane protein C (ACA) antibody, anti-flagellin antibody (AFA), and combinations thereof.

2.29. Any preceding method wherein the one or more IBD-associated antibodies comprise anti-flagellin antibody (AFA) which binds to one or more epitopes on a bacterial flagellin encoded by a gene which is capable of being amplified by a first primer selected from one or more of SEQ ID NOS 1, 3, 5, and 7 and a second primer selected from one or more of SEQ ID NOS 2, 4, 6, and 8.

2.30. Any preceding method wherein the one or more IBD-associated antibodies comprise anti-flagellin antibody (AFA) which binds to one or more epitopes on a bacterial flagellin protein or fragment thereof comprising at least 10 (e.g., at least 20, e.g., at least 30) consecutive amino acids in a sequence selected from SEQ ID NOS 9-13.

2.31. Any preceding method, wherein the one or more IBD-associated antibodies comprise anti-outer membrane protein C antibody (ACA) which binds to one or more epitopes on a bacterial outer membrane protein C encoded by a gene which is capable of being amplified by primers corresponding to SEQ ID NOS 14 and 15.

2.32. Any preceding method wherein the one or more IBD-associated antibodies comprise antibodies to antigens from bacteria from the gut of the companion animal patient species.

2.33. Any preceding method wherein the one or more IBD-associated antibodies comprise antibodies to antigens from Gram negative bacteria from the gut of the companion animal patient species.

2.34. Any preceding method wherein the one or more IBD-associated antibodies comprise antibodies to antigens from bacteria from the gut of the companion animal patient species, wherein the bacteria is of a species selected from one or more of *Pseudomonas* (*Pseudomonas aeruginosa, Pseudomonas monteilii, Pseudomonas lundensis/taetrolens, Pseudomonas mosselii, Pseudomonas mucidolens/synxantha, Pseudomonas fluorescens* A, *Pseudomonas hibiscicola, Pseudomonas asplenii/putida, Stenotrophomonas maltophilia, Brevundimonas diminuta, Stenotrophomonas rhizophila*), *Escherichia* (*Escherichia coli, Escherichia fergusonii*), *Proteus* (*Proteus mirabilis*), *Enterobacter* (*Enterobacter* hormaechei), *Acinetobacter* (*Acinetobacter genomospecies* 10, *Acinetobacter genomospecies* 11), *Sphingobacterium* (*Sphingobacterium spiritivorum*), and *Klebsiella* (*Klebsiella pneumonia*); *Enterococcus* (*Enterococcus faecium, Enterococcus faecalis*), and *Lactobacillus* (*Lactobacillus johnsonii*); for example, wherein the bacteria includes at least one of a *Pseudomonas* species.

2.35. Any preceding method, wherein the one or more IBD-associated antibodies comprise anti-outer membrane protein C antibody (ACA) which binds to one or more epitopes on a bacterial outer membrane protein C or fragment thereof comprising at least 10 (e.g., at least 20, e.g., at least 30) consecutive amino acids in a sequence selected from SEQ ID NOS 16, 17, and 18.

2.36. Any preceding method, wherein said the one or more IBD-associated antibodies are selected from APMNA, pAPMNA, AYA-IgA, AYA-IgG, ACA, or AFA.

2.37. Any preceding method, wherein said the one or more IBD-associated antibodies are IgA antibodies.

2.38. Any preceding method, wherein the immunoassay to detect the presence or level of the one or more IBD-associated antibodies is an enzyme-linked immunosorbent assay (ELISA).

2.39. Any preceding method, wherein the immunoassay to detect the presence or level of the one or more IBD-associated antibodies is an immunohistochemical assay.

2.40. Any preceding method, wherein the immunoassay to detect the presence or level of the one or more IBD-associated antibodies is an immunofluorescence assay.

2.41. Any preceding method, wherein said sample is selected from the group consisting of serum, plasma, and whole blood.

2.42. Any preceding method, wherein the step of classifying said sample as an IBD sample or non-IBD sample is carried out using a statistical algorithm selected from the group consisting of a classification and regression tree, boosted tree, neural network, random forest, support vector machine, general chi-squared automatic interaction detector model, interactive tree, multiadaptive regression spline, machine learning classifier, and combinations thereof.

2.43. Any preceding method, comprising: (a) determining the presence or level of at least one marker selected from the group consisting of an anti-polymorphonuclear leukocyte (PMN) antibody, antimicrobial antibody, calprotectin and combinations thereof in the sample; and (b) classifying the sample as an IBD sample or non-IBD sample using a statistical algorithm based upon the presence or level of at least one marker.

2.44. Any preceding method comprising detecting a complex comprising an IBD-associated antibody and an antigen, using a labeled antibody that binds to the IBD-associated antibody.

2.45. Any preceding method wherein the one or more antigens bound to a substrate or detectable label comprise any of Reagent 1, as hereinafter described.

2.46. Any preceding method wherein the one or more antigens bound to a substrate comprise a bacterial outer membrane protein C or fragment thereof comprising at least 10 (e.g., at least 20, e.g., at least 30) consecutive amino acids in a sequence selected from SEQ ID NOS 16, 17, and 18, optionally bound to a poly-histidine tag, for example a N-terminal hexa-histadine tag, e.g., optionally comprising one or more solubility enhancing residues, e.g., an N-terminal sequence of SEQ ID NO 33 or SEQ ID NO 36, for example an antigen of SEQ ID NO 35.

2.47. Any preceding method wherein the one or more antigens bound to a substrate comprise a bacterial flagellin protein or fragment thereof comprising at least 10 (e.g., at least 20, e.g., at least 30) consecutive amino acids in a sequence selected from SEQ ID NOS 9-13, optionally bound to a poly-histidine tag, for example a N-terminal hexa-histadine tag, e.g., optionally comprising one or more solubility enhancing residues, e.g., an N-terminal sequence of SEQ ID NO 33 or SEQ ID NO 36, for example, an antigen of SEQ ID NO 34.

2.48. Any preceding method further comprising detecting the presence or level of autoantibodies to one or more inflammatory markers, e.g., selected from autoantibodies to calprotectin, β-integrins, lactoferritin, and C-reactive protein, e.g., in accordance with any of Methods 3, et seq., including any of Methods 3-1, et seq.

2.49. Any preceding method further comprising detecting the presence or level of endogenous antibodies to one or more of endogenous antibodies to gliadin, zein, amylase inhibitor, TTG2, or TG3; e.g., in accordance with any of Methods 1, et seq.

2.50. Any preceding method wherein the one or more antigens bound to a substrate or detectable label comprise an antigen of SEQ ID NO 19 and an antigen of SEQ ID NO 35.

2.51. Any preceding method wherein the one or more antigens are bound to one or more substrates, wherein the substrates comprise one or more microwell plates, such that where detecting binding to different antigens is desired, the different antigens are on different microwell plates or in different wells of the same microwell plate; e.g. wherein the microwell plate is a flat plate or strip with multiple sample wells, e.g., 6, 24, 96, 384 or 1536 sample wells, e.g., wherein each well of the microwell plate has a volume between 10 nl to 1 ml, for example between 50 µl and 500 µl.

2.52. Any preceding method, wherein the one or more antigens are bound to one or more substrates, comprising the steps of a. Affixing the one or more antigens to their respective substrates,
  b. Blocking any uncoated surfaces of the substrates with protein, e.g., bovine serum albumin
  c. Exposing the antigens to the sample to allow formation of antigen-antibody complexes,
  d. Exposing the antigen-antibody complexes thus formed to the labeled antibody to a labeled antibody that binds the immunoglobulin, e.g., IgA, from the patient species, e.g., e.g., horseradish peroxidase (HRP)-anti-IgA antibody
  e. Detecting binding of the labeled antibody to the antigen-antibody complexes, e.g., wherein the substrate is washed with buffer after each of steps a-d.

2.53. Any preceding method comprising classifying the sample from the patient as "consistent" with an inflammatory condition in the patient, e.g., inflammatory bowel disease (IBD), or "not consistent" with the inflammatory condition, wherein the presence and/or level of IgA in the sample that binds to the one or more antigens, separately or in combination, correlates with the presence of the inflammatory condition in the patient.

2.54. Any preceding method wherein the antigen comprises epitopes from one or more proteins associated with food sensitivity, e.g., selected from one or more of gliadin, zein, amylase inhibitor, TTG2, or TG3.

2.55. Any preceding method wherein the antigen comprises an antigen selected from one or more of SEQ ID NOS: 38-56.

2.56. Any foregoing method wherein the labeled antibody is labeled with an enzyme, 2.57. Any foregoing method wherein the labeled antibody is an anti-dog IgA antibody linked to an enzyme.

2.58. Any foregoing method wherein the labeled antibody is an anti-dog IgA antibody linked to an enzyme and the step of detecting binding of the labeled antibody to the antigen-antibody complexes is carried out by (i) contacting the endogenous IgA bound to antigen with the labeled antibody, (ii) providing a substrate for the enzyme, and (iii) measuring the increase in optical density caused by the reaction of the enzyme with the substrate for the enzyme, wherein the increase in optical density correlates with the presence and amount of endogenous IgA bound to antigen.

2.59. The foregoing method wherein the enzyme is horseradish peroxidase (HRP) and the substrate is 3,3',5,5'-Tetramethylbenzidine (TMB).

2.60. Any preceding method comprising classifying the sample from the patient as "consistent" with a food sensitivity in the patient, e.g., to zein or gliadin, or "not consistent" with food sensitivity, wherein the presence and/or level of IgA in the sample that binds to the one or more antigens comprising comprises epitopes from one or more proteins associated with food sensitivity, e.g., selected from one or more of gliadin, zein, amylase inhibitor, TTG2, or TG3, separately or in combination, correlates with the presence of the food sensitivity condition in the patient.

In another embodiment, the invention provides a method of diagnosing IBD comprising detecting the presence and/or level of the one or more IBD-associated antibodies, separately or in combination, in accordance with any of Method 2, et seq.

In another embodiment, the invention provides a method of classifying whether companion animals are associated with a clinical subtype of IBD, the method comprising: (a)

determining the presence or level of at least one marker selected from the group consisting of an anti-PMN antibody, antimicrobial antibody, calprotectin and combinations thereof in the sample; and (b) classifying the sample lymphoplasmacytic (LPE) IBD, eosinophilic gastroenterocolitis (EGE) IBD or granulomatous (GE) IBD or non-IBD sample using a statistical algorithm based upon the presence or level of the at least one marker; e.g. using any of Method 2, et seq.

In another aspect, the present invention provides a method for monitoring the progression or regression of IBD in companion animals, the method comprising: (a) determining the presence or level of at least one marker selected from the group consisting of an anti-PMN antibody, antimicrobial antibody, calprotectin and combinations thereof in a sample from the individual; and (b) determining the presence or severity of IBD in companion animals using a statistical algorithm based upon the presence or level of the at least one marker; e.g. using any of Method 2, et seq.

In a related aspect, the present invention provides a method for monitoring drug efficacy in companion animals receiving drugs useful for treating IBD, the method comprising: (a) determining the presence or level of at least one marker selected from the group consisting of an anti-PMN antibody, antimicrobial antibody, calprotectin and combinations thereof in a sample from the individual; and (b) determining the presence or severity of IBD in the individual using a statistical algorithm based upon the presence or level of the at least one marker.

In another embodiment, the invention provides a reagent (Reagent 2) comprising an amino acid sequence from one or more of a. An isolated peptide which is a bacterial flagellin protein or antigenic fragment thereof, from a bacteria prevalent in the companion animal patient species, e.g., comprising at least 10 (e.g., at least 20, e.g., at least 30) consecutive amino acids in a sequence selected from SEQ ID NOS 9-13, wherein the bacterial flagellin protein or antigenic fragment thereof is bound to one or more of a label, a purification tag, a solid substrate, or another bacterial flagellin protein or fragment thereof; for example, wherein the bacterial flagellin protein or fragment thereof is bound to a poly-histidine tag, for example a N-terminal hexa-histidine tag, e.g., optionally comprising one or more solubility enhancing residues, e.g., an N-terminal sequence of SEQ ID No 33 or SEQ ID NO 36, for example a flagellin fusion protein of SEQ ID NO 34; and b. An isolated peptide which is a bacterial outer membrane protein C or antigenic fragment thereof, e.g., comprising at least 10 (e.g., at least 20, e.g., at least 30) consecutive amino acids in a sequence selected from SEQ ID NOS 16, 17, and 18, wherein the bacterial outer membrane protein C or fragment thereof is bound to one or more of a label, a purification tag, solid substrate, or another bacterial outer membrane protein C or fragment thereof; for example, wherein the bacterial outer membrane protein C or fragment thereof is bound to a poly-histidine tag, for example a N-terminal hexa-histidine tag, e.g., optionally comprising one or more solubility enhancing residues, e.g., an N-terminal sequence of SEQ ID NO 33 or SEQ ID NO 36, for example an OmpC fusion protein of SEQ ID NO 35.

For example, the invention provides Reagent 2 in one aspect wherein the reagent is a heteroantigen, e.g. wherein the reagent comprises sequences from at least two different sources, e.g., (i) from at least two different bacterial flagellin proteins or antigenic fragments thereof, e.g., as described herein, e.g., each from a bacteria prevalent in the companion animal patient species, e.g., comprising at least 10 (e.g., at least 20, e.g., at least 30) consecutive amino acids in a sequence selected from SEQ ID NOS 9-13, wherein the bacterial flagellin protein or antigenic fragment thereof is bound to one or more of a label, a purification tag, a solid substrate, or another bacterial flagellin protein or fragment thereof; for example, wherein the bacterial flagellin protein or fragment thereof is bound to a poly-histidine tag, for example a N-terminal hexa-histidine tag, e.g., optionally comprising one or more solubility enhancing residues, e.g., an N-terminal sequence of SEQ ID NO 33 or SEQ ID NO 36;

(ii) from at least two different bacterial outer membrane protein Cs or antigenic fragments thereof, e.g., as described herein, e.g., each from a bacterial outer membrane protein C or antigenic fragment thereof, e.g., comprising at least 10 (e.g., at least 20, e.g., at least 30) consecutive amino acids in a sequence selected from SEQ ID NOS 16, 17, and 18, wherein the bacterial outer membrane protein C or fragment thereof is bound to one or more of a label, a purification tag, solid substrate, or another bacterial outer membrane protein C or fragment thereof; for example, wherein the bacterial outer membrane protein C or fragment thereof is bound to a poly-histidine tag, for example a N-terminal hexa-histidine tag, e.g., optionally comprising one or more solubility enhancing residues, e.g., an N-terminal sequence of SEQ ID NO 33 or SEQ ID NO 36; and/or (iii) from at least one such bacterial flagellin protein or antigenic fragment thereof, and at least one such bacterial outer membrane protein Cs or antigenic fragment thereof.

For example, in some embodiments the invention provides Reagent 2 in an aspect wherein the bacterial flagellin protein or bacterial outer membrane protein C is from a species selected from one or more of *Pseudomonas* (*Pseudomonas aeruginosa, Pseudomonas monteilii, Pseudomonas lundensis/taetrolens, Pseudomonas mosselii, Pseudomonas mucidolens/synxantha, Pseudomonas fluorescens* A, *Pseudomonas hibiscicola, Pseudomonas asplenii/ putida, Stenotrophomonas maltophilia, Brevundimonas diminuta, Stenotrophomonas rhizophila*), *Escherichia* (*Escherichia coli, Escherichia fergusonii*), *Proteus* (*Proteus mirabilis*), *Enterobacter* (*Enterobacter hormaechei*), *Acinetobacter* (*Acinetobacter genomospecies* 10, *Acinetobacter genomospecies* 11), *Sphingobacterium* (*Sphingobacterium spiritivorum*), and *Klebsiella* (*Klebsiella pneumonia*); *Enterococcus* (*Enterococcus faecium, Enterococcus faecalis*), and *Lactobacillus* (*Lactobacillus johnsonii*); for example, wherein the bacterial flagellin protein or bacterial outer membrane protein C is from a *Pseudomonas* species.

In another embodiment the invention provides a diagnostic kit comprising a reagent according to Reagent 2; for example, a diagnostic kit for the detection of IBD-associated antibodies in a sample from a dog, the kit comprising: (i) one or more reagents of Reagent 1 as described in the preceding two paragraphs; and (ii) means for detection of a complex formed between the reagent and an IBD-associated antibody. In some embodiments, the diagnostic kit is an ELISA assay. In some embodiments the kit is a strip assay, wherein antigens, e.g., according to Reagent 2, are bound to specific regions of the strip.

In another embodiment the invention provides the use of any reagent as described in Reagent 2 in the manufacture of a kit or component of a kit for carrying out a diagnostic method according to any of Methods 2, et seq.

In another embodiment, the invention provides any reagent described in Reagent 2 as a reagent for use in diagnosis, e.g. diagnosis of IBD in a companion animal patient, e.g., in a diagnostic method according to any of Methods 2, et seq.

In another embodiment, the invention provides a complex comprising an antigen, an endogenous IBD-associated antibody bound to the antigen, and a labeled antibody bound to the IBD-associated antibody, for example wherein the antigen is a reagent according to Reagent 2, as hereinbefore described.

In another embodiment, the invention provides a bacterial expression construct which expresses an antigen in accordance with any of Reagent 2, e.g., a bacterial expression construct comprising a promoter operably linked to an open reading frame encoding one or more of a. a bacterial outer membrane protein C or fragment thereof comprising at least 10 (e.g., at least 20, e.g., at least 30) consecutive amino acids in a sequence selected from SEQ ID NOS 16, 17, and 18; wherein the promoter and the open reading frame are heterologous to one another, i.e., wherein the promoter and the open reading frame are not operably linked in nature; or b. a bacterial flagellin protein or fragment thereof comprising at least 10 (e.g., at least 20, e.g., at least 30) consecutive amino acids in a sequence selected from SEQ ID NOS 9-13; wherein the promoter and the open reading frame are heterologous to one another, i.e., wherein the promoter and the open reading frame are not operably linked in nature; or c. a bacterial flagellin protein or fragment thereof comprising at least 10 (e.g., at least 20, e.g., at least 30) consecutive amino acids in a sequence selected from SEQ ID NOS 9-13, bound to another bacterial flagellin protein or fragment thereof and/or to a poly-histidine tag, for example a N-terminal hexa-histidine tag, e.g., optionally comprising one or more solubility enhancing residues, e.g., an N-terminal sequence of SEQ ID No 33 or SEQ ID NO 36, for example a flagellin fusion protein of SEQ ID NO 34; or d. a bacterial outer membrane protein C or antigenic fragment thereof, e.g., comprising at least 10 (e.g., at least 20, e.g., at least 30) consecutive amino acids in a sequence selected from SEQ ID NOS 16, 17, and 18, wherein the bacterial outer membrane protein C or fragment thereof is bound to another bacterial outer membrane protein C or fragment thereof and/or to a poly-histidine tag, for example a N-terminal hexa-histidine tag, e.g., optionally comprising one or more solubility enhancing residues, e.g., an N-terminal sequence of SEQ ID NO 33 or SEQ ID NO 36, for example an OmpC fusion protein of SEQ ID NO 35.

In another embodiment, the invention provides a bacterial cell line, for example an *E. coli* line, comprising the bacterial expression construct of the preceding paragraph.

XII. Diagnosing Inflammatory Conditions in Mammals

In one embodiment, the invention provides a method (Method 3) for detecting the presence and/or level of one or more inflammation-associated autoantibodies, e.g., endogenous antibodies to an inflammatory marker, e.g., selected from autoantibodies to calprotectin, autoantibodies to β-integrins, autoantibodies, autoantibodies to lactoferritin, and autoantibodies to C-reactive protein, in a sample obtained from a companion animal patient, wherein the sample is selected from antibody-containing physiologic materials, e.g., selected from one or more of whole blood, saliva, mucus secretions, serum, plasma, stool, and intestinal tissue; said method comprising the steps of a. Contacting one or more antigens bound to a substrate or detectable label with said sample and detecting the binding of said one or more inflammation-associated autoantibodies to said one or more antigens; and/or b. Contacting a labeled antibody with said sample, wherein the labeled antibody specifically binds immunoglobulin from the species of the patient, and detecting binding of the labeled antibody to said one or more inflammation-associated autoantibodies; and c. Optionally, classifying said sample as an inflammation sample or non-inflammation sample, wherein the presence or level of the one or more inflammation-associated autoantibodies, separately or in combination, correlates with the presence of an inflammatory condition.

3.1. Method 3 wherein the patient is selected from a cat, a dog, or a horse.

3.2. Method 3 wherein the patient is a dog.

3.3. Any preceding method wherein the patient exhibits clinical symptoms of IBD, e.g., one or more of the following symptoms:
a. Blood in the stool;
b. Elevated levels of fecal calprotectin;
c. Elevated levels of fecal lactoferrin;
d. Anemia;
e. Diarrhea;
f. Vomiting;
g. Inappetence;
h. Fever;
i. Persistent pain; or
j. Significant recent weight loss.

3.4. Any preceding method wherein the inflammation-associated autoantibody is selected from autoantibodies to calprotectin, autoantibodies to β-integrins, autoantibodies to lactoferritin, autoantibodies to C-reactive protein, and combinations thereof, for example, an autoantibody to calprotectin and/or to a β-integrin, for example, wherein the inflammation-associated autoantibody is an autoantibody to calprotectin or wherein the inflammation-associated autoantibody is an autoantibody to a β-integrin.

3.5. Any preceding method wherein the inflammation associated autoantibody is an IgA.

3.6. Any preceding method wherein the inflammation associated autoantibody is a secretory IgA.

3.7. Any preceding method wherein the inflammation associated autoantibody is a serum IgA.

3.8. Any preceding method wherein the sample comprises saliva.

3.9. Any preceding method wherein the sample comprises whole blood.

3.10. Any preceding method wherein the presence of the inflammation associated autoantibody indicates a chronic inflammatory condition.

3.11. Any preceding method wherein the presence of the inflammation associated autoantibody indicates IBD.

3.12. Any preceding method used in conjunction with any of Methods 1, et seq.

3.13. Any preceding method wherein the presence, severity and/or type of an inflammatory condition in the patient is associated with antibody class switching from IgG to IgA, for example, wherein the proportion of IgG autoantibodies relative to IgA autoantibodies to the same antigen is higher in healthy animals and lower in animals with an inflammatory condition.

3.14. Any preceding method further comprising applying a statistical algorithm to said presence or level of one or more inflammation-associated autoantibodies to obtain a diagnostic or prognostic profile for said patient, wherein the presence or relative levels of particular inflammation-associated autoantibodies correlates with the presence, type or severity of inflammation.

3.15. Any preceding method wherein the antigen bound to a substrate or a detectable label is
   a. an isolated peptide, which comprises a calprotectin or antigenic fragment thereof, comprising at least 10 (e.g., at least 20, e.g., at least 30) consecutive amino acids in a sequence from a wild type calprotectin, e.g. from a companion animal calprotectin, for example comprising any of SEQ ID NO: 19, SEQ ID NO: 20, SEQ ID NO: 21, SEQ ID NO: 22 or any combination thereof, wherein the calprotectin or antigenic fragment thereof is bound to one or more of a label, a purification tag, a solid substrate, or another protein or fragment thereof, for example another calprotectin or fragment thereof or an integrin or fragment thereof; for example, wherein the calprotectin or antigenic fragment thereof is bound to a poly-histidine tag, for example, a N-terminal hexa-histadine tag, for example an N-terminal sequence of SEQ ID NO 36; and/or
   b. An isolated peptide which is an integrin or antigenic fragment thereof, comprising at least 10 (e.g., at least 20, e.g., at least 30) consecutive amino acids in a sequence from a wild type integrin, e.g. from a companion animal integrin, for example, any of SEQ ID NO: 29, SEQ ID NO: 30, SEQ ID NO: 31, SEQ ID NO: 32, or any combination thereof, wherein the integrin or antigenic fragment thereof is bound to one or more of a label, a purification tag, a solid substrate, or another protein or fragment thereof, for example, a calprotectin or fragment thereof or another integrin or fragment thereof; for example, wherein the integrin or antigenic fragment thereof is bound to a poly-histidine tag, for example a N-terminal hexa-histadine tag, for example an N-terminal sequence of SEQ ID NO 36.

3.16. Any preceding method wherein the antigen bound to a substrate or a detectable label is a fusion protein comprising a calprotectin S100A8 monomer region and a calprotectin S100A9 monomer region, wherein the regions are linked by a linker sequence.

3.17. Any preceding method wherein the antigen bound to a substrate or a detectable label is a fusion peptide comprising one or more antigenic fragments of an integrin α (alpha) subunit and one or more antigenic fragments of an integrin β (beta) subunit, wherein the integrin α (alpha) subunit region and the integrin β (beta) subunit region are linked by a linker sequence, for example a $(Gly_4Ser)_n$ linker, where n is 2, 3 or 4, e.g. 3.

3.18. Any preceding method further comprising applying a statistical algorithm to said the presence or level of one or more inflammation-associated autoantibodies in combination with the presence or level of one or more one or more additional IBD-associated endogenous antibodies, e.g., selected from the group consisting of an anti-PMN antibody, anti-yeast antibody, antimicrobial antibody, and combinations thereof in the sample.

3.19. Any preceding method wherein said patient is diagnosed with lymphoplasmacytic enteritis (LPE), eosinophilic gastroenteritis (EGE) or granulomatous enteritis (GE).

3.20. Any preceding method wherein the sample is additionally assayed for the presence or level of one or more additional IBD-associated endogenous antibodies are selected from the group consisting of an anti-PMN antibody, anti-yeast antibody, antimicrobial antibody, and combinations thereof in said sample.

3.21. The foregoing method wherein the one or more additional IBD-associated endogenous antibodies comprise
   a. anti-PMN antibody selected from the group consisting of an anti-PMN antibody (APMNA), perinuclear anti-PMN antibody (pAPMNA), and combinations thereof; and/or
   b. anti-yeast antibody selected from the group consisting of anti-yeast immunoglobulin A (AYA-IgA), anti-yeast immunoglobulin G (AYA-IgG), anti-yeast immunoglobulin M (AYA-IgM) and combinations thereof; and/or
   c. antimicrobial antibody selected from the group consisting of an anti-outer membrane protein C (ACA) antibody, anti-flagellin antibody (AFA), and combinations thereof; and/or 3.22. Any of Method 3.20, et seq. wherein the one or more additional IBD-associated endogenous antibodies comprise anti-flagellin antibody (AFA) which binds to one or more epitopes on a bacterial flagellin encoded by a gene which is capable of being amplified by a first primer selected from one or more of SEQ ID NOS 1, 3, 5, and 7 and a second primer selected from one or more of SEQ ID NOS 2, 4, 6, and 8.

3.23. Any of Method 3.20, et seq. wherein the one or more additional IBD-associated endogenous antibodies comprise anti-flagellin antibody (AFA) which binds to one or more epitopes on a bacterial flagellin protein or fragment thereof comprising at least 10 (e.g., at least 20, e.g., at least 30) consecutive amino acids in a sequence selected from SEQ ID NOS 9-13.

3.24. Any of Method 3.20, et seq. wherein the one or more additional IBD-associated endogenous antibodies comprise anti-outer membrane protein C antibody (ACA) which binds to one or more epitopes on a bacterial outer membrane protein C encoded by a gene which is capable of being amplified by primers corresponding to SEQ ID NOS 14 and 15.

3.25. Any of Method 3.20, et seq. wherein the one or more additional IBD-associated endogenous antibodies comprise antibodies to antigens from bacteria from the gut of the companion animal patient species.

3.26. Any of Method 3.20, et seq. wherein the one or more additional IBD-associated endogenous antibodies comprise antibodies to antigens from Gram negative bacteria from the gut of the companion animal patient species.

3.27. Any of Method 3.20, et seq. wherein the one or more additional IBD-associated endogenous antibodies comprise antibodies to antigens from bacteria from the gut of the companion animal patient species, wherein the bacteria is of a species selected from one or more of *Pseudomonas* (*Pseudomonas aeruginosa, Pseudomonas monteilii, Pseudomonas lundensis/taetrolens, Pseudomonas mosselii, Pseudomonas mucidolens/synxantha, Pseudomonas fluorescens* A, *Pseudomonas hibiscicola, Pseudomonas asplenii/putida, Stenotrophomonas maltophilia, Brevundimonas diminuta, Stenotrophomonas rhizophila*), *Escherichia* (*Escherichia coli, Escherichia fergusonii*), *Proteus* (*Proteus mirabilis*), *Enterobacter* (*Enterobacter hormaechei*), *Acinetobacter* (*Acinetobacter genomospecies* 10, *Acinetobacter genomospecies* 11), *Sphingobacterium* (*Sphingobacterium spiritivorum*), and *Klebsiella* (*Klebsiella pneumonia*); *Enterococcus* (*Enterococcus faecium, Enterococcus faecalis*), and *Lac-*

*tobacillus* (*Lactobacillus johnsonii*); for example wherein the bacteria includes at least one of a *Pseudomonas* species.

3.28. Any of Method 3.20, et seq. wherein the one or more additional IBD-associated endogenous antibodies comprise anti-outer membrane protein C antibody (ACA) which binds to one or more epitopes on a bacterial outer membrane protein C or fragment thereof comprising at least 10 (e.g., at least 20, e.g., at least 30) consecutive amino acids in a sequence selected from SEQ ID NOS 16, 17, and 18.

3.29. Any of Method 3.20, et seq., wherein said the one or more additional IBD-associated endogenous antibodies are selected from APMNA, pAPMNA, AYA-IgA, AYA-IgG, ACA, or AFA.

3.30. Any of Method 3.20, et seq., wherein said the one or more additional IBD-associated endogenous antibodies are IgA antibodies.

3.31. Any preceding method wherein the immunoassay to detect the presence or level of the one or more inflammation associated autoantibodies is an enzyme-linked immunosorbent assay (ELISA).

3.32. Any preceding method wherein the immunoassay to detect the presence or level of the one or more inflammation-associated autoantibodies is an agglutination-PCR (ADAP).

3.33. Any preceding method, wherein the immunoassay to detect the presence or level of the one or more inflammation-associated autoantibodies is an immunohistochemical assay.

3.34. Any preceding method, wherein the immunoassay to detect the presence or level of the one or more inflammation-associated autoantibodies is an immunofluorescence assay.

3.35. Any preceding method, wherein said sample is selected from the group consisting of saliva, serum, plasma, and whole blood.

3.36. Any preceding method, wherein the step of classifying said sample as an inflammation sample or non-inflammation sample is carried out using a statistical algorithm selected from the group consisting of a classification and regression tree, boosted tree, neural network, random forest, support vector machine, general chi-squared automatic interaction detector model, interactive tree, multi-adaptive regression spline, machine learning classifier, and combinations thereof.

3.37. Any preceding method, comprising: (a) determining the presence or level of at least one inflammation-associated autoantibody, (b) optionally determining the presence or level of at least one marker selected from the group consisting of an anti-polymorphonuclear leukocyte (PMN) antibody, antimicrobial antibody, calprotectin and combinations thereof in the sample; and (c) classifying the sample as an inflammation sample or non-inflammation sample using a statistical algorithm based upon the presence or level of at least one marker.

3.38. Any preceding method wherein the one or more antigens bound to a substrate or detectable label is any of Reagent 3, as hereinafter described.

3.39. Any preceding method wherein the one or more antigens are bound to a substrate and comprise a bacterial outer membrane protein C or fragment thereof comprising at least 10 (e.g., at least 20, e.g., at least 30) consecutive amino acids in a sequence selected from SEQ ID NOS 16, 17, and 18, optionally bound to a poly-histidine tag, for example a N-terminal hexa-histidine tag, e.g., optionally comprising one or more solubility enhancing residues, e.g., an N-terminal sequence of SEQ ID NO 33 or SEQ ID NO 36, for example an antigen of SEQ ID NO 35.

3.40. Any preceding method wherein the one or more antigens are bound to a substrate and comprise a bacterial flagellin protein or fragment thereof comprising at least 10 (e.g., at least 20, e.g., at least 30) consecutive amino acids in a sequence selected from SEQ ID NOS 9-13, optionally bound to a poly-histidine tag, for example a N-terminal hexa-histidine tag, e.g., optionally comprising one or more solubility enhancing residues, e.g., an N-terminal sequence of SEQ ID NO 33 or SEQ ID NO 36, for example, an antigen of SEQ ID NO 34.

3.41. Any preceding method further comprising detecting the presence or level of detecting the presence and/or level of one or more endogenous antibodies associated with inflammatory bowel disease (IBD-associated antibodies), e.g., wherein the one or more IBD-associated antibodies are selected from the group consisting of an anti-PMN antibody, anti-yeast antibody, antimicrobial antibody, and combinations thereof, e.g., in accordance with any of Methods 2, et seq.

3.42. Any preceding method wherein the one or more antigens bound to a substrate or detectable label comprise an antigen of SEQ ID NO 19 and an antigen of SEQ ID NO 35.

3.43. Any preceding method wherein the one or more antigens are bound to one or more substrates, wherein the substrates comprise one or more microwell plates, such that where detecting binding to different antigens is desired, the different antigens are on different microwell plates or in different wells of the same microwell plate; e.g. wherein the microwell plate is a flat plate or strip with multiple sample wells, e.g., 6, 24, 96, 384 or 1536 sample wells, e.g., wherein each well of the microwell plate has a volume between 10 nl to 1 ml, for example between 50 µl and 500 µl.

3.44. Any preceding method, wherein the one or more antigens are bound to one or more substrates, comprising the steps of
  a. Affixing the one or more antigens to their respective substrates,
  b. Blocking any uncoated surfaces of the substrates with protein, e.g., bovine serum albumin
  c. Exposing the antigens to the sample to allow formation of antigen-antibody complexes,
  d. Exposing the antigen-antibody complexes thus formed to the labeled antibody to a labeled antibody that binds the immunoglobulin, e.g., IgA, from the patient species, e.g., e.g., horseradish peroxidase (HRP)-anti-IgA antibody
  e. Detecting binding of the labeled antibody to the antigen-antibody complexes,
e.g., wherein the substrate is washed with buffer after each of steps a-d.

3.45. Any foregoing method wherein the labeled antibody is labeled with an enzyme, 3.46. Any foregoing method wherein the labeled antibody is an anti-dog IgA antibody linked to an enzyme.

3.47. Any foregoing method wherein the labeled antibody is an anti-dog IgA antibody linked to an enzyme and the step of detecting binding of the labeled antibody to the antigen-antibody complexes is carried out by (i) contacting the endogenous IgA bound to antigen with the labeled antibody, (ii) providing a substrate for the enzyme, and (iii) measuring the increase in optical density caused by the reaction of the enzyme with the substrate for the enzyme, wherein the increase in optical density correlates with the presence and amount of endogenous IgA bound to antigen.

3.48. The foregoing method wherein the enzyme is horseradish peroxidase (HRP) and the substrate is 3,3',5,5'-Tetramethylbenzidine (TMB).

3.49. Any preceding method comprising classifying the sample from the patient as "consistent" with an inflammatory condition in the patient, e.g., inflammatory bowel disease (IBD), or "not consistent" with the inflammatory condition, wherein the presence and/or level of IgA in the sample that binds to the one or more antigens, separately or in combination, correlates with the presence of the inflammatory condition in the patient.

3.50. Any preceding method further comprising detecting the presence or level of endogenous antibodies to one or more of endogenous antibodies to gliadin, zein, amylase inhibitor, TTG2, or TG3; e.g., in accordance with any of Methods 1, et seq.

In a particular embodiment of Method 3 (Method 3-1), the invention provides a method for detecting the presence and/or level of at least the following IgA markers in serum obtained from a canine patient
  (i) endogenous IgA to a bacterial outer membrane protein C (OmpC), and
  (ii) endogenous IgA to canine calprotectin,
said method comprising the steps of
  a) contacting a first antigen bound to a substrate and a second antigen bound to a substrate, with said serum, and
  b) detecting the binding of said one or more IgA markers to said one or more antigens using a labeled antibody to canine IgA,
wherein
  (i) the first antigen comprises one or more antigenic sequences from bacterial OmpC; and
  (ii) the second antigen comprises one or more antigenic sequences from a canine calprotectin.

For example, Method 3-1 provides 3-1.1. Method 3-1 wherein the first antigen comprises at least 20 consecutive amino acids in a sequence selected from SEQ ID NOS 16, 17, and 18.

3-1.2. Any foregoing Method 3-1 wherein the second antigen comprises at least 20 consecutive amino acids in a sequence selected from SEQ ID NO: 20, SEQ ID NO: 21, and SEQ ID NO: 22.

3-1.3. Any foregoing Method 3-1 wherein the second antigen is a fusion protein comprising a calprotectin S100A8 monomer region and a calprotectin S100A9 monomer region, wherein the regions are linked by a linker sequence; e.g. wherein the calprotectin S100A8 monomer region comprises at least 20 amino acid residues in sequence from SEQ ID NO: 21 and the calprotectin S100A9 monomer region comprises at least 20 amino acid residues in sequence from SEQ ID NO: 22.

3-1.4. Any foregoing Method 3-1 wherein the first and second antigens each comprise a polyhistidine tag; for example an N-terminal hexa-histidine tag, e.g., optionally further comprising one or more solubility-enhancing residues, e.g., serine residues, for example, wherein the first and second antigens each comprise an N-terminal sequence selected from SEQ ID NO 33 and SEQ ID NO 36.

3-1.5. Any foregoing Method 3-1 wherein the substrate comprises one or more microwell plates, wherein the first antigen and the second antigen are on different microwell plates or in different wells of the same microwell plate, e.g. wherein the microwell plate is a flat plate or strip with multiple sample wells, e.g., 6, 24, 96, 384 or 1536 sample wells, e.g., wherein each well of the microwell plate has a volume between 10 nl to 1 ml, for example between 50 µl and 500 µl.

3-1.6. Any foregoing Method 3-1 comprising the steps of
  a. Affixing the first and second antigens to their respective substrates,
  b. Blocking any uncoated surfaces of the substrates with protein, e.g., bovine serum albumen,
  c. Exposing the antigens to the serum sample to allow formation of antigen-antibody complexes,
  d. Exposing the antigen-antibody complexes thus formed to the labeled antibody to canine IgA, e.g., horseradish peroxidase (HRP)-anti-dog IgA antibody,
  e. Detecting binding of the labeled antibody to canine IgA to the antigen-antibody complexes.

3-1.7. Any foregoing Method 3-1 wherein the first antigen comprises a fusion protein of SEQ ID NO: 35.

3-1.8. Any foregoing Method 3-1 wherein the second antigen comprises a fusion protein of SEQ ID NO: 19.

3-1.9. Any foregoing Method 3-1 wherein the first antigen comprises a fusion protein according to SEQ ID NO: 35 and the second antigen comprises a fusion protein according to SEQ ID NO: 19.

3-1.10. Any foregoing method wherein the labeled antibody is labeled with an enzyme, 3-1.11. Any foregoing method wherein the labeled antibody is an anti-dog IgA antibody linked to an enzyme.

3-1.12. Any foregoing method wherein the labeled antibody is an anti-dog IgA antibody linked to an enzyme and the step of detecting binding of the labeled antibody to the antigen-antibody complexes is carried out by contacting the labeled antibody bound to the antigen-antibody complexes with a substrate for the enzyme, wherein the reaction of the enzyme with the substrate causes an increase in Optical Density (OD) as measured using an ELISA plate reader.

3-1.13. The foregoing method wherein the enzyme is horseradish peroxidase (HRP) and the substrate is 3,3',5,5'-Tetramethylbenzidine (TMB).

3-1.14. Any foregoing Method 3-1 further comprising classifying the serum from the canine patient as consistent with inflammatory bowel disease (IBD), or not consistent with IBD, wherein the presence and/or level of IgA in the serum that binds to the first antigen and the presence and/or level of IgA in the serum that binds to the second antigen, separately or in combination, correlates with the presence of IBD in the canine patient.

In another embodiment, the invention provides a method of diagnosing an inflammatory condition comprising detecting the presence and/or level of the one or more IBD-associated antibodies, separately or in combination, in accordance with any of Method 3, et seq.

In another embodiment, the invention provides a method of classifying whether a patient is associated with a clinical subtype of inflammation, the method comprising: (a) determining the presence or level of at least one inflammation-associated autoantibody, (b) optionally determining the presence or level of at least one marker selected from the group consisting of an anti-polymorphonuclear leukocyte (PMN) antibody, antimicrobial antibody, calprotectin and combinations thereof in the sample; and (c) classifying the sample lymphoplasmacytic (LPE) IBD, eosinophilic gastroenterocolitis (EGE) IBD or granulomatous (GE) IBD or non-IBD sample using a statistical algorithm based upon the presence or level of the at least one marker; e.g. using any of Method 3, et seq.

In another aspect, the present invention provides a method for monitoring the progression or regression of inflammation in a mammal, the method comprising: (a) determining the presence or level of at least one inflammation-associated autoantibody, (b) optionally determining the presence or level of at least one marker selected from the group consisting of an anti-polymorphonuclear leukocyte (PMN) antibody, antimicrobial antibody, calprotectin and combinations thereof in the sample; and (c) determining the presence or severity of inflammation using a statistical algorithm based upon the presence or level of the at least one marker; e.g., using any of Method 3, et seq.

In a related aspect, the present invention provides a method for monitoring drug efficacy in a patient receiving drugs useful for treating inflammation, the method comprising: (a) determining the presence or level of at least one inflammation-associated autoantibody, (b) optionally determining the presence or level of at least one marker selected from the group consisting of an anti-polymorphonuclear leukocyte (PMN) antibody, antimicrobial antibody, calprotectin and combinations thereof in the sample; and (c) determining the presence or severity of inflammation using a statistical algorithm based upon the presence or level of the at least one marker; e.g. using any of Method 3, et seq.

In another embodiment, the invention provides a reagent (Reagent 3) comprising an amino acid sequence selected from one or more of
  a. An isolated peptide which is a calprotectin or antigenic fragment thereof, comprising at least 10 (e.g., at least 20, e.g., at least 30) consecutive amino acids in a sequence from a wild type calprotectin, e.g., from a companion animal calprotectin, for example, any of SEQ ID NO: 19, SEQ ID NO: 20, SEQ ID NO: 21, SEQ ID NO: 22 or any combination thereof, wherein the calprotectin or antigenic fragment thereof is bound to one or more of a label, a purification tag, a solid substrate, or another protein or fragment thereof, for example another calprotectin or fragment thereof or an integrin or fragment thereof; for example, wherein the calprotectin or antigenic fragment thereof is bound to a poly-histidine tag, for example a N-terminal hexa-histidine tag, e.g., an N-terminal sequence of SEQ ID NO: 36; for example, a fusion protein according to SEQ ID NO: 19; and
  b. An isolated peptide which is an integrin or antigenic fragment thereof, comprising at least 10 (e.g., at least 20, e.g., at least 30) consecutive amino acids in a sequence from a wild type integrin, e.g. from a companion animal integrin, for example any of SEQ ID NO: 29, SEQ ID NO: 30, SEQ ID NO: 31, SEQ ID NO: 32, or any combination thereof, wherein the integrin or antigenic fragment thereof is bound to one or more of a label, a purification tag, a solid substrate, or another protein or fragment thereof, for example, a calprotectin or fragment thereof or another integrin or fragment thereof; for example, wherein the integrin or antigenic fragment thereof is bound to a poly-histidine tag, for example a N-terminal hexa-histidine tag, e.g., an N-terminal sequence of SEQ ID NO: 36.

For example, in some embodiments, Reagent 3 is a fusion protein comprising a calprotectin S100A8 monomer region, e.g., with sequence comprising at least 20 amino acid residues in sequence from SEQ ID NO: 21 and a calprotectin S100A9 monomer region, e.g., with sequence comprising at least 20 amino acid residues in sequence from SEQ ID NO: 22, wherein the regions are linked by a linker sequence, e.g., a fusion protein comprising SEQ ID NO: 19; or a fusion peptide comprising an integrin α (alpha) subunit region, e.g., comprising at least 20 amino acid residues in sequence from SEQ ID NO: 29 or 30, and an integrin β (beta) subunit region, e.g., comprising at least 20 amino acid residues in sequence from SEQ ID NO: 31 or 32, wherein the regions are linked by a linker sequence. Linker sequences may, for example, comprise sequences of 10-30, e.g., about 15, amino acid residues, e.g. non-charged amino acid residues, for example glycine and serine residues, e.g., a $(Gly_4Ser)_n$ linker, where n is an integer 2 through 5, e.g. 3.

For example, in certain embodiments, Reagent 3 comprises a canine calprotectin S100A8 monomer region and a canine calprotectin S100A9 monomer region, wherein the regions are linked by a linker sequence, e.g., wherein the canine calprotectin S100A8 monomer region comprises at least 20 amino acid residues in sequence from SEQ ID NO: 21 and the canine calprotectin S100A9 monomer region comprises at least 20 amino acid residues in sequence from SEQ ID NO: 22; for example, a fusion protein comprising a sequence of SEQ ID NO: 19.

In another embodiment the invention provides a diagnostic kit comprising a reagent according to Reagent 3; for example, a diagnostic kit for the detection of inflammation-associated antibodies in a sample from a dog, the kit comprising: (i) one or more reagents of Reagent 3 as described above; and (ii) means for detection of a complex formed between the reagent and an inflammation-associated autoantibody. In some embodiments, the diagnostic kit is an ELISA assay. In some embodiments the kit is a strip assay, wherein antigens, e.g., according to Reagent 1, are bound to specific regions of the strip. In some embodiments, the diagnostic kit is an Agglutination-PCR (ADAP) kit.

In some embodiments, the invention provides a diagnostic kit comprising a reagent according to Reagent 3 and a reagent according to Reagent 2, e.g., for use in any of Method 2, et seq. or Method 3, et seq. (including Method 3-1, et seq.). For example, in one embodiment, the invention provides a diagnostic kit, for example an ELISA assay, comprising (i) an antigen comprising an antigenic sequence from bacterial OmpC, e.g., a fusion protein according to SEQ ID NO: 35, together with (ii) a second antigen comprising one or more antigenic sequences from calprotectin, e.g., a fusion protein according to SEQ ID NO: 19.

In another embodiment the invention provides the use of any reagent as described in Reagent 3 in the manufacture of a kit or component of a kit for carrying out a diagnostic method according to any of Method 3, et seq., e.g., a diagnostic kit as described above.

In another embodiment, the invention provides any reagent described in Reagent 3 for use in diagnosis, e.g., diagnosis of inflammation in a companion animal patient, e.g., in a diagnostic method according to any of Method 3, et seq.

In another embodiment, the invention provides a complex comprising an antigen, an endogenous inflammation-associated antibody bound to the antigen, and a labeled antibody bound to the inflammation-associated antibody, for example wherein the antigen is a reagent according to Reagent 3, as hereinbefore described.

In another embodiment, the invention provides a bacterial expression construct comprising a promoter operably linked to an open reading frame encoding one or more of comprising at least 10 (e.g., at least 20, e.g., at least 30) consecutive amino acids in a sequence from a wild type calprotectin, e.g.

from a companion animal calprotectin, and/or comprising at least 10 (e.g., at least 20, e.g., at least 30) consecutive amino acids in a sequence from a wild type integrin, e.g. from a companion animal integrin, each optionally linked to an additional sequence, e.g. a polyhistidine tag; wherein the promoter and the open reading frame are heterologous to one another, i.e., wherein the promoter and the open reading frame are not operably linked in nature.

In another embodiment, the invention provides a bacterial cell line, for example an *E. coli* line, comprising the bacterial expression construct of the preceding paragraph.

XIII. Therapy and Therapeutic Monitoring

Once a patient sample has been classified as an inflammation sample, for example, once a companion animal sample has been classified as IBD, the methods, systems, and code of the present invention can further comprise administering to the individual a therapeutically effective amount of a drug useful for treating one or more symptoms associated with the particular inflammatory condition, for example, IBD or the IBD subtype. For therapeutic applications, the drug can be administered alone or co-administered in combination with one or more additional anti-inflammatory or anti-IBD drugs and/or one or more drugs that reduce the side-effects associated with the anti-inflammatory or anti-IBD drug.

Anti-inflammatory or anti-IBD drugs can be administered with a suitable pharmaceutical excipient as necessary and can be carried out via any of the accepted modes of administration. Thus, administration can be, for example, intravenous, topical, subcutaneous, transcutaneous, transdermal, intramuscular, oral, buccal, sublingual, gingival, palatal, parenteral, intradermal, intranasal, rectal, vaginal, or by inhalation. By "co-administer" it is meant that an anti-inflammatory or anti-IBD drug is administered at the same time, just prior to, or just after the administration of a second drug (e.g., another IBD drug, a drug useful for reducing the side-effects of the IBD drug, etc.).

A therapeutically effective amount of an anti-inflammatory or anti-IBD drug may be administered repeatedly, e.g., at least 2, 3, 4, 5, 6, 7, 8, or more times, or the dose may be administered by continuous infusion. The dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, that can be delivered in unit dosage forms suitable for simple administration of precise dosages.

As used herein, the term "unit dosage form" includes physically discrete units suitable as unitary dosages for companion animals, each unit containing a predetermined quantity of a drug calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the anti-inflammatory or anti-IBD drug.

Methods for preparing such dosage forms are known to those skilled in the art (see, e.g., Remington's Pharmaceutical Sciences, 18$^{th}$ Ed., Mack Publishing Co., Easton, Pa. (1990). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., Remington's Pharmaceutical Sciences, supra).

Examples of suitable excipients include, but are not limited to, lactose, dextrose, sucrose, sorbitol, mannitol, starches, gum acacia, calcium phosphate, alginates, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates; pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with an IBD drug, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. An IBD drug can also be formulated into a suppository disposed, for example, in a polyethylene glycol (PEG) carrier.

Liquid dosage forms can be prepared by dissolving or dispersing an IBD drug and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. An IBD drug can also be formulated into a retention enema.

For topical administration, the therapeutically effective dose can be in the form of emulsions, lotions, gels, foams, creams, jellies, solutions, suspensions, ointments, and transdermal patches. For administration by inhalation, an IBD drug can be delivered as a dry powder or in liquid form via a nebulizer. For parenteral administration, the therapeutically effective dose can be in the form of sterile injectable solutions and sterile packaged powders. Injectable solutions can be formulated at a pH of from about 4.5 to about 7.5. The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to a patient.

In therapeutic use for the treatment of IBD or a clinical subtype thereof, an IBD drug can be administered at the initial dosage of from about 0.001 mg/kg to about 1000 mg/kg daily. A daily dose range of from about 0.01 mg/kg to about 500 mg/kg, from about 0.1 mg/kg to about 200 mg/kg, from about 1 mg/kg to about 100 mg/kg, or from about 10 mg/kg to about 50 mg/kg, can be used. The dosages, however, may be varied depending upon the requirements of the individual, the severity of IBD symptoms, and the IBD drug being employed. For example, dosages can be empirically determined considering the severity of IBD symptoms in an individual classified as having IBD according to the methods described herein. The dose administered to a companion animal patient, in the context of the present invention, should be sufficient to affect a beneficial therapeutic response over time. The size of the dose can also be determined by the existence, nature, and extent of any adverse side-effects that accompany the administration of a particular IBD drug in such companion animal patient. Determination of the proper dosage for a particular situation is within the skill of the practitioner. Generally, treatment is initiated with smaller dosages which are less than the optimum dose of the IBD drug. Thereafter, the dosage is increased by small increments until the optimum effect under circumstances is reached. For convenience, the total daily dosage may be divided and administered in portions during the day, if desired.

As used herein, the term "IBD drug" includes all pharmaceutically acceptable forms of a drug that is useful for treating one or more symptoms associated with IBD. For example, the IBD drug can be in a racemic or isomeric mixture, a solid complex bound to an ion exchange resin, or the like. In addition, the IBD drug can be in a solvated form. The term is also intended to include all pharmaceutically acceptable salts, derivatives, and analogs of the IBD drug being described, as well as combinations thereof. For example, the pharmaceutically acceptable salts of an IBD drug include, without limitation, the tartrate, succinate, tartarate, bitartarate, dihydrochloride, salicylate, hemisuccinate, citrate, maleate, hydrochloride, carbamate, sulfate, nitrate, and benzoate salt forms thereof, as well as combinations thereof and the like. Any form of an IBD drug is suitable for use in the methods of the present invention, e.g., a pharmaceutically acceptable salt of an IBD drug, a free base of an IBD drug, or a mixture thereof.

As used herein, an anti-inflammatory drug includes IBD drugs, and drugs for treating other inflammatory conditions, including corticosteroids, NSAIDS, and monoclonal antibodies or soluble receptors binding inflammatory cytokines, for example monoclonal antibodies to TNFα.

For example, suitable drugs that are useful for treating one or more symptoms associated with inflammatory conditions such as IBD or a clinical subtype thereof include, but are not limited to, aminosalicylates (e.g., mesalazine, sulfasalazine, and the like), corticosteroids (e.g., prednisone), thiopurines (e.g., azathioprine, 6-mercaptopurine, and the like), methotrexate, monoclonal antibodies (e.g., infliximab), free bases thereof, pharmaceutically acceptable salts thereof, derivatives thereof, analogs thereof, and combinations thereof. One skilled in the art will know of additional anti-inflammatory or IBD drugs suitable for use in the present invention.

A patient can also be monitored at periodic time intervals to assess the efficacy of a certain therapeutic regimen once a sample from such patient has been classified as an IBD sample. For example, the levels of certain markers change based on the therapeutic effect of a treatment such as a drug. The patient is monitored to assess response and understand the effects of certain drugs or treatments in an individualized approach. Additionally, patients may not respond to a drug, but the markers may change, suggesting that these companion animal patients belong to a special population (not responsive) that can be identified by their marker levels. These patients can be discontinued on their current therapy and alternative treatments prescribed.

For example, in another embodiment, the invention provides a method (Method 4) for treating an inflammatory condition, e.g., IBD, in a companion animal patient, comprising detecting the presence and/or level of one or more endogenous antibodies accordance with a method according to any one of Method 1, et seq., Method 2, et seq., and/or any one of Method 3, et seq. and administering to said patient a therapeutically effective amount of a drug useful for treating one or more symptoms associated with the inflammatory condition, e.g., IBD, for example, 4.1. Method 4 wherein the companion animal patient is a cat, a dog, or a horse, for example, a dog.

4.2. Any of Method 4, et seq. wherein the companion animal patient exhibits one or more clinical symptoms of an inflammatory condition, e.g., IBD, for example one or more of the following symptoms:
  a. Blood in the stool;
  b. Elevated levels of fecal calprotectin;
  c. Elevated levels of fecal lactoferrin;
  d. Anemia;
  e. Diarrhea;
  f. Vomiting
  g. Inappetence; or
  h. Significant recent weight loss.

4.3. Any of Method 4, et seq. wherein the patient has failed to respond to antibiotics.

4.4. Any of Method 4, et seq. wherein said drug is selected from the group known to veterinarian consisting of aminosalicylates, corticosteroids, thiopurines, methotrexate, monoclonal antibodies, free bases thereof, pharmaceutically acceptable salts thereof, derivatives thereof, analogs thereof, and combinations thereof; e.g., selected from one or more of
  i. olsalazine (dogs: 10-20 mg/kg, orally (PO), three times a day (tid))
  ii. mesalamine (dogs: 10 mg/kg, PO, tid);
  iii. prednisone or prednisolone (2 mg/kg/day dogs or cats);
  iv. dexamethasone (0.25 mg/kg/day dogs or cats);
  v. budesonide (enteric coated) (1 mg/m$^2$/day, PO, in dogs, or 1 mg/cat/day, PO);
  vi. azathioprine (2.2 mg/kg/day, PO, in dogs);
  vii. cyclosporine (5-10 mg/kg/day, PO, in dogs or cats).

4.5. Any of Method 4, et seq. wherein the companion animal patient is a dog.

4.6. Any of Method 4, et seq. wherein the method further comprises assessing the patient's response to treatment by repeating the step of comprising detecting the presence and/or level of one or more endogenous antibodies the patient in accordance with a method according to any one of Method 3, et seq.

4.7. Any of Method 4, et seq. further comprising the step of classifying the sample from the companion animal patient analyzed in accordance with Method 1, et seq., or Method 3, et seq., as being associated with a clinical subtype of IBD, said method comprising:
  a. determining the presence or level of one or more markers selected from the group consisting of an anti- PMN antibody, anti-yeast antibody, antimicrobial antibody, calprotectin and combinations thereof in said sample; and b. classifying said sample as a lymphoplasmacytic enteritis (LPE) sample, eosinophilic gastroenteritis (EGE) sample, granulomatous enteritis (GE) or non-IBD sample using a statistical algorithm based upon the presence or level of said one or more markers.

4.8. The preceding method wherein said statistical algorithm is selected from the group consisting of a classification and regression tree, boosted tree, neural network, random forest, support vector machine, general chi-squared automatic interaction detector model, interactive tree, multi-adaptive regression spline, machine learning classifier, and combinations thereof.

4.9. Any of Method 4, et seq. further comprising giving the companion animal patient a diet with antigen-limited or hydrolyzed protein and/or high levels of insoluble fiber.

XIV. Detection of Combinations of Markers

In some embodiments, the invention provides a method of detecting multiple types of endogenous antibody in a companion animal patient, e.g. a dog, including detecting endogenous antibody to food antigens, e,g, according to any of Method 1, et seq., endogenous antibody to bacterial antigens, e.g., according to any of Method 2, et seq., and/or endogenous antibody to inflammatory markers, e.g., according to any of Method 3, et seq. For example, in some embodiments, the invention provides use of Methods 1, 2, and 3 in combination, Methods 2 and 3 in combination, Methods 1 and 2 in combination, or Methods 1 and 3 in combination.

Detecting combinations of IgA to different antigens is especially valuable for differential diagnosis among gastrointestinal disorders, for example IBD and food sensitivity. For example, the absolute and relative levels of endogenous IgA to gliadin, OmpC and calprotectin, e.g., detected using Methods 1, 2 and 3 respectively, provides particularly useful information for diagnosis of gastrointestinal disorders in dogs.

For example, the invention provides a method (Method A) for detecting the presence and/or level of combinations of at least the following endogenous IgA markers in serum obtained from a canine patient:
 a. endogenous IgA to gliadin;
 b. endogenous IgA to a bacterial outer membrane protein C (OmpC),
 c. endogenous IgA to canine calprotectin, and
said method comprising the steps (carried out simultaneously or sequentially in any order) of
 a1) contacting said serum with a gliadin antigen bound to a substrate, wherein the gliadin antigen comprises one or more antigenic sequences from gliadin;
 a2) detecting the binding of endogenous IgA markers to the gliadin antigen using a labeled antibody which binds canine IgA;
 b1) contacting said serum with an OmpC antigen bound to a substrate, wherein the OmpC antigen comprises one or more antigenic sequences from bacterial OmpC;
 b2) detecting the binding of endogenous IgA markers to the OmpC antigen using a labeled antibody which binds canine IgA;
 c1) contacting said serum with a calprotectin antigen bound to a substrate, wherein the calprotectin antigen comprises one or more antigenic sequences from canine calprotectin, e.g., at least 20 consecutive amino acids in a sequence selected from SEQ ID NO: 20, SEQ ID NO: 21, and SEQ ID NO: 22;
 c2) detecting the binding of endogenous IgA markers to the calprotectin antigen using a labeled antibody which binds canine IgA; for example A.1. Method A wherein the gliadin antigen is an isolated peptide comprising one or more sequences from gliadin that do not contain protease cleavage sites for proteases from canine gastric fluid, i.e., are not digested by canine gastric fluid, but not comprising sequences from gliadin that do contain such protease cleavage sites, i,e., that are digested by canine gastric fluid, e.g.,
 i. wherein the isolated gliadin peptide comprises one or more sequences selected from SEQ ID NOS 37-40;
 ii. wherein the isolated gliadin peptide is a fusion peptide comprising two or more sequences selected from SEQ ID NOS 37-40;
 iii. wherein the isolated zein peptide is bound to one or more of a label, a purification tag, a solid substrate, or another protein or fragment thereof; for example, wherein the isolated zein peptide is bound to a poly-histidine tag, for example an N-terminal hexa-histidine tag, e.g., optionally comprising one or more solubility enhancing residues;
 iv. wherein the isolated gliadin peptide is bound to an N-terminal hexa-histidine tag of SEQ ID NO: 36; and/or
 v. wherein the isolated gliadin peptide comprises SEQ ID NO: 58.

A.2. Any foregoing method wherein the gliadin antigen comprises at least two sequences selected from SEQ ID NOS: 37-40.

A.3. Any foregoing method wherein the gliadin antigen comprises SEQ ID NO: 58.

A.4. Any foregoing method wherein the OmpC antigen is an isolated peptide which is a bacterial outer membrane protein C or antigenic fragment thereof, e.g., comprising at least 10 (e.g., at least 20, e.g., at least 30) consecutive amino acids in a sequence selected from SEQ ID NOS 16, 17, and 18, wherein the bacterial outer membrane protein C or fragment thereof is bound to one or more of a label, a purification tag, solid substrate, or another bacterial outer membrane protein C or fragment thereof; for example, wherein the bacterial outer membrane protein C or fragment thereof is bound to a poly-histidine tag, for example a N-terminal hexa-histidine tag, e.g., optionally comprising one or more solubility enhancing residues, e.g., an N-terminal sequence of SEQ ID NO 33 or SEQ ID NO 36, for example an OmpC fusion protein of SEQ ID NO 35.

A.5. Any foregoing method wherein the OmpC antigen comprises at least 20 consecutive amino acids in a sequence selected from SEQ ID NOS 16, 17, and 18.

A.6. Any foregoing method wherein the OmpC antigen comprises SEQ ID NO 35.

A.7. Any foregoing method wherein the calprotectin antigen is an isolated peptide, which comprises a calprotectin or antigenic fragment thereof, comprising at least 10 (e.g., at least 20, e.g., at least 30) consecutive amino acids in a sequence from a wild type calprotectin, e.g. from a companion animal calprotectin, for example comprising any of SEQ ID NO: 19, SEQ ID NO: 20, SEQ ID NO: 21, SEQ ID NO: 22 or any combination thereof, wherein the calprotectin or antigenic fragment thereof is bound to one or more of a label, a purification tag, a solid substrate, or another protein or fragment thereof, for example another calprotectin or fragment thereof or an integrin or fragment thereof; for example, wherein the calprotectin or antigenic fragment thereof is bound to a poly-histidine tag, for example, a N-terminal hexa-histadine tag, for example an N-terminal sequence of SEQ ID NO 36;

A.8. Any foregoing method wherein the calprotectin antigen comprises at least 20 consecutive amino acids in a sequence selected from SEQ ID NO: 20, SEQ ID NO: 21, and SEQ ID NO: 22.

A.9. Any foregoing method wherein the calprotectin antigen is a fusion protein comprising a calprotectin S100A8 monomer region and a calprotectin S100A9 monomer region, wherein the regions are linked by a linker sequence.

A.10. Any foregoing method wherein the calprotectin antigen is a fusion protein comprising a calprotectin S100A8 monomer region and a calprotectin S100A9 monomer region, wherein the regions are linked by a linker sequence, and wherein the calprotectin S100A8 monomer region comprises at least 20 amino acid residues in sequence from SEQ ID NO: 21 and the calprotectin S100A9 monomer region comprises at least 20 amino acid residues in sequence from SEQ ID NO: 22.

A.11. Any foregoing method wherein the calprotectin antigen comprises SEQ ID NO: 19.

A.12. Any foregoing method wherein the gliadin antigen, the OmpC antigen, and the calprotectin antigen each comprises a polyhistidine tag, e.g., an N-terminal hexahistadine tag, e.g., of SEQ ID NO: 36.

A.13. Any foregoing method wherein the substrates comprise one or more microwell plates, wherein the gliadin antigen, the OmpC antigen, and calprotectin antigen are on different microwell plates or in different wells of the same microwell plate.

A.14. Any foregoing method comprising the steps of
  a. Affixing the gliadin antigen, the OmpC antigen, and the calprotectin antigen to their respective substrates,
  b. Blocking any uncoated surfaces of the substrates with protein,
  c. Exposing the antigens to the serum sample to allow formation of antigen-antibody complexes,
  d. Exposing the antigen-antibody complexes thus formed to the labeled antibody,
  e. Detecting binding of the labeled antibody to the antigen-antibody complexes.

A.15. The foregoing method wherein the substrate is washed with buffer after each of steps a-d.

A.16. Any foregoing method wherein the gliadin antigen comprises SEQ ID NO: 58, the OmpC antigen comprises SEQ ID NO 35, and the calprotectin antigen comprises SEQ ID NO: 19.

A.17. Any foregoing method wherein the labeled antibody is labeled with an enzyme, A.18. Any foregoing method wherein the labeled antibody is an anti-dog IgA antibody linked to an enzyme.

A.19. Any foregoing method wherein the labeled antibody is an anti-dog IgA antibody linked to an enzyme and the steps a2, b2, and c2 are carried out by (i) contacting the endogenous IgA bound to antigen with the labeled antibody, (ii) providing a substrate for the enzyme, and (iii) measuring the increase in optical density caused by the reaction of the enzyme with the substrate for the enzyme, wherein the increase in optical density correlates with the presence and amount of endogenous IgA bound to antigen.

A.20. The foregoing method wherein the enzyme is horseradish peroxidase (HRP) and the substrate for the enzyme is 3,3',5,5'-Tetramethylbenzidine (TMB).

A.21. Any foregoing method further comprising classifying the serum from the canine patient as "consistent" or "not consistent" with inflammatory bowel disease (IBD) and "consistent" or "not consistent" with food sensitivity, wherein the presence and/or level of IgA in the serum that binds to the gliadin antigen, the OmpC antigen, and calprotectin antigen, separately or in combination, is used to determine the presence or absence of IBD and/or food sensitivity in the canine patient.

In certain embodiments, the invention provides a method of diagnosing and differentiating among inflammation (for example, IBD or other inflammatory condition), gastrointestinal infection, and food sensitivity (for example to grain, e.g., to gliadin) in a canine patient, comprising detecting endogenous IgA to gliadin; endogenous IgA to a bacterial outer membrane protein C (OmpC), and endogenous IgA to canine calprotectin in the serum of the patient, in accordance with any of Method A, et seq., and
  a. diagnosing the presence of inflammation when relatively high levels of endogenous IgA to canine calprotectin are detected in the serum of the patient,
  b. diagnosing gastrointestinal infection when relatively high levels of endogenous IgA to a bacterial outer membrane protein C (OmpC) are detected in the serum of the patient, and
  c. diagnosing food sensitivity when relatively high levels of endogenous IgA to gliadin are detected in the serum of the patient.

In certain embodiments, the invention provides a method of treating gastrointestinal disorders in a canine patient, comprising
  a. diagnosing the patient in accordance with the method of diagnosing and differentiating among IBD, gastrointestinal infection, and food sensitivity in a canine patient, as set forth in the preceding paragraph, and
  b. when inflammation is diagnosed, treating in accordance with any of Method 4, et seq., e.g., administering to said patient an effective amount of an anti-inflammatory drug (e.g., selected from one or more of corticosteroids, NSAIDS, and monoclonal antibodies or soluble receptors binding inflammatory cytokines (for example monoclonal antibodies to TNFα), and combinations thereof);
  c. when gastrointestinal infection is diagnosed, administering an effective amount of an antibiotic to said patient (for example a β-lactam antibiotic, e.g., penicillin, amoxycillin, amoxycillin plus clavulanic acid), and
  d. when food sensitivity is diagnosed, placing the patient on a grain-free diet or hypoallergenic diet.

In certain embodiments, the invention provides kits that contain (i) reagents selected from Reagent 1, et seq., e.g., gliadin antigen as hereinbefore described; (ii) reagents selected from Reagent 2, et seq., eg. OmpC antigen as hereinbefore described; (iii) reagents selected from Reagent 3, et seq., e.g., calprotectin antigen as hereinbefore described; and (iv) labeled antibody to canine IgA.

Other features and advantages of the invention are apparent from the following description of the embodiments thereof, and from the claims.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

The following examples are offered to illustrate, but not to limit, the claimed invention in any manner.

Example 1—Identification of Microorganisms Isolated from Biopsy Samples from Dogs Presenting IBD This example illustrates the identification of microorganism isolated from biopsy samples from dogs with IBD.

Microorganism cultures are isolated from biopsy samples from 20 dogs with inflammatory bowel disease (IBD) after obtaining informed consent from owners and genotyped using 16S rRNA gene sequencing.

The following organisms including the genus, the species, and their respective percentage of representation, are isolated from biopsy samples from dogs with IBD. Gram negative microorganisms are represented in a greater proportion than Gram positive microorganisms:
(i) Gram negative: *Pseudomonas* (47.9%) (*Pseudomonas aeruginosa, Pseudomonas monteilii, Pseudomonas lundensis/taetrolens, Pseudomonas mosselii, Pseudomonas mucidolens/synxantha, Pseudomonas fluorescens* A, *Pseudomonas hibiscicola, Pseudomonas asplenii/putida, Stenotrophomonas maltophilia, Brevundimonas diminuta, Stenotrophomonas rhizophila*), *Escherichia* (10.4%) (*Escherichia coli, Escherichia fergusonii*), *Proteus* (8.3%) (*Proteus mirabilis*), *Enterobacter* (6.3%) (*Enterobacter* hormaechei), *Acinetobacter* (4.2%) (*Acinetobacter* genomospecies 10, *Acinetobacter* genomospecies 11), *Sphingobacterium* (2.1%) (*Sphingobacterium spiritivorum*), and *Klebsiella* (2.1%) (*Klebsiella pneumonia*);
(ii) Gram positive: *Enterococcus* 16.7% (*Enterococcus faecium, Enterococcus faecalis*), and *Lactobacillus* (2.1%) (*Lactobacillus johnsonii*).

Example 2—Determination of APMNA Levels

This example illustrates an analysis of APMNA levels in a sample using a direct ELISA assay.

A polymorphonuclear leukocyte (PMN) enzyme-linked immunosorbent assay (ELISA) is used to detect levels of APMNA in dog sera. Briefly, microtiter plates are coated with $12.5 \times 10^3$ to $200 \times 10^3$ PMN per well isolated from dog blood sample collected from a single dog or from multiple dogs. A layer of PMN is recovered after centrifugation of the whole blood at 18-25° C. and treated with a hypotonic solution to lyse red blood cells. PMN are treated with cold 95% methanol and 5% acetic acid for 20±10 minutes to fix the cells. Cells are incubated for 60±30 minutes at 18-25° C. with 1% bovine serum albumin (BSA) in phosphate-buffered saline to block nonspecific antibody binding. Next, after 3 washes with Tris Buffered Saline-Tween (TBS-T: Tris Buffered Saline Tween, 25.0 mM Tris-HCl, 2.7 mM potassium chloride, 137 mM Sodium Chloride, 0.05% Tween-20, pH 7.4±0.2), control sera and test sample sera are added at a 1:100 to 1:200 dilutions to the microtiter plates and incubated for 60±30 minutes at 18-25° C. After 3 washes with TBS-T, alkaline phosphatase-conjugated anti-dog immunoglobulin A antibody is added at a 1:2000 dilution to label PMN-bound antibody and incubated for 60±30 minutes at 18-25° C. A solution of p-nitrophenol phosphate substrate is added, and color development is allowed to proceed for 30±30 minutes. The Optical Density (OD) is measured at 405 nm using an ELISA plate reader.

To determine the base cut-off value for APMNA-IgA, calibrators and negative control samples having fixed ELISA Unit (EU/mL) values can be used. For example, OD values for patient samples are compared to the OD value for the calibrators and multiplied by the calibrator assigned values. Patient samples having an average EU value greater than the base cut-off are marked as ELISA positive for APMNA reactivity. Similarly, a test sample having an average EU value less than or equal to the base cut-off is determined to be negative for APMNA reactivity.

Typical results obtained with serum samples from disease dogs and apparently healthy dogs (control) using the ELISA method described above are reported below. Data are compared using an unpaired t test and are expressed as Mean±Standard Error of the Mean (SEM) using EU (Elisa Units/mL). These results indicate that PMNs are differentially reactive with IBD sera as compared to normal sera and that the immunoreactivity to PMN can be used to diagnose IBD.

TABLE 1

APMNA-IgA levels in serum samples from disease dogs and control dogs.

| | |
|---|---|
| Mean of APMNA-IgA ± SEM in samples from disease dogs | 141.9 ± 18.06 |
| Mean of APMNA-IgA ± SEM in samples from control dogs | 42.21 ± 4.90 |
| p value | <0.0001 |

Example 3—Isolation of Flagellin Coding Regions

The flagellin coding regions are cloned from cultures isolated biopsy samples from dogs with inflammatory bowel disease (IBD) after obtaining informed consent from owners. Genomic DNA is extracted from frozen microorganism cultures isolated from biopsy samples according to the manufacturer's protocol using the ZR fungal/bacterial DNA Isolation Kit (Zymo-Research) with ultra-high density bashing beads. The DNA preparations are stored at −20° C. The coding region of the genes of interest is amplified by PCR amplification. PCR reactions are carried out in a 25 μl final volume containing the reaction master mix supplemented with a Taq DNA polymerase (Thermo Fisher scientific), the DNA template, and 0.5 μM of each of the forward and reverse primers. The PCR reaction mix is denatured at 94° C. for 4-5 min followed by amplification for 30 cycles (95° C. for 30 s, 50° C. for 30 s, 72° C. for 60 s) and an extension at 72° C. for 10 min using the primers of SEQ ID NO:1, SEQ ID NO:2, SEQ ID NO:3, SEQ ID NO:4, SEQ ID NO:5, SEQ ID NO:6, SEQ ID NO:7, SEQ ID NO:8. The PCR product is cloned into the vector pJET1.2 and sequenced. The amino-acid sequence of the flagellin genes isolated from biopsy samples of dogs presenting with IBD are reported as SEQ ID NO: 9, SEQ ID NO: 10, SEQ ID NO: 11, SEQ ID NO: 12, and SEQ ID NO: 13. The coding region is then cloned into a bacterial expression vector containing a histidine tag according to the manufacturer's recommendations (Life Technologies). The histidine tags are expressed at the N-terminal of the protein, just after the N-terminal methionine, and contain additional serine and glycine to enhance presentation of the histidine tag. The N-terminal sequence comprising the additional serine and glycine together with a hexahistidine sequence is as set forth in SEQ ID NO 36. The recombinant product is purified using a nickel-charged purification resin.

Example 4—Determination of Anti-Flagellin Antibody (AFA) Levels

This example illustrates the preparation of recombinant flagellin protein and the analysis of anti-flagellin antibody (AFA) levels in a sample using a direct ELISA assay.

The following protocol describes the purification of a flagellin protein. The nucleic acid sequence is cloned into a polyhistidine tagged-protein expression vector to create a HIS-flagellin fusion protein with an N-terminal sequence of SEQ ID No. 33. For example, the final sequence comprising the flagellin sequence of SEQ ID NO. 9 is the fusion protein of SEQ ID No. 34. Fusion proteins of the various flagellin proteins to be used as antigen are expressed in the same way. After expression in E. coli, the fusion protein is purified using a nickel purification column. The purified protein is shown to be of the expected molecular weight by Coomassie staining.

Dog IgA and IgG antibodies that bind flagellin are detected by direct ELISA assays essentially as follows. Sera from healthy and disease dogs are analyzed in duplicate for IgA reactivity to flagellin. Microtiter plates are coated overnight at 4° C. with 100 µL/well flagellin at 0.2 µg/mL in carbonate solution (100.0 mM $NaHCO_3$—$Na_2CO_3$ Buffer, pH 9.5±0.5). The plates are washed thrice with TBS-T (Tris Buffered Saline Tween, 25.0 mM Tris-HCl, 2.7 mM potassium chloride, 137 mM Sodium Chloride, 0.05% Tween-20, pH 7.4±0.2) and blocked with 200 µL/well TBS/BSA (Tris Buffered Saline, 25.0 mM Tris-HCl, 2.7 mM potassium chloride, 137 mM Sodium Chloride, pH 7.4±0.2, 1% BSA) for 1 hour at 18-25° C. After washing the plates thrice with TBS-T, the standard and sample preparations are added to each well and incubated at 18-25° C. for 1 hour. The plates are then washed thrice with TBS-T and incubated for 1 hour at 18-25° C. with horseradish peroxidase (HRP)-anti-dog IgA antibody diluted 1:5,000 in TBS/BSA. The plates are washed thrice with TBS-T and developed using 100 µL/well of 3,3',5,5'-Tetramethylbenzidine (TMB) substrate. The reaction is stopped with 0.33 M $H_2SO_4$ and the Optical Density (OD) is measured at 450 nm using an ELISA plate reader. The standard curve is fitted using a four parameter equation and used to estimate the antibody levels in the samples. Anti-flagellin positive reactivity is defined as reactivity greater than two standard deviations above the mean reactivity obtained with control sera.

Typical results obtained with serum samples from disease dogs and apparently healthy dogs (control) using the ELISA method described above are reported below. Data are compared using the Mann Whitney test and are expressed as Mean±Standard Error of the Mean (SEM) using EU (Elisa Units/mL). These results indicate that the flagellin protein is differentially reactive with IBD sera as compared to control sera and that the immunoreactivity to the flagellin polypeptide, can be used to diagnose IBD.

TABLE 2

AFA-IgA levels in serum samples from disease dogs and control dogs.

| Source of Flagellin | Disease dogs Mean ± SEM | Control dogs Mean ± SEM | p value |
|---|---|---|---|
| SEQ ID NO: 9 | 328.90 ± 50.55 | 48.84 ± 10.64 | <0.0001 |
| SEQ ID NO: 10 | 303.90 ± 41.08 | 78.63 ± 12.62 | 0.0009 |
| SEQ ID NO: 11 | 186.60 ± 33.08 | 50.83 ± 9.66 | 0.0019 |
| SEQ ID NO: 12 | 244.40 ± 37.31 | 26.78 ± 10.26 | <0.0001 |
| SEQ ID NO: 13 | 181.80 ± 35.00 | 20.15 ± 6.39 | 0.1784 |

Example 5—Isolation of OMPC Coding Regions

This example illustrates the cloning of outer membrane protein C (OmpC) coding regions.

The OmpC coding regions are cloned from cultures isolated biopsy samples from dogs with IBD. Genomic DNA is extracted from frozen microorganism cultures isolated from biopsy samples according to the manufacturer's protocol using the ZR fungal/bacterial DNA Isolation Kit (Zymo-Research) with ultra-high density bashing beads. The DNA preparations are stored at −20° C. until analysis. The coding region of the genes of interest is amplified by PCR amplification. PCR reactions are carried out in a 25 µl final volume containing the reaction master mix supplemented with a Taq DNA polymerase (Thermo Fisher scientific), the DNA template, and 0.5 µM of each of the forward primer of SEQ ID NO: 14 and the reverse primer of SEQ ID NO: 15. The PCR reaction mix is denatured at 94° C. for 4-5 min followed by amplification for 30 cycles (95° C. for 30 s, 50° C. for 30 s, 72° C. for 60 s) and an extension at 72° C. for 10 min. The PCR product is cloned into the vector pJET1.2 and sequenced. The coding region is then cloned into a bacterial expression vector containing a histidine tag according to the manufacturer's recommendations (Life Technologies). The recombinant product is purified using a nickel-charged purification resin. The amino-acid sequence of the OmpC genes isolated from biopsy samples of dogs presenting with IBD are reported as SEQ ID NO: 16, SEQ ID NO: 17, and SEQ ID NO: 18.

Example 6—Determination of Anti-OmpC Antibody (ACA) Levels

This example illustrates the preparation of OmpC protein fraction and an analysis of anti-OmpC antibody (ACA) levels in a sample using a direct ELISA assay.

The following protocol describes the purification of an OmpC protein. The nucleic acid sequence is cloned into a polyhistidine tagged-protein expression vector with an additional solubility sequence, to create a HIS-OmpC fusion protein with an N-terminal sequence of SEQ ID No. 33. For example, the final sequence comprising the OmpC sequence of SEQ ID No. 16 is the fusion protein of SEQ ID No. 35. Fusion proteins of the various OmpC proteins to be used as antigen are expressed in the same way. After expression in E. coli, the fusion protein is purified under denaturing conditions using a nickel purification column. The purified protein is shown to be of the expected molecular weight by Coomassie staining.

Detection of dog IgA antibodies that bind OmpC (ACA-IgA) is performed by direct ELISA assays essentially as follows. ELISA plates are coated overnight at 4° C. with 100 µl/well OmpC at 0.5 µg/ml in carbonate solution (100.0 mM $NaHCO_3$—$Na_2CO_3$ Buffer, pH 9.5±0.5). The plates are washed thrice with TBS-T (Tris Buffered Saline Tween, 25.0 mM Tris-HCl, 2.7 mM potassium chloride, 137 mM Sodium Chloride, 0.05% Tween-20, pH 7.4±0.2) and blocked with 200 µL/well TBS/BSA (Tris Buffered Saline, 25.0 mM Tris-HCl, 2.7 mM potassium chloride, 137 mM Sodium Chloride, pH 7.4±0.2, 1% BSA) for 1 hour at 18-25° C. After washing the plates thrice with TBS-T, the standard and sample preparations are added to each well and incubated at 18-25° C. for 1 hour. The plates are then washed thrice with TBS-T and incubated for 1 hour at 18-25° C. with horseradish peroxidase (HRP)-anti-dog IgA antibody diluted 1:5,000 in TBS/BSA, horseradish peroxidase (HRP)-anti-dog IgG1 antibody diluted 1:10,000 in TBS/BSA, horseradish peroxidase (HRP)-anti-dog IgG2 antibody diluted 1:10,000 in TBS/BSA, and horseradish peroxidase (HRP)-anti-dog IgM antibody diluted 1:10,000 in TBS/BSA. The plates are washed thrice with TBS-T and developed using 100 of 3,3',5,5'-tetramethylbenzidine (TMB) substrate. The reaction is stopped with 0.33 M $H_2SO_4$ and the Optical Density (OD) is measured at 450 nm using an ELISA plate reader. The standard curve is fitted using a four parameter equation and used to estimate the antibody levels in the samples. OmpC positive reactivity is defined as reactivity greater than two standard deviations above the mean reactivity obtained with apparently normal (control) sera.

Typical results obtained with serum samples from disease dogs and apparently healthy dogs (control) using the ELISA method described above are reported below. Data are compared using the Mann Whitney test and are expressed as Mean±Standard Error of the Mean (SEM) using EU (Elisa Units/mL). These results indicate that the OmpC protein derived from clones expressing SEQ ID NO: 16, SEQ ID NO: 17, and SEQ ID NO: 18 is differentially reactive with IBD sera as compared to normal sera and that the immunoreactivity to the OmpC polypeptide, can be used to diagnose IBD. The K12 OmpC is purified from strain *Escherichia coli* K12.

TABLE 3

ACA-IgA levels in serum samples from disease dogs and control dogs.

| Source of OmpC | Disease dogs Mean ± SEM | Control dogs Mean ± SEM | p value |
|---|---|---|---|
| E. coli K12 | 37.15 ± 7.27 | 41.3 ± 10.06 | 0.3374 |
| SEQ ID NO: 16 | 270.30 ± 39.06 | 10.47 ± 3.45 | <0.0001 |
| SEQ ID NO: 17 | 317.90 ± 48.91 | 53.18 ± 12.17 | <0.0001 |
| SEQ ID NO: 18 | 236.70 ± 37.87 | 12.90 ± 2.57 | <0.0001 |

Example 7—Isolation of Canine Calprotectin Coding Regions and Preparation of Recombinant Polypeptides This example illustrates the cloning of calprotectin coding regions and the preparation of calprotectin polypeptide fractions.

The coding regions of the calprotectin genes are cloned by assembling synthetic oligonucleotides. The synthetic constructs include NdeI and HindIII as flanking restriction sites on the 5'- and 3'-end of the gene of interest, respectively, and a histidine tag at the N-terminal region to create a HIS-calprotectin fusion polypeptide. The coding region sequences are designed to optimize polypeptide expression in *E. coli*. The assembled products are then subcloned into an expression vector with the N-terminal region of the coding gene operably linked to a start codon and an inducible promoter system. The expression constructs are transformed in *E. coli* BL21 and plated on LB agar plates containing kanamycin (50 µg/mL) for selection. Whole cell lysates are analyzed for clone selection. The amino-acid sequence of the genes are reported as SEQ ID NO: 19, SEQ ID NO: 20, SEQ ID NO: 21, and SEQ ID NO: 22 and correspond to nucleotide sequence of canine heterochimeric polypeptide S100A8/A9, canine polypeptide S100A12, canine polypeptide S100A8, and canine polypeptide S100A9, respectively.

The following protocol describes the purification of a calprotectin polypeptide. The nucleic acid sequence of the calprotectin coding region is designed to include a polyhistidine tag to create a HIS-calprotectin fusion polypeptide. After expression in *E. coli*, the fusion polypeptide is purified using a nickel purification column. For inoculum preparation and for production, the recombinant *E. coli* cells are cultivated overnight (seed culture). The seed culture is then inoculated into a culture medium in larger flasks or mini-bioreactors at a ratio of 1 to 25 and cultured until reaching an optical density (OD) of 0.6-0.9 at 600 nm. At this cell density, cells are induced with 1 mM IPTG (Isopropyl β-D-1-thiogalactopyranoside) and the fermentation is carried out for another 4-16 hours. The cells are then harvested and lysed. The recombinant polypeptides are purified from the whole cell lysates using a nickel-charged purification resin. The purified recombinant polypeptides are shown to be of the expected molecular weight by Coomassie staining. Purified polypeptide preparations are diluted 5 times in a dimerization buffer (Dulbecco's Phosphate Buffered Saline (DPBS) with calcium, magnesium, 20% glycerol, 0.02% sodium azide, pH 7.0-7.2) and the reactions are incubated at 2-8° C. for at least 24 hours.

Example 8—Determination of Anti-Calprotectin Antibody (ACN) Levels in Dog Serum Samples This example illustrates an analysis of anti-calprotectin antibody (ACN) levels in serum samples using a direct ELISA assay using various calprotectin polypeptides.

Detection of dog IgA antibodies that bind calprotectin (ACN-IgA) is performed by direct ELISA assays essentially as follows. ELISA plates are coated overnight at 4° C. with 100 µl/well Calprotectin at 0.5 µg/mL in carbonate solution (100.0 mM $NaHCO_3$—$Na_2CO_3$ Buffer, pH 9.5±0.5). The plates are washed thrice with TBS-T (Tris Buffered Saline Tween, 25.0 mM Tris-HCl, 2.7 mM potassium chloride, 137 mM Sodium Chloride, 0.05% Tween-20, pH 7.4±0.2) and blocked with 200 µL/well TBS/BSA (Tris Buffered Saline, 25.0 mM Tris-HCl, 2.7 mM potassium chloride, 137 mM Sodium Chloride, pH 7.4±0.2, 1% BSA) for 1 hour at 18-25° C. After washing the plates thrice with TBS-T, the standard and sample preparations are added to each well and incubated at 18-25° C. for 1 hour. The plates are then washed thrice with TBS-T and incubated for 1 hour at 18-25° C. with horseradish peroxidase (HRP)-anti-dog IgA antibody diluted 1:5,000 in TBS/BSA. The plates are washed thrice with TBS-T and developed using 100 µL/well of 3,3',5,5'-tetramethylbenzidine (TMB) substrate. The reaction is stopped with 0.33 M $H_2SO_4$ and the Optical Density (OD) is measured at 450 nm using an ELISA plate reader. The standard curve is fitted using a four parameter equation and used to estimate the antibody levels in the samples.

Typical results obtained with serum samples from diseased dogs and apparently healthy dogs (control) using the ELISA method described above are reported below. Data are compared using the Mann Whitney test and are expressed as Mean±Standard Error of the Mean (SEM) using Optical Density values. These results indicate that the calprotectin polypeptides derived from clones expressing SEQ ID NO:19, SEQ ID NO:20, SEQ ID NO:21, and SEQ ID NO:22 are differentially reactive with IBD sera as compared to normal sera and that the immunoreactivity to the calprotectin polypeptide, can be used to diagnose IBD.

TABLE 1

ACN-IgA levels in serum samples from diseased dogs and control dogs.

| Source of Calprotectin | Description | Diseased dogs Mean ± SEM | Control dogs Mean ± SEM | p value |
|---|---|---|---|---|
| SEQ ID NO: 19 | Dimers of heterochimeric peptide S100A8/S100A9 | 0.488 ± 0.126 | 0.068 ± 0.017 | 0.0027 |
| SEQ ID NO: 20 | Dimers of peptide S100A12 | 0.539 ± 0.138 | 0.062 ± 0.017 | 0.0021 |
| SEQ ID NO: 21 and SEQ ID NO: 22 | Dimers of peptide S100A8 and peptide S100A9 | 0.623 ± 0.151 | 0.110 ± 0.029 | 0.0027 |

Example 9—Determination of Anti-Calprotectin Antibody (ACN) Levels in Dog Serum Samples This example illustrates an analysis of anti-calprotectin antibody (ACN) levels in a sample using a direct ELISA assay using the calprotectin polypeptide of SEQ ID NO: 19.

Detection of dog IgA antibodies that bind calprotectin (ACN-IgA) is performed by direct ELISA assays essentially as follows. ELISA plates are coated overnight at 4° C. with 100 µl/well Calprotectin at 0.5 µg/mL in carbonate solution (100.0 mM $NaHCO_3$—$Na_2CO_3$ Buffer, pH 9.5±0.5). The plates are washed thrice with TBS-T (Tris Buffered Saline Tween, 25.0 mM Tris-HCl, 2.7 mM potassium chloride, 137 mM Sodium Chloride, 0.05% Tween-20, pH 7.4±0.2) and blocked with 200 µL/well TBS/BSA (Tris Buffered Saline, 25.0 mM Tris-HCl, 2.7 mM potassium chloride, 137 mM Sodium Chloride, pH 7.4±0.2, 1% BSA) for 1 hour at 18-25° C. After washing the plates thrice with TBS-T, the standard and sample preparations are added to each well and incubated at 18-25° C. for 1 hour. The plates are then washed thrice with TBS-T and incubated for 1 hour at 18-25° C. with horseradish peroxidase (HRP)-anti-dog IgA antibody diluted 1:5,000 in TBS/BSA. The plates are washed thrice with TBS-T and developed using 100 µL/well of 3,3',5,5'-tetramethylbenzidine (TMB) substrate. The reaction is stopped with 0.33 M $H_2SO_4$ and the Optical Density (OD) is measured at 450 nm using an ELISA plate reader. The standard curve is fitted using a four parameter equation and used to estimate the antibody levels in the samples.

Typical results obtained with serum samples from diseased dogs (N=60) confirmed with the diagnosis of IBD by endoscopy followed by biopsy and apparently healthy dogs (controls, N=28) using the ELISA method described above are reported below. Data are compared using the Mann Whitney test and are expressed as Mean±Standard Error of the Mean (SEM) using EU (Elisa Units). These results indicate that the calprotectin polypeptide derived from clones expressing SEQ ID NO:1 is differentially reactive with IBD sera as compared to normal sera and that the immunoreactivity to the calprotectin polypeptide, can be used to diagnose IBD.

TABLE 2

ACN-IgA levels in serum samples from diseased dogs and control dogs.

| Source of Calprotectin | Description | Diseased dogs Mean ± SEM (EU) | Control dogs Mean ± SEM (EU) | p value |
|---|---|---|---|---|
| SEQ ID NO: 19 | Dimers of heterochimeric peptide S100A8/ S100A9 | 45.45 ± 12.71 | 3.849 ± 0.488 | <0.0001 |

Example 10—Isolation of Canine Integrin Coding Regions and Preparation of Recombinant Polypeptides This example illustrates the cloning of integrin coding regions and the preparation of integrin polypeptide fractions.

Fragments of the coding regions of canine integrin alpha-4 and canine integrin beta-7 are cloned by PCR amplification using cDNA isolated from dog as template. PCR reactions are carried out in a 25 µL final volume containing the reaction master mix supplemented with a Taq DNA polymerase (Thermo Fisher scientific), the DNA template, and 0.5 µM of each of a forward primer and of reverse primer. For amplification of fragments of the integrin alpha-4 coding region, forward primers of SEQ ID NO:23 and SEQ ID NO:24 and reverse primer of SEQ ID NO:25 are used. For amplification of fragments of the integrin beta-7 coding region, forward primer of SEQ ID NO:26 and reverse primers of SEQ ID NO:27 and SEQ ID NO:28 are used. The PCR reaction mix is denatured at 94° C. for 4-5 min followed by amplification for 30 cycles (95° C. for 30 s, 50° C. for 30 s, 72° C. for 60 s) and an extension at 72° C. for 10 min. The amino-acid sequence of the cloned fragments of the integrin alpha-4 coding region are reported as SEQ ID NO:29 and SEQ ID NO:30. The amino-acid sequence of the cloned fragments of the integrin beta-7 coding region are reported as SEQ ID NO:31 and SEQ ID NO:32. The PCR products are cloned into a bacterial expression vector containing a histidine tag according to the manufacturer's recommendations (Life Technologies).

The following protocol describes the preparation of purified recombinant integrin polypeptides. The nucleic acid sequence of the integrin coding region includes a polyhistidine tag to create a HIS-Integrin fusion polypeptide. After expression in *E. coli*, the fusion polypeptide is purified using a nickel purification column. For inoculum preparation and for production, the recombinant E. coli cells are cultivated overnight (seed culture). The seed culture is inoculated into culture medium in larger flasks or mini-bioreactors at a ratio of 1 to 25 and cultured until reaching an optical density (OD) of 0.6-0.9 at 600 nm. At this cell density, cells are induced with 1 mM IPTG (Isopropyl β-D-1-thiogalactopyranoside) and the fermentation is carried out for another 4-16 hours. The cells are then harvested and lysed. The recombinant polypeptides are purified from the whole cell lysates using a nickel-charged purification resin. The purified recombinant polypeptides are shown to be of the expected molecular weight by Coomassie staining.

Example 11—Determination of Anti-Integrin Antibody (AIN) Levels in Dog Serum Samples This example illustrates an analysis of anti-integrin antibody (AIN) levels in a sample using a direct ELISA assay.

Detection of dog IgA antibodies that bind integrin (AIN-IgA) is performed by direct ELISA assays essentially as follows. ELISA plates are coated overnight at 4° C. with 100 µL/well with the integrin polypeptide preparation at 0.2 µg/mL in carbonate solution (100.0 mM NaHCO$_3$—Na$_2$CO$_3$ Buffer, pH 9.5±0.5). The plates are washed thrice with TBS-T (Tris Buffered Saline Tween, 25.0 mM Tris-HCl, 2.7 mM potassium chloride, 137 mM Sodium Chloride, 0.05% Tween-20, pH 7.4±0.2) and blocked with 200 µL/well TBS/BSA (Tris Buffered Saline, 25.0 mM Tris-HCl, 2.7 mM potassium chloride, 137 mM Sodium Chloride, pH 7.4±0.2, 1% BSA) for 1 hour at 18-25° C. After washing the plates thrice with TBS-T, the standard and sample preparations are added to each well and incubated at 18-25° C. for 1 hour. The plates are then washed thrice with TBS-T and incubated for 1 hour at 18-25° C. with horseradish peroxidase (HRP)-anti-dog IgA antibody diluted 1:5,000 in TBS/BSA. The plates are washed thrice with TBS-T and developed using 100 µL/well of 3,3',5,5'-tetramethylbenzidine (TMB) substrate. The reaction is stopped with 0.33 M H$_2$SO$_4$ and the Optical Density (OD) is measured at 450 nm using an ELISA plate reader. The standard curve is fitted using a four parameter equation and used to estimate the antibody levels in the samples.

Typical results obtained with serum samples from diseased dogs and apparently healthy dogs (control) using the ELISA method described above are reported below. Data are compared using the Mann Whitney test and are expressed as Mean±Standard Error of the Mean (SEM) using EU (Elisa Units). In addition, area under the curve (AUC) from receiver operating characteristics (ROC) curves generated by plotting sensitivity versus 1☐specificity for each integrin polypeptide are shown.

These results indicate that the integrin polypeptide preparations derived from clones expressing SEQ ID NO: 29, SEQ ID NO: 30, SEQ ID NO: 31, and SEQ ID NO: 32 are differentially reactive with IBD sera as compared to normal sera and that the immunoreactivity to the integrin polypeptide, can be used to diagnose IBD.

TABLE 3

AIN-IgA levels in serum samples from diseased dogs and control dogs.

| Integrin | Integrin Polypeptides | Diseased Dogs Mean ± SEM (EU) | Control Dogs Mean ± SEM (EU) | p value |
|---|---|---|---|---|
| SEQ ID NO: 29 | α4 | 168.8 ± 55.74 | 16.92 ± 6.49 | 0.0001 |
| SEQ ID NO: 30 | α4 | 149.1 ± 54.65 | 24.78 ± 5.81 | 0.002 |
| SEQ ID NO: 31 | β7 | 149.3 ± 51.56 | 16.06 ± 4.12 | 0.0002 |
| SEQ ID NO: 32 | β7 | 145.9 ± 48.17 | 26.43 ± 6.26 | 0.0057 |
| SEQ ID NO: 29 & SEQ ID NO: 31 | α4 & β7 | 165.2 ± 55.95 | 23.73 ± 6.43 | 0.0013 |

TABLE 4

Area under the curve values (AUC) obtained for ROC curves using different integrin polypeptides for differentiation between control dogs and diseased dogs.

| | AUC | Std. Error | P value |
|---|---|---|---|
| SEQ ID NO: 29 | 0.844 | 0.069 | 0.0005 |
| SEQ ID NO: 30 | 0.784 | 0.079 | 0.0038 |
| SEQ ID NO: 31 | 0.850 | 0.062 | 0.0004 |
| SEQ ID NO: 32 | 0.750 | 0.088 | 0.0109 |
| SEQ ID NO: 29 and SEQ ID NO: 31 | 0.797 | 0.079 | 0.0025 |

Example 12—Determination of Anti-Calprotectin Antibody IgA (ACN-IgA) Levels in Human Serum Samples This example illustrates an analysis of anti-calprotectin antibody IgA (ACN) levels in human serum samples using a direct ELISA assay.

Detection of human IgA antibodies that bind calprotectin (ACN-IgA) is performed by direct ELISA assays essentially as follows using human serum from apparently normal (N) and Inflammatory Bowel Disease (IBD) subjects, in particular Ulcerative Colitis (UC), and Crohn's Disease (CD) subjects.

ELISA plates are coated overnight at 4° C. with 100 µL/well with a recombinant, E. coli derived, human calprotectin S100A8/S100A9 heterodimer (R&D Systems, Cat No. 8226-S8) at 0.2 µg/mL in carbonate solution (100.0 mM NaHCO$_3$—Na$_2$CO$_3$ Buffer, pH 9.5±0.5). The plates are washed thrice with TBS-T (Tris Buffered Saline Tween, 25.0 mM Tris-HCl, 2.7 mM potassium chloride, 137 mM Sodium Chloride, 0.05% Tween-20, pH 7.4±0.2) and blocked with 200 µL/well TBS/BSA (Tris Buffered Saline, 25.0 mM Tris-HCl, 2.7 mM potassium chloride, 137 mM Sodium Chloride, pH 7.4±0.2, 1% BSA) for 1 hour at 18-25° C. After washing the plates thrice with TBS-T, the standard and sample preparations are added to each well and incubated at 18-25° C. for 1 hour. The plates are then washed thrice with TBS-T and incubated for 1 hour at 18-25° C. with horseradish peroxidase (HRP)-anti-human IgA antibody diluted 1:2,000 in TBS/BSA. The plates are washed thrice with TBS-T and developed using 100 µL/well of 3,3',5,5'-tetramethylbenzidine (TMB) substrate. The reaction is stopped with 0.33 M H$_2$SO$_4$ and the Optical Density (OD) is measured at 450 nm using an ELISA plate reader.

Results obtained using the ELISA method described above with human serum samples from IBD subjects, in particular Ulcerative Colitis (UC) and Crohn's Disease (CD)

subjects and apparently normal subjects are reported below. Data are compared using the Mann Whitney test and are expressed as Mean±Standard Error of the Mean (SEM) using Optical Density values. These results indicate that the calprotectin is differentially reactive with IBD sera as compared to normal sera and that the immunoreactivity to the calprotectin polypeptide, can be used to diagnose IBD.

TABLE 5

ACN-IgA levels in human serum samples from control subjects (normal) and diseased subjects (Ulcerative Colitis and Crohn's disease)

| Subject Groups | Description | Mean ± SEM |
|---|---|---|
| Group 1 | Ulcerative Colitis (UC) | 0.527 ± 0.052 |
| Group 2 | Apparently Normal (N) | 0.442 ± 0.023 |
| Group 3 | Crohn's Disease (CD) | 0.779 ± 0.068 |

| Mann Whitney Test | | P value |
|---|---|---|
| Group 1 vs Group 2 | UC vs N | 0.17 |
| Group 2 vs Group 3 | N vs CD | <0.0001 |

Example 13—Determination of Anti-Calprotectin Antibody IgG (ACN-IgG) Levels in Human Serum Samples This example illustrates an analysis of anti-calprotectin antibody IgG (ACN-IgG) levels in human serum samples using a direct ELISA assay.

Detection of human IgG antibodies that bind calprotectin (ACN-IgG) is performed by direct ELISA assays essentially as follows using human serum from apparently normal (N) and Inflammatory Bowel Disease (IBD) subjects, in particular Ulcerative Colitis (UC), and Crohn's Disease (CD) subjects.

ELISA plates are coated overnight at 4° C. with 100 µL/well with a recombinant, E. coli derived, human calprotectin S100A8/S100 A9 heterodimer (R&D Systems, Cat No. 8226-S8) at 0.2 µg/mL in carbonate solution (100.0 mM NaHCO$_3$—Na$_2$CO$_3$ Buffer, pH 9.5±0.5). The plates are washed thrice with TBS-T (Tris Buffered Saline Tween, 25.0 mM Tris-HCl, 2.7 mM potassium chloride, 137 mM Sodium Chloride, 0.05% Tween-20, pH 7.4±0.2) and blocked with 200 µL/well TBS/BSA (Tris Buffered Saline, 25.0 mM Tris-HCl, 2.7 mM potassium chloride, 137 mM Sodium Chloride, pH 7.4±0.2, 1% BSA) for 1 hour at 18-25° C. After washing the plates thrice with TBS-T, the standard and sample preparations are added to each well and incubated at 18-25° C. for 1 hour. The plates are then washed thrice with TBS-T and incubated for 1 hour at 18-25° C. with horseradish peroxidase (HRP)-anti-human IgG antibody diluted 1:10,000 in TBS/BSA. The plates are washed thrice with TBS-T and developed using 100 µL/well of 3,3',5,5'-tetramethylbenzidine (TMB) substrate. The reaction is stopped with 0.33 M H$_2$SO$_4$ and the Optical Density (OD) is measured at 450 nm using an ELISA plate reader.

Results obtained using the ELISA method described above with human serum samples from IBD subjects, in particular Ulcerative Colitis (UC) and Crohn's Disease (CD) subjects and apparently normal subjects are reported below. Data are compared using the Mann Whitney test and are expressed as Mean±Standard Error of the Mean (SEM) using Optical Density values.

TABLE 6

ACN-IgG levels in human serum samples from control subjects (normal) and diseased subjects (Ulcerative Colitis and Crohn's disease)

| Subject Groups | Description | Mean ± SEM |
|---|---|---|
| Group 1 | Ulcerative Colitis (UC) | 0.584 ± 0.078 |
| Group 2 | Apparently Normal (N) | 0.510 ± 0.048 |
| Group 3 | Crohn's Disease (CD) | 0.639 ± 0.076 |

| Mann Whitney Test | | P value |
|---|---|---|
| Group 1 vs Group 2 | UC vs N | 0.2949 |
| Group 2 vs Group 3 | N vs CD | 0.3093 |

Example 14—Determination of Anti-Integrin Antibody IgA (AIN-IgA) Levels in Human Serum Samples This example illustrates an analysis of anti-integrin antibody IgA (AIN-IgA) levels in human serum samples using a direct ELISA assay.

Detection of human IgA antibodies that bind integrin (AIN-IgA) is performed by direct ELISA assays essentially as follows using human serum from apparently normal (N) and Inflammatory Bowel Disease (IBD) subjects, in particular Ulcerative Colitis (UC), and Crohn's Disease (CD) subjects.

ELISA plates are coated overnight at 4° C. with 100 µL/well with a recombinant, CHO cell derived, human Integrin alpha-4 beta-7 (R&D Systems, Cat No. 5397-A3) at 0.2 µg/mL in carbonate solution (100.0 mM NaHCO$_3$—Na$_2$CO$_3$ Buffer, pH 9.5±0.5). The plates are washed thrice with TBS-T (Tris Buffered Saline Tween, 25.0 mM Tris-HCl, 2.7 mM potassium chloride, 137 mM Sodium Chloride, 0.05% Tween-20, pH 7.4±0.2) and blocked with 200 µL/well TBS/BSA (Tris Buffered Saline, 25.0 mM Tris-HCl, 2.7 mM potassium chloride, 137 mM Sodium Chloride, pH 7.4±0.2, 1% BSA) for 1 hour at 18-25° C. After washing the plates thrice with TBS-T, the standard and sample preparations are added to each well and incubated at 18-25° C. for 1 hour. The plates are then washed thrice with TBS-T and incubated for 1 hour at 18-25° C. with horseradish peroxidase (HRP)-anti-human IgA antibody diluted 1:2,000 in TBS/BSA. The plates are washed thrice with TBS-T and developed using 100 µL/well of 3,3',5,5'-tetramethylbenzidine (TMB) substrate. The reaction is stopped with 0.33 M H$_2$SO$_4$ and the Optical Density (OD) is measured at 450 nm using an ELISA plate reader.

Results obtained using the ELISA method described above with human serum samples from IBD subjects, in particular Ulcerative Colitis (UC) and Crohn's Disease (CD) subjects and apparently normal subjects are reported below. Data are compared using the Mann Whitney test and are expressed as Mean±Standard Error of the Mean (SEM) using Optical Density values. These results indicate that the integrin alpha-4 beta-7 is differentially reactive with IBD sera as compared to normal sera and that the immunoreactivity to the integrin polypeptide, can be used to diagnose IBD.

TABLE 7

AIN-IgA levels in human serum samples from control subjects (normal) and diseased subjects (Ulcerative Colitis and Crohn's disease)

| Subject Groups | Description | Mean ± SEM |
|---|---|---|
| Group 1 | Ulcerative Colitis (UC) | 0.485 ± 0.043 |
| Group 2 | Apparently Normal (N) | 0.387 ± 0.024 |
| Group 3 | Crohn's Disease (CD) | 0.695 ± 0.057 |

| Mann Whitney Test | | P value |
|---|---|---|
| Group 1 vs Group 2 | UC vs N | 0.065 |
| Group 2 vs Group 3 | N vs CD | <0.0001 |

Example 15—Determination of Anti-Integrin Antibody IgG (AIN-IgG) Levels in Human Serum Samples This example illustrates an analysis of anti-integrin antibody IgG (AIN-IgG) levels in human serum samples using a direct ELISA assay.

Detection of human IgG antibodies that bind integrin (AIN-IgG) is performed by direct ELISA assays essentially as follows using human serum from apparently normal (N) and Inflammatory Bowel Disease (IBD) subjects, in particular Ulcerative Colitis (UC), and Crohn's Disease (CD) subjects.

ELISA plates are coated overnight at 4° C. with 100 µL/well with a recombinant, CHO cell derived, human Integrin alpha-4 beta-7 (R&D Systems, Cat No. 5397-A3) at 0.2 µg/mL in carbonate solution (100.0 mM $NaHCO_3$—$Na_2CO_3$ Buffer, pH 9.5±0.5). The plates are washed thrice with TBS-T (Tris Buffered Saline Tween, 25.0 mM Tris-HCl, 2.7 mM potassium chloride, 137 mM Sodium Chloride, 0.05% Tween-20, pH 7.4±0.2) and blocked with 200 µL/well TBS/BSA (Tris Buffered Saline, 25.0 mM Tris-HCl, 2.7 mM potassium chloride, 137 mM Sodium Chloride, pH 7.4±0.2, 1% BSA) for 1 hour at 18-25° C. After washing the plates thrice with TBS-T, the standard and sample preparations are added to each well and incubated at 18-25° C. for 1 hour. The plates are then washed thrice with TBS-T and incubated for 1 hour at 18-25° C. with horseradish peroxidase (HRP)-anti-human IgG antibody diluted 1:10,000 in TBS/BSA. The plates are washed thrice with TBS-T and developed using 100 µL/well of 3,3',5,5'-tetramethylbenzidine (TMB) substrate. The reaction is stopped with 0.33 M $H_2SO_4$ and the Optical Density (OD) is measured at 450 nm using an ELISA plate reader.

Results obtained using the ELISA method described above with human serum samples from IBD subjects, in particular Ulcerative Colitis (UC) and Crohn's Disease (CD) subjects and apparently normal subjects are reported below. Data are compared using the Mann Whitney test and are expressed as Mean±Standard Error of the Mean (SEM) using Optical Density values.

TABLE 8

AIN-IgG levels in human serum samples from control subjects (normal) and diseased subjects (Ulcerative Colitis and Crohn's disease)

| Subject Groups | Description | Mean ± SEM |
|---|---|---|
| Group 1 | Ulcerative Colitis (UC) | 0.477 ± 0.057 |
| Group 2 | Apparently Normal (N) | 0.510 ± 0.050 |
| Group 3 | Crohn's Disease (CD) | 0.596 ± 0.072 |

| Mann Whitney Test | | P value |
|---|---|---|
| Group 1 vs Group 2 | UC vs N | 0.2034 |
| Group 2 vs Group 3 | N vs CD | 0.1186 |

Example 16—Determination of ACA, APMNA, ACNA, and AFA Levels in Dog Serum Samples This example illustrates an analysis of anti-OmpC antibody level (ACA), anti-canine polymorphonuclear leukocytes antibody level (APMNA), anti-calprotectin antibody level (ACNA), and anti-flagellin antibody level (AFA) using a direct ELISA assay in serum samples. Serum samples are collected from three cohorts of dogs: (i) the "IBD Dog" cohort includes dogs confirmed with the diagnosis of IBD based on the chronicity of gastrointestinal signs, the exclusion of underlying infectious, endocrine or neoplastic diseases, and the histological inflammatory findings; (ii) the "Non-IBD" cohort includes dogs predominantly with acute gastrointestinal symptoms; and (iii) the "Normal Dog" cohort includes dogs with no apparent gastrointestinal symptoms.

Study Design and Inclusion Criteria.

This is a multicenter study designed to develop methods and systems to accurately detect and measure the presence and/or levels of endogenous antibodies to markers associated with inflammatory bowel disease (IBD) in dogs. Such methods and systems identify whether a sample from the patient is associated with an inflammatory condition, by using non-invasive means, thus conveniently providing information useful for guiding treatment decisions. In this study, serum samples are collected once from dogs of the IBD cohort with gastrointestinal symptoms and from dogs of the Normal cohort with no apparent gastrointestinal symptoms. Dog owners sign an informed consent form for their dogs to participate in the study. IBD Dogs are considered eligible for participation if they meet the following inclusion criteria: vomiting, diarrhea, anorexia, weight loss, or some combination of these signs for at least 3 weeks; no immunosuppresive drugs or antibiotics administered for at least 10 days before sample collection; and confirmation of IBD by histopathology analysis of biopsy samples. Dogs are confirmed with the diagnosis of IBD based on the chronicity of gastrointestinal signs, the exclusion of underlying infectious, endocrine or neoplastic diseases, and the histological inflammatory findings. A complete clinical evaluation is performed, including hematology, clinical biochemistry, and as required, fecal flotation, *Giardia* antigen test, and abdominal ultrasound to exclude infectious, endocrine or neoplastic diseases. Gastroduodenoscopy is performed in all dogs of the IBD cohort, and biopsy samples from the stomach, duodenum, and colon, are collected with flexible endoscopy biopsy forceps. All IBD dogs are scored according to the canine inflammatory bowel disease activity index (CIBDAI). Full thickness biopsies and/or endoscopy biopsies are immediately placed in ice-cold phosphate-buffered saline (PBS) and 4% buffered paraformaldehyde solution until processed. All tissue samples are processed and graded by a clinical pathologist according using the World Small Animal Veterinary Association (WSAVA) guidelines. Multiple morphological parameters (i.e. epithelial injury, crypt distension, lacteal dilatation, mucosal fibrosis) and inflammatory histological parameters (such as plasma cells, lamina propria lymphocyte, eosinophils and neutrophils) are scored, and the resulting final scores are subdivided into histological severity groups: WSAVA score of 0=normal, 1-6=mild, 7-12=moderate, >13=severe.

Determination of Antibody Levels in Dog Sera to OMPC, PMN, Calprotectin, and Flagellin.

Canine IgA antibody levels against specific antigens are detected by direct ELISA assays. Sera from the IBD Dog, Non-IBD Dog, and Normal Dog cohorts are analyzed in duplicate for IgA reactivity to OmpC (ACA-IgA), canine polymorphonuclear leukocytes (APMNA-IgA), canine calprotectin (ACNA-IgA), and flagellin (AFA-IgA) as described previously.

The recombinant polypeptides for OmpC, calprotectin, and flagellin, utilized for the preparation of the coating material are peptides of sequences SEQ ID No: 35, SEQ ID No: 19, and SEQ ID No: 34, respectively. PMNs are isolated from canine blood as described in Example 2.

Briefly, for determination of APMNA-IgA levels in serum, microtiter plates are coated with $12.5 \times 10^3$ to $200 \times 10^3$ PMN per well isolated from blood sample collected from a single dog. A layer of PMN is recovered after centrifugation of the whole blood at 18-25° C. and treated with a hypotonic solution to lyse red blood cells. PMN are treated with cold 95% methanol and 5% acetic acid for $20 \pm 10$ minutes to fix the cells. Cells are incubated for $60 \pm 30$ minutes at 18-25° C. with 1% bovine serum albumin (BSA) in phosphate-buffered saline to block nonspecific antibody binding. Next, after 3 washes with Tris Buffered Saline-Tween (TBS-T: Tris Buffered Saline Tween, 25.0 mM Tris-HCl, 2.7 mM potassium chloride, 137 mM Sodium Chloride, 0.05% Tween-20, pH 7.4±0.2), control sera and test sample sera are added at a 1:50 to 1:100 dilutions to the microtiter plates and incubated for $60 \pm 30$ minutes at 18-25° C. After 3 washes with TBS-T, alkaline phosphatase-conjugated anti-dog IgA is added at a 1:2000 dilution to label PMN-bound antibody and incubated for $60 \pm 30$ minutes at 18-25° C. A solution of p-nitrophenol phosphate substrate is added, and color development is allowed to proceed for $30 \pm 10$ minutes. The Optical Density (OD) is measured at 405 nm using an ELISA plate reader.

For all other markers, microtiter plates are coated overnight at 4° C. with 100 µL/well at 0.2 µg/mL to 0.5 µg/mL antigen in carbonate solution (100.0 mM $NaHCO_3$—$Na_2CO_3$ Buffer, pH 9.5±0.5). The plates are washed thrice with TBS-T (Tris Buffered Saline Tween, 25.0 mM Tris-HCl, 2.7 mM potassium chloride, 137 mM Sodium Chloride, 0.05% Tween-20, pH 7.4±0.2) and blocked with 200 µL/well TBS/BSA (Tris Buffered Saline, 25.0 mM Tris-HCl, 2.7 mM potassium chloride, 137 mM Sodium Chloride, pH 7.4±0.2, 1% BSA) for 1 hour at 18-25° C. After washing the plates thrice with TBS-T, the standard and sample preparations are added to each well and incubated at 18-25° C. for 1 hour. The plates are then washed thrice with TBS-T and incubated for 1 hour at 18-25° C. with horseradish peroxidase (HRP)-anti-dog IgA antibody diluted 1:5,000 in TBS/BSA. The plates are washed thrice with TBS-T and developed using 100 µL/well of 3,3',5,5'-Tetramethylbenzidine (TMB) substrate. The reaction is stopped with 0.33 M $H_2SO_4$ and the Optical Density (OD) is measured at 450 nm using an ELISA plate reader.

Antibody levels are determined relative to a standard/calibrator/reference obtained from a dog with a positive signal using the Softmax software (Molecular Devices). Results with test samples are expressed as ELISA units/mL. Sera with circulating ACA, APMNA, ACNA, and AFA levels greater than two standard deviations above the mean value of the normal cohort may respectively be termed ACA positive, APMNA positive, ACNA positive, and AFA positive whereas numerical values that are less than the reference values may be termed negative.

Statistical Analysis

Statistical analysis is conducted using the Graphpad Prism (GraphPad Software, La Jolla Calif. USA) or Microsoft Office Excel (2013, Microsoft, Redmond, Wash., USA). Mean, median, minimum, maximum, and percentile are calculated. Data are analyzed by ANOVA with Bonferroni's post hoc multiple comparison test and presented as the mean (±SEM) and p values. Statistical analyses include area under receiver operating characteristic (ROC) curves and calculations of diagnostic sensitivity and specificity as appropriate for each of the markers (univariate analysis) and for a combination of markers (multivariate analysis). Measures of performance, sensitivity and specificity, may be computed using multiple reference values. A p-value <0.05 is considered significant.

Results.

The IBD-Dog cohort includes seventy dogs of various ages, gender and breeds presenting with chronic gastrointestinal signs. The Non-IBD-Dog cohort includes twenty-three dogs predominantly presenting with acute gastrointestinal symptoms. The Normal-Dog cohort consists of fifty eight dogs of various ages, gender, and breeds presenting no significant gastrointestinal symptoms at the time of visit at the clinical site.

Levels of IgA antibodies to OmpC (ACA), canine polymorphonuclear leukocytes (APMNA), calprotectin (ACNA), and flagellin (AFA) are determined in all enrolled subjects.

Typical results obtained with serum samples from IBD-Dogs and Normal-Dogs using the ELISA method described above are reported below. Data are compared between groups using the area under the curve (AUC) from receiver operating characteristics (ROC) curves generated by plotting sensitivity versus 1☐specificity for each marker. These results indicate that the markers are differentially reactive with IBD-Dog sera as compared to Normal-Dog sera and Non-IBD-Dog sera, and that the immunoreactivity to the markers can be used to detect IBD.

TABLE 9

Area under the curve values (AUC) obtained for ROC curves using OmpC (ACA), PMN (APMNA), calprotectin (ACNA), and flagellin (AFA) markers for differentiation between the IBD Dog and Normal Dog cohorts.

|  | ACA-IgA | APMNA-IgA | ACNA-IgA | AFA-IgA |
|---|---|---|---|---|
| Area under the ROC curve | 0.915 | 0.924 | 0.774 | 0.766 |
| P value | <0.0001 | <0.0001 | <0.0001 | <0.0001 |
| Specificity | 93% | 91% | 86% | 80% |
| Sensitivity | 87% | 86% | 66% | 64% |
| Indeterminate | 4% | 10% | 7% | 21% |

The table below summarizes the percent of positive samples identified in the IBD, Non-IBD, and Normal cohort. Samples with values greater than two standard deviations above the mean value of the normal cohort are identified as positive samples. The data show that the number of positive samples is significantly higher in the IBD cohorts.

TABLE 10

Percentage of positive serum samples per cohort.

| Cohort | ACA-IgA | APMNA-IgA | ACNA-IgA | AFA-IgA |
|---|---|---|---|---|
| IBD-Dogs | 75.7 | 77.1 | 42.9 | 38.6 |
| Non-IBD Dogs | 13.0 | 13.0 | 13.0 | 0.0 |
| Normal Dogs | 3.4 | 8.6 | 8.6 | 8.6 |

Data are analyzed by ANOVA with Bonferroni's post hoc multiple comparison test and the p value and the mean (±SEM) are is presented in the table below. The data show that there is a significant statistical difference between the IBD Dog vs the Non-IBD Dog cohorts and IBD Dog vs the Normal Dog cohorts. There is no significant statistical difference between the Normal Dog vs Non-IBD Dog cohorts.

TABLE 11

P values results obtained for four markers, ACA, APMNA, ACNA, and AFA, by ANOVA analysis with Bonferroni's post hoc multiple comparison test.

| Cohort Comparison | ACA | APMNA | ACNA | AFA |
|---|---|---|---|---|
| Normal vs IBD | <0.0001 | 0.0005 | 0.0009 | <0.0001 |
| Non-IBD vs IBD | <0.0001 | <0.0001 | 0.0166 | <0.0001 |
| Normal vs Non-IBD | 0.6231 | 0.7873 | 0.9051 | 0.7770 |

TABLE 12

Mean ± SEM results obtained for four markers, ACA, APMNA, ACNA, and AFA for the IBD Dog, Non-IBD Dog, and Normal Dog cohorts.

| Cohort | IBD | Non-IBD | Normal |
|---|---|---|---|
| ACA | 251.5 ± 29.40 | 31.51 ± 18.48 | 10.15 ± 1.96 |
| APMNA | 121.8 ± 12.42 | 26.04 ± 5.15 | 20.96 ± 1.42 |
| ACNA | 47.22 ± 11.04 | 9.072 ± 1.50 | 6.852 ± 0.68 |
| AFA | 189.7 ± 31.82 | 13.5 ± 3.11 | 26.66 ± 5.14 |

Overall, these results indicate that the method of detecting in a sample the presence and/or level of endogenous antibodies to OmpC, canine polymorphonuclear leukocytes, calprotectin, and flagellin, markers associated with inflammatory bowel disease (IBD), can be utilized to evaluate IBD in dogs.

Example 17—Determination of ACA and ACNA in Dog Serum Samples in a Longitudinal Study This example illustrates an analysis of anti-OmpC antibody level (ACA) and anti-calprotectin antibody level (ACNA) using dog serum samples to monitor the marker levels during the evolution of the disease.

In this study, serum samples are collected from dogs with gastrointestinal symptoms such as vomiting, diarrhea, anorexia, weight loss, or some combination for a long period of time. Serum samples are collected at the initial visit and may be collected as a follow-up visit after completion of treatment prescribed by the attending clinician.

Serum samples are collected and stored for short period of time at 2 to 8° C. and for long period of time at −10 to −20° C. until analysis.

Levels of canine IgA antibodies to OmpC (ACA) and calprotectin (ACNA) are determined using a direct ELISA method described previously.

Antibody levels are determined relative to a standard/calibrator/reference obtained from a dog with a positive signal using the Softmax software (Molecular Devices). Results with test samples are expressed as ELISA units/mL. Sera with circulating ACA and ACNA levels may be categorized as low, intermediate, or high. These three categories are defined by analysis of area under receiver operating characteristic (ROC) curves and calculations of diagnostic sensitivity and specificity as appropriate for each of the markers (univariate analysis) and for a combination of markers (multivariate analysis).

Typical results are listed below for dogs categorized as positive by testing for immunoreactivity to OmpC and calprotectin.

TABLE 13

ACA-IgA and ACNA-IgA level results obtained by using a direct ELISA method from serum samples collected from dogs with gastrointestinal symptoms.

| Subject | Serum Samples | ACA-IgA (EU/mL) | ACNA-IgA (EU/mL) |
|---|---|---|---|
| Dog 1 | Initial Visit | 2,021.6 (High) | 60.5 (High) |
| Dog 1 | Follow-up Visit | 497.6 (High) | 60.1 (High) |
| Dog 2 | Initial Visit | 42.4 (High) | 9.5 (Intermediate) |
| Dog 2 | Follow-up Visit | 2.7 (Low) | 4.9 (Low) |

Evidence of inflammatory bowel disease is confirmed by a pathologist based on a biopsy performed on the dog tested for seropositivity for OmpC and calprotectin. For instance, moderate lymphomplasmacytic enteritis with eosinophils and mild lymphoplasmacytic gastritis is observed for dog 2: sections of tissue from the stomach are characterized by mild inflammation with a mild accumulation of lymphocytes and plasma cells within the gastric mass; sections of tissue from the intestine are characterized by a moderate inflammation with a moderate accumulation of lymphocytes and plasma cells within the lamina propria, villous structures are swollen and lacteals are occasionally dilated at the villous tips.

These results indicate that the method of detecting the presence and/or level of one or more endogenous antibodies associated with inflammatory bowel disease (IBD) in a sample can be utilized to detect and monitor IBD.

Example 18—Identification of Polypeptides Generated from Gliadin Extracts Subjected to Dog Gastric Fluids Digestion This example illustrates the identification of polypeptides obtained after subjecting gliadin extracts to dog gastric fluids digestion.

In a 1.5 mL Eppendorf tube, 70 µL of gliadin solution at 100 mg/mL solubilized in 60% ethanol (Ethanol, Fisher Scientific, Cat No. BP2818-500) are placed. The tube containing the gliadin solution (ACROS Organics, Cat No. 179311000) is incubated at 37° C. under various conditions. Under condition 1, 280 µL of dog gastric fluids collected during a biopsy procedure from a dog are added to the gliadin solution. Under condition 2, 280 µL of simulated gastric fluids (RICCA Chemical Company, Cat No. 7108.16) supplemented with 1 mg/mL of pepsin from porcine gastric mucosa with an activity of 8.60 European Units/mg (ACROS Organics, Cat No. 41707-1000) are added to the gliadin solution. Under condition 3, 280 µL of simulated gastric fluids (RICCA Chemical Company, Cat No. 7108.16) are added to the gliadin solution. Under condition 4, 280 µL of reagent grade water (Thermo Scientific, Cat No. 9800-5) are added to the gliadin solution. 50 µL aliquots of the reaction mixtures are taken at various time points (0, 5, 15, 30, 60 and 120 min) and the reactions are immediately stopped by adding 5 µL of cold stop solution (1M Tris-Base, Teknova, Cat No. T0550).

Digestibility of the gliadin extracts by the dog gastric fluids is assessed by comparing the migration patterns of the gliadin solution and control solutions subjected to digestion under various conditions for various time periods using 4-12% Bis-Tris SDS-PAGE gels (Novex, Cat No. NP0322BOX) under reducing conditions (NuPAGE Sample Reducing Agent, Novex, Cat No. NP004) and Coomassie staining (Colloidal blue staining kit, Novex, Cat No. LC6025). A certain number of proteolytic fragments are observed even after extended exposure to dog gastric fluids and are considered to be resistant to digestion. These polypeptides are collected and their sequences are determined by mass spectrometry with the Quadrupole-time-of-flight Sciex 5600 QTOF 5600 instrument.

The proteolytic polypeptides recovered after exposure of gliadin extracts to dog gastric fluids for a long period of time are considered to be resistant to digestion. As such, they may be immunogenic and causing symptoms observed in subjects susceptible to food sensitivity. Sequences of the polypeptides identified under these conditions are listed as SEQ ID NOs. 37 to 45.

Example 19—Identification of Polypeptides Generated from Zein Extracts Subjected to Dog Gastric Fluids Digestion This example illustrates the identification of polypeptides obtained after subjecting zein extracts to dog gastric fluids digestion.

In a 1.5 mL Eppendorf tube, 70 µL of zein solution at 100 mg/mL solubilized in 60% ethanol (Ethanol, Fisher Scientific, Cat No. BP2818-500) are placed. The tube containing the zein solution (MP, Cat No. 101778) is incubated at 37° C. under various conditions. Under condition 1, 280 µL of dog gastric fluids collected during a biopsy procedure from a dog are added to the zein solution. Under condition 2, 280 µL of simulated gastric fluids (RICCA Chemical Company, Cat No. 7108.16) supplemented with 1 mg/mL of pepsin from porcine gastric mucosa with an activity of 8.60 European Units/mg (ACROS Organics, Cat No. 41707-1000) are added to the zein solution. Under condition 3, 280 µL of simulated gastric fluids (RICCA Chemical Company, Cat No. 7108.16) are added to the zein solution. Under condition 4, 280 µL of reagent grade water (Thermo Scientific, Cat No. 9800-5) are added to the zein solution. 50 µL aliquots of the reaction mixtures are taken at various time points (0, 5, 15, 30, 60 and 120 min) and the reactions are immediately stopped by adding 5 µL of cold stop solution (1M Tris-Base, Teknova, Cat No. T0550).

Digestibility of the zein extracts by the dog gastric fluids is assessed by comparing the migration patterns of the zein solution and control solutions subjected to digestion under various conditions for various time periods using 4-12% Bis-Tris SDS-PAGE gels (Novex, Cat No. NP0322BOX) under reducing conditions (NuPAGE Sample Reducing Agent, Novex, Cat No. NP004) and Coomassie staining (Colloidal blue staining kit, Novex, Cat No. LC6025). A certain number of proteolytic fragments are observed even after extended exposure to dog gastric fluids and are considered to be resistant to digestion. These polypeptides are collected and their sequences are determined by mass spectrometry with the Quadrupole-time-of-flight Sciex 5600 QTOF 5600 instrument.

The proteolytic polypeptides recovered after exposure of zein extracts to dog gastric fluids for a long period of time are considered to be resistant to digestion. As such, they may be immunogenic and causing symptoms observed in subjects susceptible to food sensitivity. Sequences of the polypeptides identified under these conditions are listed as SEQ ID NOs. 46 to 57.

Example 20—Cloning of Proteolytic Polypeptide Coding Regions and Preparation of Recombinant Polypeptides This example illustrates the cloning of the coding regions of proteolytic polypeptides identified after digestion of gliadin extracts and zein extracts with dog gastric fluids and the preparation of recombinant polypeptides.

The coding regions encompassing the proteolytic polypeptide sequences are cloned by assembling synthetic oligonucleotides. The synthetic constructs which are codon optimized for expression in *E. coli* include NdeI and HindIII as flanking restriction sites on the 5'- and 3'-end of the gene of interest, respectively, and a histidine tag at the N-terminal region to create a HIS fusion polypeptide. The assembled products are then subcloned into an expression vector with the N-terminal region of the coding gene operably linked to a start codon and an inducible promoter system. The expression constructs are transformed into *E. coli* BL21. The amino-acid sequence of the synthetic constructs are reported as SEQ ID NO: 58, SEQ ID NO: 59, SEQ ID NO: 60.

The following protocol describes the purification of the recombinant polypeptides. The nucleic acid sequence of the polypeptide coding region is designed to include a polyhistidine tag to create a HIS-fusion polypeptide. After expression in *E. coli*, the fusion polypeptide is purified using a nickel purification column under denaturing conditions. For inoculum preparation and for production, the recombinant *E. coli* cells are cultivated overnight to generate the seed culture. The seed culture is then inoculated into a culture medium in larger flasks or mini-bioreactors at a ratio of 1 to 25 and cultured until reaching an optical density (OD) of 0.6-0.9 at 600 nm. At this cell density, cells are induced with 1 mM IPTG (Isopropyl β-D-1-thiogalactopyranoside) and the fermentation is carried out for another 4-24 hours. The cells are then harvested and lysed. The recombinant polypeptides are purified from the whole cell lysates using a nickel-charged purification resin under denaturing conditions. The purified recombinant polypeptides are shown to be of the expected molecular weight by Coomassie staining. Purified recombinant polypeptide preparations are diluted 5 times in a refolding buffer (25 mM Tris-Cl, pH 7.5, 100 mM NaCl, 10% glycerol, 0.2M Urea, 0.02% Sodium Azide) and the reactions are incubated at 2-8° C. for at least 24 hours.

Example 21—Determination of Anti-gliadin Antibody (AGA) Levels in Dog Serum Samples This example illustrates an assay to determine anti-gliadin antibody (AGA) levels using a direct ELISA assay in serum samples collected from diseased and control dogs.

Serum samples collected from diseased dogs enrolled in the study are from dogs diagnosed with conditions related to gastrointestinal disorders. Diagnosis includes histopathological assessment of gastrointestinal biopsies. Histopathological observations include but is not limited to shortened, eroded, and blunted villous structures, swollen villous structures, cyst distension, inflammation at villous tips, sloughed epithelial cells, dilated lacteals, glandular degeneration, and in some cases lymphangiectasia.

Detection of dog IgA antibodies that bind gliadin (AGA-IgA) is performed by direct ELISA assays essentially as follows. ELISA plates are coated overnight at 4° C. with 100 µL/well gliadin extracts at 10 µg/mL in carbonate solution supplemented with urea (100.0 mM $NaHCO_3$—$Na_2CO_3$ Buffer, pH 9.5±0.5, 3 M Urea). The plates are washed thrice with TBS-T (Tris Buffered Saline Tween, 25.0 mM Tris-HCl, 2.7 mM potassium chloride, 130 mM Sodium Chloride, 0.05% Tween-20, pH 7.4±0.2) and blocked with 200 µL/well TBS/BSA (Tris Buffered Saline, 25.0 mM Tris-HCl, 2.7 mM potassium chloride, 130 mM Sodium Chloride, pH 7.4±0.2, 1% BSA) for 1 hour at 18-25° C. After washing the plates thrice with TBS-T, the standard and sample preparations are added to each well and incubated at 18-25° C. for 1 hour. The plates are then washed thrice with TBS-T and incubated for 1 hour at 18-25° C. with horseradish peroxidase (HRP)-anti-dog IgA antibody diluted 1:5,000 in TBS/BSA. The plates are washed thrice with TBS-T and developed using 100 µL/well of 3,3',5,5'-tetramethylbenzidine (TMB) substrate. The reaction is stopped with 0.33 M $H_2SO_4$ and the Optical Density (OD) is measured at 450 nm using an ELISA plate reader. The standard curve is fitted using a four parameter equation and used to estimate the antibody levels in the samples.

Example 22—Determination of Anti-Zein Antibody (AZA) Levels in Dog Serum Samples This example illustrates an assay to determine anti-zein antibody (AZA) levels using a direct ELISA assay in serum samples collected from diseased and control dogs.

Serum samples collected from diseased dogs enrolled in the study are from dogs diagnosed with conditions related to gastro-intestinal disorders. Diagnosis includes histopathological assessment of gastrointestinal biopsies. Histopathological observations include but is not limited to shortened, eroded, and blunted villous structures, swollen villous structures, cyst distension, inflammation at villous tips, sloughed epithelial cells, dilated lacteals, glandular degeneration, and in some cases lymphangiectasia.

Detection of dog IgA antibodies that bind zein (AZA-IgA) is performed by direct ELISA assays essentially as follows. ELISA plates are coated overnight at 4° C. with 100 µL/well zein extracts at 2 µg/mL in carbonate solution supplemented with urea (100.0 mM $NaHCO_3$—$Na_2CO_3$ Buffer, pH 9.5±0.5, 3 M Urea). The plates are washed thrice with TBS-T (Tris Buffered Saline Tween, 25.0 mM Tris-HCl, 2.7 mM potassium chloride, 130 mM Sodium Chloride, 0.05% Tween-20, pH 7.4±0.2) and blocked with 200 µL/well TBS/BSA (Tris Buffered Saline, 25.0 mM Tris-HCl, 2.7 mM potassium chloride, 130 mM Sodium Chloride, pH 7.4±0.2, 1% BSA) for 1 hour at 18-25° C. After washing the plates thrice with TBS-T, the standard and sample preparations are added to each well and incubated at 18-25° C. for 1 hour. The plates are then washed thrice with TBS-T and incubated for 1 hour at 18-25° C. with horseradish peroxidase (HRP)-anti-dog IgA antibody diluted 1:5,000 in TBS/BSA. The plates are washed thrice with TBS-T and developed using 100 µL/well of 3,3',5,5'-tetramethylbenzidine (TMB) substrate. The reaction is stopped with 0.33 M $H_2SO_4$ and the Optical Density (OD) is measured at 450 nm using an ELISA plate reader. The standard curve is fitted using a four parameter equation and used to estimate the antibody levels in the samples.

Example 23—Determination of Anti-Recombinant-Gliadin-Antibody (ARGA) Anti-Recombinant-Amylase-Inhibitor-Antibody (ARAIA) Levels in Dog Serum Samples This example illustrates an analysis of anti-Recombinant-Gliadin-Antibody (ARGA) and anti-Recombinant-Amylase-Inhibitor-Antibody (ARAIA) levels using a direct ELISA assay in serum samples collected from diseased and control dogs.

Serum samples collected from diseased dogs enrolled in the study are from dogs diagnosed with conditions related to gastro-intestinal disorders. Diagnosis includes histopathological assessment of gastrointestinal biopsies. Histopathological observations include but is not limited to shortened, eroded, and blunted villous structures, swollen villous structures, cyst distension, inflammation at villous tips, sloughed epithelial cells, dilated lacteals, glandular degeneration, and in some cases lymphangiectasia.

Detection of dog IgA antibodies that bind recombinant gliadin derived polypeptide (ARGA-IgA) and recombinant amylase inhibitor polypeptide (ARAI-IgA) is performed by direct ELISA assays essentially as follows. ELISA plates are coated overnight at 4° C. with 100 µL/well recombinant polypeptides of SEQ ID No: 58 alone at 2.5 µg/mL, SEQ ID No: 59 alone at 2.5 µg/mL or a mixture of SEQ ID No: 58 and SEQ ID No: 59 at 1.25 µg/mL each in carbonate solution (100.0 mM $NaHCO_3$—$Na_2CO_3$ Buffer, pH 9.5±0.5). Additional ELISA plates are coated overnight at 4° C. with 100 µL/well gliadin extracts at 10 µg/mL in carbonate solution supplemented with urea (100.0 mM $NaHCO_3$—$Na_2CO_3$ Buffer, pH 9.5±0.5, 3 M Urea). The plates are washed thrice with TBS-T (Tris Buffered Saline Tween, 25.0 mM Tris-HCl, 2.7 mM potassium chloride, 130 mM Sodium Chloride, 0.05% Tween-20, pH 7.4±0.2) and blocked with 200 µL/well TBS/BSA (Tris Buffered Saline, 25.0 mM Tris-HCl, 2.7 mM potassium chloride, 130 mM Sodium Chloride, pH 7.4±0.2, 1% BSA) for 1 hour at 18-25° C. After washing the plates thrice with TBS-T, the standard and sample preparations are added to each well and incubated at 18-25° C. for 1 hour. The plates are then washed thrice with TBS-T and incubated for 1 hour at 18-25° C. with horseradish peroxidase (HRP)-anti-dog IgA antibody diluted 1:5,000 in TBS/BSA. The plates are washed thrice with TBS-T and developed using 100 µL/well of 3,3',5,5'-tetramethylbenzidine (TMB) substrate. The reaction is stopped with 0.33 M $H_2SO_4$ and the Optical Density (OD) is measured at 450 nm using an ELISA plate reader. The standard curve is fitted using a four parameter equation and used to estimate the antibody levels in the samples.

Typical results obtained with serum samples from diseased dogs and apparently healthy dogs (control) using the ELISA method described above are reported below. Data are compared using the Mann Whitney test and are expressed as Mean±Standard Error of the Mean (SEM) using ELISA units. These results indicate that the polypeptide preparations derived from clones expressing SEQ ID NO:58 and SEQ ID NO:59 are differentially reactive with diseased sera as compared to apparently normal sera and that the immunoreactivity to the recombinant polypeptides can be used to diagnose food sensitivity.

TABLE 1

ARGA-IgA levels and ARAA-IgA levels in serum samples from diseased dogs and control dogs.

| Description | Sequence | Diseased Dogs (N = 20) Mean ± SEM | Control Dogs (N = 20) Mean ± SEM | p value |
|---|---|---|---|---|
| Recombinant Gliadin | SEQ ID: 58 | 56.87 ± 20.41 | 6.425 ± 2.99 | <0.0001 |
| Recombinant Amylase | SEQ ID: 59 | 56.82 ± 21.08 | 4.831 ± 1.60 | 0.0004 |
| Recombinant Gliadin and Recombinant Amylase | SEQ ID: 58 and SEQ ID: 59 | 68.11 ± 21.14 | 9.454 ± 2.30 | <0.0001 |

Example 24—Determination of Anti-Recombinant-Zein-Antibody (ARZA) Levels in Dog Serum Samples This example illustrates an analysis of anti-Recombinant-Zein-Antibody (ARZA) levels using a direct ELISA assay in serum samples collected from diseased and control dogs.

Serum samples collected from diseased dogs enrolled in the study are from dogs diagnosed with conditions related to gastro-intestinal disorders. Diagnosis includes histopathological assessment of gastrointestinal biopsies. Histopathological observations include but is not limited to shortened, eroded, and blunted villous structures, swollen villous structures, cyst distension, inflammation at villous tips, sloughed epithelial cells, dilated lacteals, glandular degeneration, and in some cases lymphangiectasia.

Detection of dog IgA antibodies that bind recombinant zein polypeptide (ARZA-IgA) is performed by direct ELISA assays essentially as follows. ELISA plates are coated overnight at 4° C. with 100 µL/well recombinant polypeptide of SEQ ID No: 60 at 2.5 µg/mL in carbonate solution (100.0 mM $NaHCO_3$—$Na_2CO_3$ Buffer, pH 9.5±0.5). Additional ELISA plates are coated overnight at 4° C. with 100 µL/well zein extracts at 2 µg/mL in carbonate solution supplemented with urea (100.0 mM $NaHCO_3$—$Na_2CO_3$ Buffer, pH 9.5±0.5, 3 M Urea). The plates are washed thrice with TBS-T (Tris Buffered Saline Tween, 25.0 mM Tris-HCl, 2.7 mM potassium chloride, 130 mM Sodium Chloride, 0.05% Tween-20, pH 7.4±0.2) and blocked with 200 µL/well TBS/BSA (Tris Buffered Saline, 25.0 mM Tris-HCl, 2.7 mM potassium chloride, 130 mM Sodium Chloride, pH 7.4±0.2, 1% BSA) for 1 hour at 18-25° C. After washing the plates thrice with TBS-T, the standard and sample preparations are added to each well and incubated at 18-25° C. for 1 hour. The plates are then washed thrice with TBS-T and incubated for 1 hour at 18-25° C. with horseradish peroxidase (HRP)-anti-dog IgA antibody diluted 1:5,000 in TBS/BSA. The plates are washed thrice with TBS-T and developed using 100 µL/well of 3,3',5,5'-tetramethylbenzidine (TMB) substrate. The reaction is stopped with 0.33 M $H_2SO_4$ and the Optical Density (OD) is measured at 450 nm using an ELISA plate reader. The standard curve is fitted using a four parameter equation and used to estimate the antibody levels in the samples.

Typical results obtained with serum samples from diseased dogs and apparently healthy dogs (control) using the ELISA method described above are reported below. Data are compared using the Mann Whitney test and are expressed as Mean±Standard Error of the Mean (SEM) using ELISA units. These results indicate that the polypeptide preparation derived from clone expressing SEQ ID NO:24 is differentially reactive with diseased sera as compared to normal sera and that the immunoreactivity to the recombinant polypeptide can be used to diagnose food sensitivity.

TABLE 2

ARZA-IgA levels (EU/mL) in serum samples from diseased dogs and control dogs.

| Description | Sequence | Diseased Dogs (N = 20) Mean ± SEM | Control Dogs (N = 20) Mean ± SEM | p value |
|---|---|---|---|---|
| Recombinant Zein | SEQ ID: 60 | 73.51 ± 21.51 | 9.116 ± 2.37 | <0.0001 |

Example 25—Isolation of Canine TTG2 Coding Region and Preparation of Recombinant Polypeptide This example illustrates the cloning of canine Tissue Transglutaminase 2 (TTG2) coding region and the preparation of TTG2 polypeptide.

Fragment of the coding regions of canine TTG2 is cloned by PCR amplification using cDNA isolated from dog as template. PCR reactions are carried out in a 25 µL final volume containing the reaction master mix supplemented with a Taq DNA polymerase (Thermo Fisher scientific), the DNA template, and 0.5 µM of each of a forward primer of SEQ ID NO:61 and of reverse primer of SEQ ID NO:62. The PCR reaction mix is denatured at 94° C. for 4-5 min followed by amplification for 30 cycles (95° C. for 30 s, 50° C. for 30 s, 72° C. for 60 s) and an extension at 72° C. for 10 min. The amino-acid sequence of the cloned fragment is reported as SEQ ID NO: 27. The PCR products are cloned into a bacterial expression vector containing a histidine tag according to the manufacturer's recommendations (Life Technologies).

The following protocol describes the preparation of the purified recombinant polypeptide. The nucleic acid sequence of the Tissue Transglutaminase 2 coding region includes a polyhistidine tag to create a HIS fusion polypeptide. After expression in E. coli, the fusion polypeptide is purified using a nickel purification column. For inoculum preparation and for production, the recombinant E. coli cells are cultivated overnight (seed culture). The seed culture is inoculated into culture medium in larger flasks or mini-bioreactors at a ratio of 1 to 25 and cultured until reaching an optical density (OD) of 0.6-0.9 at 600 nm. At this cell density, cells are induced with 1 mM. IPTG (Isopropyl β-D-1-thiogalactopyranoside) and the fermentation is carried out for another 4-24 hours. The cells are then harvested and lysed under denaturing conditions. The recombinant polypeptide is purified from the whole cell lysate using a nickel-charged purification resin. The purified recombinant polypeptide is shown to be of the expected molecular weight by Coomassie staining. The purified polypeptide preparation is diluted 10 times in a refolding buffer (25 mM Tris-Cl, pH 7.5, 100 mM NaCl, 10% glycerol, 0.2M Urea, 0.02% Sodium Azide) and the reaction is incubated at 2-8° C. for at least 24 hours.

Example 26—Determination of Anti-TTG2 Antibody (ATTGA) Levels in Dog Serum Samples This example illustrates an assay to determine anti-TTG antibody (ATTGA) levels using a direct ELISA assay in serum samples collected from diseased and control dogs.

Serum samples collected from diseased dogs enrolled in the study are from dogs diagnosed with conditions related to gastro-intestinal disorders. Diagnosis includes histopathological assessment of gastrointestinal biopsies. Histopathological observations include but is not limited to shortened, eroded, and blunted villous structures, swollen villous structures, cyst distension, inflammation at villous tips, sloughed epithelial cells, dilated lacteals, glandular degeneration, and in some cases lymphangiectasia.

Detection of dog IgA antibodies that bind TTG (ATTGA-IgA) is performed by direct ELISA assays essentially as follows. ELISA plates are coated overnight at 4° C. with 100 µL/well recombinant TTG2 at 2.5 µg/mL in carbonate solution (100.0 mM $NaHCO_3$—$Na_2CO_3$ Buffer, pH 9.5±0.5,). The plates are washed thrice with TBS-T (Tris Buffered Saline Tween, 25.0 mM Tris-HCl, 2.7 mM potassium chloride, 130 mM Sodium Chloride, 0.05% Tween-20, pH 7.4±0.2) and blocked with 200 µL/well TBS/BSA (Tris Buffered Saline, 25.0 mM Tris-HCl, 2.7 mM potassium chloride, 130 mM Sodium Chloride, pH 7.4±0.2, 1% BSA) for 1 hour at 18-25° C. After washing the plates thrice with TBS-T, the standard and sample preparations are added to each well and incubated at 18-25° C. for 1 hour. The plates are then washed thrice with TBS-T and incubated for 1 hour at 18-25° C. with horseradish peroxidase (HRP)-anti-dog IgA antibody diluted 1:5,000 in TBS/BSA. The plates are washed thrice with TBS-T and developed using 100 µL/well of 3,3',5,5'-tetramethylbenzidine (TMB) substrate. The reaction is stopped with 0.33 M $H_2SO_4$ and the Optical Density (OD) is measured at 450 nm using an ELISA plate reader. The standard curve is fitted using a four parameter equation and used to estimate the antibody levels in the samples.

Example 27—Isolation of Canine TG3 Coding Region and Preparation of Recombinant Polypeptide This example illustrates the cloning of canine Transglutaminase 3 (TG3) coding region and the preparation of TG3 polypeptide.

Fragment of the coding regions of canine TG3 is cloned by PCR amplification using cDNA isolated from dog as template. PCR reactions are carried out in a 25 µL final volume containing the reaction master mix supplemented with a Taq DNA polymerase (Thermo Fisher scientific), the DNA template, and 0.5 µM of each of a forward primer of SEQ ID NO:28 and of reverse primer of SEQ ID NO:29. The PCR reaction mix is denatured at 94° C. for 4-5 min followed by amplification for 30 cycles (95° C. for 30 s, 50° C. for 30 s, 72° C. for 60 s) and an extension at 72° C. for 10 min. The amino-acid sequence of the cloned fragment is reported as SEQ ID NO: 30. The PCR products are cloned into a bacterial expression vector containing a histidine and a Small Ubiquitin-like Modifier (SUMO) tag according to the manufacturer's recommendations (Life Technologies).

The following protocol describes the preparation of the purified recombinant polypeptide. The nucleic acid sequence of the Transglutaminase 3 coding region includes a polyhistidine tag to create a HIS fusion polypeptide. After expression in *E. coli*, the fusion polypeptide is purified using a nickel purification column. For inoculum preparation and for production, the recombinant *E. coli* cells are cultivated overnight (seed culture). The seed culture is inoculated into culture medium in larger flasks or mini-bioreactors at a ratio of 1 to 25 and cultured until reaching an optical density (OD) of 0.6-0.9 at 600 nm. At this cell density, cells are induced with 1 mM IPTG (Isopropyl β-D-1-thiogalactopyranoside) and the fermentation is carried out for another 4-24 hours. The cells are then harvested and lysed under denaturing conditions. The recombinant polypeptide is purified from the whole cell lysate using a nickel-charged purification resin. The purified recombinant polypeptide is shown to be of the expected molecular weight by Coomassie staining. The purified polypeptide preparation is diluted 10 times in a refolding buffer (25 mM Tris-Cl, pH 7.5, 100 mM NaCl, 10% glycerol, 0.2M Urea, 0.02% Sodium Azide) and the reaction is incubated at 2-8° C. for at least 24 hours.

Example 28—Determination of Anti-TG3 Antibody (ATG3A) Levels in Dog Serum Samples This example illustrates an assay to determine anti-TTG antibody (ATTG3A) levels using a direct ELISA assay in serum samples collected from diseased and control dogs.

Serum samples collected from diseased dogs enrolled in the study are from dogs presenting with skin disorders such as pruritus, rash, lesion, blister, and the like, with or without gastro-intestinal symptoms.

Detection of dog IgA antibodies that bind TG3 (ATG3A-IgA) is performed by direct ELISA assays essentially as follows. ELISA plates are coated overnight at 4° C. with 100 µL/well recombinant TG3 at 2.5 µg/mL in carbonate solution (100.0 mM $NaHCO_3$—$Na_2CO_3$ Buffer, pH 9.5±0.5,). The plates are washed thrice with TBS-T (Tris Buffered Saline Tween, 25.0 mM Tris-HCl, 2.7 mM potassium chloride, 130 mM Sodium Chloride, 0.05% Tween-20, pH 7.4±0.2) and blocked with 200 µL/well TBS/BSA (Tris Buffered Saline, 25.0 mM Tris-HCl, 2.7 mM potassium chloride, 130 mM Sodium Chloride, pH 7.4±0.2, 1% BSA) for 1 hour at 18-25° C. After washing the plates thrice with TBS-T, the standard and sample preparations are added to each well and incubated at 18-25° C. for 1 hour. The plates are then washed thrice with TBS-T and incubated for 1 hour at 18-25° C. with horseradish peroxidase (HRP)-anti-dog IgA antibody diluted 1:5,000 in TBS/BSA. The plates are washed thrice with TBS-T and developed using 100 µL/well of 3,3',5,5'-tetramethylbenzidine (TMB) substrate. The reaction is stopped with 0.33 M $H_2SO_4$ and the Optical Density (OD) is measured at 450 nm using an ELISA plate reader. The standard curve is fitted using a four parameter equation and used to estimate the antibody levels in the samples.

Example 29—Determination of AGA, AZA, and ATTGA Levels in Dog Serum Samples

This example illustrates an analysis of anti-gliadin antibody level (AGA), anti-zein antibody level (AZA), and anti-tissue transglutaminase antibody level (ATTGA) using a direct ELISA assay in serum samples. Serum samples are collected from two cohorts of dogs: the "Symptomatic" cohort includes dogs with GI-related symptoms and the "Asymptomatic" cohort including dogs with no apparent gastrointestinal symptoms at the time of the visit at the clinical site.

Study Design and Inclusion Criteria.

This is a multicenter study designed to develop methods and systems to accurately detect and measure the presence and/or levels of endogenous antibodies to markers associated with food sensitivity in dogs. Such methods and systems identify whether a sample from the patient is associated with food sensitivity, by using non-invasive means, thus conveniently providing information useful for guiding treatment decisions. In this study, serum samples are collected once from dogs of the symptomatic cohort with gastrointestinal symptoms and from dogs of the asymptomatic cohort with no apparent gastrointestinal symptoms. Dog owners sign an informed consent form for their dogs to participate in the study. Dogs are considered eligible for participation if they meet the following inclusion criteria: vomiting, diarrhea, anorexia, weight loss, or some combination of these signs for at least 3 weeks; no immunosuppressive drugs or antibiotics administered for at least 10 days before sample collection. Dogs are confirmed with the diagnosis of GI-related symptoms based on the chronicity of gastrointestinal signs, the exclusion of underlying infectious, endocrine or neoplastic diseases, and the histological inflammatory findings. A complete clinical evaluation is performed, including hematology, clinical biochemistry, and as required, fecal flotation, *Giardia* antigen test, and abdominal ultrasound to exclude infectious, endocrine or neoplastic diseases. Gastroduodenoscopy is performed in all dogs of the symptomatic cohort, and biopsy samples from the stomach, duodenum, and colon, are collected with flexible endoscopy biopsy forceps.

Determination of Antibody Levels to Gliadin, Zein, and Tissue Transglutaminase in Dog Sera.

Canine IgA antibody levels against specific antigens are detected by direct ELISA assays essentially as described above. Sera from the Symptomatic Dog and Asymptomatic Dog cohorts are analyzed in duplicate for IgA reactivity to gliadin (AGA-IgA), zein (AZA-IgA), and tissue transglutaminase (ATTGA-IgA).

Antibody levels are determined relative to a standard/calibrator/reference obtained from a dog with a positive signal using the Softmax software (Molecular Devices). Results with test samples are expressed as ELISA units/mL. Sera with circulating AGA, AZA, and ATTGA levels greater than two standard deviations above the mean value of the asymptomatic cohort may respectively be termed AGA positive, AZA positive, and ATTGA positive, whereas numerical values that are less than the reference values may be termed negative.

Statistical Analysis

Statistical analysis is conducted using the Graphpad Prism (GraphPad Software, La Jolla Calif. USA) or Microsoft Office Excel (2013, Microsoft, Redmond, Wash., USA). Mean, median, minimum, maximum, and percentile are calculated. Data are analyzed by the Mann Whitney test. Statistical analyses include area under receiver operating characteristic (ROC) curves and calculations of diagnostic sensitivity and specificity as appropriate for each of the markers (univariate analysis) and for a combination of markers (multivariate analysis). Measures of performance, sensitivity and specificity, may be computed using multiple reference values. A p-value <0.05 is considered significant.

Results.

The symptomatic cohort includes seventy dogs of various ages, gender and breeds presenting with chronic gastrointestinal signs. The asymptomatic cohort includes fifty eight dogs with no apparent gastrointestinal symptoms.

Levels of IgA antibodies to gliadin (AGA-IgA), zein (AZA-IgA), and tissue transglutaminase (ATTGA-IgA) are determined for all enrolled subjects.

Typical results obtained with serum samples from symptomatic-Dogs and Asymptomatic-Dogs using the ELISA method described above are reported below. Data are compared between groups using the area under the curve (AUC) from receiver operating characteristics (ROC) curves generated by plotting sensitivity versus 1-specificity for each marker. These results indicate that the markers are differentially reactive with symptomatic sera as compared to asymptomatic sera, and that the immunoreactivity to the markers can be used to detect food sensitivity.

TABLE 3

Area under the curve (AUC) values obtained for receiver operating characteristics (ROC) curves using gliadin (AGA), zein (AZA), and tissue transglutaminase (ATTGA) markers for differentiation between the symptomatic and asymptomatic cohorts.

|  | AGA-IgA | AZA-IgA | ATTGA-IgA |
|---|---|---|---|
| Area under the ROC curve | 0.843 | 0.7049 | 0.6222 |
| p value | <0.0001 | <0.0001 | 0.0176 |
| Specificity | 92% | 94% | 95% |
| Sensitivity | 69% | 47% | 42% |
| Indeterminate | 16% | 19% | 11% |

The table below summarizes the percent of positive samples identified in the symptomatic and asymptomatic cohorts. Samples with values greater than two standard deviations above the mean value of the asymptomatic cohort are identified as positive samples. The data show that the number of positive samples is significantly higher in the Symptomatic cohorts.

TABLE 4

Percentage of positive serum samples per cohort.

| Cohort | AGA-IgA | AZA-IgA | ATTGA-IgA |
|---|---|---|---|
| Symptomatic Dogs | 54.3 | 15.7 | 37.1 |
| Asymptomatic Dogs | 3.4 | 1.7 | 5.2 |

Data are compared using the Mann Whitney test and are expressed as Mean±Standard Error of the Mean (SEM) using ELISA units. The data show that there is a significant statistical difference between the symptomatic cohort vs the asymptomatic cohort.

TABLE 5

Mean ± SEM of ELISA results (EU/mL) obtained for three markers, AGA, AZA, and ATTGA, for serum collected from the symptomatic and asymptomatic cohorts.

| Cohort | Symptomatic Dogs | Asymptomatic Dogs | p Values |
|---|---|---|---|
| AGA | 208.3 ± 28.57 | 29.05 ± 4.60 | <0.0001 |
| AZA | 59.57 ± 12.65 | 13.68 ± 5.897 | <0.0001 |
| ATTGA | 92.69 ± 18.36 | 16.04 ± 1.954 | 0.006 |

Overall, these results indicate that the method of detecting in a sample the presence and/or level of endogenous antibodies to gliadin, zein, tissue transglutaminase, and amylase inhibitors can be utilized to evaluate food sensitivity in dogs.

SEQUENCE LISTING

| SEQ ID NO | Gene | Sequence |
|---|---|---|
| SEQ ID NO: 1 | Flagellin | FW: 5'-gctttaactgtaaacaccaac-3' |
| SEQ ID NO: 2 | Flagellin | REV: 5'-ctactgaagcagtttcagga-3' |

SEQUENCE LISTING

| SEQ ID NO | Gene | Sequence |
|---|---|---|
| SEQ ID NO: 3 | Flagellin | FW: 5'-gctttatctgttaataccaacatc-3' |
| SEQ ID NO: 4 | Flagellin | REV: 5'-ttactgaagcagtttcagtaccg-3' |
| SEQ ID NO: 5 | Flagellin | FW: 5'-gcacaagtcattaataccaac-3' |
| SEQ ID NO: 6 | Flagellin | REV: 5'-ttaacgtaacagagacagaac-3' |
| SEQ ID NO: 7 | Flagellin | FW: 5'-gcacaagtcattaataccaac-3' |
| SEQ ID NO: 8 | Flagellin | REV: 5'-ttaaccctgcagcagaga-3' |
| SEQ ID NO: 9 | Flagellin | MALTVNTNIASVTTQVNLNKASTAQTTSMQRLSSGL<br>RINSAKDDAAGLQIANRLTSQINGLGQAVKNANDGI<br>SIAQTAEGAMQASTDILQKMRTLALSSATGSLSPDD<br>RKSNNDEYQALTAELNRISATTTFGGQKLLDGSYGT<br>KAIQVGANANETINLTLDNVSAKSIGSQQLKTGNIS<br>ISKDGLAAGELAVTGNGQTKTVNYGPGASAKDVAAQ<br>LNGAIGGLTATASTEVKLDASGATAAAPANFDLTVG<br>GSTVSFVGVTDNASLADQLKSNAAKLGISVNYDEST<br>KNLEIKSDTGENITFAPKAGAPGVKIAAKNGSGTYG<br>AAVPLNAAAGDKSVVTGQISLDSAKGYSIADGAGAN<br>GAGSTAALYGTGVTSVSSKKTNVSDTDVTSATNAQN<br>AVAVIDKAIGSIDSVRSGLGATQNRLTTTVDNLQNI<br>QKNSTAARSTVQDVDFASETAELTKQQTLQQASTAI<br>LSQANQLPSSVLKLLQ |
| SEQ ID NO: 10 | Flagellin | MALSVNTNIASITTQGNLTKASTAQTTSMQRLSSGL<br>RINSAKDDAAGLQISNRLTSQINGLGQAVKNANDGI<br>SIAQTAEGAMQASTDILQKMRTLALSSATGSLSADD<br>RKSNNDEYQALTAELTRISQTTTFGGQKLLDGSYGT<br>KAIQVGANANETINLTLDNVAANNIGSQQVKSVAIT<br>PSATGVDAGTVTVTGNGQTKDVTVTAGDSAKTIAAN<br>LNGAIGGLTATASTEVQFSVDKTAPAANFELTVGSQ<br>KVSFVGVTDTASLADQLKSNAAKLGISVNYDESNGG<br>SLSVKSDTGENLVFGAGDAAAQAGIKVNAKDGNGEY<br>AASGTALTAADLYVTGAISLDSAKGYSLTGGGVTKL<br>FSAAGTAATSVKTTIADTDVTDATKAQNALAVIDKA<br>IGSIDSVRSGLGATQNRLQTTVDNLQNIQKNSTAAR<br>STVQDVDFASETAELTKQQTLQQASTAILSQANQLP<br>SSVLKLLQ |
| SEQ ID NO: 11 | Flagellin | MAQVINTNYLSLVTQNNLNKSQGTLGSAIERLSSGL<br>RINSAKDDAAGQAIANRFTSNVNGLTQASRNANDGI<br>SIAQTTEGALNEINNNLQRIRELTVQAKNGTNSNSD<br>ITSIQNEVKERLDEINRISEQTQFNGVKVLSGEKSE<br>MVIQVGTNDNETIKFNLDKVDNDTLGVASDKLFDTK<br>TEKKGVTEAGAAIDAKDIGVTGATKYEGGTVKEYKV<br>DGKVSADKVIFNDGTKDYLVSKSDFKLKAGTADTAE<br>FTGSKTTEFKADAGKDVKTLNVKDDALATLDKAINT<br>IDESRSKLGAIQNRFESTINNLNNTVNNLSASRSRI<br>LDADYATEVSNMSRGQILQQAGTSVLAQANQVPQTV<br>LSLLR |
| SEQ ID NO: 12 | Flagellin | MAQVINTNSLSLITQNNINKNQSALSSSIERLSSGL<br>RINSAKDDAAGQAIANRFTSNIKGLTQAARNANDGI<br>SLAQTTEGALSEINNNLQRVRELTVQATTGTNSDSD<br>LSSIQDEIKSRLDEIDRVSGQTQFNGVNVLAKNGTM<br>KIQVGANDGQTIAIDLQKIDSSTLGLNGLSVSKNSL<br>NVSEPVTQINNAANTAPLKVDLSAVATDLGVDASSL<br>TLSNVLDKDGNATKNYVVKSGNDYFAASVDRATGKV<br>ALNKADVEYTDPANGLTTAATQAGQFVKVSADKDGN<br>ATAPFVTFQGKNYAAKAASLVDTGDATTAAQGTAATT<br>NKVTLQLSDKAAVIGTGTAANPQFPATSATAEFAGT<br>ATNDPLALLDKAIASVDKFRSSLGAVQNRLSSAVTN<br>LNNTTTNLSEAQSRIQDADYATEVSNMSKAQIVQQA<br>GNSVLSKANQVPQQVLSLLQG |
| SEQ ID NO: 13 | Flagellin | MAQVINTNSLSLITQNNINKNQSALSSSIERLSSGL<br>RINSAKDDAAGQAIANRFTSNIKGLTQAARNANDGI<br>SVAQTTEGALSEINNNLQRVRELTVQATTGTNSQSD<br>LDSIQDHIKSRLDEIDRVSGQTQFNGVNVPAKDGSM<br>KIQVGANDGQTITIDLKKIDSSTLKLTGFNVNGSGS<br>VANTAATKADLAAAAIGTPGAADSTGAIAYTVSAGL |

-continued

| SEQ ID NO | Gene | Sequence |
|---|---|---|
| | | TKTTAADVLSSLADGTTITATGVKNGFAAGATSNAY<br>KLNKDNNTFTYDTTATTAELQSYLTPKAGDTATFSV<br>EIGGTTQDVVLSSDGKLTAKDGSKLYIDTTGNLTQN<br>GGNNGVGTLAEATLSGLALNNNNGAAAVKSTITTAD<br>NTSIVLNGSSNGTEGTIAVTGAVISSAALQSASKTT<br>GFTVGTADTAGYISVGTDGSVQAYDVATSGNKDSYT<br>NTDGTLTTDNTTKLYLQKDGSVTNGSGKAVYVEADG<br>DFTTDAATKAATTTDPLAALDDAISQIDKFRSSLGA<br>IQNRLDSAVTNLNNTTTNLSEAQSRIQDADYATEVS<br>NMSKAQIIQQAGNSVLAKANQVPQQVLSLLQG |
| SEQ ID NO: 14 | OMPC | FW: 5'-ctgaagtttacaacaaagac-3' |
| SEQ ID NO: 15 | OMPC | REV: 5'-ttagaactggtaaaccagacc-3' |
| SEQ ID NO: 16 | OMPC | AEVYNKDGNKLDLYGKVDGLHYFSDNKSEDGDQTYV<br>RLGFKGETQVTDQLTGYGQWEYQIQGNTSEDNKENS<br>WTRVAFAGLKFQDVGSFDYGRNYGVVYDVTSWTDVL<br>PEFGGDTYGSDNFMQQRGNGFATYRNTDFFGLVDGL<br>NFAVQYQGKNGSVSGEGMTNNGRGALRQNGDGVGGS<br>ITYDYEGFGIGAAVSSSKRTDDQNGSYTSNGVVRNY<br>IGTGDRAETYTGGLKYDANNIYLAAQYTQTYNATRV<br>GSLGWANKAQNFEAVAQYQFDFGLRPSLAYLQSKGK<br>NLGVINGRNYDDEDILKYVDVGATYYFNKNMSTYVD<br>YKINLLDDNQFTRDAGINTDNIVALGLVYQF |
| SEQ ID NO: 17 | OMPC | AEVYNKDGNKLDLYGKVDGLHYFSDNKDVDGDQTYM<br>RLGFKGETQVTDQLTGYGQWEYQIQGNSAENENNSW<br>TRVAFAGLKFQDVGSFDYGRNYGVVYDVTSWTDVLP<br>EFGGDTYGSDNFMQQRGNGFATYRNTDFFGLVDGLN<br>FAVQYQGKNGSVSGEGMTNNGRGALRQNGDGVGGSI<br>TYDYEGFGIGGAISSSKRTDDQNSPLYIGNGDRAET<br>YTGGLKYDANNIYLAAQYTQTYNATRVGSLGWANKA<br>QNFEAVAQYQFDFGLRPSVAYLQSKGKNLGVINGRN<br>YDDEDILKYVDVGATYYFNKNMSTYVDYKINLLDDN<br>QFTRDAGINTDNIVALGLVYQF |
| SEQ ID NO: 18 | OMPC | AEVYNKDGNKLDLYGKVDGLHYFSDNDSKDGDKTYM<br>RLGFKGETQVTDQLTGYGQWEYQIQGNEPESDNSSW<br>TRVAFAGLKFQDVGSFDYGRNYGVVYDVTSWTDVLP<br>EFGGDTYDSDNFMQQRGNGFATYRNTDFFGLVDGLD<br>FAVQYQGKNGSAHGEGMTTNGRDDVFEQNGDGVGGS<br>ITYNYEGFGIGAAVSSSKRTWDQNNTGLIGTGDRAE<br>TYTGGLKYDANNIYLAAQYTQTYNATRVGSLGWANK<br>AQNFEAVAQYQFDFGLRPSLAYLQSKGKNLGRGYDD<br>EDILKYVDVGATYYFNKNMSTYVDYKINLLDDNRFT<br>RDAGINTDDIVALGLVYQF |
| SEQ ID NO: 19 | Hetero-<br>chimeric<br>S100A8/<br>S100A9 | MGSSHHHHHHGLTELESAINSLIEVYHKYSLVKGNY<br>HALYRDDLKKLLETECPQYMKKKADDTWFQELDVNS<br>DGAINFEEFLILVIKVGVASHKDIHKEGGGGSGGGG<br>SGGGGSADQMSQLECSIETIINIFHQYSVRLEHPDK<br>LNQKEMKQLVKKELPNFLKKQKKNDAINKIMEDLD<br>TNGDKELNFEEFSILVARLTVASHEEMHKNAPEGEG<br>HSHGPGFGEGSQGHCSHGGHGHGHSH |
| SEQ ID NO: 20 | S100A12 | MGSSHHHHHHGTKLEDHLEGIVDVFHRYSARVGHPD<br>TLSKGEMKQLIIRELPNTLKNTKDQATVDKLFQDLD<br>ADKDGQVNFNEFISLVSVVLDTSHKNTHKE |
| SEQ ID NO: 21 | S100A8 | MGSSHHHHHHGLTELESAINSLIEVYHKYSLVKGNY<br>HALYRDDLKKLLETECPQYMKKKADDTWFQELDVNS<br>DGAINFEEFLILVIKVGVASHKDIHKE |
| SEQ ID NO: 22 | S100A9 | MGSSHHHHHHGADQMSQLECSIETIINIFHQYSVRL<br>EHPDKLNQKEMKQLVKKELPNFLKKQKKNDAINKI<br>MEDLDTNGDKELNFEEFSILVARLTVASHEEMHKNA<br>PEGEGHSHGPGFGEGSQGFFIXHGGHGHGHSH |
| SEQ ID NO: 23 | α4 | FW: 5'-GTGTCTGCCTCTCGACCTCGG-3' |
| SEQ ID NO: 24 | α4 | FW: 5'-CAGAGAATTGAAGGATTTCAAATCAG<br>C-3' |

| SEQ ID NO | Gene | Sequence |
|---|---|---|
| SEQ ID NO: 25 | α4 | REV: 5'-TTATGTGAAATGACGTTTGGGTCTTT G-3' |
| SEQ ID NO: 26 | β7 | FW: 5'-GAATTGGATGCCAAGATCTCC-3' |
| SEQ ID NO: 27 | β7 | REV: 5'-TTACAGTGTGTGCAGCTCCACAGTCA G-3' |
| SEQ ID NO: 28 | β7 | REV: 5'-TTAGTGATCCGCGCCTCTCTCTTG-3' |
| SEQ ID NO: 29 | α4 | WLVVGAPTARWLANASVVNPGAIYRCRIGGNPGLTC EQLQLGSPSGEPCGKTCLEERDNQWLGVTLSRQPGE NGSIVTCGHRWKNIFYIKNENKLPMGVCYGMPSDLR TELSKRIAPCYQDYVRKFGENFASCQAGISSFYTED LIVMGAPGSSYWTGSLFVYNITTNKYKAFLDRQNQV KFGSYLGYSVGAGHFRSPHTTEVVGGAPQHEQIGKA YIFSIEAKELSILHEMKGKKLGSYFGASVCAVDLNA DGFSDLLVGAPMQSTIREEGRVFVYINSGSGAVMNE METELIGSDKYAARFGESIVNLGDIDNDGFEDVAVG APQEDDLRGAVYIYNGRADGISTAFSQRIEGFQISK SLSMFGQSISGQIDADNNGYVDVAVGAFRSDSAVLL RTRPVVIVEVSLNHPESVNRTNFDCVENGLPSVCMD LTLCFSYKGKEVPGYIVLLYNMSLDVNRKIDSPSRF YFSSNGTSDVITGSMKVSSKVPNCRTHQAFMRKDVR DILTPIQIEAAYRLGQHVIRKRSTEEFPPLQPILQQ KKERDIIEKTINFARFCAHENCSADLQVSARIGFLK PHENKTYVAVGSMKTVMLNVSLFNAGDDAYETALHI RLPSGLYFIKILDLEEKQINCEVTDSSGSVKLDCSI GYIYMDRLSRMDISFLLDVSSLSQAEEDLSLTVHAT CANEREMDNLNKVTLAIPLKYEVMLSVHGFVNPTSF IYGPKEENEPDTCMAEKMNFTFHVINTTGHSMAPNV SVEIMVPNSFAPQTDKLFNILDVQPAGECHFKTYQR KCALEQEKGAMKILKDIFTFLSKTDKKLLFCMKADP YCLTILCHLGKMESGKEASVHIQLEGRPYLSEMDET SALKFEVRVTAFPEPNPKVIELNKDENVAHVLLEGL HHQRPKRHFT |
| SEQ ID NO: 30 | α4 | VSASRPRPGSTPPPPPWQVYPVAEAWEGGASSSGSG EQGPRAGGCGAPAGSSPKVLVAKSGARGLSSSWWGR RGDAQARGFGAGSWELEGDLAHVCAHLHGCPLGLWL VVGAPTARWLANASVVNPGAIYRCRIGGNPGLTCEQ LQLGSPSGEPCGKTCLEERDNQWLGVTLSRQPGENG SIVTCGHRWKNIFYIKNENKLPMGVCYGMPSDLRTE LSKRIAPCYQDYVRKFGENFASCQAGISSFYTEDLI VMGAPGSSYWTGSLFVYNITTNKYKAFLDRQNQVKF GSYLGYSVGAGHFRSPHTTEVVGGAPQHEQIGKAYI FSIEAKELSILHEMKGKKLGSYFGASVCAVDLNADG FSDLLVGAPMQSTIREEGRVFVYINSGSGAVMNEME TELIGSDKYAARFGESIVNLGDIDNDGFEDVAVGAP QEDDLRGAVYIYNGRADGISTAFSQRIEGFQISKSL SMFGQSISGQIDADNNGYVDVAVGAFRSDSAVLLRT RPVVIVEVSLNHPESVNRTNFDCVENGLPSVCMDLT LCFSYKGKEVPGYIVLLYNMSLDVNRKIDSPSRFYF SSNGTSDVITGSMKVSSKVPNCRTHQAFMRKDVRDI LTPIQIEAAYRLGQHVIRKRSTEEFPPLQPILQQKK ERDIIEKTINFARFCAHENCSADLQVSARIGFLKPH ENKTYVAVGSMKTVMLNVSLFNAGDDAYETALHIRL PSGLYFIKILDLEEKQINCEVTDSSGSVKLDCSIGY IYMDRLSRMDISFLLDVSSLSQAEEDLSLTVHATCA NEREMDNLNKVTLAIPLKYEVMLSVHGFVNPTSFIY GPKEENEPDTCMAEKMNFTFHVINTGHSMAPNVSVE IMVPNSFAPQTDKLFNILDVQPAGECHFKTYQRKCA LEQEKGAMKILKDIFTFLSKTDKKLLFCMKADPYCL TILCHLGKMESGKEASVHIQLEGRPYLSEMDETSAL KFEVRVTAFPEPNPKVIELNKDENVAHVLLEGLHHQ RPKRHFT |
| SEQ ID NO: 31 | β7 | ELDAKISSAEKATEWRDPDLSLLGSCQPAPSCRECI LSHPSCAWCKQLFWGLGIRDQDASPFGSWGGPSPWP AHRCRPALWCLFCDPPPPPASAPRLSPGPSRRCTL DPLLCRRLHRAPCALCPAPCTLHPALRLGTPCATST WPARPLAQPSPCPLPGFGSFVDKTVLPFVSTVPAKL RHPCPTRLERCQPPFSFRHVLSLTGDATAFEREVGR QSVSGNLDSPEGGFDAILQAALCQEKIGWRNVSRLL |

| SEQ ID NO | Gene | Sequence |
|---|---|---|
| | | VFTSDDTFHTAGDGKLGGIFMPSDGHCHLDSNGLYS<br>RSPEFDYPSVGQVAQALSTANIQPIFAVTSATLPVY<br>QELSKLIPKSAVGELSEDSSNVVQLIMDAYNSLSST<br>VTLEHSALPPGVHISYESLCGDPEKREAEAGDRGQC<br>SHVPINHTVNFLVTLQATRCLPEPHLLRLRALGFSE<br>ELTVELHL |
| SEQ ID NO: 32 | β7 | ELDAKISSAEKATEWRDPDLSLLGSCQPAPSCRECI<br>LSHPSCAWCKQLFWGLGIRDQDASPFGSWGGPSPWP<br>AHRCRPALWCLFCDPPPPPPASAPRLSPGPSRRCTL<br>DPLLCRRLHRAPCALCPAPCTLHPALRLGTPCATST<br>WPARPLAQPSPCPLPGFGSFVDKTVLPFVSTVPAKL<br>RHPCPTRLERCQPPFSFRHVLSLTGDATAFEREVGR<br>QSVSGNLDSPEGGFDAILQAALCQEKIGWRNVSRLL<br>VFTSDDTFHTAGDGKLGGIFMPSDGHCHLDSNGLYS<br>RSPEFDYPSVGQVAQALSTANIQPIFAVTSATLPVY<br>QELSKLIPKSAVGELSEDSSNVVQLIMDAYNSLSST<br>VTLEHSALPPGVHISYESLCGDPEKREAEAGDRGQC<br>SHVPINHTVNFLVTLQATRCLPEPHLLRLRALGFSE<br>ELTVELHTLCDCNCSDTQPQAPHCSDGQGLLQCGVC<br>SCAPGRLGRLCECSEAELSSPDLESGCRAPNGTGPL<br>CSGKGRCQCGRCSCSGQSSGPLCECDDASCERHEGI<br>LCGGFGHCQCGRCHCHANRTGSACECSMDTDSCLGP<br>EGEVCSGHGDCKCNRCQCRDGYFGALCEQCSGCKTS<br>CERHRDCAECGAFGTGPLATNCSVACAHYNVTLALV<br>PVLDDGWCKERTLDNQLLFFLVEEEAGGMVVLTVRP<br>QERGADH |
| SEQ ID NO: 33 | TAG | MGSSHHHHHHGSGLVPRGSASMSDSEVNQEAKPEVK<br>PEVKPETHINLKVSDGSSEIFFKIKKTTPLRRLMEA<br>FAKRQGKEMDSLRFLYDGIRIQADQTPEDLDMEDND<br>IIEAHREQIGG |
| SEQ ID NO: 34 | Flagellin | MGSSHHHHHHGSGLVPRGSASMSDSEVNQEAKPEVK<br>PEVKPETHINLKVSDGSSEIFFKIKKTTPLRRLMEA<br>FAKRQGKEMDSLRFLYDGIRIQADQTPEDLDMEDND<br>IIEAHREQIGGALTVNTNIASVTTQVNLNKASTAQT<br>TSMQRLSSGLRINSAKDDAAGLQIANRLTSQINGLG<br>QAVKNANDGISIAQTAEGAMQASTDILQKMRTLALS<br>SATGSLSPDDRKSNNDEYQALTAELNRISATTTFGG<br>QKLLDGSYGTKAIQVGANANETINLTLDNVSAKSIG<br>SQQLKTGNISISKDGLAAGELAVTGNGQTKTVNYGP<br>GASAKDVAAQLNGAIGGLTATASTEVKLDASGATAA<br>APANFDLTVGGSTVSFVGVTDNASLADQLKSNAAKL<br>GISVNYDESTKNLEIKSDTGENITFAPKAGAPGVKJ<br>AAKNGSGTYGAAVPLNAAAGDKSVVTGQISLDSAKG<br>YSIADGAGANGAGSTAALYGTGVTSVSSKKTNVSDT<br>DVTSATNAQNAVAVIDKAIGSIDSVRSGLGATQNRL<br>TTTVDNLQNIQKNSTAARSTVQDVDFASETAELTKQ<br>QTLQQASTAILSQANQLPSSVLKLLQ |
| SEQ ID NO: 35 | OMPC | MGSSHHHHHHGSGLVPRGSASMSDSEVNQEAKPEVK<br>PEVKPETHINLKVSDGSSEIFFKIKKTTPLRRLMEA<br>FAKRQGKEMDSLRFLYDGIRIQADQTPEDLDMEDND<br>IIEAHREQIGGAEVYNKDGNKLDLYGKVDGLHYFSD<br>NKSEDGDQTYVRLGFKGETQVTDQLTGYGQWEYQIQ<br>GNTSEDKENSWTRVAFAGLKFQDVGSFDYGRNYGV<br>VYDVTSWTDVLPEFGGDTYGSDNFMQQRGNGFATYR<br>NTDFFGLVDGLNFAVQYQGKNGSVSGEGMTNNGRGA<br>LRQNGDGVGGSITYDYEGFGIGAAVSSSKRTDDQNG<br>SYTSNGVVRNYIGTGDRAETYTGGLKYDANNIYLAA<br>QYTQTYNATRVGSLGWANKAQNFEAVAQYQFDFGLR<br>PSLAYLQSKGKNLGVINGRNYDDEDILKYVDVGATY<br>YFNKNMSTYVDYKINLLDDNQFTRDAGINTDNIVAL<br>GLVYQF |
| SEQ ID NO: 36 | Poly-His tag | MGSSHHHHHHG |
| SEQ ID No: 37 | Gliadin | QPQPQPQPQPQMNTCAAFLQQCSQTAYVQSQMWQAS<br>GCQLMRQQCCQPLAQISEQAR |
| SEQ ID No: 38 | Gliadin | QQQGQR |
| SEQ ID No: 39 | Gliadin | FGQPQQQQGQSFGQPQQQVPVEIMGM |

| SEQUENCE LISTING | | |
|---|---|---|
| SEQ ID NO | Gene | Sequence |
| SEQ ID No: 40 | Gliadin | VFLQQQCSPVAMPQHLAR |
| SEQ ID No: 41 | Amylase inhibitor | AFQVPALPACRPLLR |
| SEQ ID No: 42 | Amylase inhibitor | LQCNGSQVPEAVLRDCCQQLAHISEWCR |
| SEQ ID No: 43 | Amylase inhibitor | EHGAQEGQAGTGAFPR |
| SEQ ID No: 44 | Amylase inhibitor | LTAASITAVCRLPIVVDASGDGAYVCK |
| SEQ ID No: 45 | Amylase inhibitor | YKEHGAQEGQAGTGAFPR |
| SEQ ID No: 46 | Zein | ATIFPQCSQAPIA |
| SEQ ID No: 47 | Zein | PYLPS |
| SEQ ID No: 48 | Zein | IIASICENPALQPYRLQQAIAASNIPLSPL |
| SEQ ID No: 49 | Zein | LFQQSPALS |
| SEQ ID No: 50 | Zein | LVQSLVQTIR |
| SEQ ID No: 51 | Zein | SQQQQFLPFNQL |
| SEQ ID No: 52 | Zein | SQLATAYSQQQQLLPF |
| SEQ ID No: 53 | Zein | QILLPFSQLAAANRASFLTQQQLLPFYQQF |
| SEQ ID No: 54 | Zein | AANPATLLQLQQLL |
| SEQ ID No: 55 | Zein | VQLALTDPAASYQQH |
| SEQ ID No: 56 | Zein | IIGGALF |
| SEQ ID No: 57 | Zein | AQQLQQLVLAN |
| SEQ ID No: 58 | Gliadin | MGSSHHHHHHGQPQPQPQPQMNTCAAFLQQCSQT AYVQSQMWQASGCQLMRQQCCQPLAQISEQARCQAV CSVAQIIMRQQQGQRFGQPQQQQGQSFGQPQQQVPV EIMGM |
| SEQ ID No: 59 | Amylase inhibitor | MGSSHHHHHHGAFQVPALPACRPLLRLQCNGSQVPE AVLRDCCQQLAHISEWCRCGALYSMLDSMYKEHGAQ EGQAGTGAFPRCRREVVKLTAASITAVCRLPIVVDA SGDGAYVCK |
| SEQ ID No: 60 | Zein | MGSSHHHHHHGIIASICENPALQPYRLQQAIAASNI PLSPLLFQQSPALSLVQSLVQTIRAQQLQQLVLPLI NQVALANLSPYSQQQQFLPFNQLSTLNPAAYLQQQL LPFSQLATAYSQQQQLLPFNQLAALNPAAYLQQQIL LPFSQLAAANRASFLTQQQLLPFYQQFAANPATLLQ LQQLLPFVQLALTDPAASYQQHIIGGALF |
| SEQ ID No: 61 | TTG2 | 5'-GCCGAGGATCTGGTTCTCGAG-3' |
| SEQ ID No: 62 | TTG2 | 5'-TTAGGCGGGACCAATGAGGAC-3' |
| SEQ ID No: 63 | TTG2 | MGSSHHHHHHSGLVPRGSASMSDSEVNQEAKPEVK PEVKPETHINLKVSDGSSEIFFKIKKTTPLRRLMEA FAKRQGKEMDSLRFLYDGIRIQADQTPEDLDMEDND IIEAHREQIGGAEDLVLEKCDLELEANGRDHHTAGL CQGRLVVRRGQPFWLTLHFTGRSYESSVDSLTFSAV TGPDPSEEAGTKARFSLSSAVEEGAWTAWMDQQDSV LSLQLSTPPNAPVGLYRLSLEASTGYQGSSFVLGHF TLLFNSWCPADAVYLDSDEERREYVLSQQGFIYQGS VKFIKSIPWNFGQFEDGILDICLMLLDRNPKFLKDA CRDCSSRSNPIYVGRVVSAMVNCNDDQGVLLGRWDN NYKDGISPMFWIGSVDILRRWKTSGCQRVKYGQCWV FAAVACTVLRCLGIPTRVVTNFNSAHDQNSNLLIEY |

SEQUENCE LISTING

| SEQ ID NO | Gene | Sequence |
|---|---|---|
| | | VYNKFGEIQKEKSEMIWNYHCWVESWMSRPDLQPGY<br>EGWQALDPTPQEKSEGTYCCGPVPVRAIKEGDLSTK<br>YDAAFVFAEVNADVVNWIQQDDGSLCKSTNNSQTVG<br>MKISTKSVGRDEREDITHNYKYPEGSPEEREAFRKA<br>NHLNKLTEKEETGLAMRIRVSESMSMGSDFDVFAYI<br>NNNTSESHSCRLLLHARTVSYNGILGPECGTKDLLN<br>LSLEPFSEKSIPLRILYEKYCECLTESNLIKVRGLL<br>VEQAANNYLLAERDIYLENPEIKIRILGEPKQNRKL<br>VAEASLRNPLTVPLLGCSFTMEGAGLTEEQKVMDVP<br>DPVEAGEEVKVRVDLLPRHVGRHKLVVNFESDKLKA<br>VKGFRNVLIGPA |
| SEQ ID No: 64 | TG3 | FW: 5'-ACG GCT TTA GAA CCC CAG AGT ATC-3' |
| SEQ ID No: 65 | TG3 | REV: 5'-CTT CAC TCG GCC ACG TCA ATG GAC-3' |
| SEQ ID No: 66 | TG3 | MGSSHHHHHHGSGLVPRGSASMSDSEVNQEAKPEVK<br>PEVKPETHINLKVSDGSSEIFFKIKKTTPLRRLMEA<br>FAKRQGKEMDSLRFLYDGIRIQADQTPEDLDMEDND<br>IIEAHREQIGGTALEPQSINWQATSNRRAHHTDRFS<br>SQEPILRRGQSFNFSLSLNRSLGTGESLGFVVSTGP<br>QPSESARTKAVFPLSNRTSRGGWSAELVSNKDNILT<br>ISISSPVNAPVGWYTLSTQISSQGKDFILKLGMFIL<br>LFNPWLQEDGVFMDNHVEREEYVLEDAGIIYVGSTN<br>RIGMVGCNFGQFEEGELNICLSILDHSLNFRRDPAT<br>DVARRNDPKYVGRVLSAMVNGNDDNGVLSGNWSGNY<br>TGGRDPRNWNGSVEILKEWKKSGFRPVRFGQCWVFA<br>GTLNTVLRSFGIPSRVVTNFNSAHDTDRNLSVHVYY<br>DPYGRPMDKGSDSVWNFHVWNEAWFVRTDLGPLYNG<br>WQVLDATPQERSQGVFQCGPASVAAVREGDVNLDFD<br>MPFVFAEVNADRITWIYDVYNSTQKQNASDAHSIGR<br>YISTKAVGSNSRMDITEKYKHPEGSSQERQVFEKAL<br>GKLKPHASFGATSARHLADKLR |

REFERENCES

Xavier, R. J. & Podolsky, D. K. Nature 448: 427-434 (2007).
Cerquetella, M. et al. World J. Gastroent. 16: 1050-1056 (2010).
Hall, E J. Hill's Pet Nutrition (2009).
Hasida, et al., J. Clin. Lab. Anal. 11: 267-286 (1997).
Braun, J. U.S. Pat. No. 6,033,864 Pub. Date Mar. 7 (2000).
Walsh & Rose U.S. Pat. No. 6,218,129 Pub. Date Apr. 17 (2001).
Lindberg et al., Gut, 33:909-913 (1992).
Sendid et al., Clin. Diag. Lab. Immunol., 3:219-226 (1996).
Frosh et al., Proc. Natl. Acad. Sci. USA, 82:1194-1198 (1985).
Fukazawa, Y. In "Immunology of Fungal Disease," E. Kurstak et al. (eds.), Marcel Dekker Inc., New York, pp. 37-62 (1989).
Kikuchi et al., Planta, 190:525-535 (1993).
Nikaido, H. Microbiol. Mol. Biol. Rev. 67:593-656 (2003).
Braun & Sutton U.S. Pat. No. 6,309,643 Pub. Date Oct. 30 (2001).
Scalice, E. R. & Daiss, J. L. U.S. Pat. No. 6,838,250 Pub. Date Jan. 4 (2005).
Krakauer, T. U.S. Pat. No. 6,406,862 Pub. Date Jun. 18 (2002).
Melnick, J. L. & Wallis, C. U.S. Pat. No. 4,277,250 Pub. Date Jul. 7, 1981
Okuda, S. & Uchida, K. U.S. Pat. No. 4,920,045 Pub. Date Apr. 24 (1990).
Nolan, J. P. & Mandy, F. Cytometry 69: 318-325 (2006).
Felici, F. et al. Methods Enzymol. 267:116-129 (1996).
The immunoassay handbook 4th edition, D. Wild ed. Newnes, (2013).
Harlow and Lane. Antibodies: A Laboratory Manual, Cold Spring Harbor Laboratory, New York (1988).
Buechler, K. U.S. Pat. No. 6,019,944 Pub. Date Feb. 1 (2000).
Anderson, M. Nucleic Acid Hybridization, Springer Verlag, New York (1999).
Hardinam, G. Microarray Methods and Applications: The Nuts and Bolts Series, DNA Press (2003).
Baldi, P. & G. Westley Hatfield. DNA Microarrays and Gene Expression: From Experiments to Data Analysis and Modeling, Cambridge University Press, (2002).
Remington's Pharmaceutical Sciences, 18th Ed., Mack Publishing Co., Easton, Pa. (1990).

The invention claimed is:

1. An isolated antigen comprising a sequence selected from the group consisting of SEQ ID NO: 19, SEQ ID NO: 20, SEQ ID NO: 21, SEQ ID NO: 22, SEQ ID NO: 29, SEQ ID NO: 30, SEQ ID NO: 31, and SEQ ID NO: 32, wherein the sequence is bound to one or more of a label, a purification tag, or another protein or fragment thereof.

2. The isolated antigen of claim 1, comprising a first region comprising SEQ ID NO: 21 and a second region comprising SEQ ID NO: 22, wherein the first and second regions are linked by a linker sequence.

3. The isolated antigen of claim 2, comprising a sequence according to SEQ ID NO: 19.

4. The isolated antigen of claim 1, comprising a first region comprising SEQ ID NO: 29 or 30, and a second region comprising SEQ ID NO: 31 or 32, wherein the regions are linked by a linker sequence.

5. The isolated antigen of claim 1, wherein the antigen is bound to a solid substrate.

6. The isolated antigen of claim 5, wherein the antigen is bound to purification tag which is a polyhistidine tag according to SEQ ID NO: 36.

7. A fusion protein comprising a first region comprising a canine calprotectin S100A8 monomer region, and a second region comprising a calprotectin S100A9 monomer region, wherein the regions are linked by a linker sequence, and wherein the fusion protein is optionally bound to one or more of a label, a purification tag, a solid substrate, or another protein or fragment thereof, wherein the canine calprotectin S100A8 monomer region comprises SEQ ID NO: 21 and the calprotectin S100A9 monomer region comprises SEQ ID NO: 22.

8. The fusion protein of claim 7, wherein the linker sequence comprises a sequence of 10-30 non-charged amino acid residues.

9. The fusion protein of claim 7, wherein the protein is bound to a solid substrate.

10. The fusion protein of claim 7, wherein the protein is linked to a purification tag which is a polyhistidine tag according to SEQ ID NO: 36.

11. A kit comprising the isolated antigen of claim 1.

12. The kit of claim 11, wherein the isolated antigen is bound to a solid substrate.

13. The kit of claim 11 further comprising one of more additional reagents selected from:
 a. bacteria-derived peptides comprising at least 10 consecutive amino acids from a sequence selected from the group consisting of SEQ ID NO 9, 10, 11, 12, 13, 16, 17, and 18, optionally bound to one or more of a label, a purification tag, a solid substrate, or another protein or fragment thereof, and
 b. gluten-derived peptides selected from the group consisting of wheat extract and peptides comprising SEQ ID NO 37, 38, 39, 40, or 58, optionally bound to one or more of a label, a purification tag, a solid substrate, or another protein or fragment thereof.

14. The kit of claim 11 further comprising means for detection of a complex formed between the isolated antigen and an endogenous antibody from a dog.

15. The kit of claim 11 further comprising a labeled antibody specific for canine IgA and capable of binding to a complex formed between the isolated antigen and an endogenous IgA antibody from a dog.

16. The kit of claim 11 further comprising a labeled antibody specific for canine IgA and capable of binding to a complex formed between the isolated antigen and an endogenous IgG antibody from a dog.

17. A kit comprising the fusion protein of claim 7.

18. The kit of claim 17, wherein the fusion protein is bound to a solid substrate.

19. The kit of claim 17 further comprising one of more additional reagents selected from:
  a. bacteria-derived peptides comprising at least 10 consecutive amino acids from a sequence selected from the group consisting of SEQ ID NO 9, 10, 11, 12, 13, 16, 17, and 18, optionally bound to one or more of a label, a purification tag, a solid substrate, or another protein or fragment thereof, and
  b. gluten-derived peptides selected from the group consisting of wheat extract and peptides comprising SEQ ID NO 37, 38, 39, 40, or 58, optionally bound to one or more of a label, a purification tag, a solid substrate, or another protein or fragment thereof.

20. The kit of claim 17 further comprising means for detection of a complex formed between the fusion protein and an endogenous antibody from a dog.

21. The kit of claim 17 further comprising a labeled antibody specific for canine IgA and capable of binding to a complex formed between the fusion protein and an endogenous IgA antibody from a dog.

22. The kit of claim 17 further comprising a labeled antibody specific for canine IgG and capable of binding to a complex formed between the fusion protein and an endogenous IgG antibody from a dog.

* * * * *

UNITED STATES PATENT AND TRADEMARK OFFICE
CERTIFICATE OF CORRECTION

PATENT NO. : 11,099,195 B2
APPLICATION NO. : 16/029373
DATED : August 24, 2021
INVENTOR(S) : Estruch et al.

Page 1 of 1

It is certified that error appears in the above-identified patent and that said Letters Patent is hereby corrected as shown below:

In the Claims

Column 195, Line 56; in Claim 6, the phrase "bound to purification tag" should read -- bound to a purification tag --.

Column 196, Line 46; in Claim 13, the phrase "one of more" should read -- one or more --.

Column 197, Line 6; in Claim 19, the phrase "one of more" should read -- one or more --.

Signed and Sealed this
Twenty-first Day of December, 2021

Drew Hirshfeld
*Performing the Functions and Duties of the
Under Secretary of Commerce for Intellectual Property and
Director of the United States Patent and Trademark Office*